United States Patent
Jiang et al.

(10) Patent No.: US 11,974,969 B2
(45) Date of Patent: *May 7, 2024

(54) ARTIFICIALLY SYNTHESIZED SPHINGOSINE DERIVATIVE LIPOID MONOMER AND USE OF SAME FOR DELIVERING NUCLEIC ACID

(71) Applicant: INSTITUTE OF BASIC MEDICAL SCIENCES CHINESE ACADEMY OF MEDICAL SCIENCES, Beijing (CN)

(72) Inventors: Chengyu Jiang, Beijing (CN); Yuhao Qin, Beijing (CN); Xiaoyun Li, Beijing (CN); Cong Zhang, Beijing (CN)

(73) Assignee: INSTITUTE OF BASIC MEDICAL SCIENCES CHINESE ACADEMY OF MEDICAL SCIENCES, Beijing (CN)

( * ) Notice: Subject to any disclaimer, the term of this patent is extended or adjusted under 35 U.S.C. 154(b) by 0 days.

This patent is subject to a terminal disclaimer.

(21) Appl. No.: 17/042,931

(22) PCT Filed: Mar. 29, 2019

(86) PCT No.: PCT/CN2019/080519
§ 371 (c)(1),
(2) Date: Sep. 29, 2020

(87) PCT Pub. No.: WO2019/185038
PCT Pub. Date: Oct. 3, 2019

(65) Prior Publication Data
US 2021/0015767 A1    Jan. 21, 2021

(30) Foreign Application Priority Data

Mar. 29, 2018 (WO) ............... PCT/CN2018/081155

(51) Int. Cl.
| | |
|---|---|
| *A61K 31/133* | (2006.01) |
| *A61K 9/00* | (2006.01) |
| *A61K 31/14* | (2006.01) |
| *A61K 31/661* | (2006.01) |
| *A61K 31/7016* | (2006.01) |
| *A61K 31/702* | (2006.01) |
| *A61K 47/18* | (2017.01) |
| *A61K 47/24* | (2006.01) |

(Continued)

(52) U.S. Cl.
CPC .......... *A61K 31/133* (2013.01); *A61K 9/0053* (2013.01); *A61K 31/14* (2013.01); *A61K 31/661* (2013.01); *A61K 31/7016* (2013.01); *A61K 31/702* (2013.01); *A61K 47/18* (2013.01); *A61K 47/24* (2013.01); *A61P 35/00* (2018.01); *C07C 69/003* (2013.01); *C07C 69/587* (2013.01); *C07C 215/10* (2013.01); *C07C 233/18* (2013.01); *C07F 9/10* (2013.01); *C12N 15/113* (2013.01); *C12N 2310/141* (2013.01); *C12N 2320/32* (2013.01)

(58) Field of Classification Search
CPC .... A61K 31/133; A61K 9/0053; A61K 31/14; A61K 31/661; A61K 31/7016; A61K 31/702; A61K 47/18; A61K 47/24; A61P 35/00; C07C 69/003; C07C 69/587; C07C 215/10; C07C 233/18; C07F 9/10; C12N 15/113; C12N 2310/141; C12N 2320/32
See application file for complete search history.

(56) References Cited

U.S. PATENT DOCUMENTS

| | | | | |
|---|---|---|---|---|
| 6,074,667 | A * | 6/2000 | Kinnunen | A61K 9/127 435/254.11 |
| 2003/0049310 | A1* | 3/2003 | Gao | C07C 219/08 554/107 |

(Continued)

FOREIGN PATENT DOCUMENTS

| | | | | |
|---|---|---|---|---|
| CN | 101939027 A | | 1/2011 | |
| CN | 102409044 A | * | 4/2012 | ......... C12N 15/1065 |

(Continued)

OTHER PUBLICATIONS

English translation of CN102409044 (Shenzhen BGI Technology Co LTD). Published on Apr. 11, 2012. Retrieved from Espacenet.com on Feb. 15, 2022, https://worldwide.espacenet.com/patent/search/family/045873443/publication/CN102409044A?q=2012037879. (Year: 2012).*

(Continued)

*Primary Examiner* — Brandon J Fetterolf
*Assistant Examiner* — Lauren Wells
(74) *Attorney, Agent, or Firm* — Jun He Law Offices P.C.; Zhaohui Wang

(57) ABSTRACT

The invention provides an artificially synthesized single sphingosine lipid and use of delivering a nucleic acid thereof. More particularly, the invention provides Use or method for delivering a nucleic acid to a cell or a subject using a compound of Formula (I), a stereoisomer or a pharmaceutical acceptable salt thereof, or a combination comprising a compound of Formula (I), a stereoisomer or a pharmaceutical acceptable salt thereof,

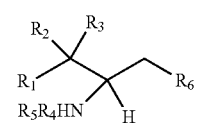

17 Claims, 184 Drawing Sheets
Specification includes a Sequence Listing.

Figure 1A:
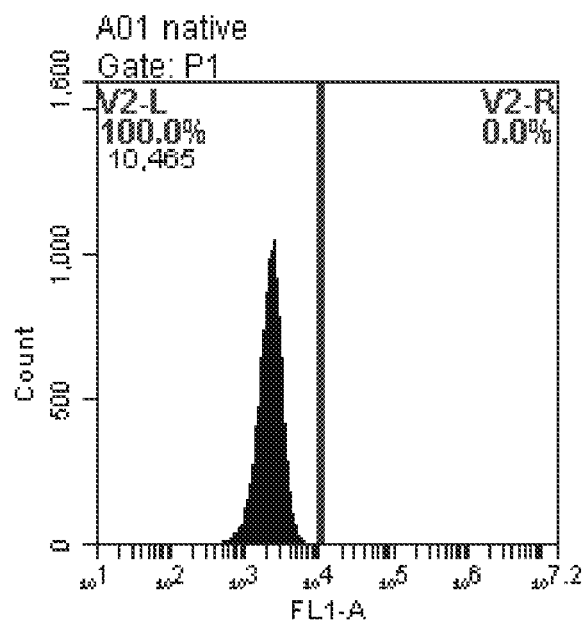
Figure 1B:
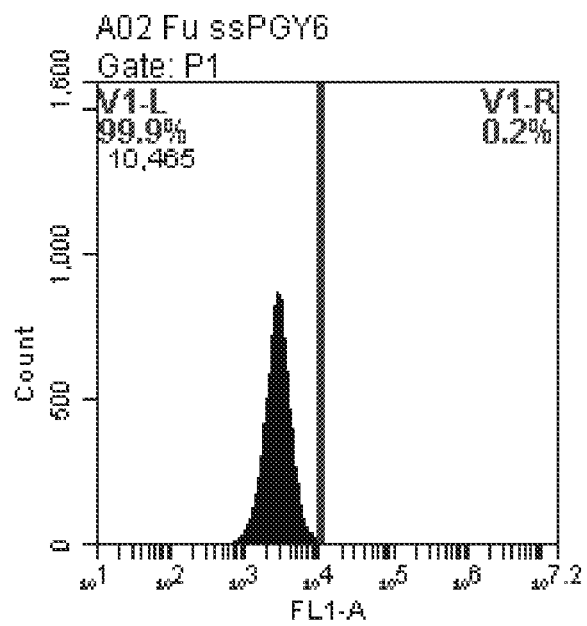
Figure 1C:
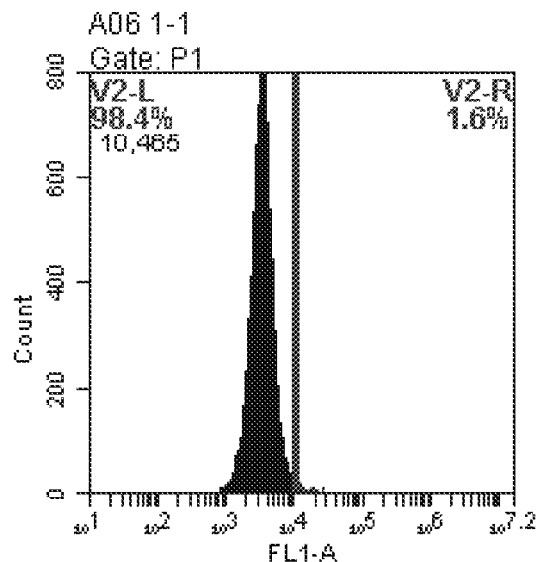
Figure 1D:
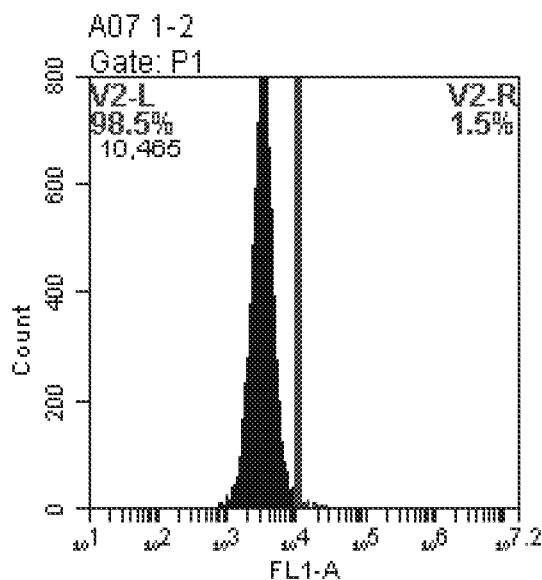
Figure 1E:
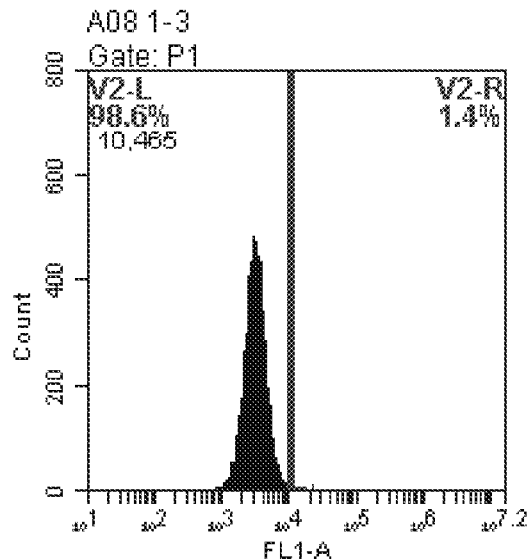
Figure 2A:
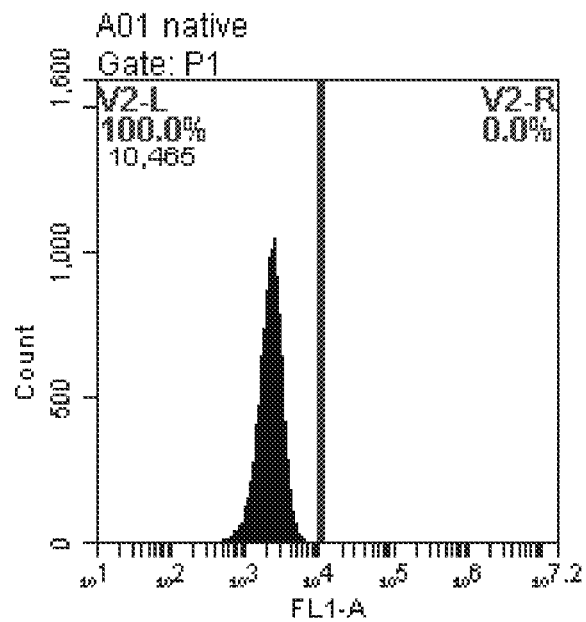
Figure 2B:
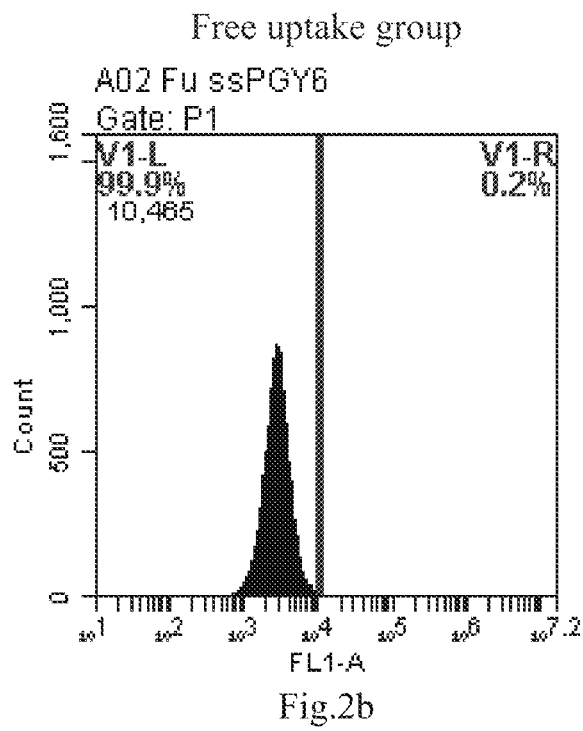
Figure 2C:
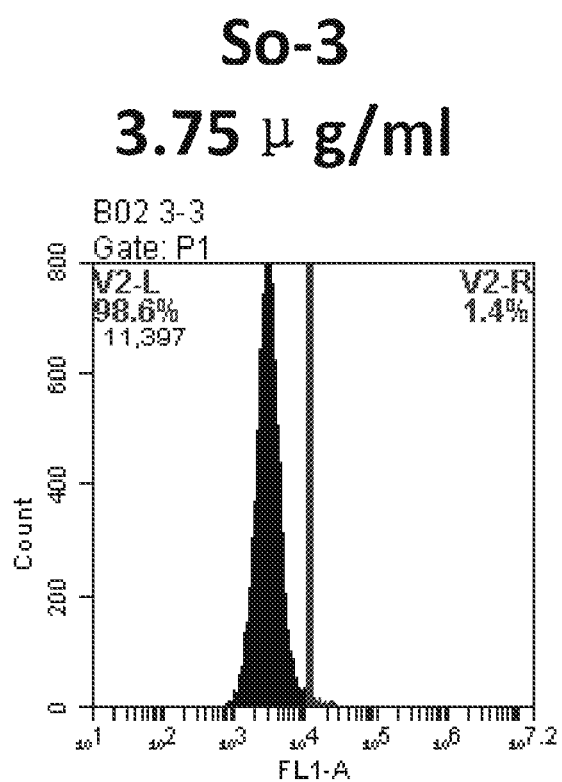
Figure 2D:
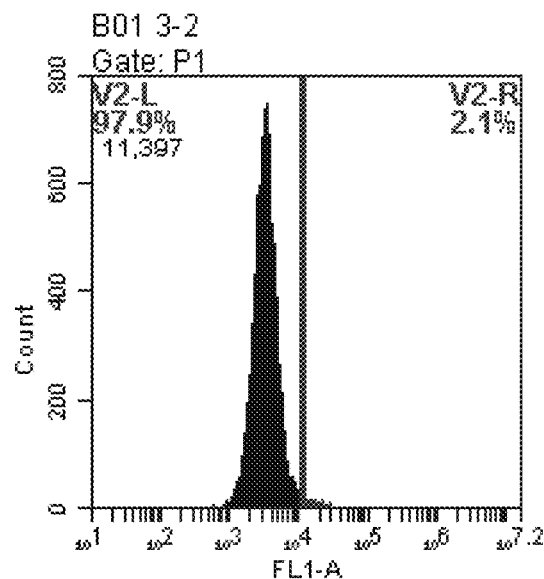
Figure 2E:
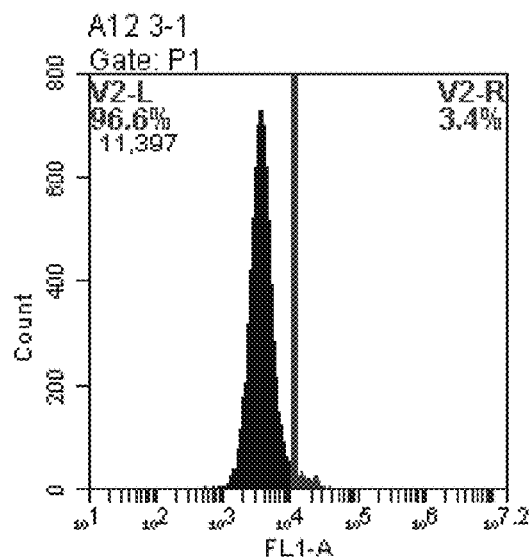
Figure 3A:
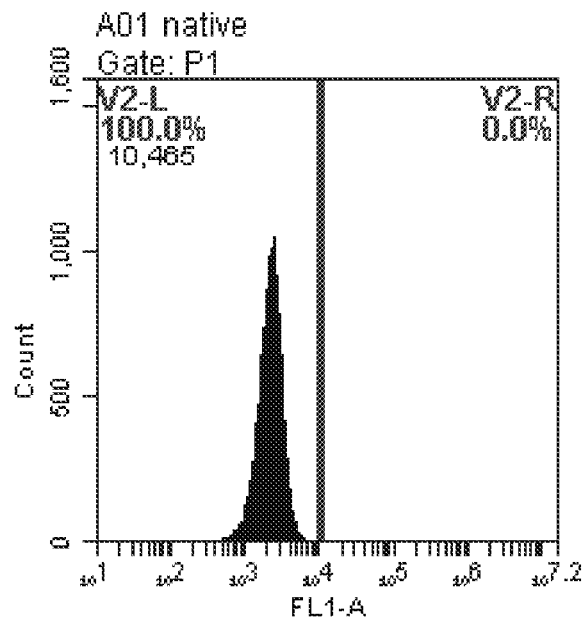
Figure 3B:
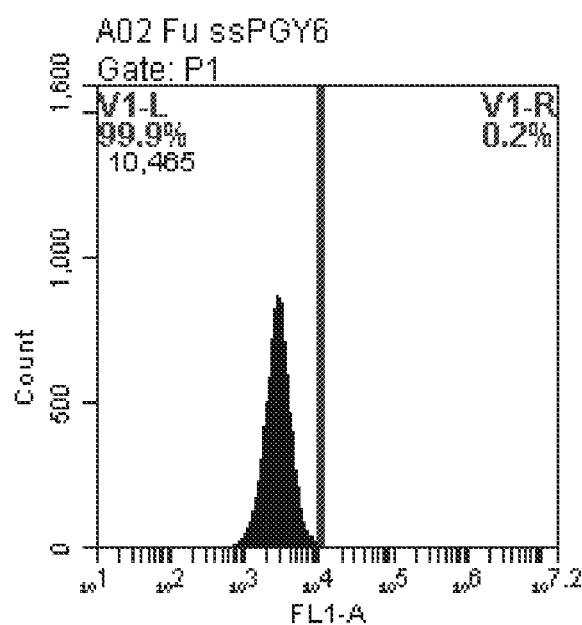
Figure 3C:
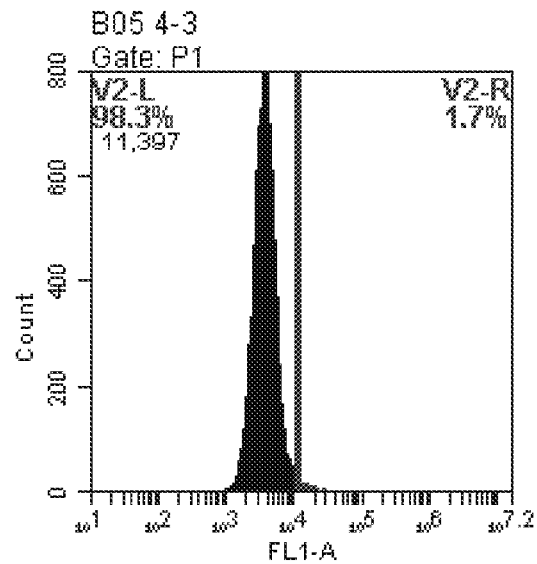
Figure 3D:
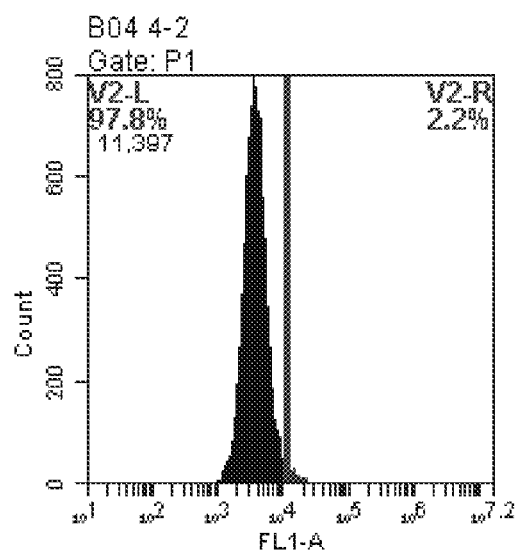
Figure 3E:
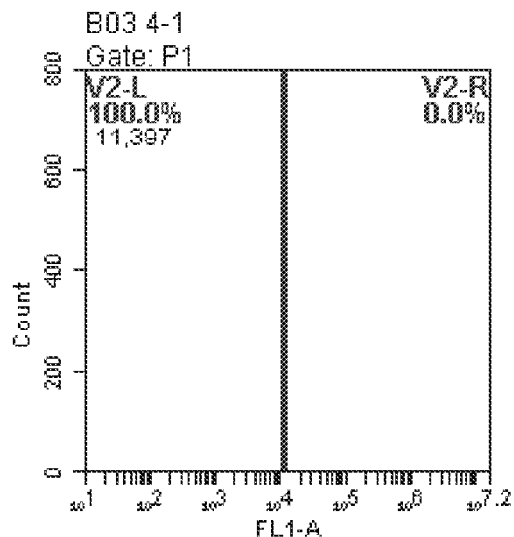
Figure 4A:
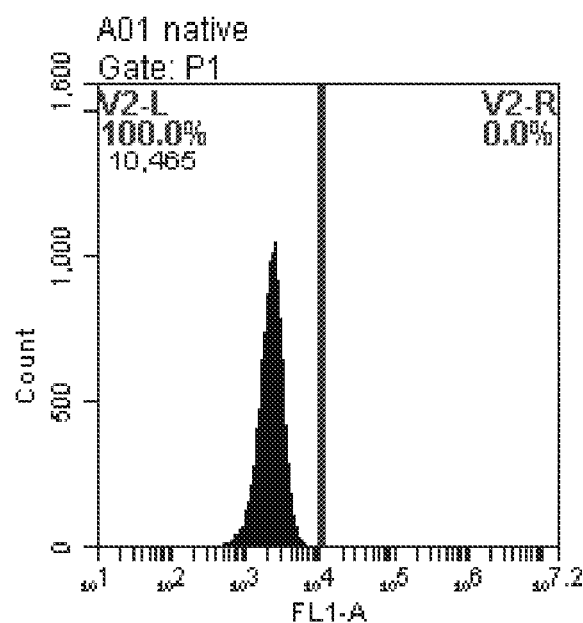
Figure 4B:
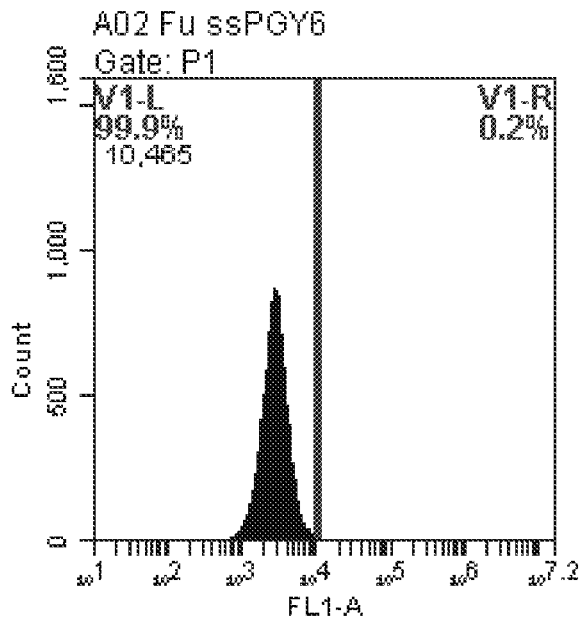
Figure 4C:
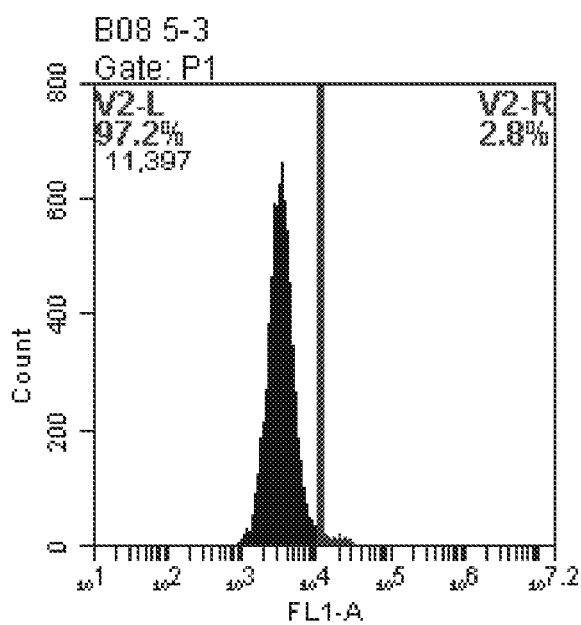
Figure 4D:
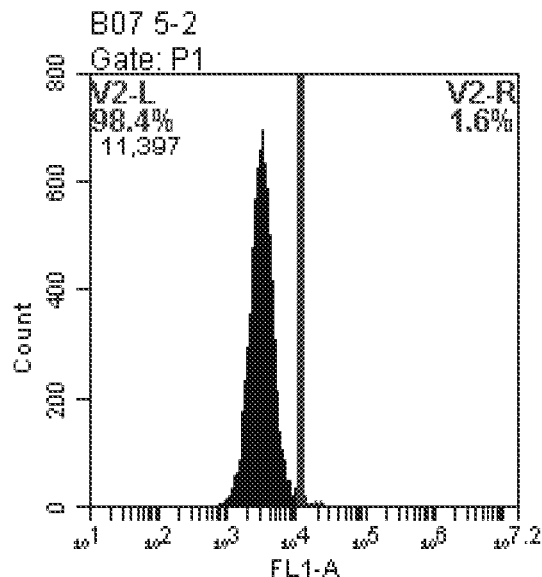
Figure 4E:
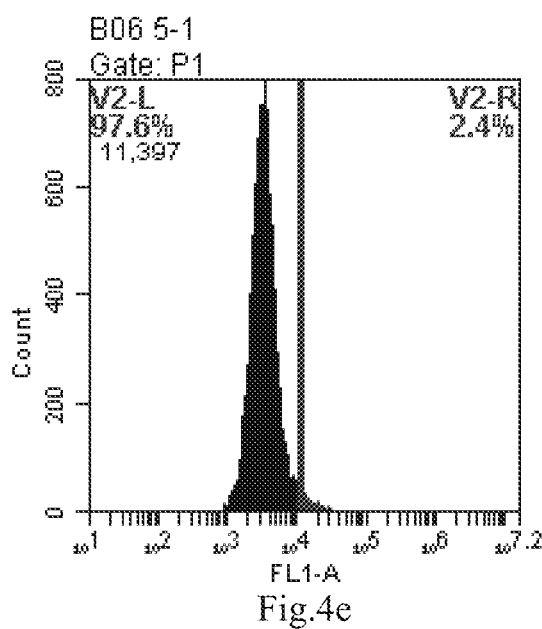
Figure 5A:
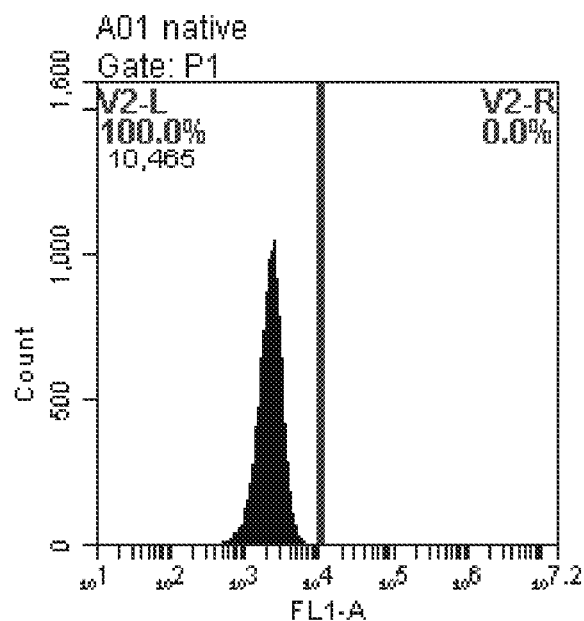
Figure 5B:
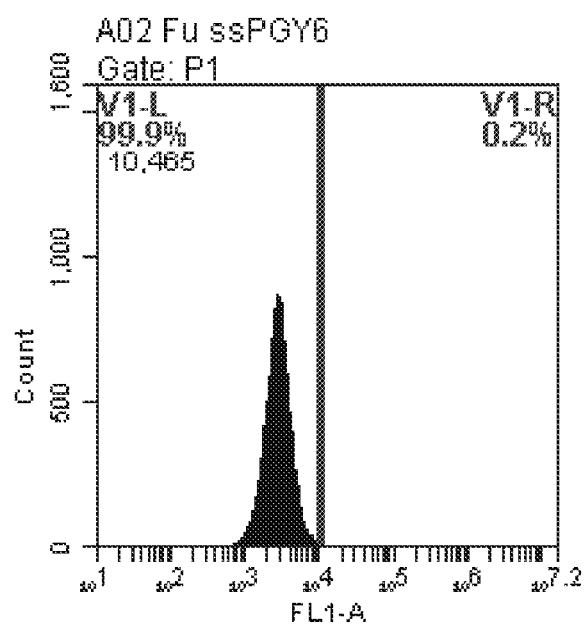
Figure 5C:
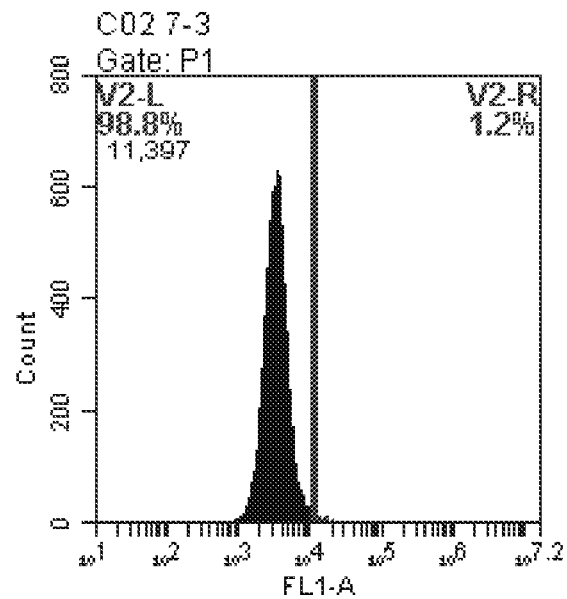
Figure 5D:
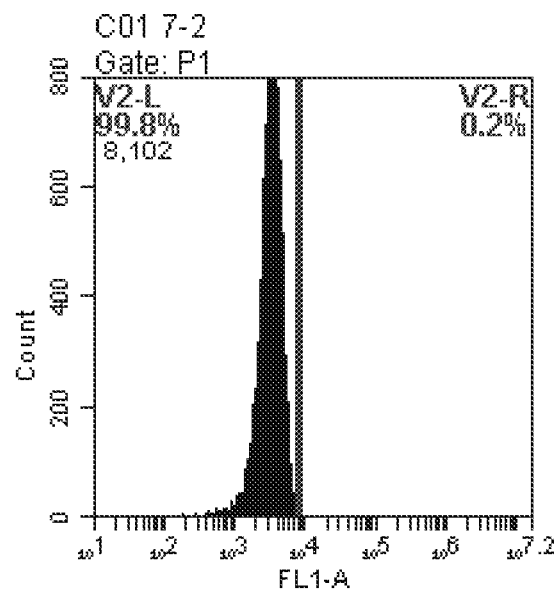
Figure 5E:
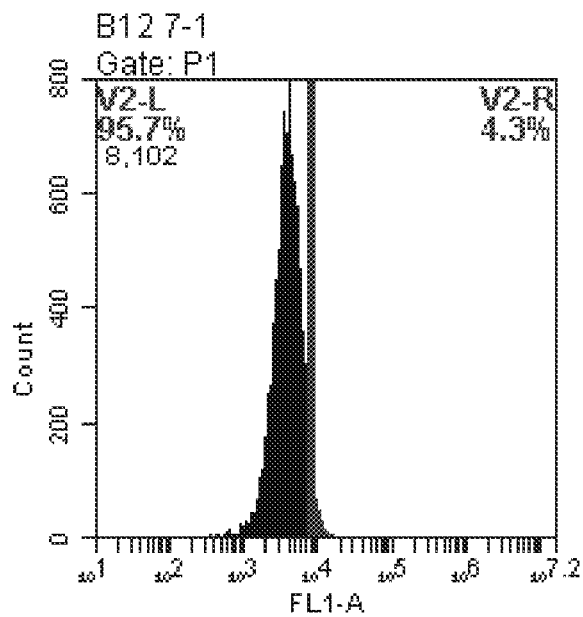
Figure 6A:
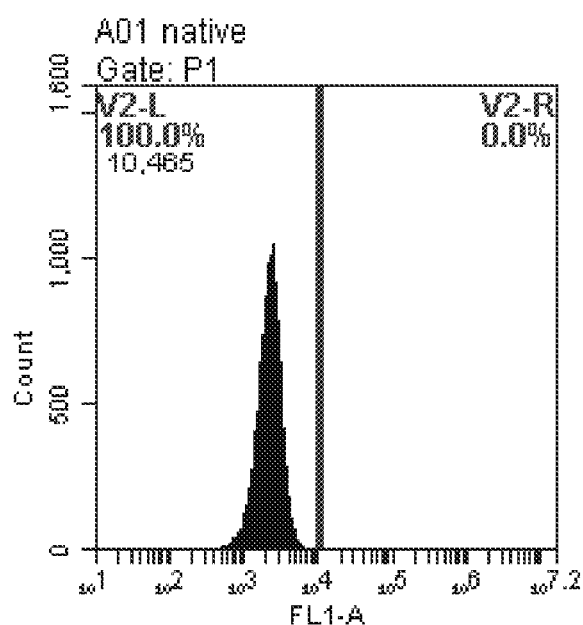
Figure 6B:
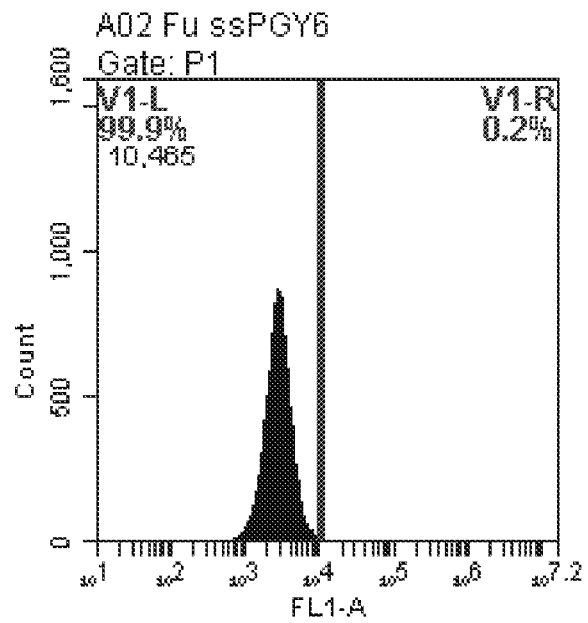
Figure 6C:
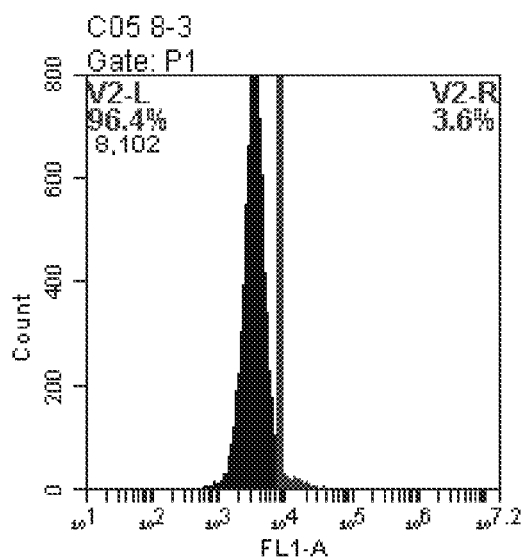
Figure 6D:
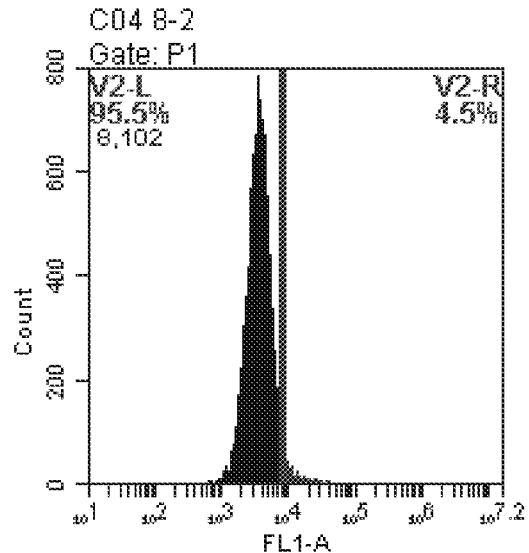
Figure 6E:
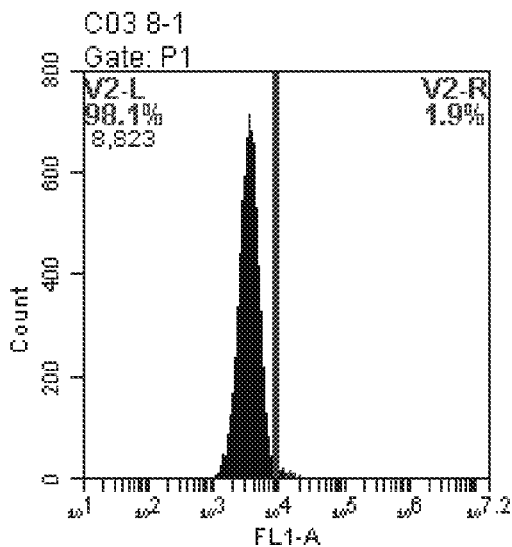
Figure 7A:
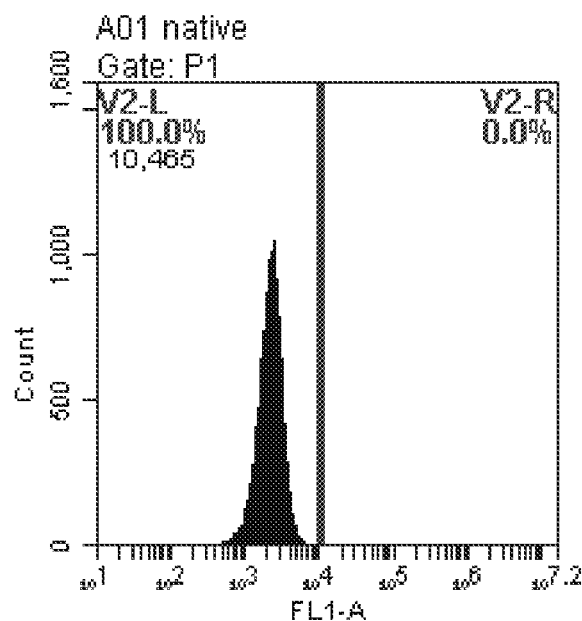
Figure 7B:
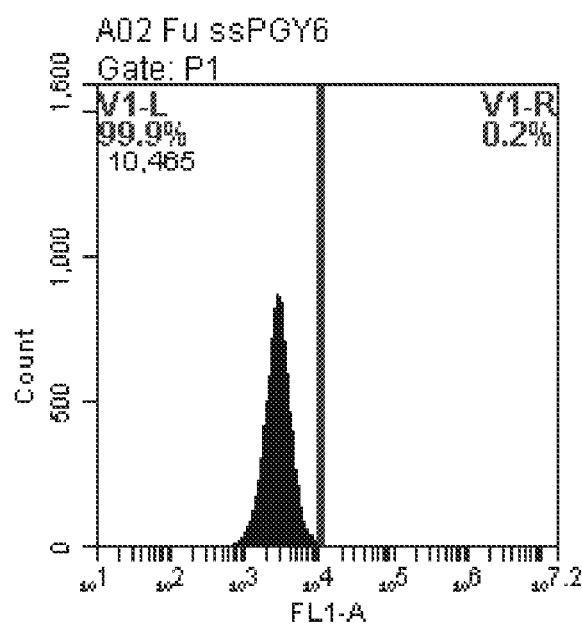
Figure 7C:
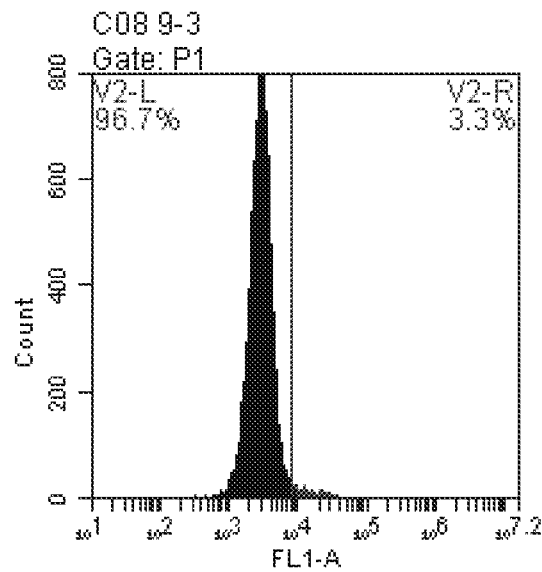
Figure 7D:
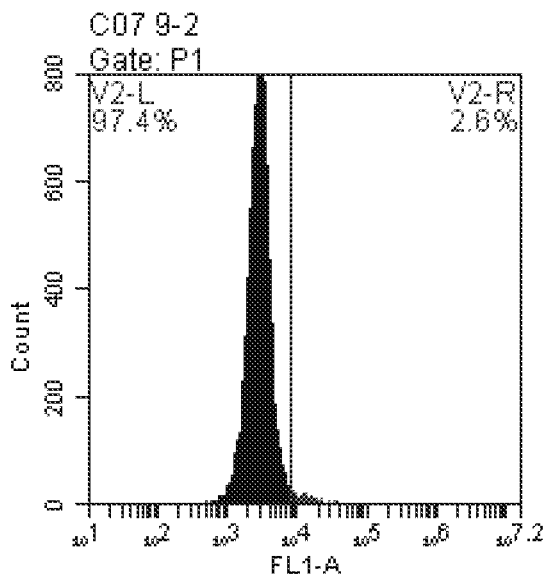
Figure 7E:
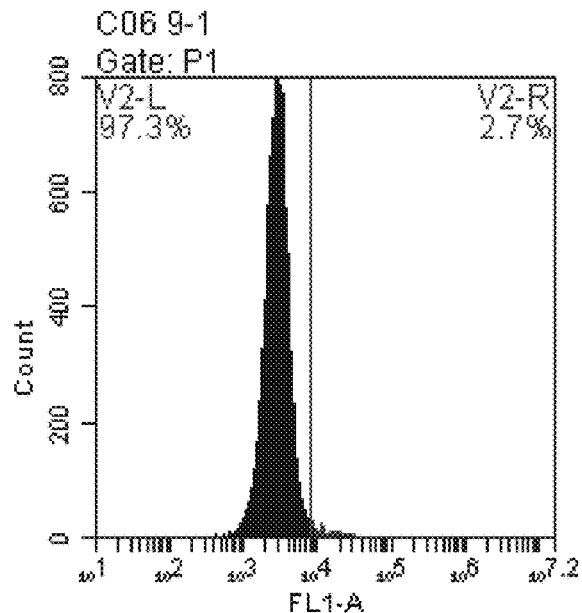
Figure 8A:
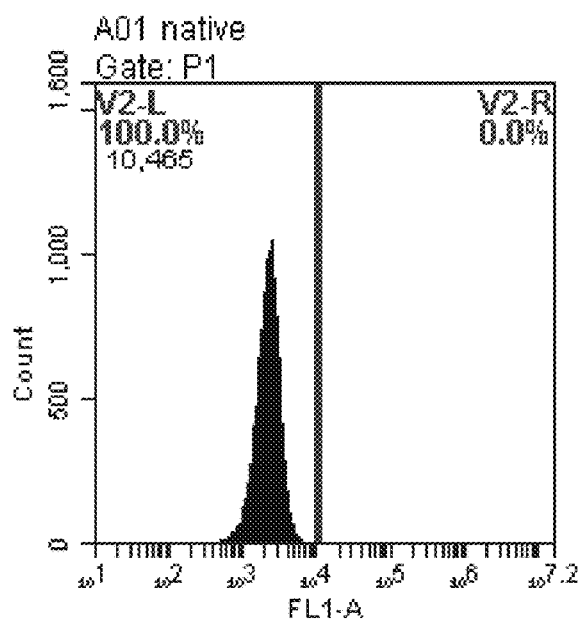
Figure 8B:
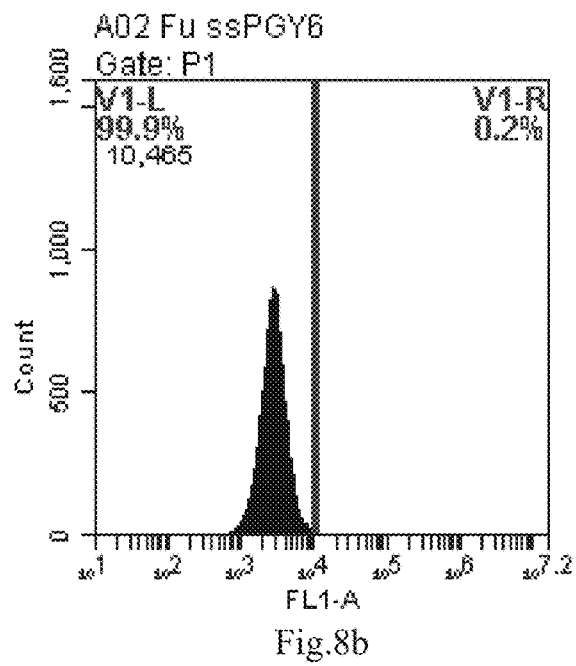
Figure 8C:
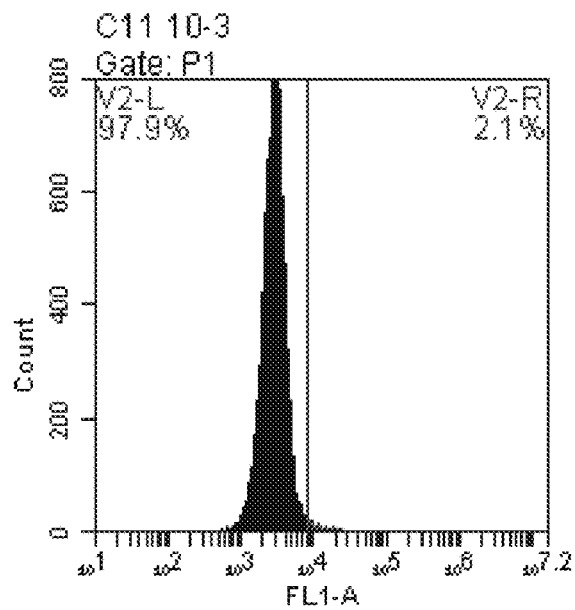
Figure 8D:
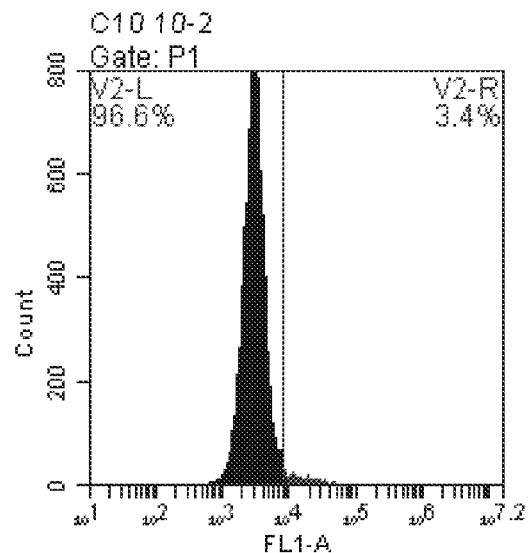
Figure 8E:
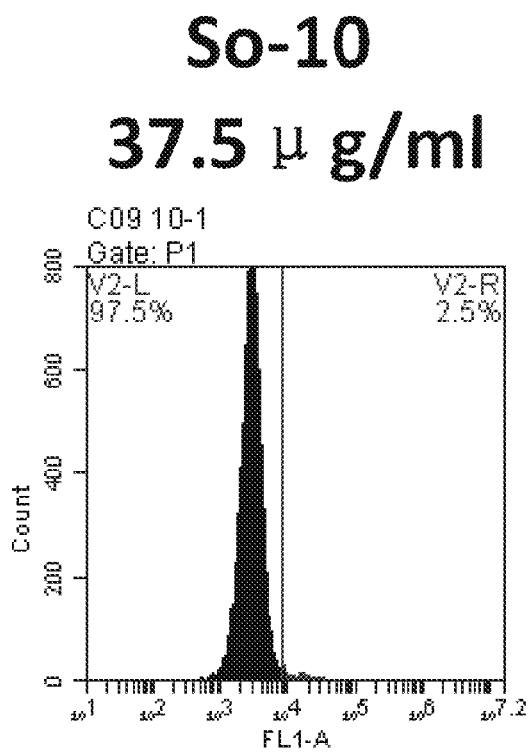
Figure 9A:
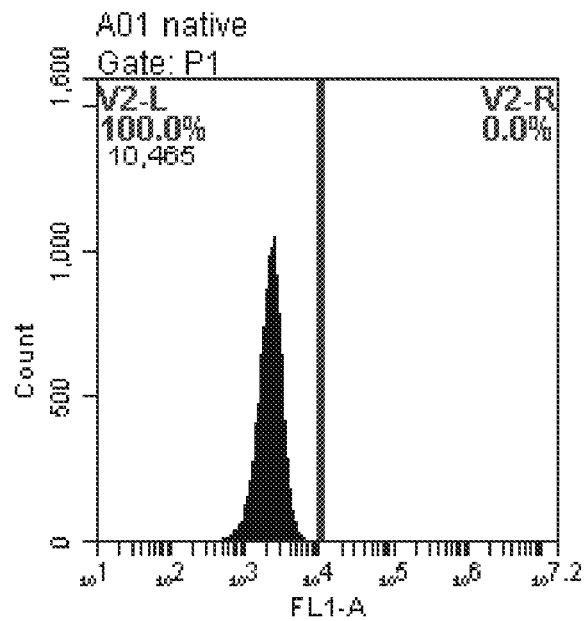
Figure 9B:
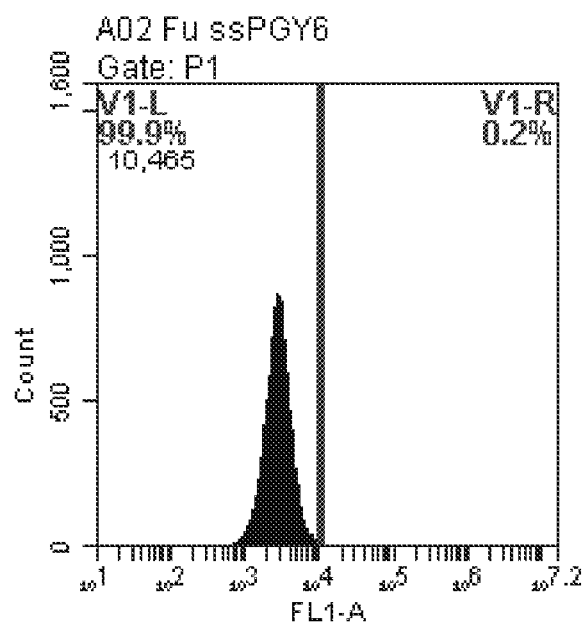
Figure 9C:
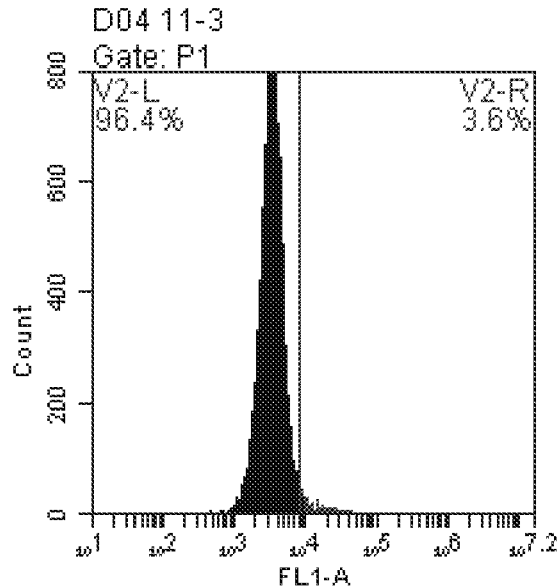
Figure 9D:
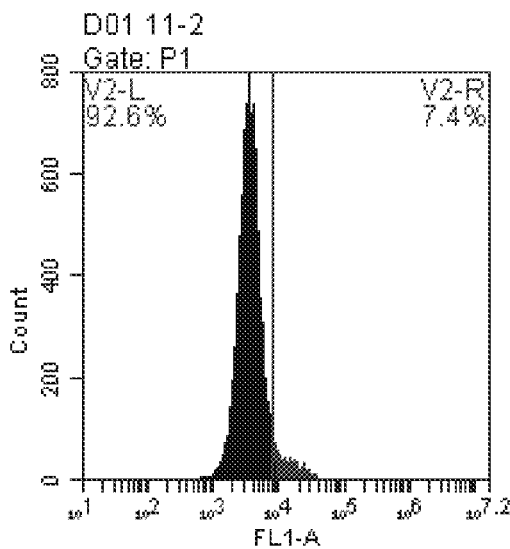
Figure 9E:
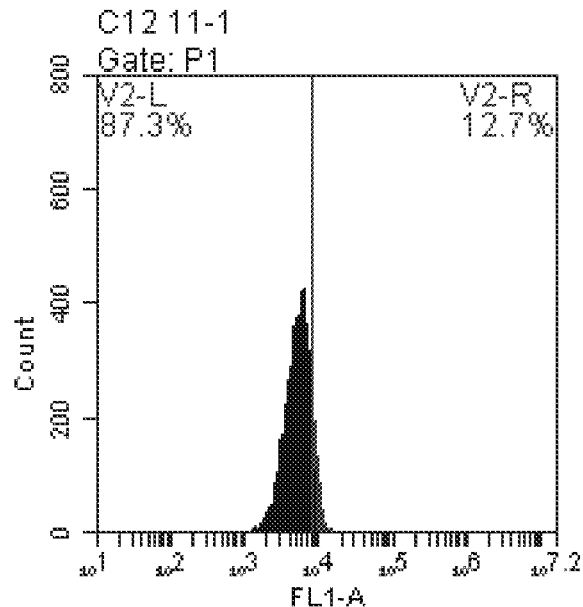
Figure 10A:
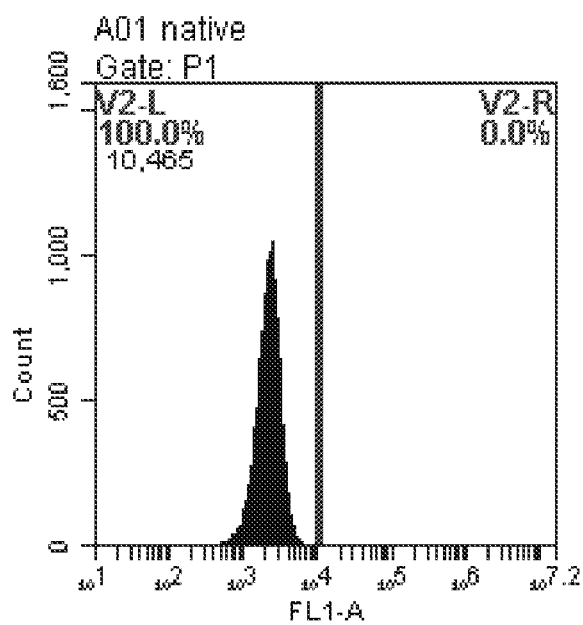
Figure 10B:
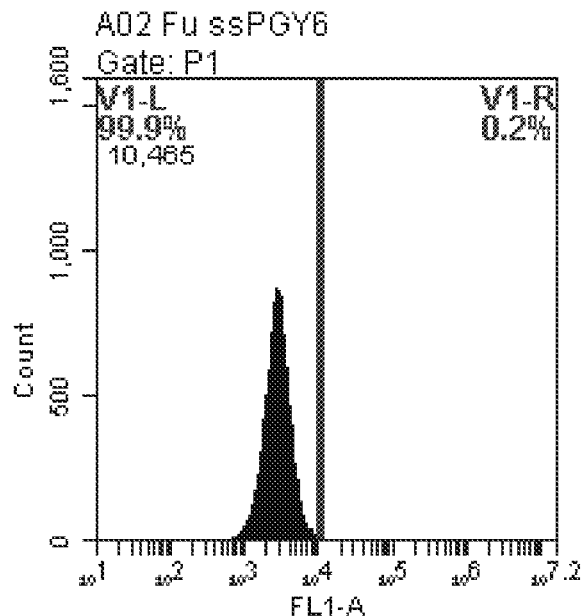
Figure 10C:
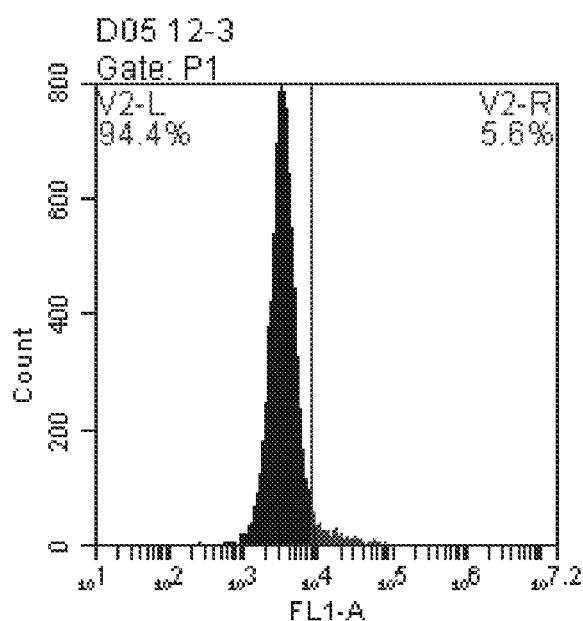
Figure 10D:
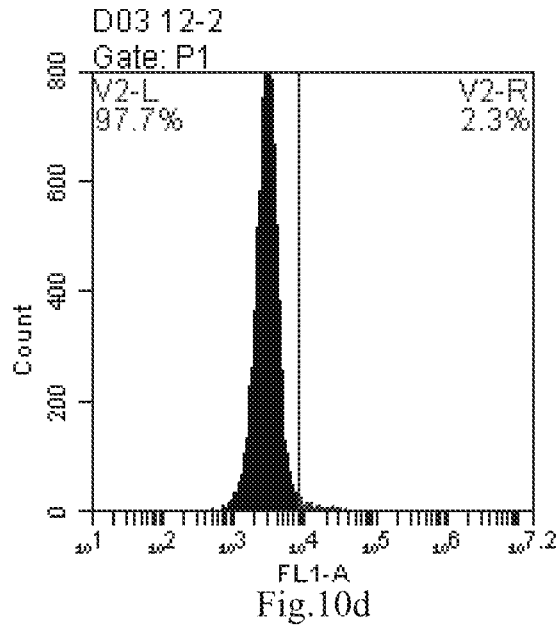
Figure 10E:
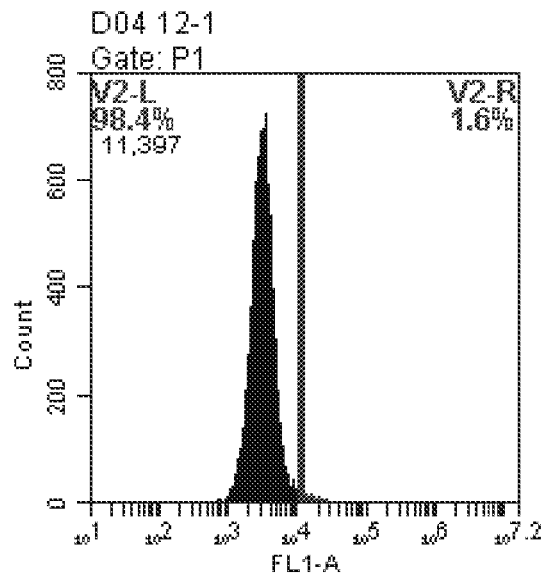
Figure 11A:
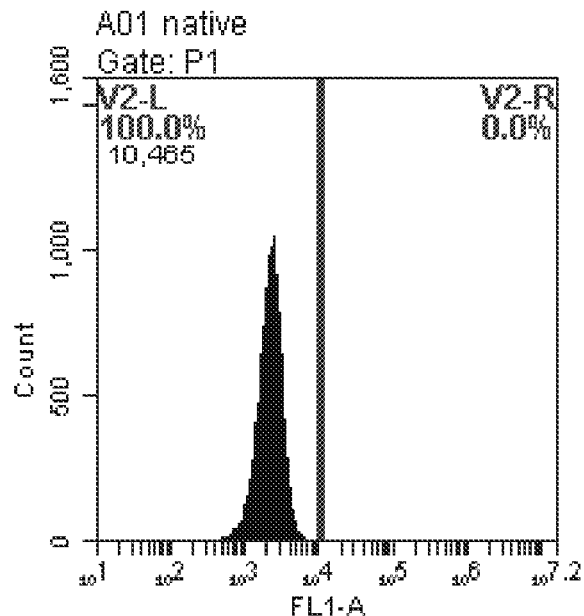
Figure 11B:
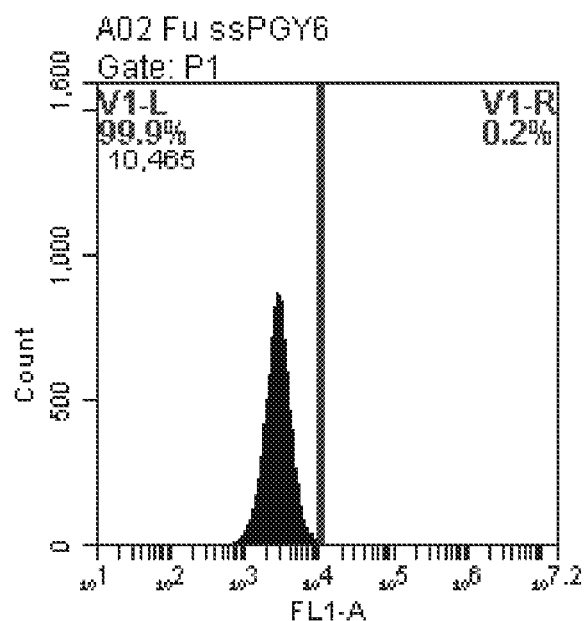
Figure 11C:
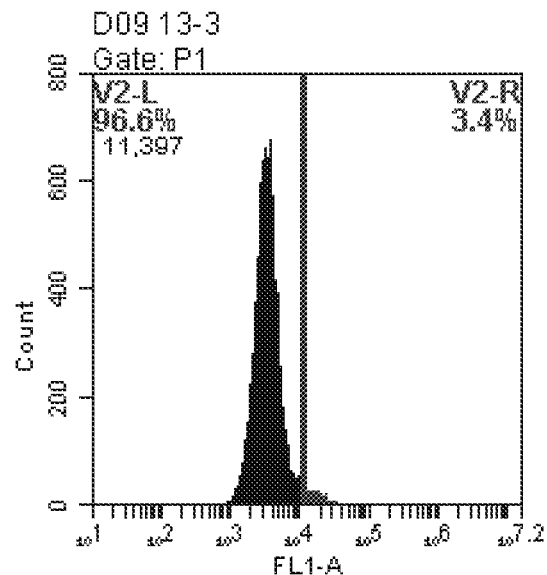
Figure 11D:
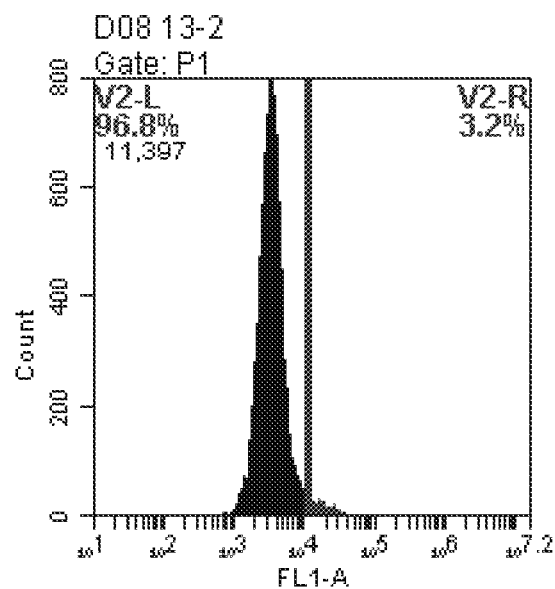
Figure 11E:
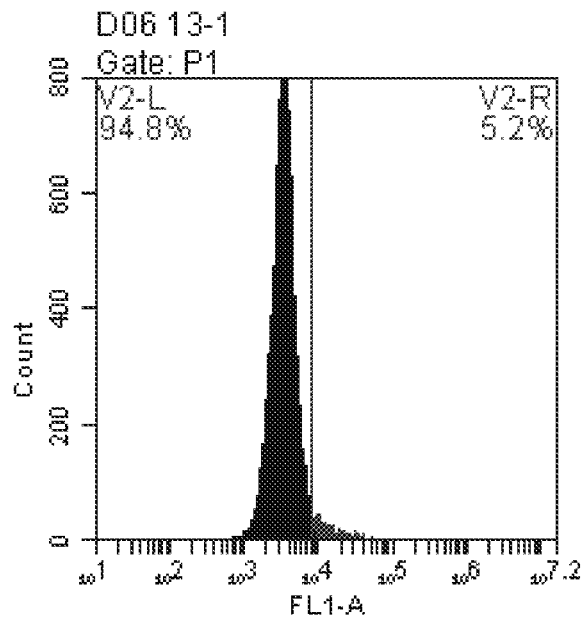
Figure 12A:
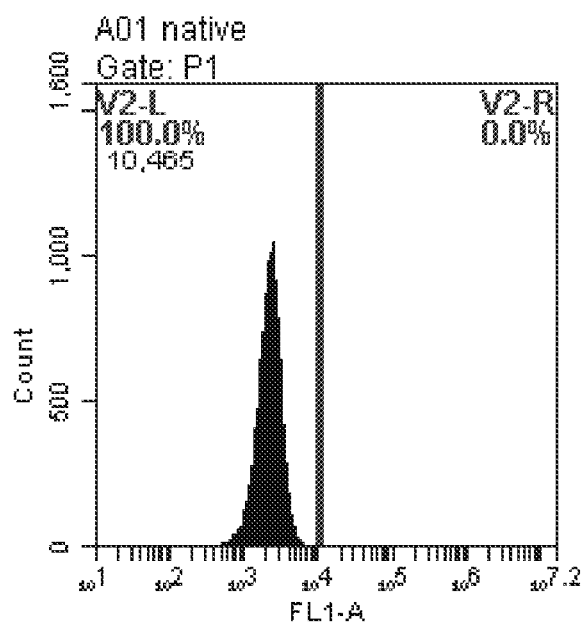
Figure 12B:
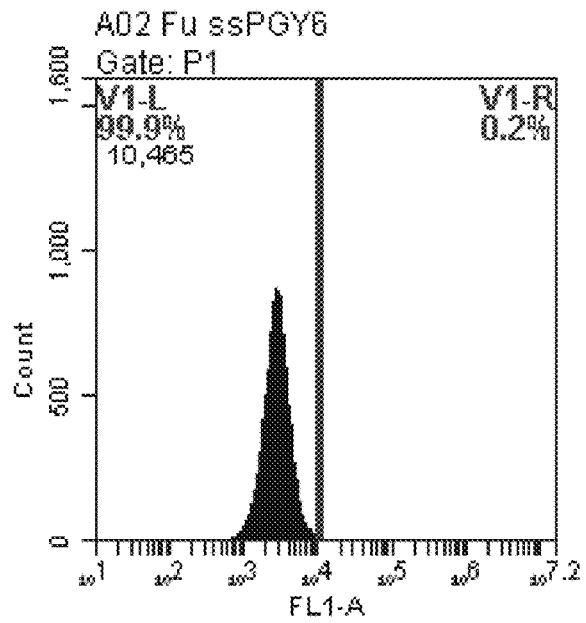
Figure 12C:
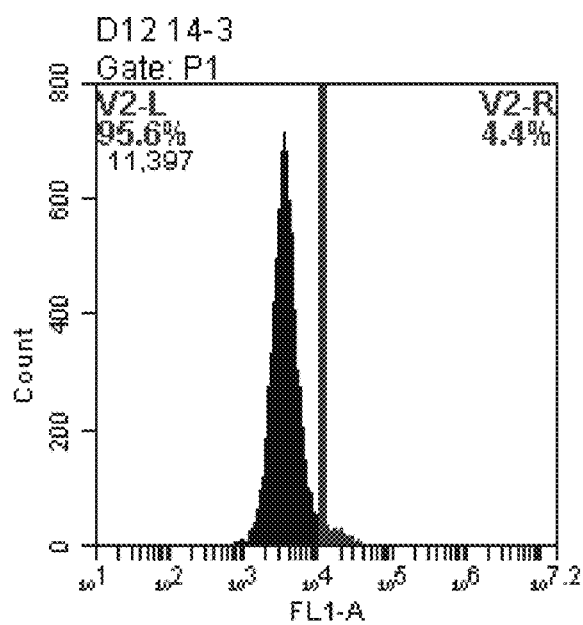
Figure 12D:
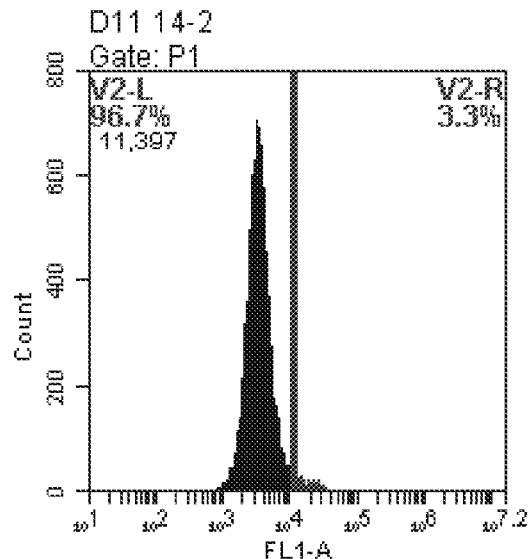
Figure 12E:
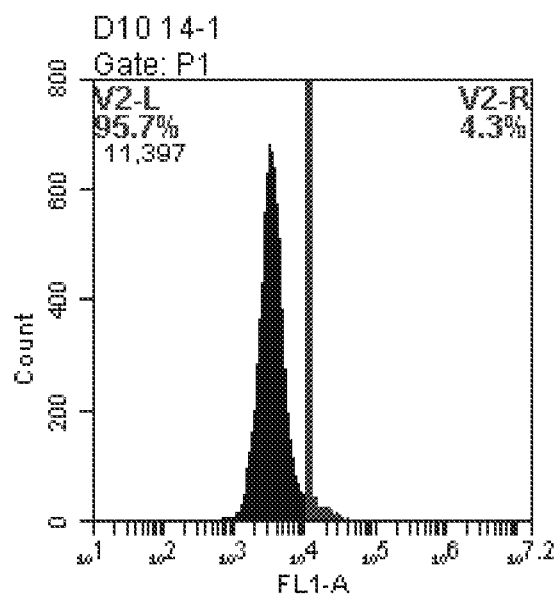
Figure 13A:
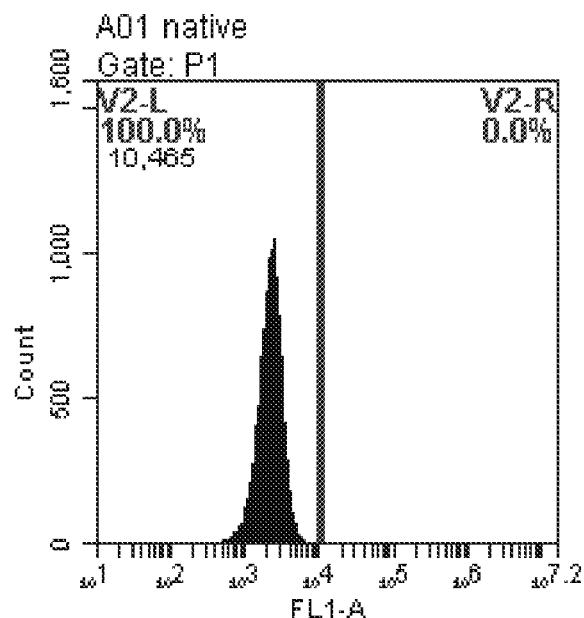
Figure 13B:
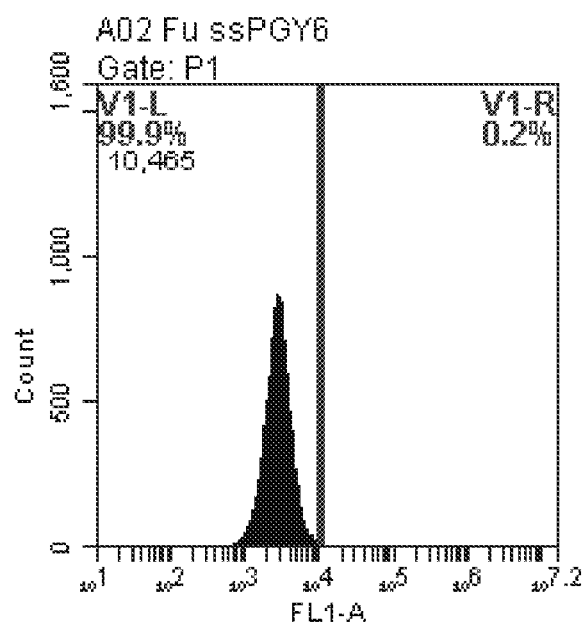
Figure 13C:
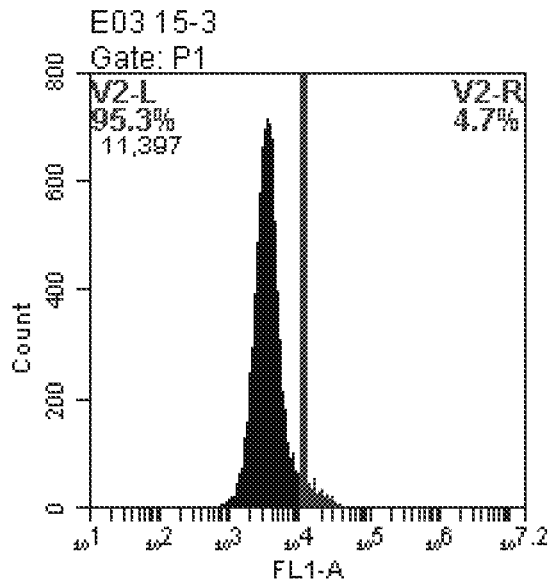
Figure 13D:
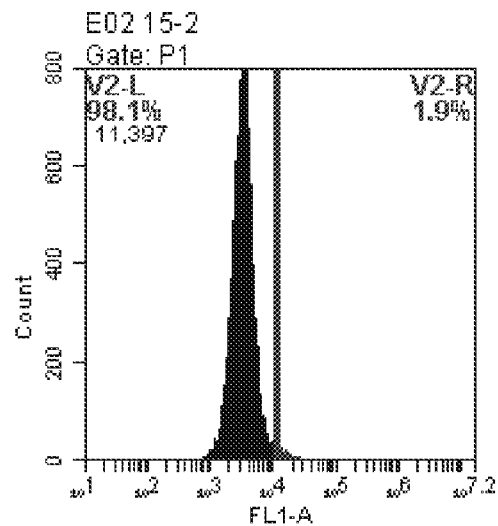
Figure 13E:
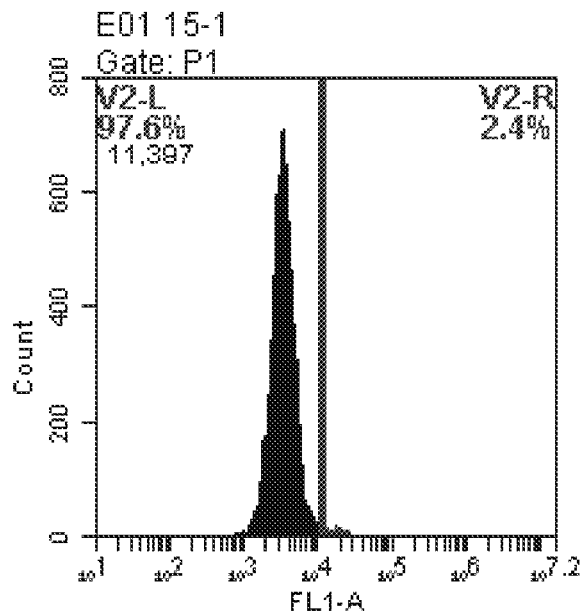
Figure 14A:
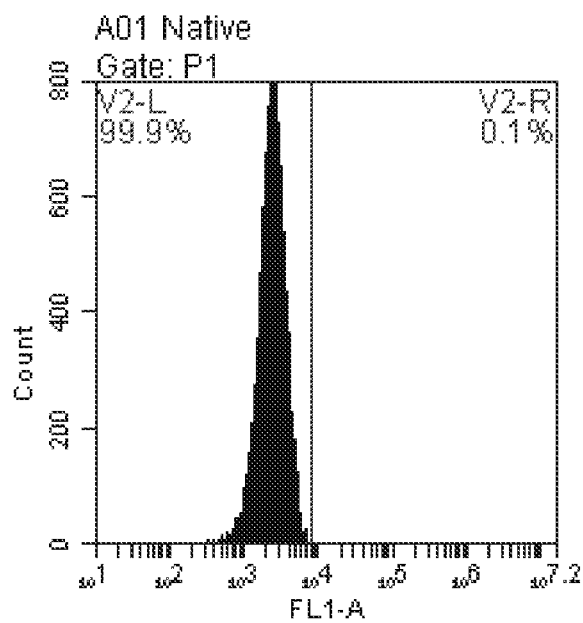
Figure 14B:
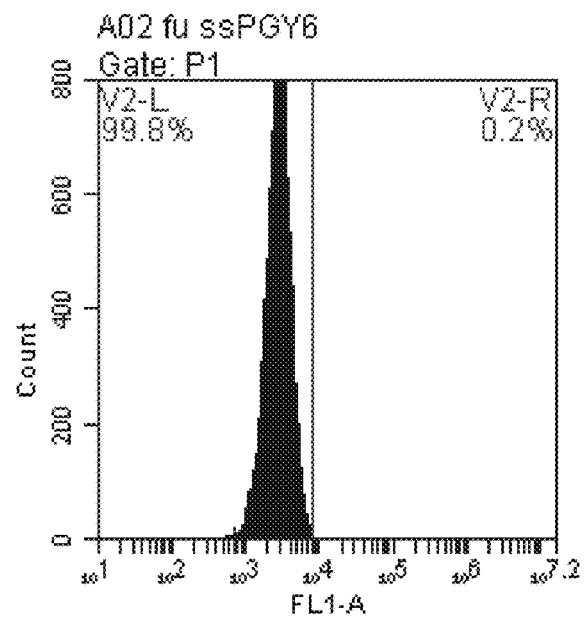
Figure 14C:
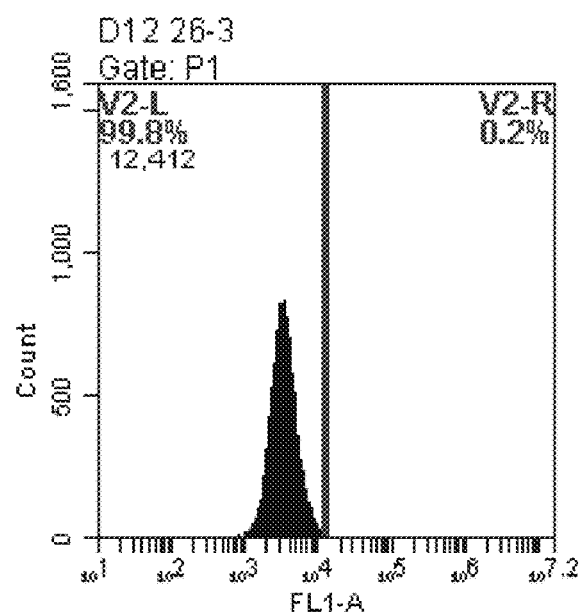
Figure 14D:
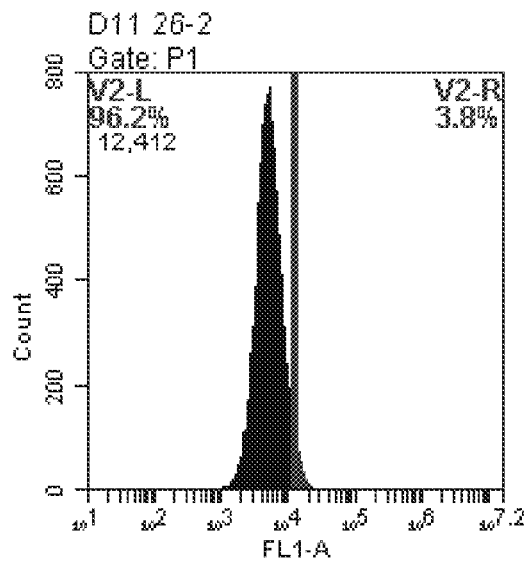
Figure 14E:
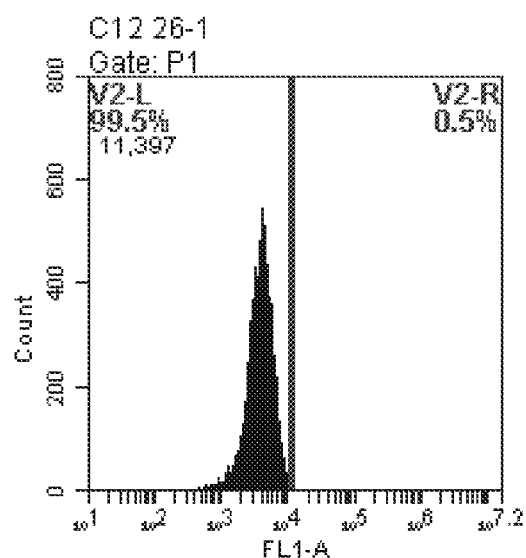
Figure 15A:
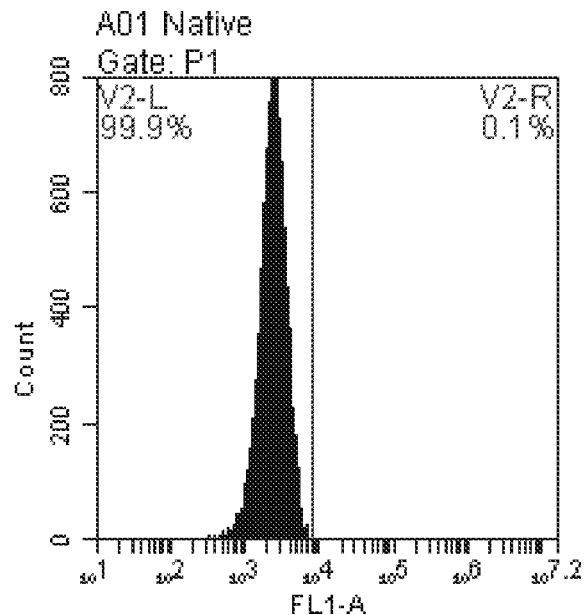
Figure 15B:
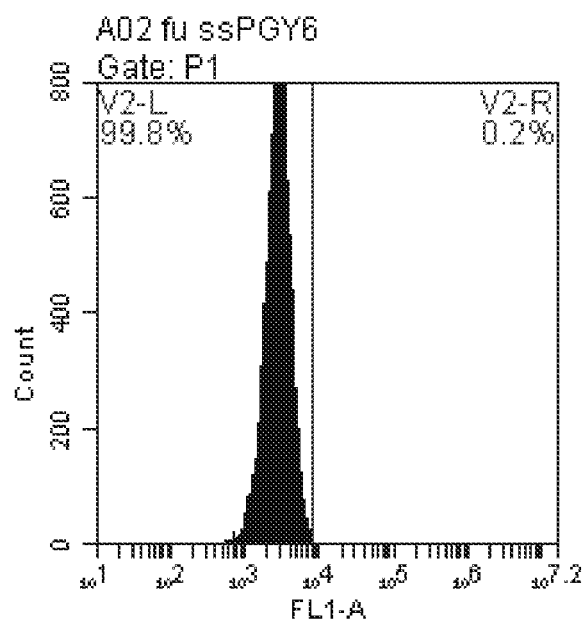
Figure 15C:
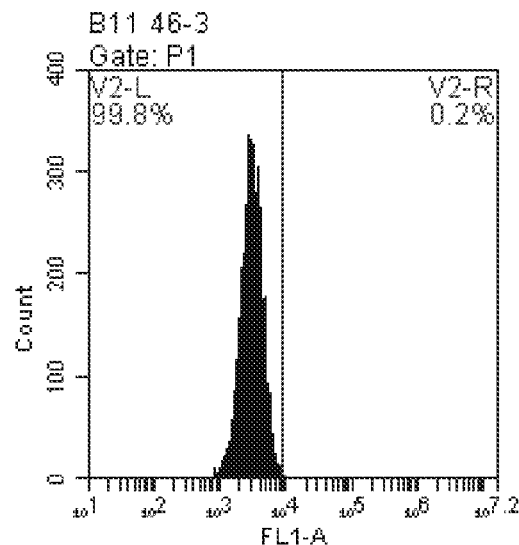
Figure 15D:
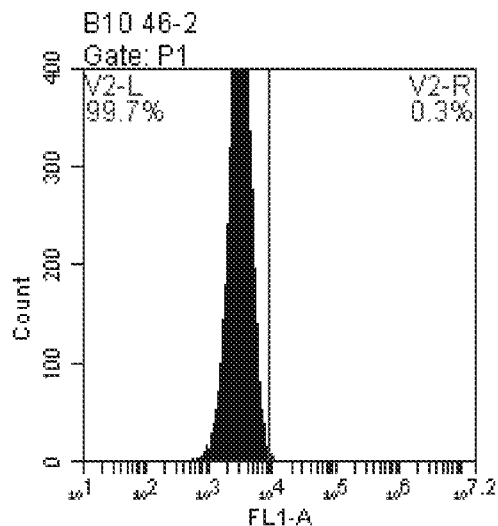
Figure 15E:
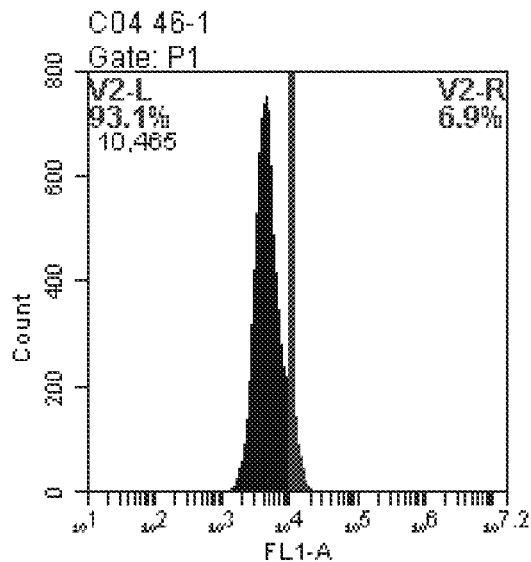
Figure 16A:
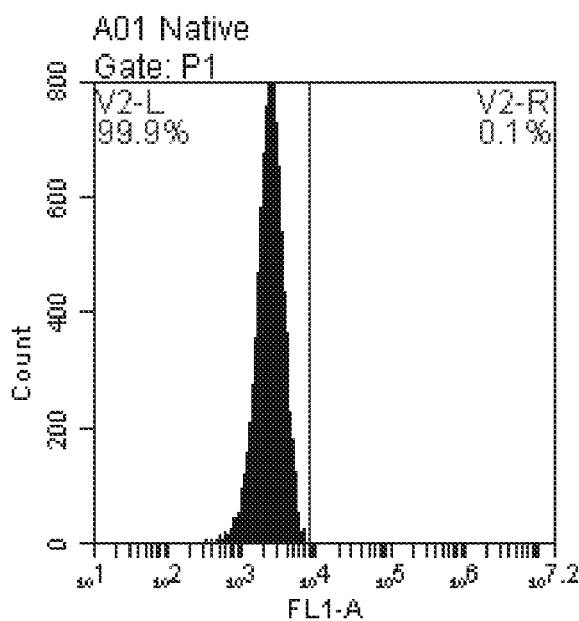
Figure 16B:
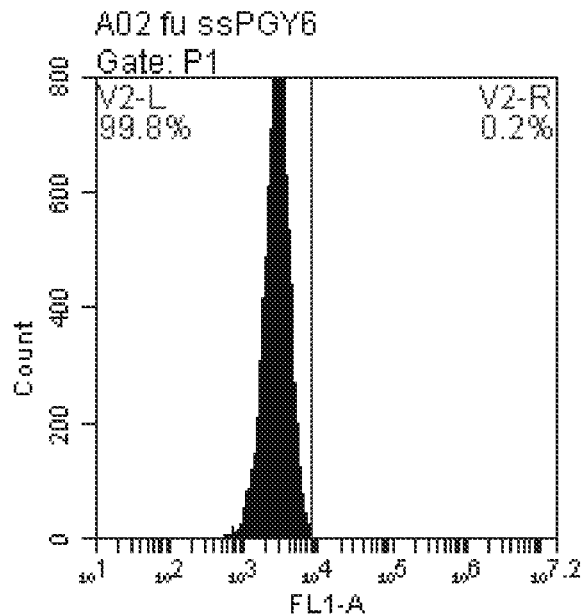
Figure 16C:
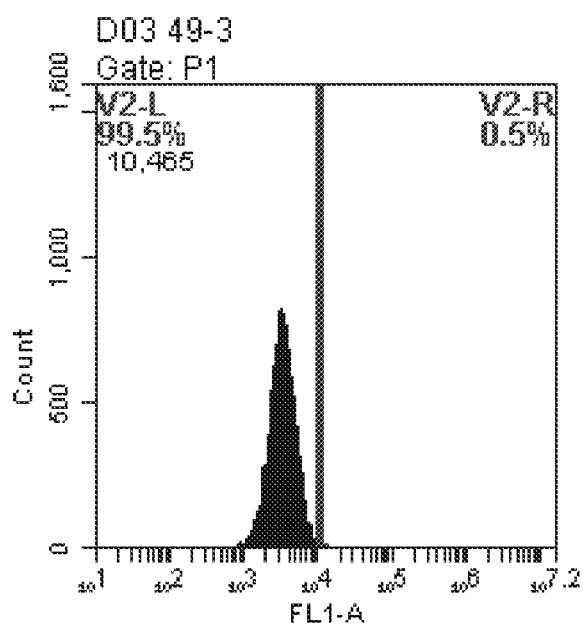
Figure 16D:
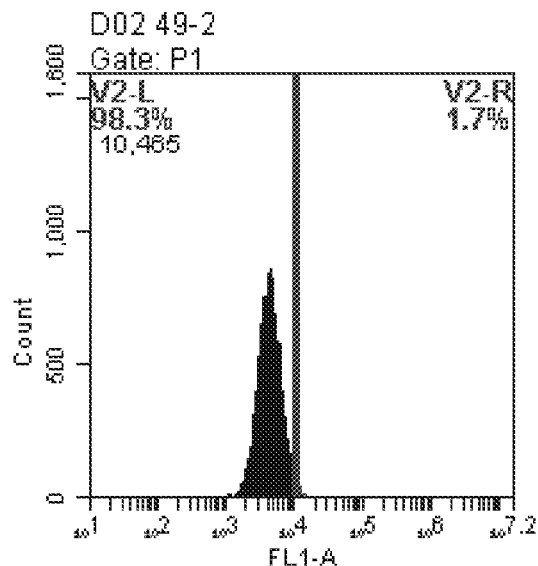
Figure 16E:
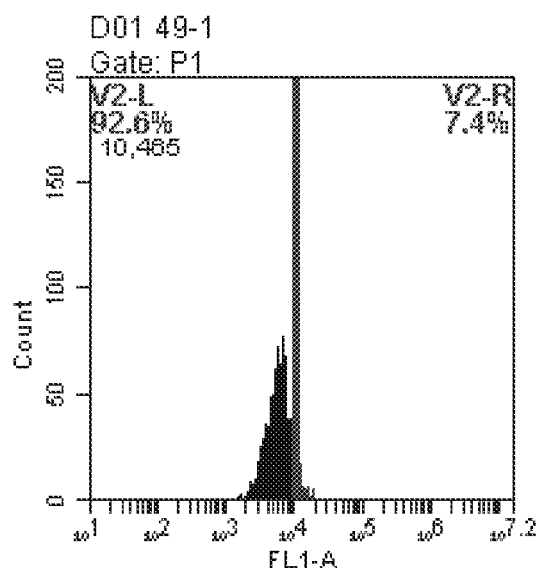
Figure 17A:
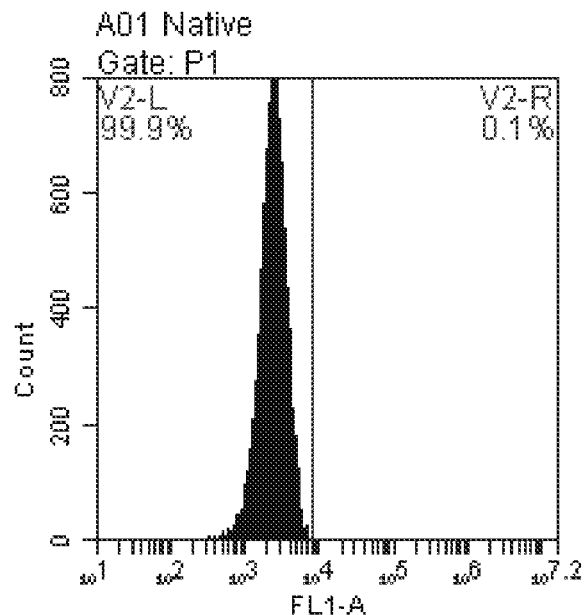
Figure 17B:
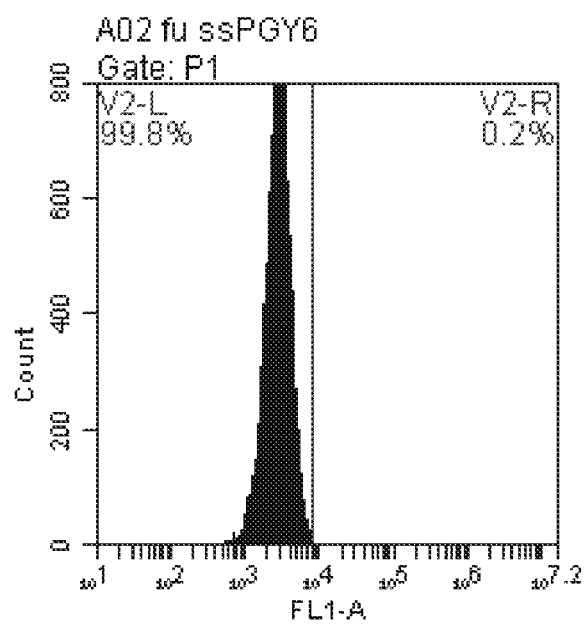
Figure 17C:
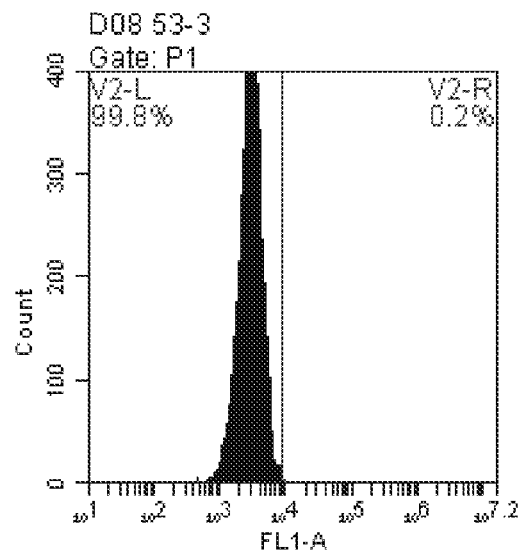
Figure 17D:
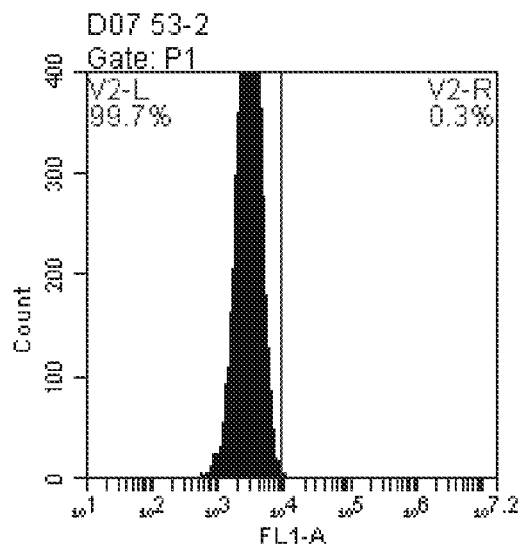
Figure 17E:
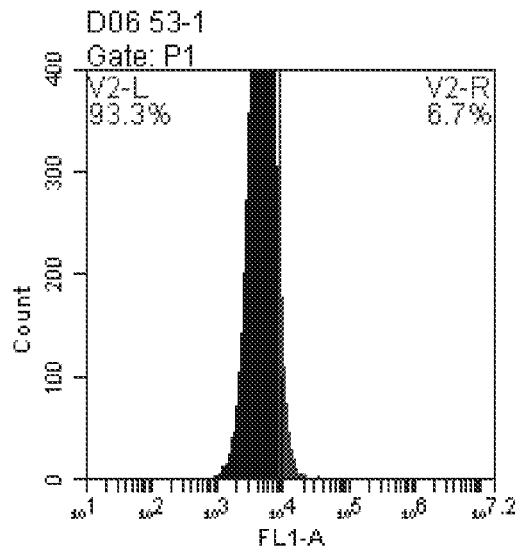
Figure 18A:
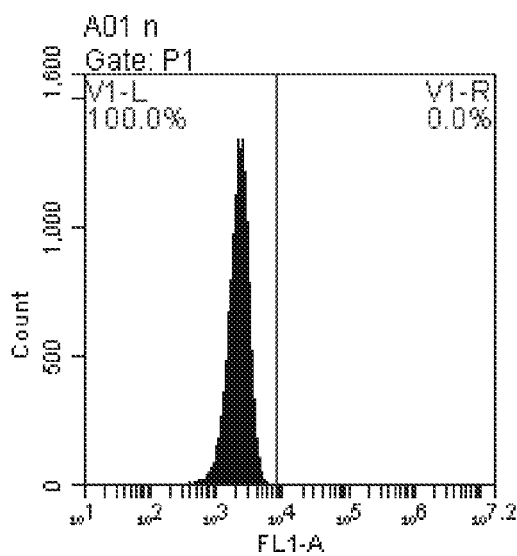
Figure 18B:
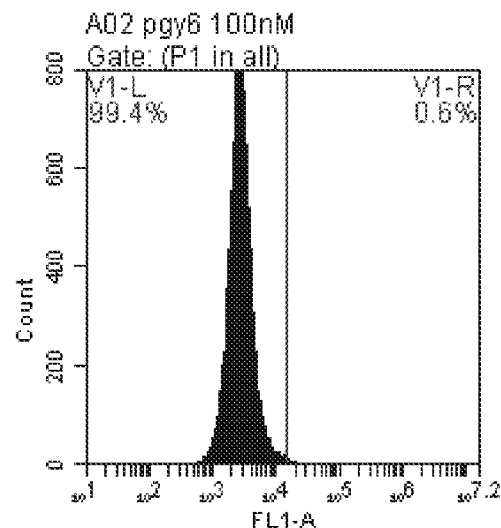
Figure 18C:
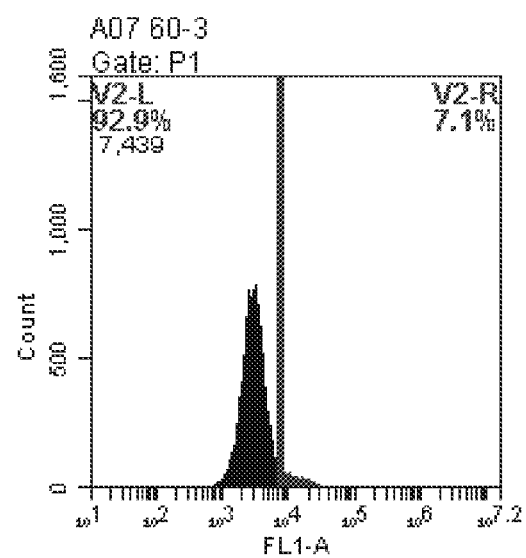
Figure 18D:
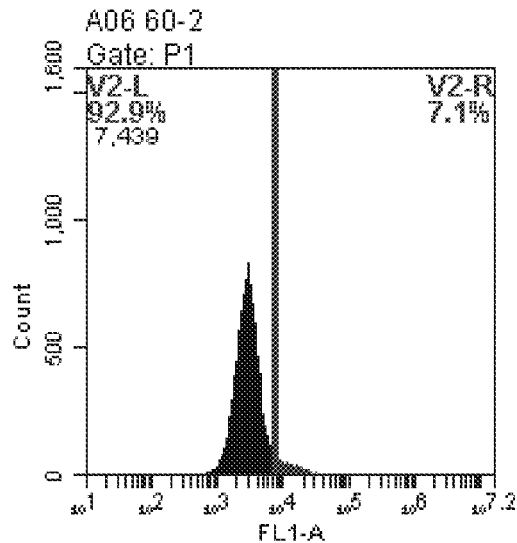
Figure 18E:
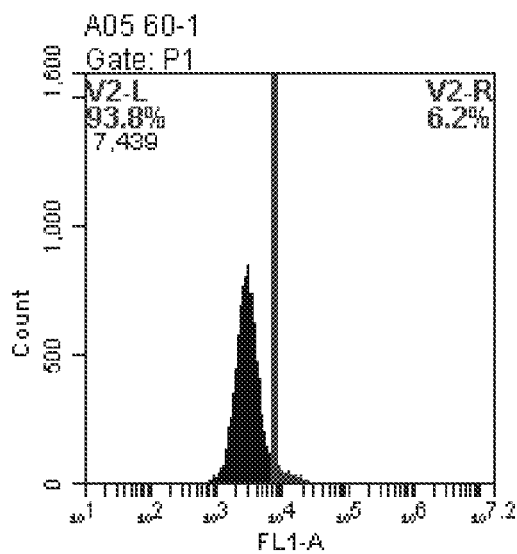
Figure 19A:
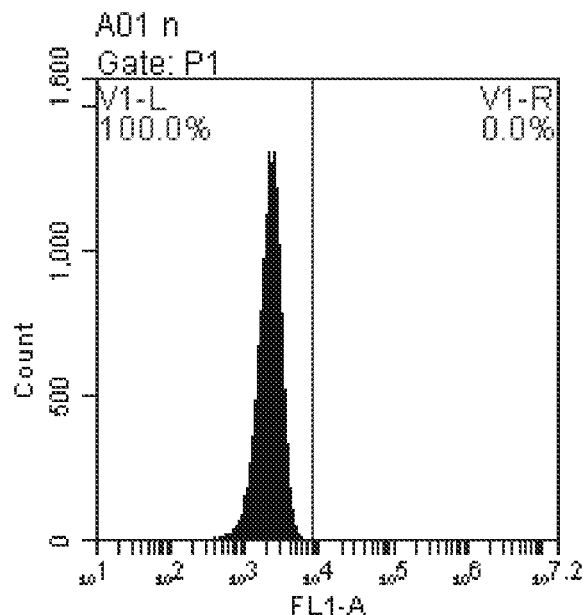
Figure 19B:
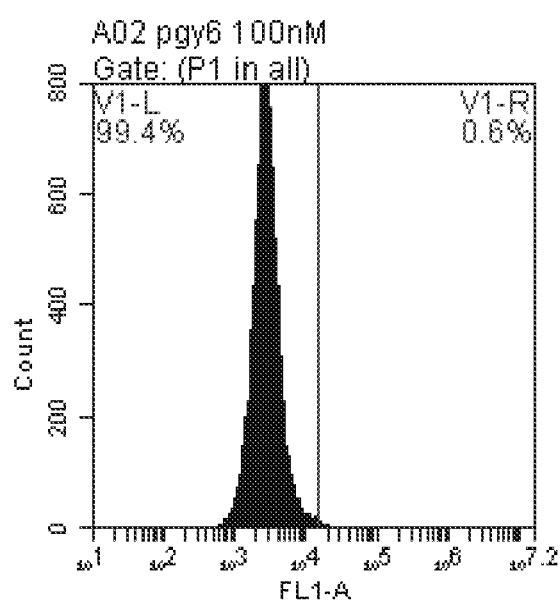
Figure 19C:
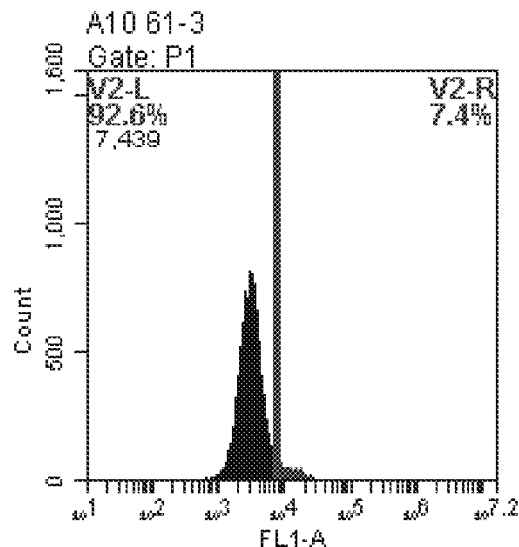
Figure 19D:
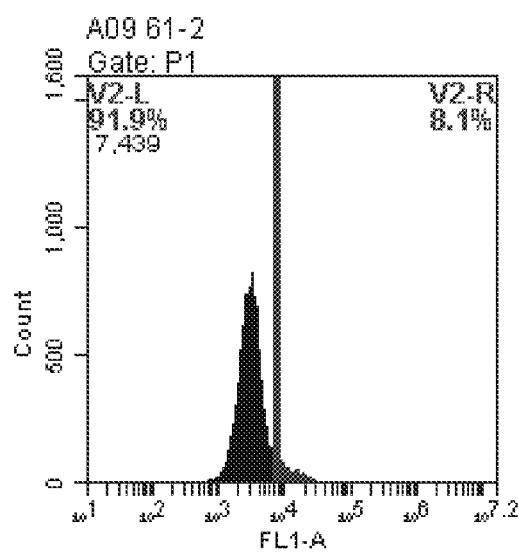
Figure 19E:
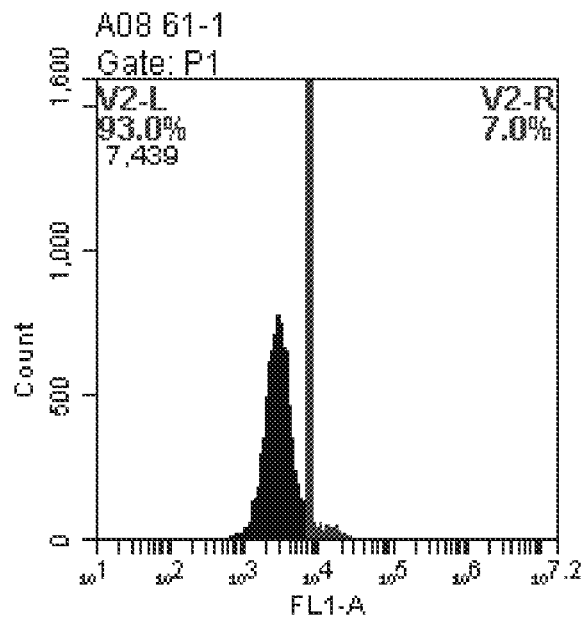
Figure 20A:
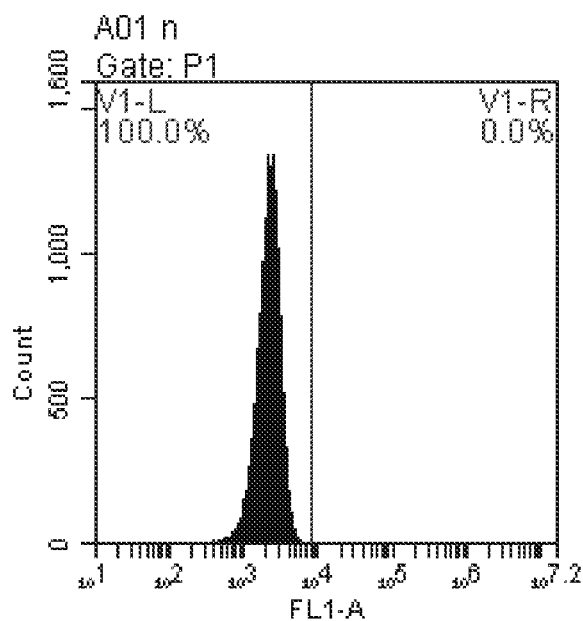
Figure 20B:
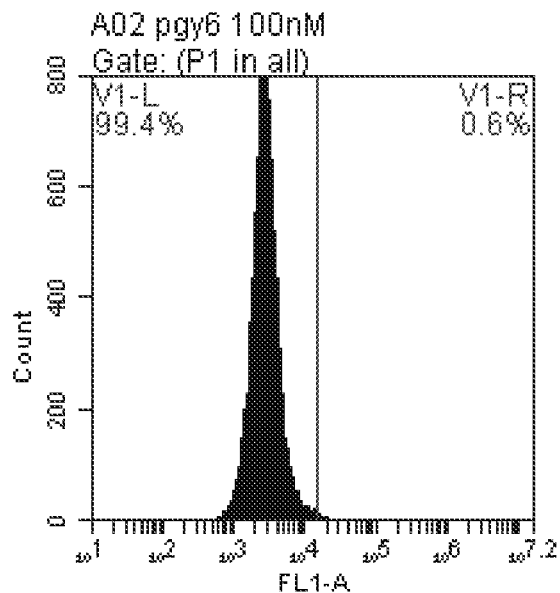
Figure 20C:
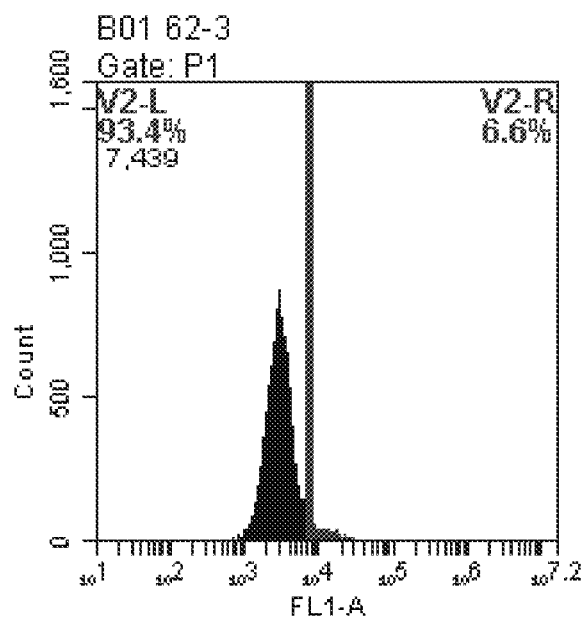
Figure 20D:
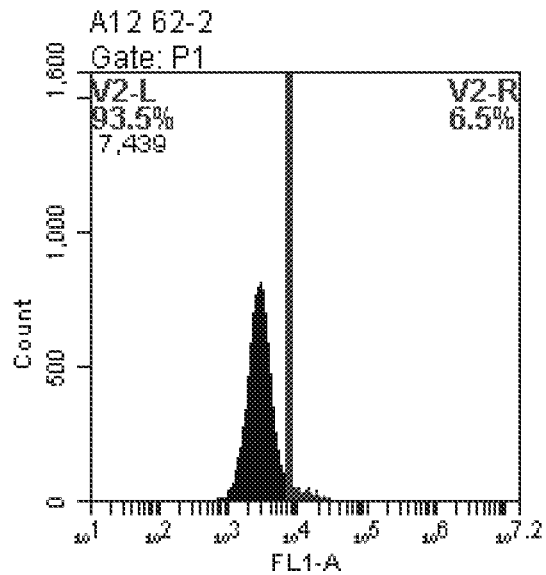
Figure 20E:
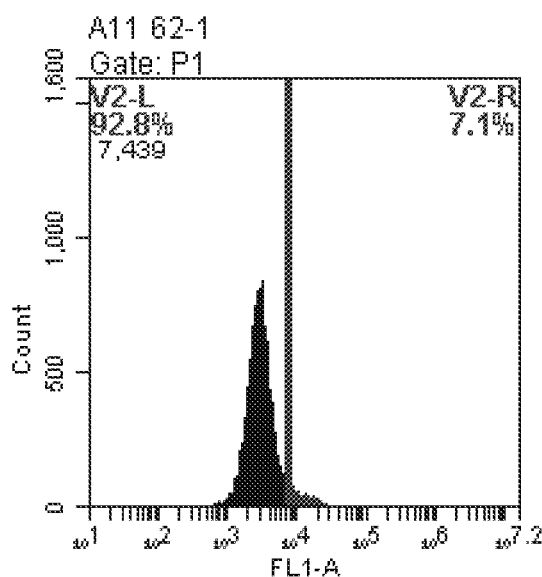
Figure 21A:
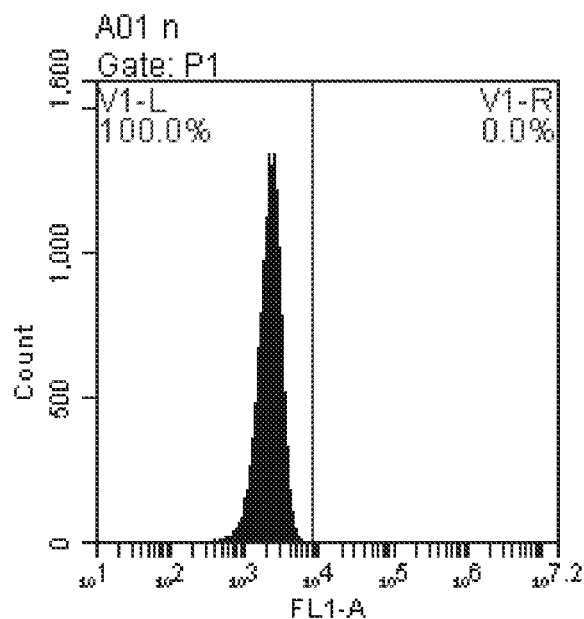
Figure 21B:
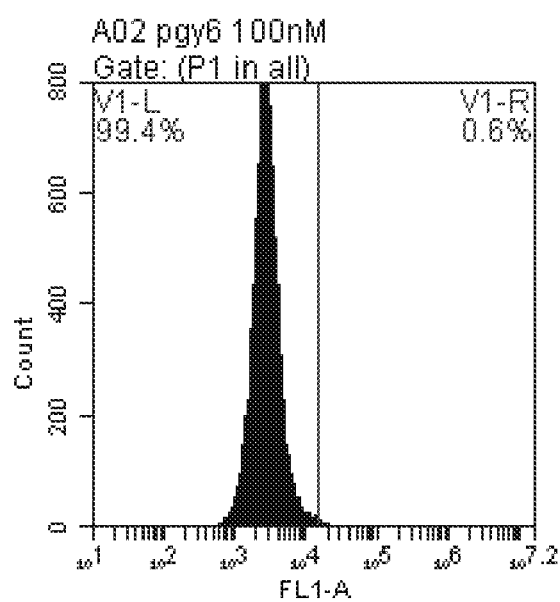
Figure 21C:
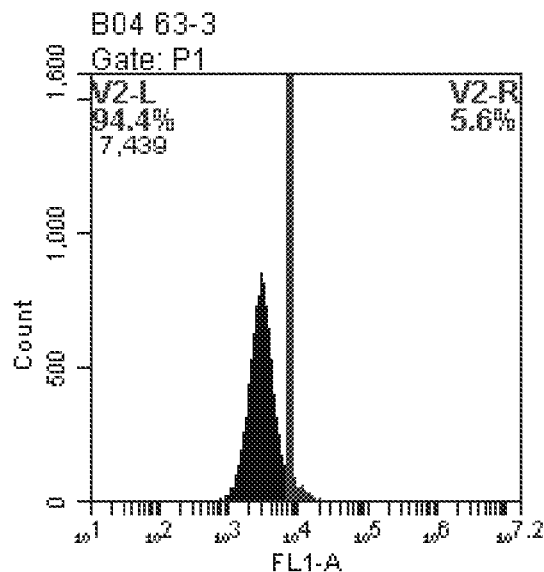
Figure 21D:
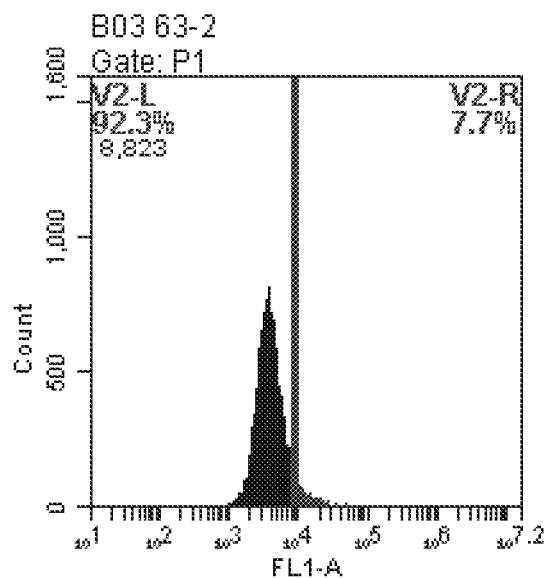
Figure 21E:
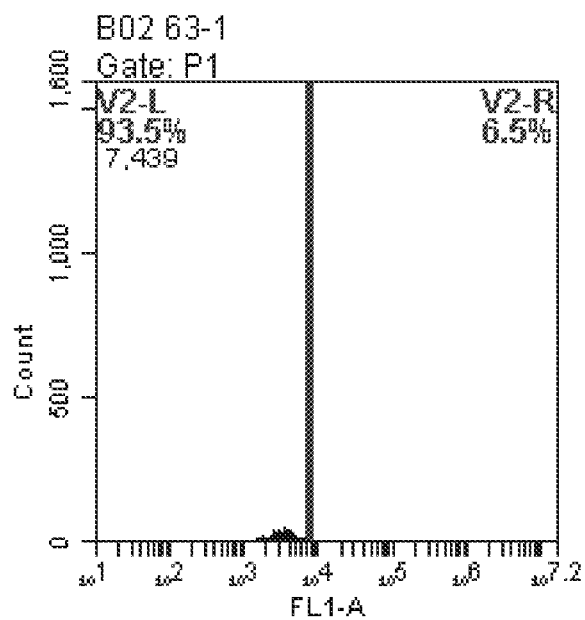
Figure 22A:
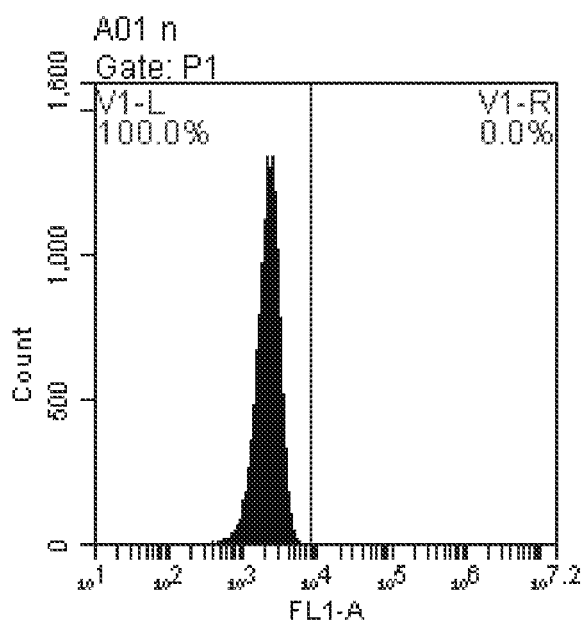
Figure 22B:
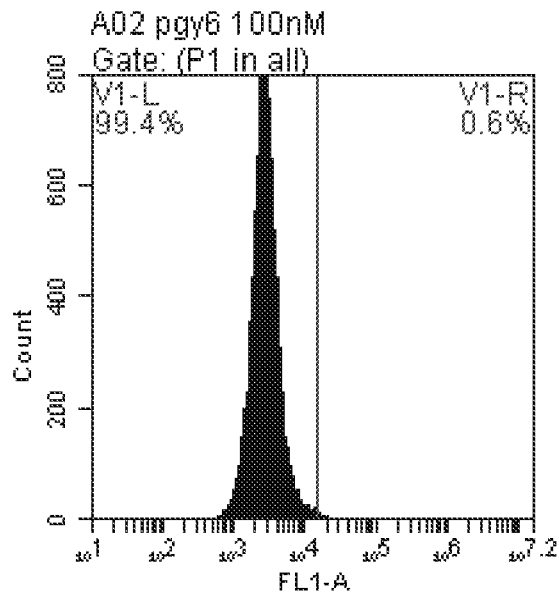
Figure 22C:
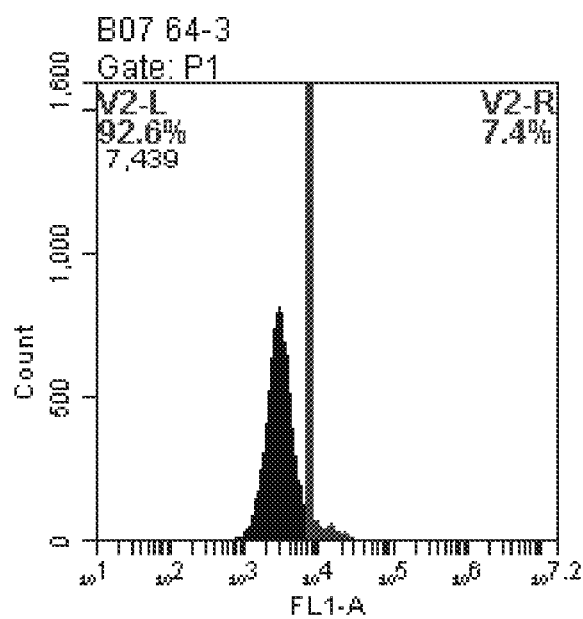
Figure 22D:
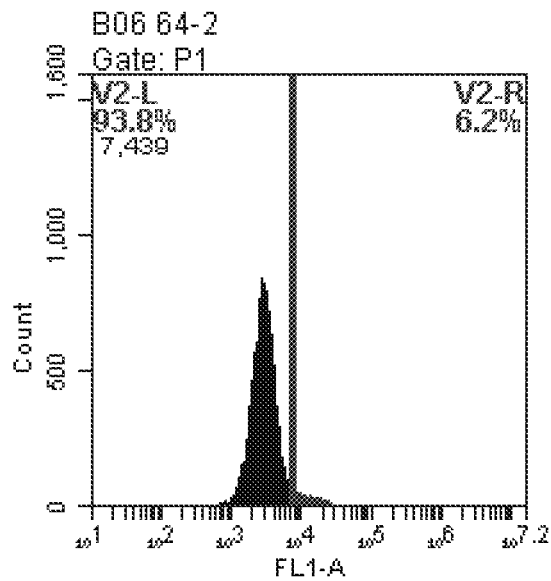
Figure 22E:
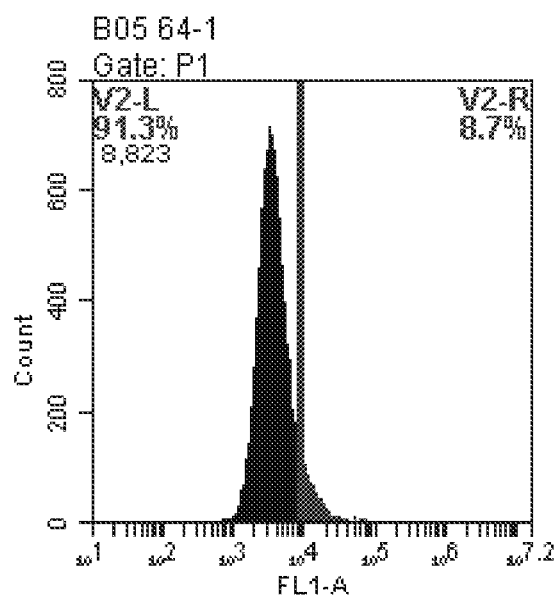
Figure 23A:
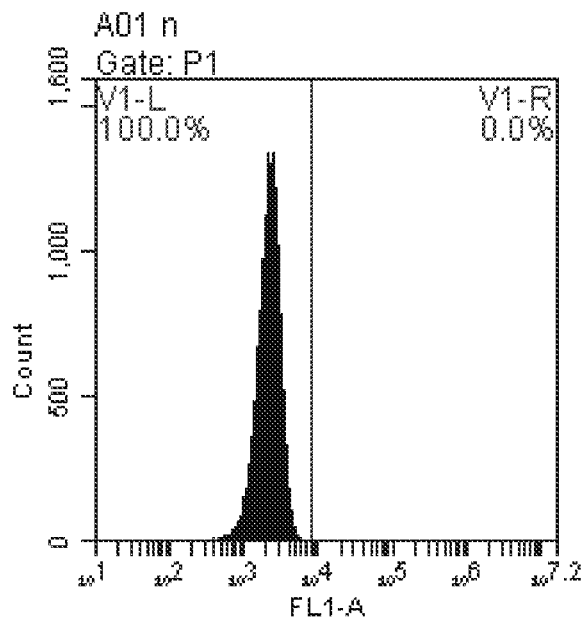
Figure 23B:
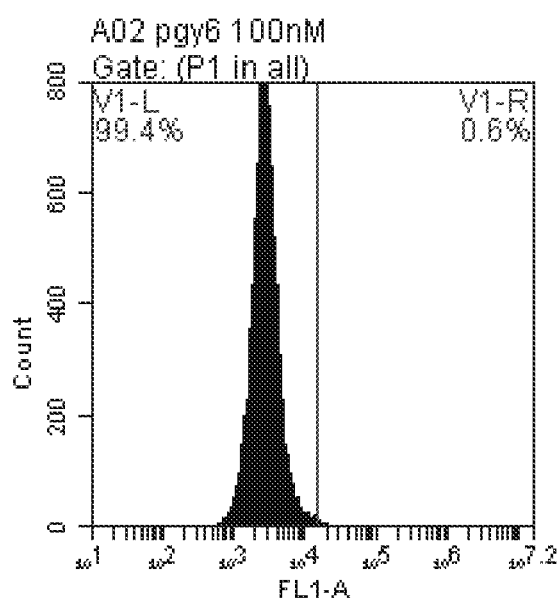
Figure 23C:
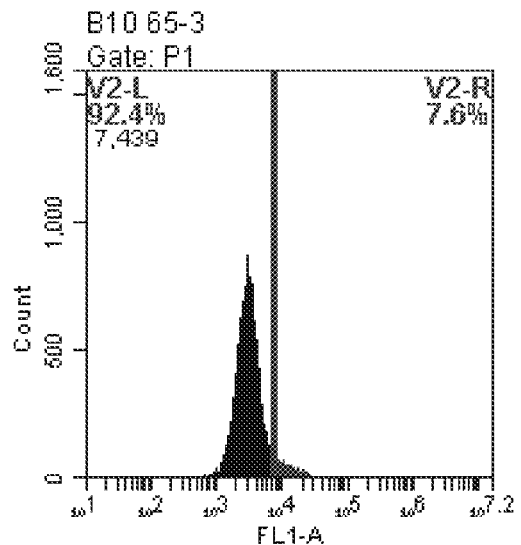
Figure 23D:
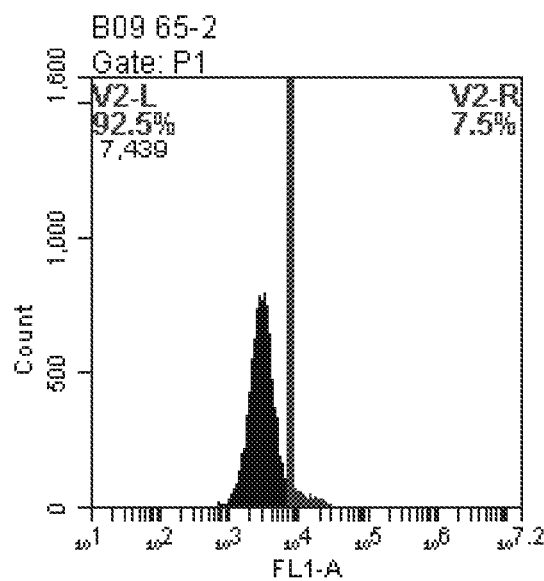
Figure 23E:
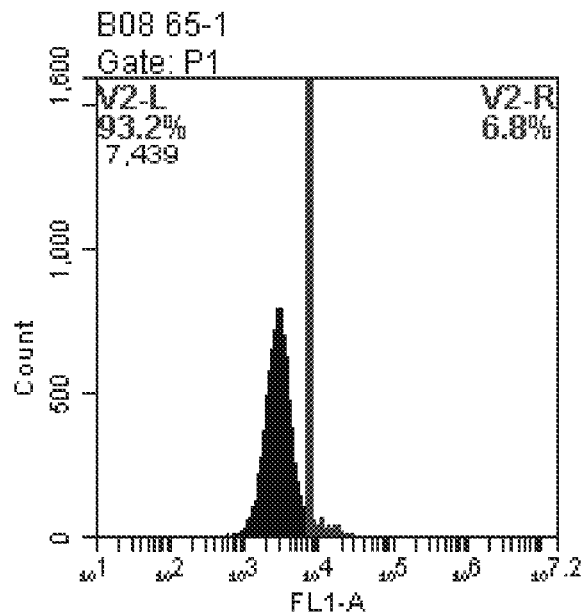
Figure 24A:
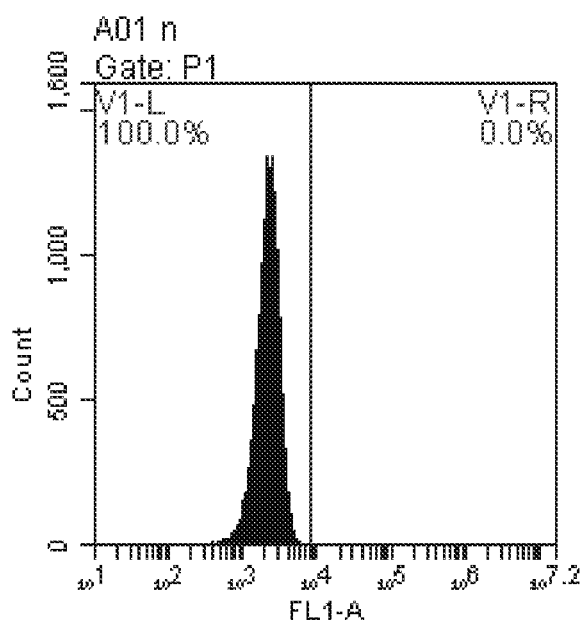
Figure 24B:
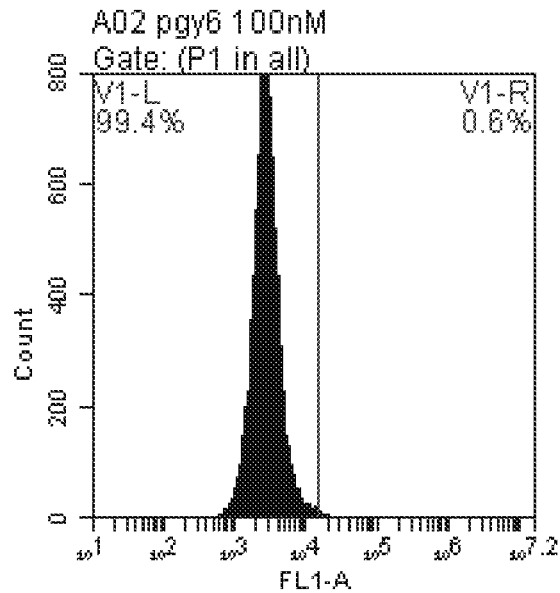
Figure 24C:
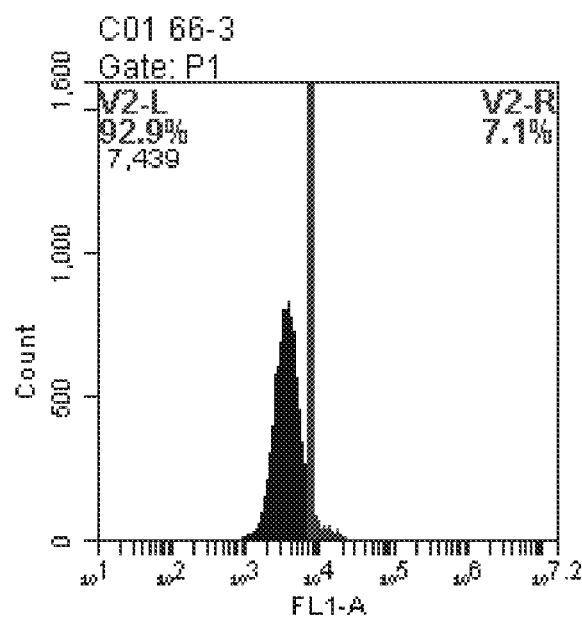
Figure 24D:
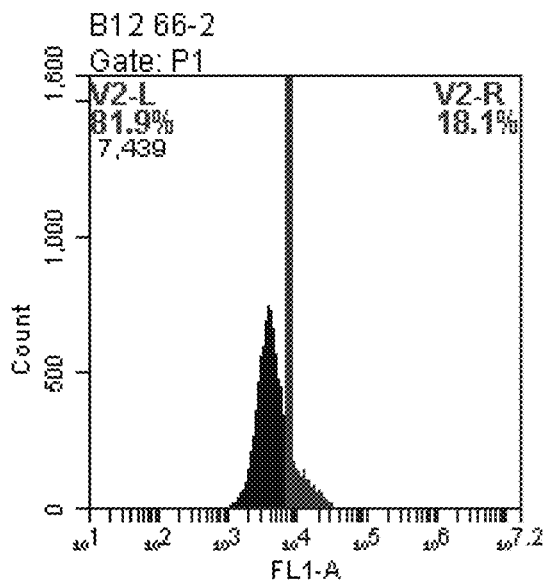
Figure 24E:
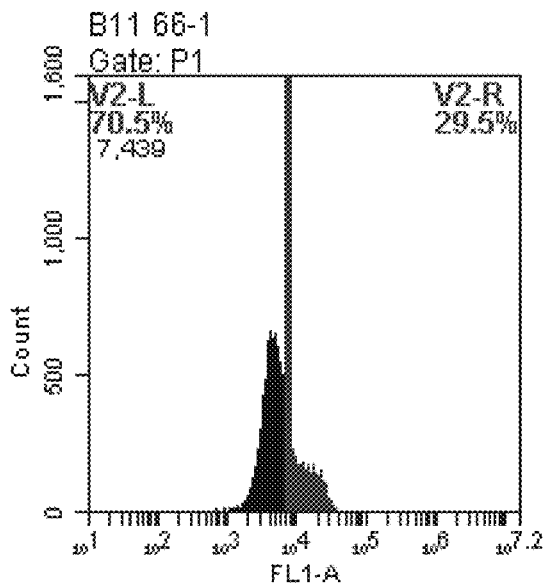
Figure 25A:
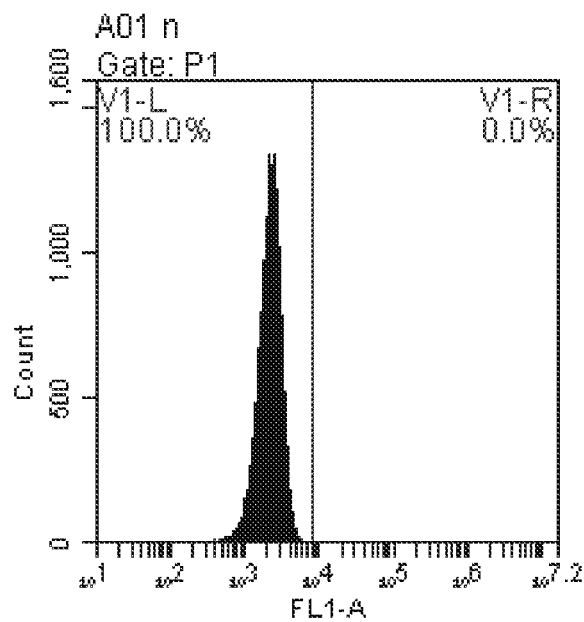
Figure 25B:
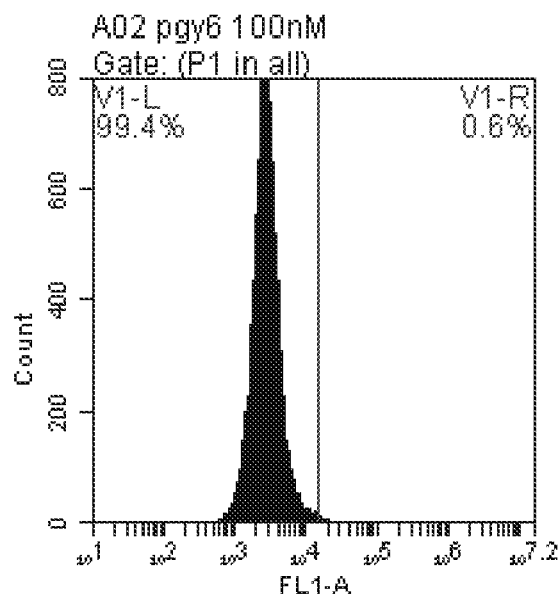
Figure 25C:
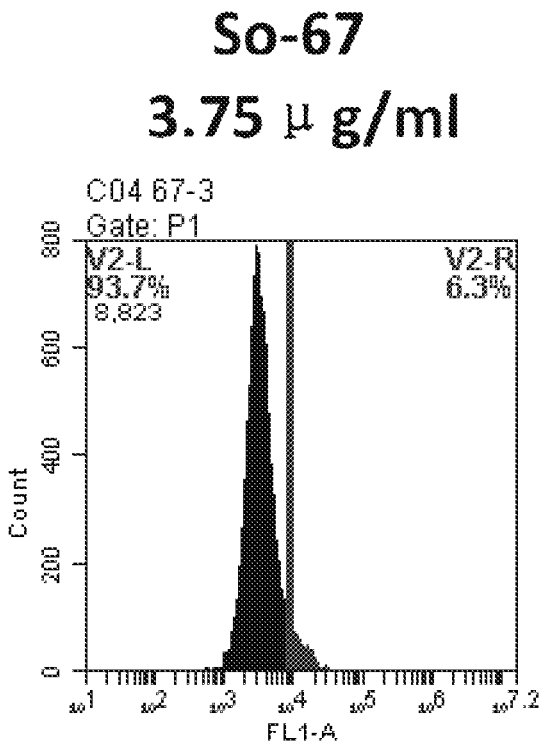
Figure 25D:
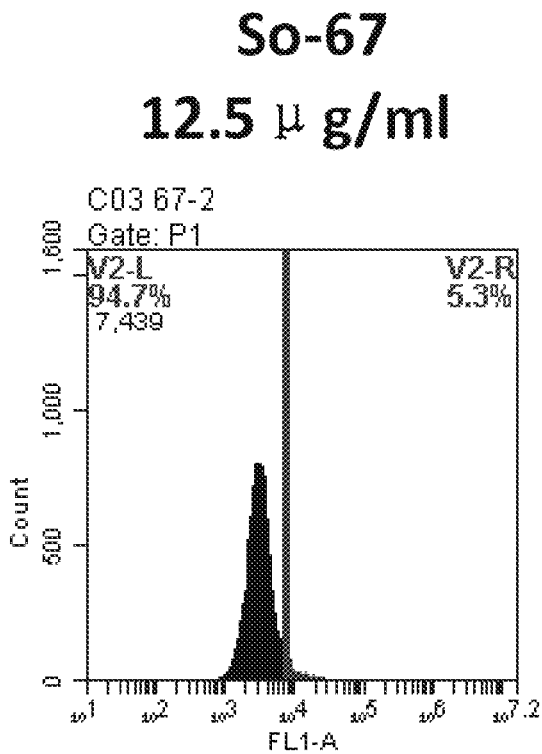
Figure 25E:
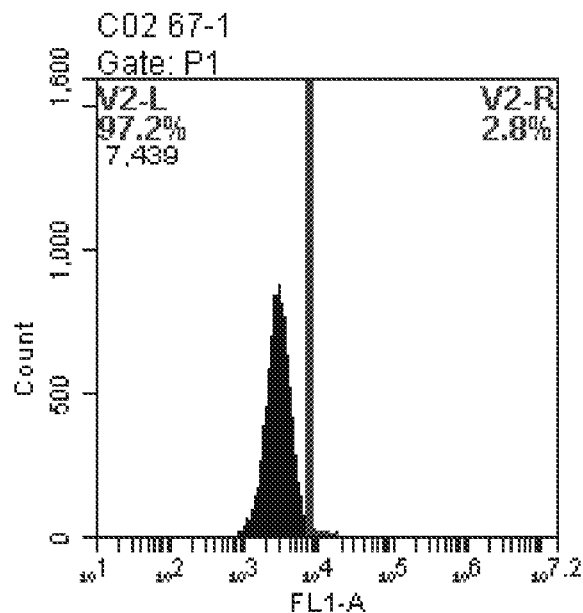
Figure 26A:
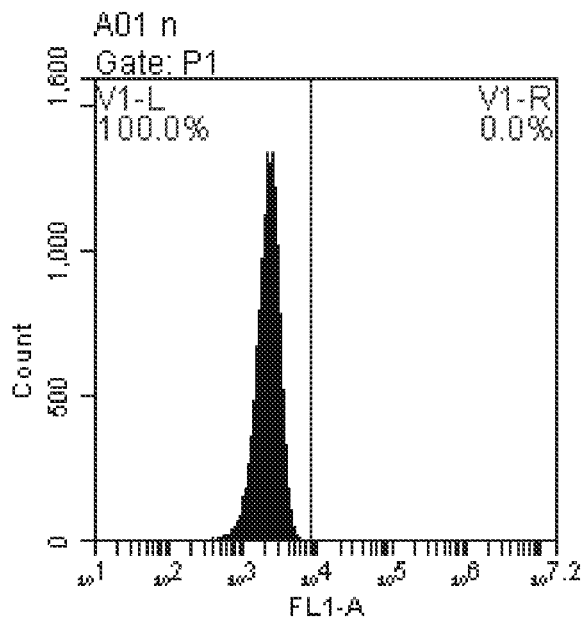
Figure 26B:
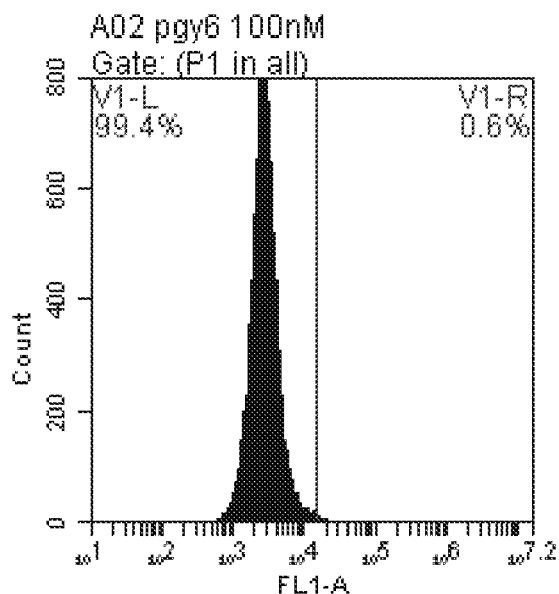
Figure 26C:
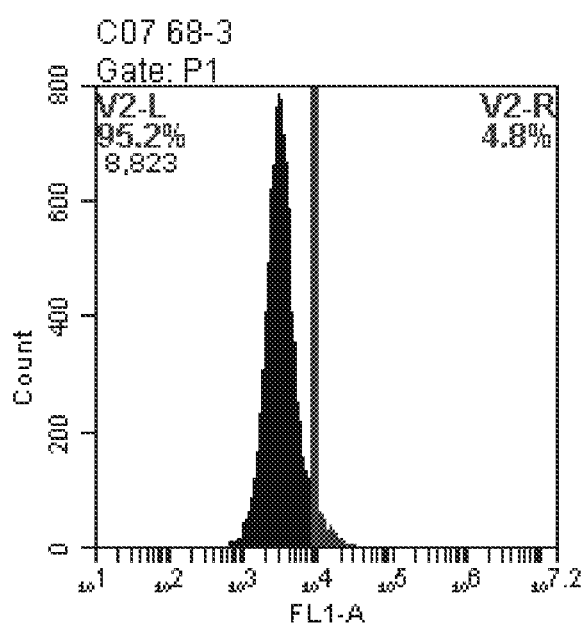
Figure 26D:
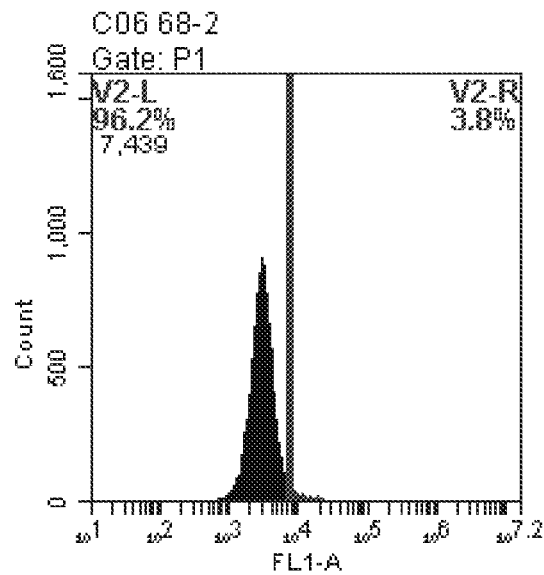
Figure 26E:
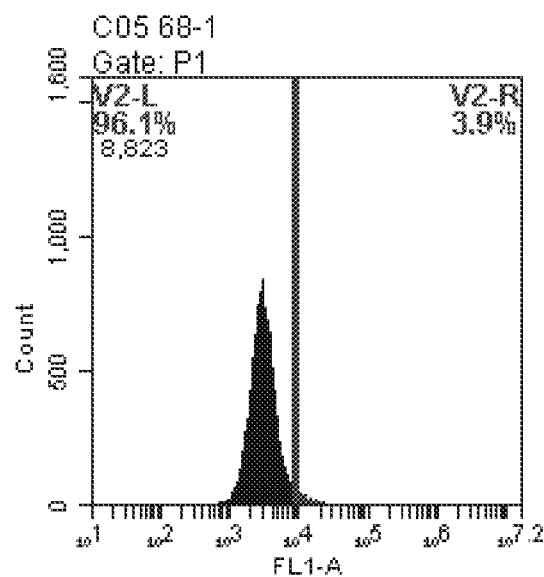
Figure 27A:
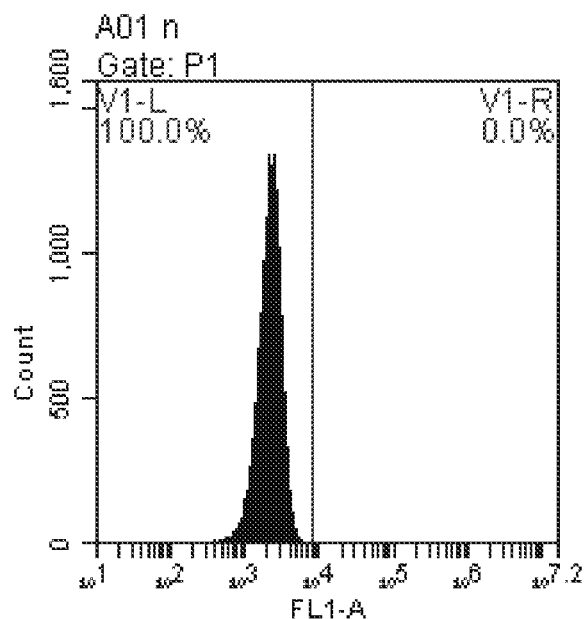
Figure 27B:
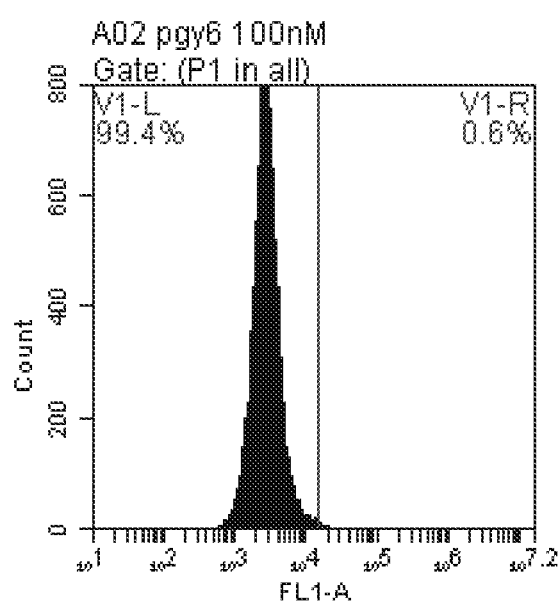
Figure 27C:
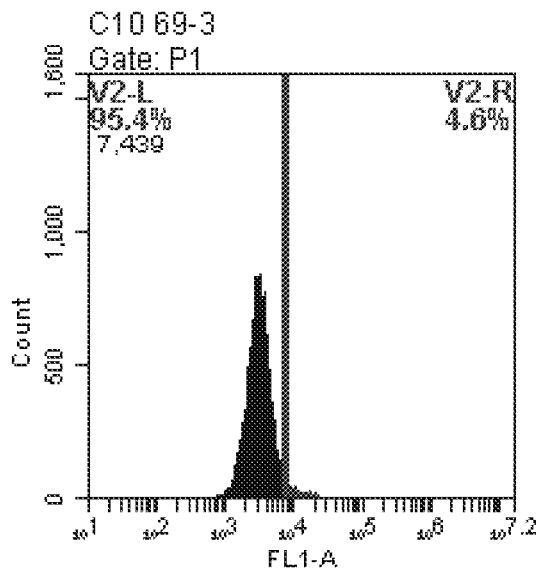
Figure 27D:
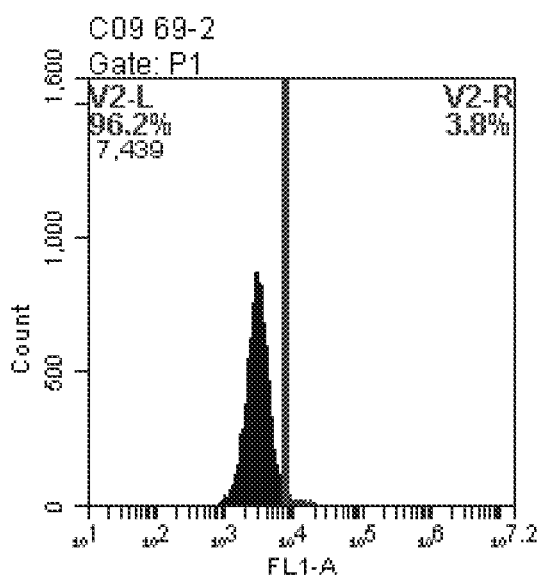
Figure 27E:
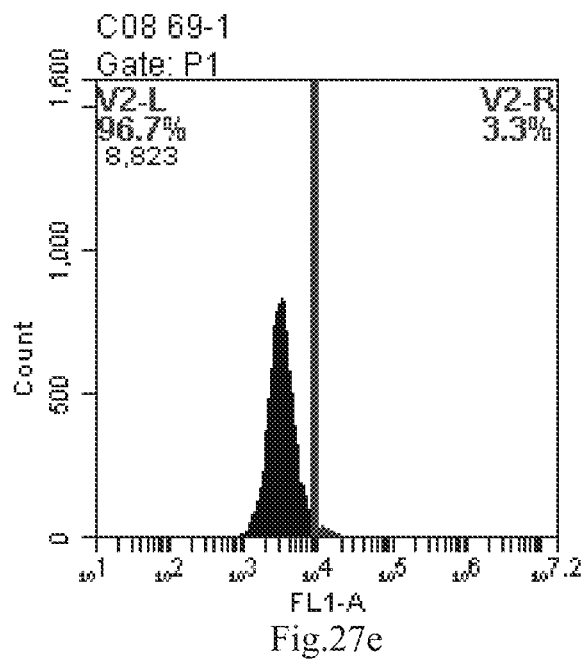
Figure 28A:
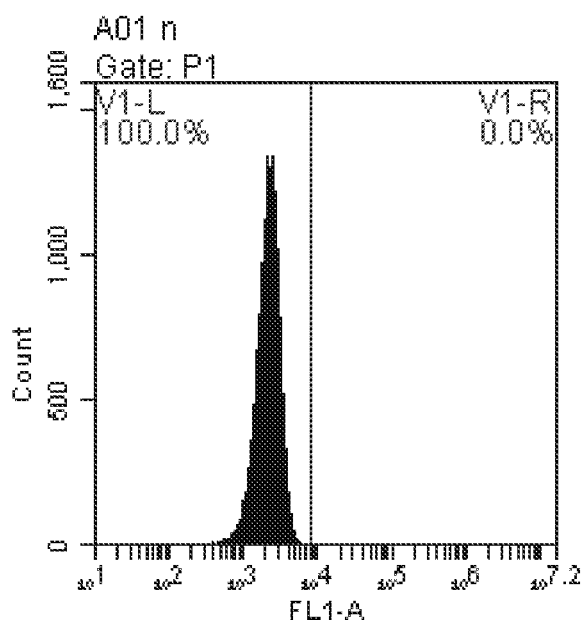
Figure 28B:
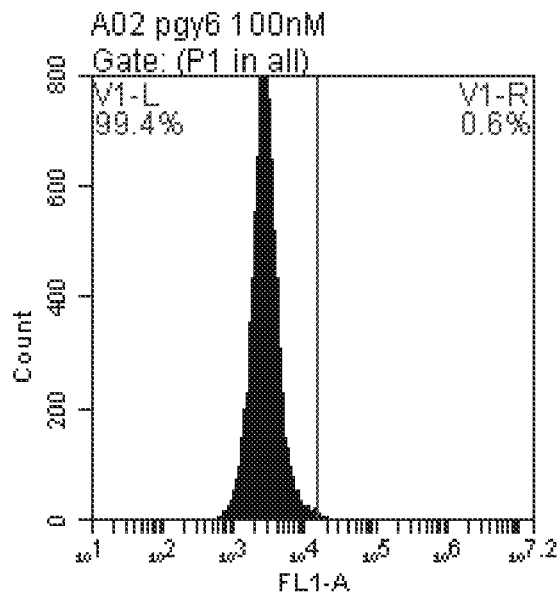
Figure 28C:
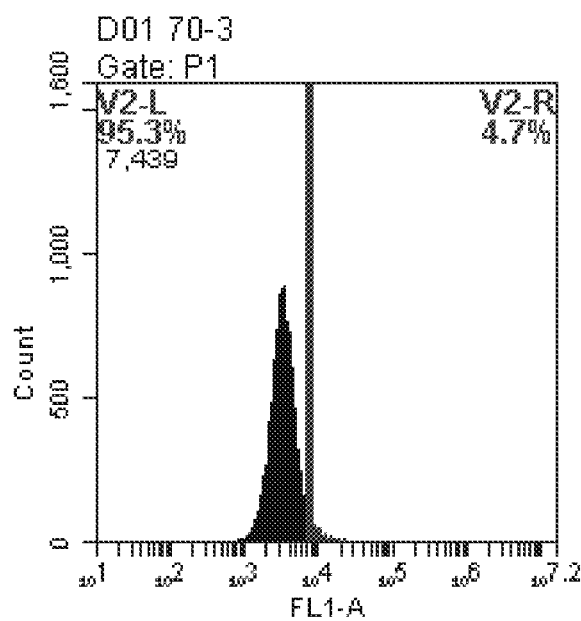
Figure 28D:
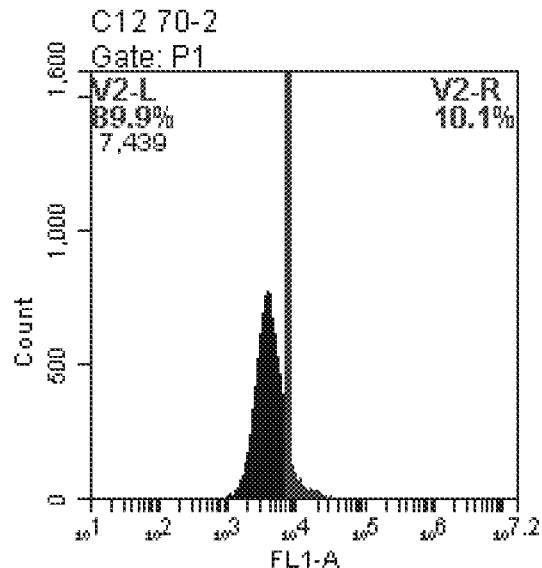
Figure 28E:
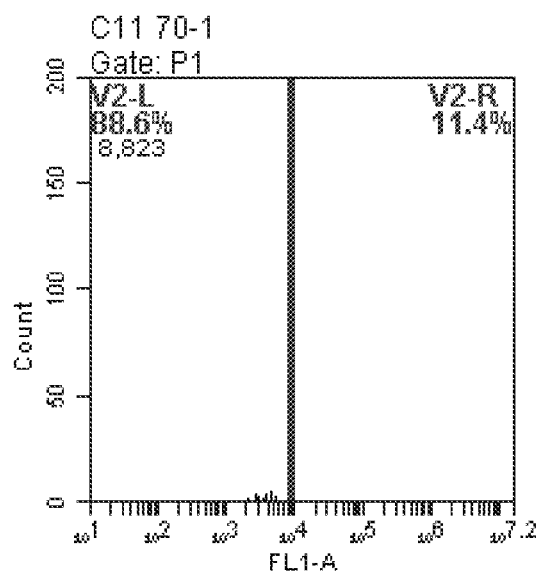
Figure 29A:
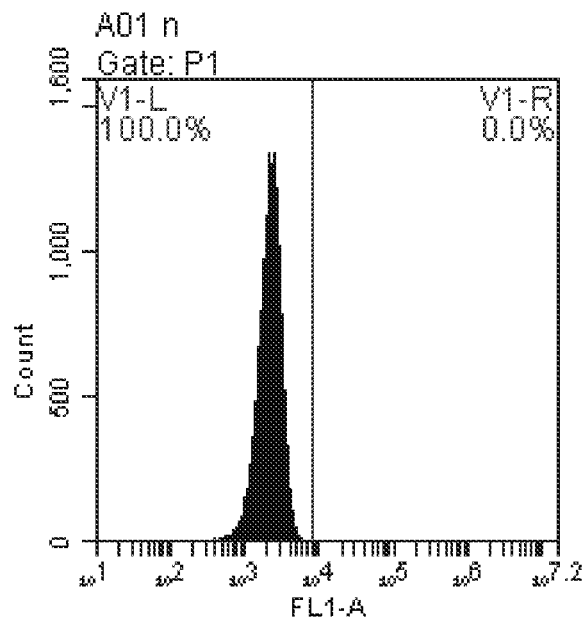
Figure 29B:
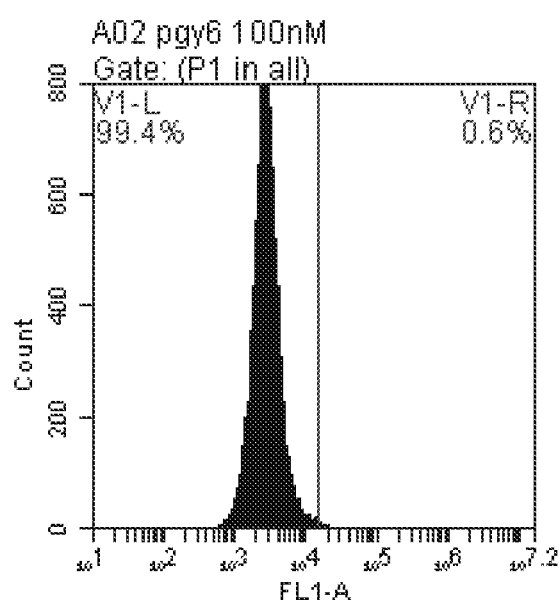
Figure 29C:
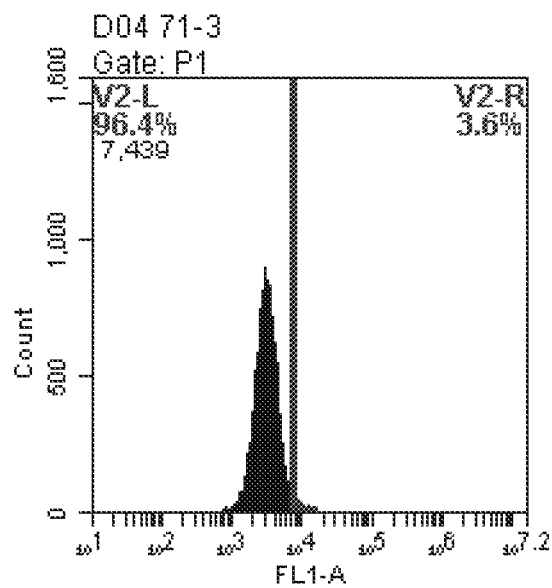
Figure 29D:
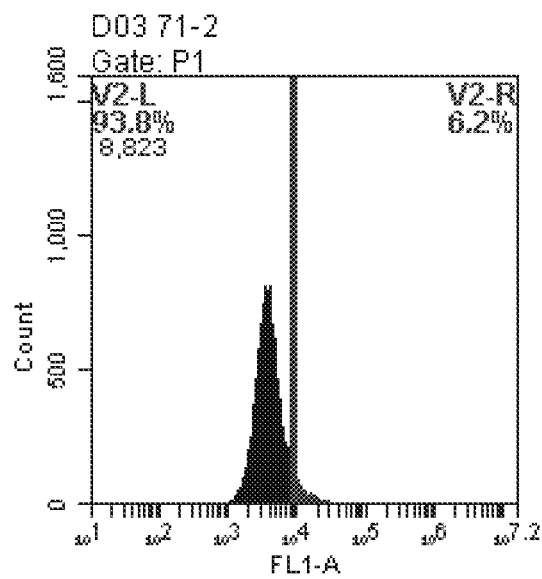
Figure 29E:
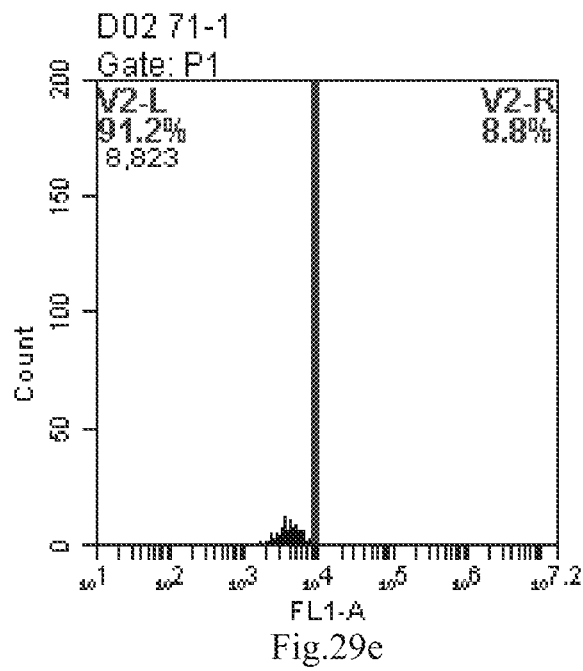
Figure 30A:
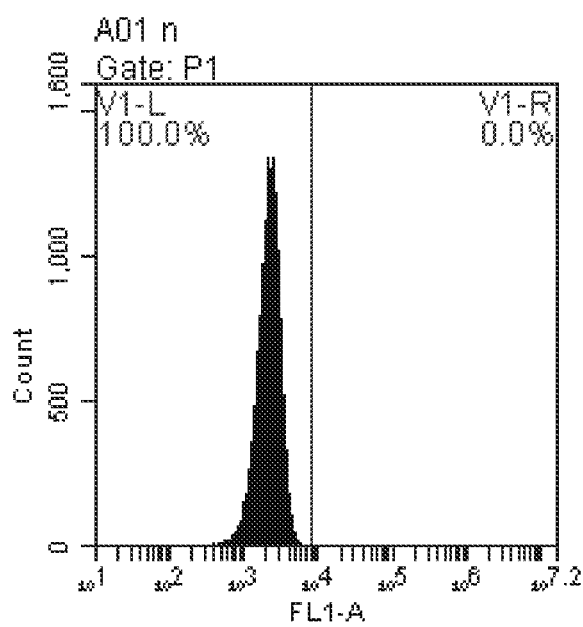
Figure 30B:
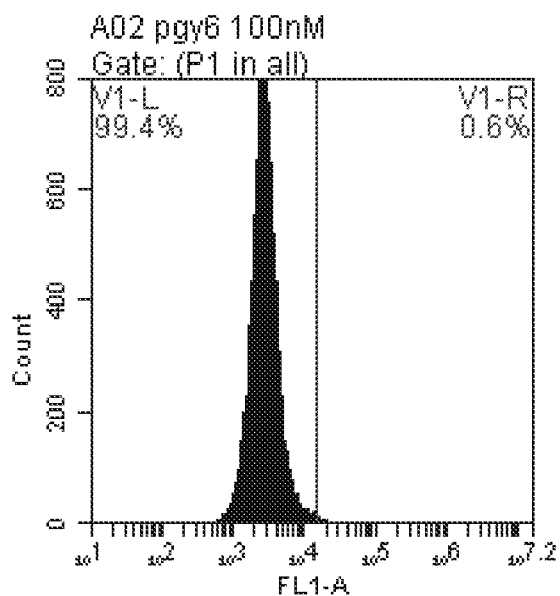
Figure 30C:
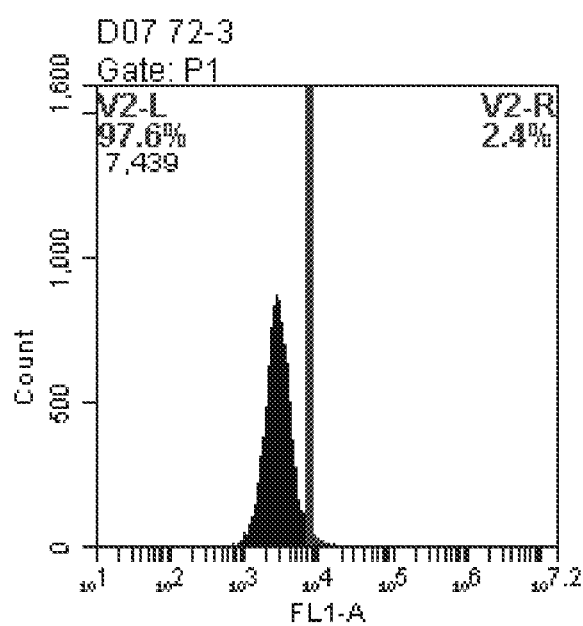
Figure 30D:
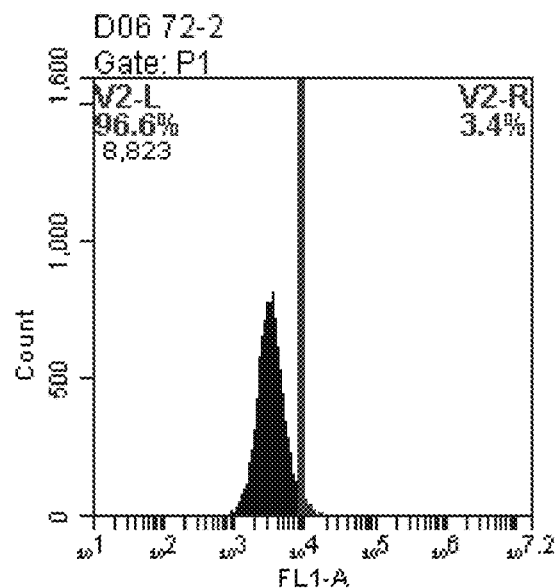
Figure 30E:
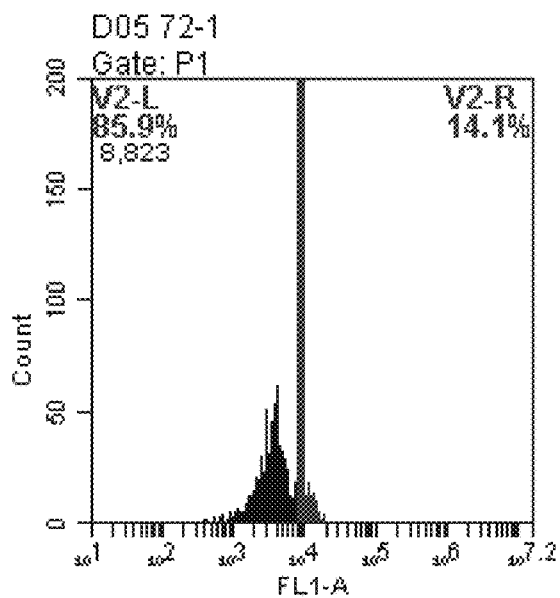
Figure 31A:
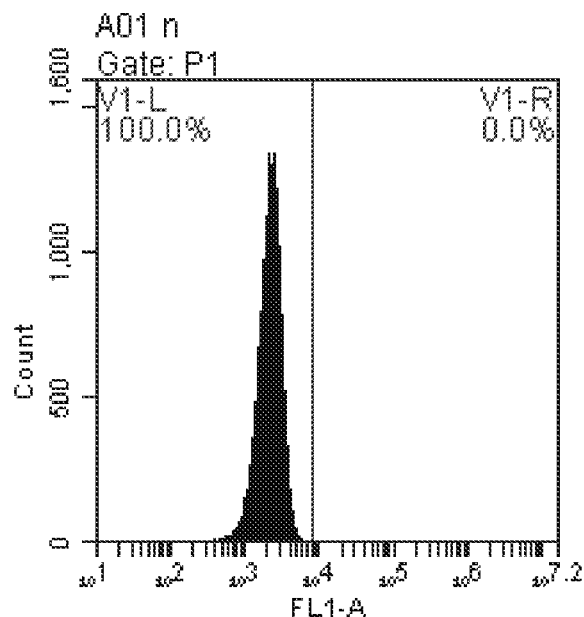
Figure 31B:
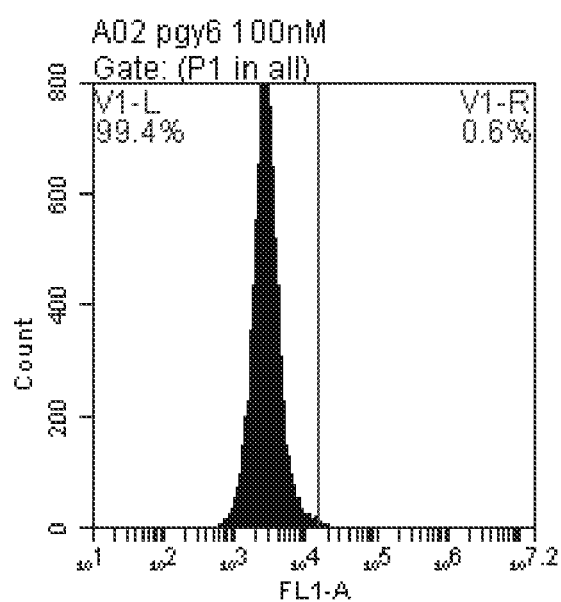
Figure 31C:
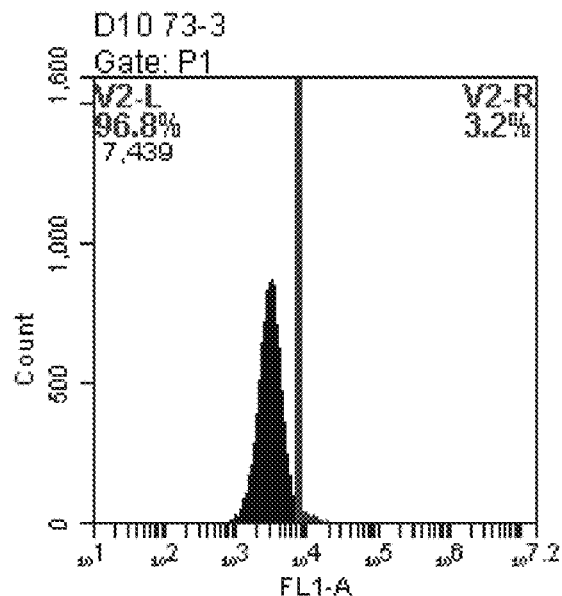
Figure 31D:
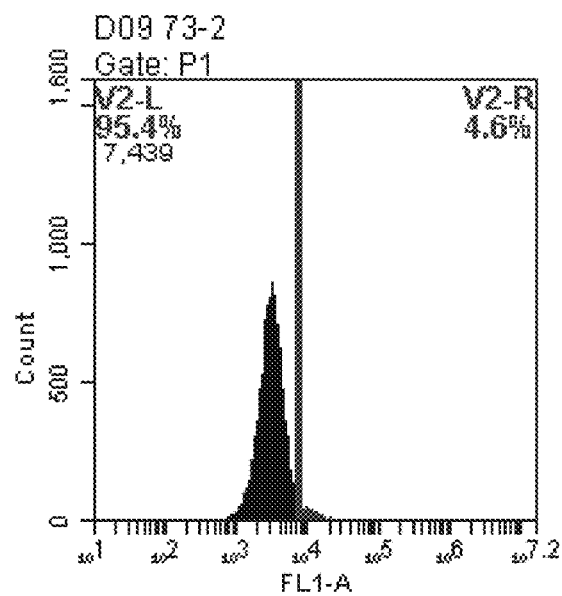
Figure 31E:
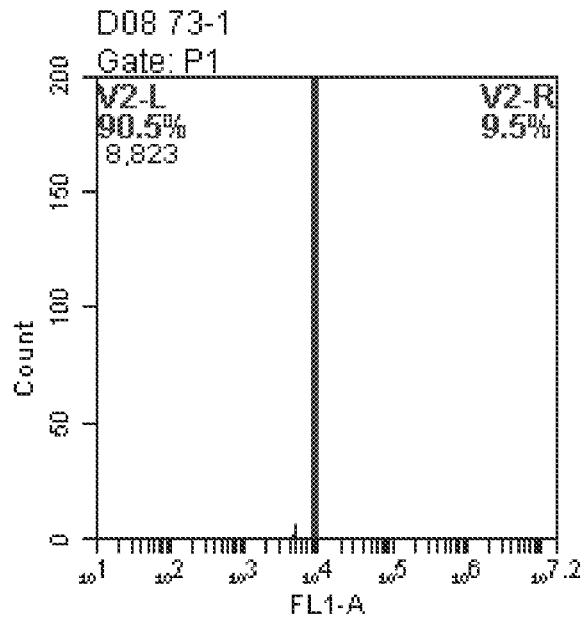
Figure 32A:
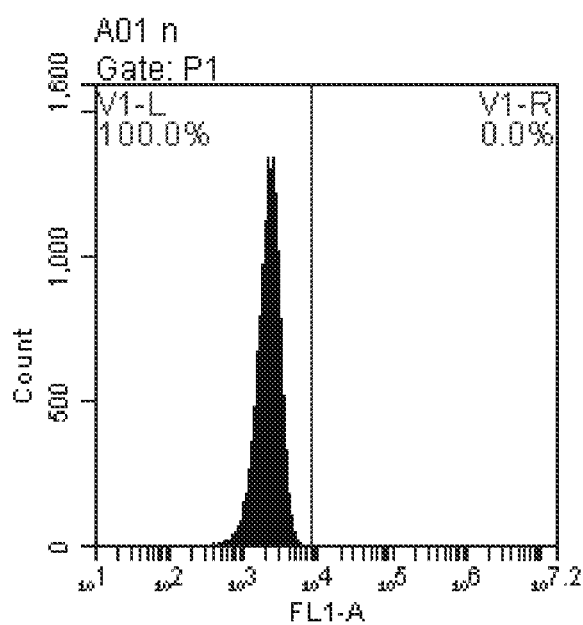
Figure 32B:
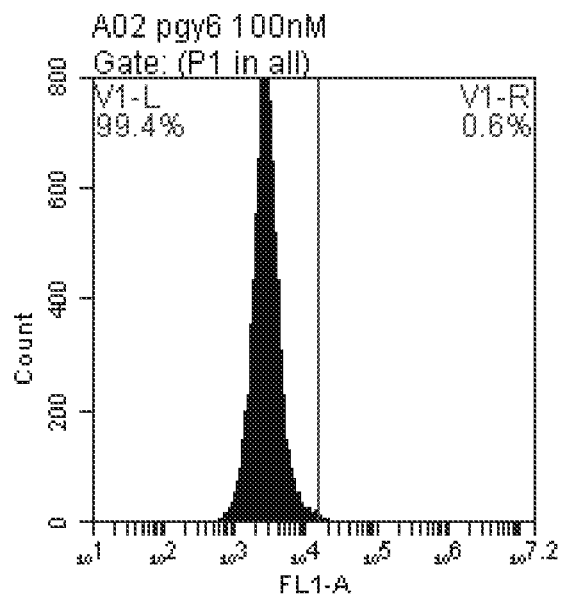
Figure 32C:
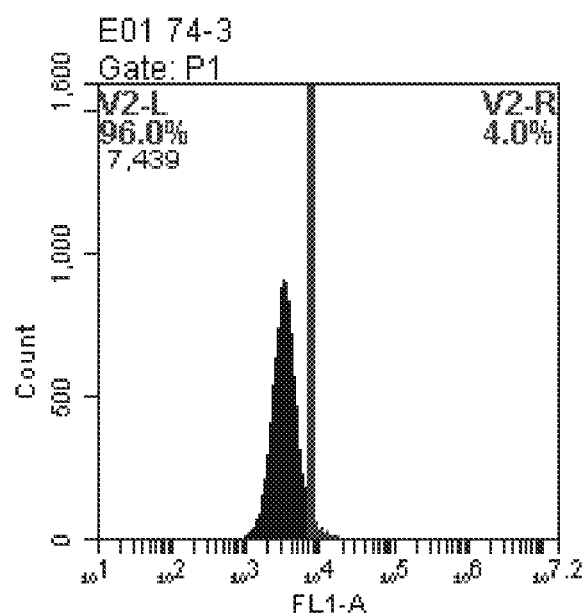
Figure 32D:
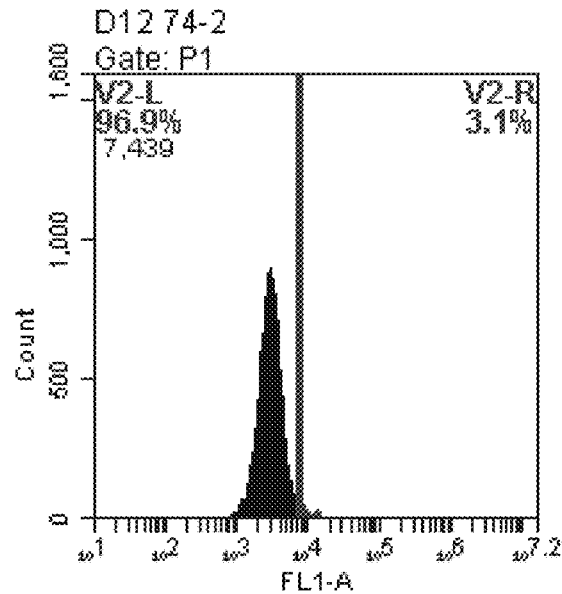
Figure 32E:
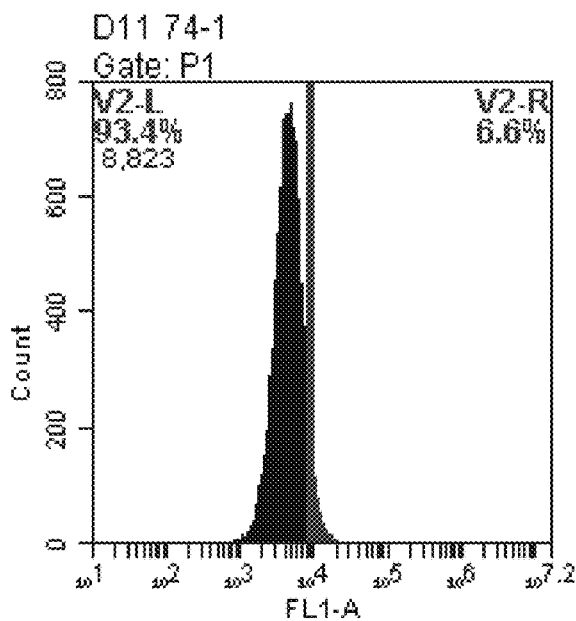
Figure 33A:
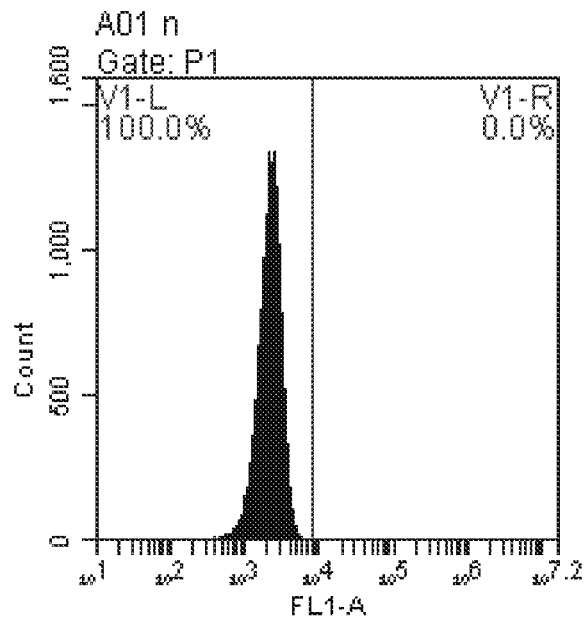
Figure 33B:
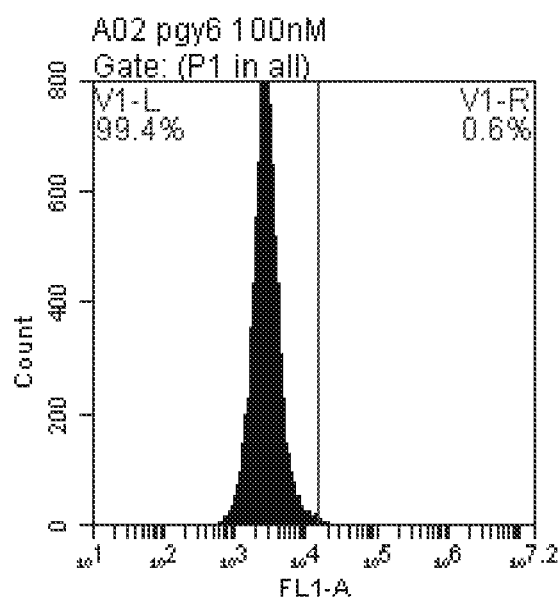
Figure 33C:
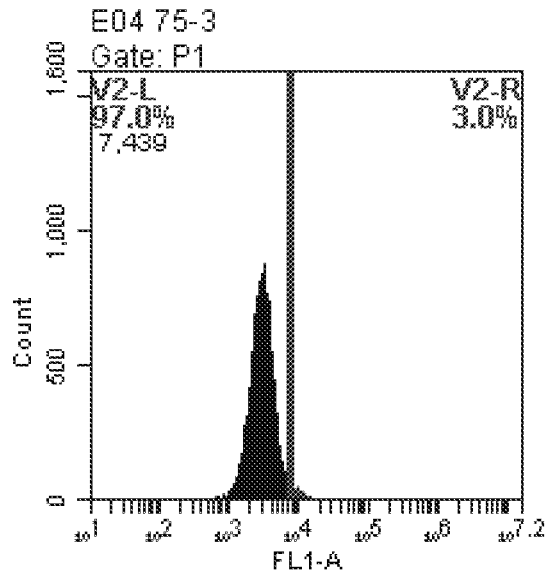
Figure 33D:
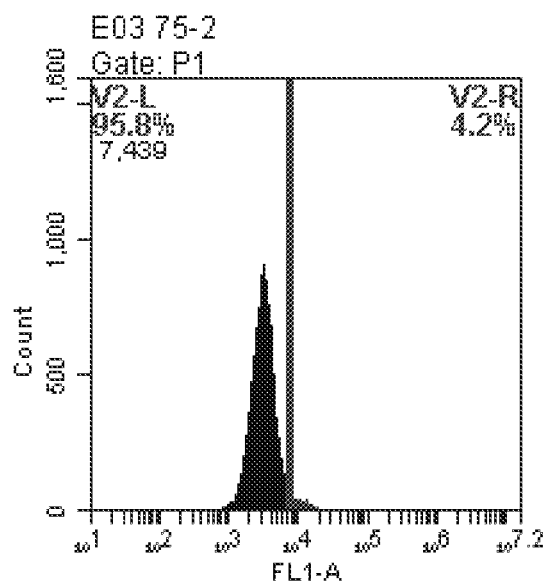
Figure 33E:
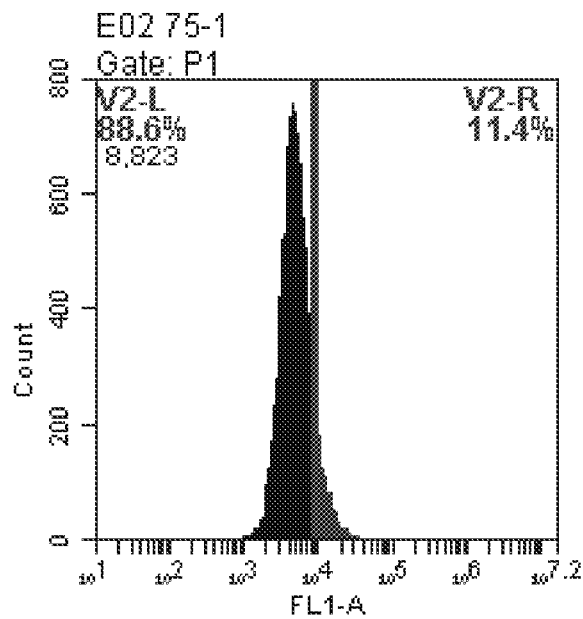

(51) Int. Cl.
  *A61P 35/00* (2006.01)
  *C07C 69/003* (2006.01)
  *C07C 69/587* (2006.01)
  *C07C 215/10* (2006.01)
  *C07C 233/18* (2006.01)
  *C07F 9/10* (2006.01)
  *C12N 15/113* (2010.01)

(56) References Cited

U.S. PATENT DOCUMENTS

| | | | | |
|---|---|---|---|---|
| 2012/0142765 | A1* | 6/2012 | Jimenez | C12N 15/111 435/375 |
| 2013/0065944 | A1* | 3/2013 | Maurel | A61P 31/00 514/44 R |
| 2020/0069587 | A1* | 3/2020 | Radovic-Moreno | A61P 31/12 |

FOREIGN PATENT DOCUMENTS

| | | |
|---|---|---|
| CN | 105078889 A | 11/2015 |
| KR | 20120035775 A | 4/2012 |
| WO | 94/23694 A1 | 10/1994 |
| WO | 97/19184 A1 | 5/1997 |

OTHER PUBLICATIONS

Allegood. Application of Liquid Chromatography Tandem Mass Spectrometry for the Separation and Quantitative Analysis of Sphingolipids, Georgia Institute of Technology, Dec. 2011. (Year: 2011).*

Human Metabolomics Database—PE(P-16:0/16:1(9Z). Published on Sep. 19, 2018. Retrieved from the Wayback Machine, https://web.archive.org/web/20180919184730/https://hmdb.ca/metabolites/HMDB0011339. (Year: 2018).*

Avanti Polar Lipids—Sphingosine (d22:1). PUblished on Nov. 15, 2018. Retrived from the internet, https://avantilipids.com/product/860663. (Year: 2018).*

Cayman Chemical, 3-keto Sphinganine(d6:0)(hydrochloride). Published on Mar. 9, 2018. Retrieved from the Internet, https://cdn.caymanchem.com/cdn/insert/24381.pdf. (Year: 2018).*

Goni et al.Biophysics of sphingolipids I. Membrane properties of sphingosine, ceramides and other simple sphingolipids, Biochimica et Biophysica Acta (BBA)—Biomembranes, vol. 1758, Issue 12, 2006, pp. 1902-1921, ISSN 0005-2736 (Year: 2006).*

Dabkowska et al. The effect of neutral helper lipids on the structure of cationic lipid monolayers, J R Soc Interface. Mar. 7, 2012; 9(68): 548-561. Published online Aug. 10, 2011. (Year: 2011).*

Merriam-Webster Online Dictionary, "Composition." Retrieved from the internet on Jun. 1, 2022. https://www.merriam-webster.com/dictionary/composition (Year: 2022).*

CAS SciFindern, CAS Registry No. 123-78-4, retrieved from the internet on Nov. 1, 2022, https://scifinder-n.cas.org/searchDetail/substance/63614f9e42ba3c59e9b224a2/substanceDetails (Year: 2022).*

CAS SciFindern, CAS Registry No. 26993-30-6, retrieved from the internet on Nov. 1, 2022, https://scifinder-n.cas.org/searchDetail/substance/6361252242ba3c59e9b01d3e/substanceDetails (Year: 2022).*

CAS SciFindern, CAS Registry No. 764-22-7, retrieved from the internet on Nov. 1, 2022, https://scifinder-n.cas.org/searchDetail/substance/6361245542ba3c59e9b0123d/substanceDetails (Year: 2022).*

Tokudome, Y. et al., "Preparation and Characterization of Ceramide-Based Liposomes with High Fusion Activity and High Membrane Fluidity", Colloids and Surfaces B: Biointerfaces, No. 73, May 12, 2009 (May 12, 2009), pp. 92-96.

Mi, Jia-ning et al., "New Immunosuppressive Sphingoid Base and Ceramide Analogues in Wild Cordyceps", Scientific Reports, vol. 6, Dec. 14, 2016 (Dec. 14, 2016), 38641.

Paukku Tommi et al: "Novel cationic liposomes for DNA-transfection with high efficiency and low toxicity", Chemistry and Physics of Lipids., vol. 87, No. 1, May 1, 1997 (May 1, 1997), pp. 23-29, XP055887294, IR ISSN: 0009-3084, DOI: 10.1016/S0009-3084(97)00020-0.

The extended European search report for the corresponding EP Application No. 19775142.3, dated Feb. 23, 2022.

* cited by examiner

Naïve group

Free uptake group

So-1
3.75 μg/ml

So-1
12.5 μg/ml

So-1
37.5 μ g/ml

Naïve group

Free uptake group

So-3
3.75 μg/ml

So-3
12.5 µg/ml

So-3
37.5 µg/ml

Naïve group

Free uptake group

So-4

3.75 μg/ml

So-4

12.5 μg/ml

So-4
37.5 μg/ml

Naïve group

Free uptake group

So-5
3.75 μg/ml

So-5
12.5 μg/ml

So-5
37.5 μg/ml

Naïve group

Free uptake group

So-7
3.75 μg/ml

So-7
12.5 μg/ml

So-7
37.5 μ g/ml

Naïve group

Free uptake group

So-8

3.75 µg/ml

So-8
12.5 μg/ml

So-8
37.5 μg/ml

Naïve group

Free uptake group

So-9
3.75 μg/ml

So-9
12.5 μg/ml

So-9
37.5 μg/ml

Naïve group

Free uptake group

So-10
3.75 μg/ml

So-10
12.5 μ g/ml

So-10
37.5 μ g/ml

Naïve group

Free uptake group

So-11
3.75 μg/ml

So-11
12.5 μg/ml

So-11
37.5 μg/ml

Naïve group

Free uptake group

So-12
3.75 μg/ml

So-12
12.5 μg/ml

So-12
37.5 μg/ml

Naïve group

Free uptake group

So-13
3.75 µg/ml

So-13
12.5 µg/ml

So-13
37.5 μ g/ml

Naïve group

Free uptake group

So-14
3.75 μg/ml

So-14
12.5 μg/ml

So-14
37.5 μg/ml

Naïve group

Free uptake group

So-15
3.75 μg/ml

So-15
12.5 μg/ml

So-15
37.5 μg/ml

Naïve group

Free uptake group

So-26
3.75 μg/ml

So-26
12.5 μg/ml

So-26
37.5 μg/ml

Naïve group

Free uptake group

So-46
3.75 μg/ml

So-46
12.5 μg/ml

So-46
37.5 μg/ml

Naïve group

Free uptake group

So-49
3.75 μg/ml

So-49
12.5 µg/ml

So-49
37.5 µg/ml

So-53
3.75 μg/ml

So-53
12.5 μg/ml

So-53
37.5 μ g/ml

Naïve group

Free uptake group

So-60

3.75 μg/ml

So-60
12.5 μg/ml

So-60
37.5 μg/ml

Naïve group

Free uptake group

So-61

3.75 μg/ml

So-61

12.5 μg/ml

So-61
37.5 μg/ml

Naïve group

Free uptake group

So-62
3.75 μg/ml

So-62
12.5 μg/ml

So-62
37.5 μg/ml

Naïve group

Free uptake group

So-63

3.75 μg/ml

So-63

12.5 μg/ml

So-63
37.5 μg/ml

Naïve group

Free uptake group

So-64
3.75 μg/ml

So-64
12.5 μg/ml

So-64
37.5 μg/ml

Naïve group

Free uptake group

So-65
3.75 µ g/ml

So-65
12.5 µ g/ml

So-65
37.5 μ g/ml

Naïve group

Free uptake group

So-66
3.75 μg/well

So-66
12.5 µg/ml

So-66
37.5 µg/ml

Naïve group

Free uptake group

So-67
3.75 μg/ml

So-67
12.5 μg/ml

So-67
37.5 μg/ml

Naïve group

Free uptake group

So-68
3.75 μg/ml

So-68
12.5 μ g/ml

So-68
37.5 μ g/ml

Naïve group

Free uptake group

So-69
3.75 μg/ml

So-69
12.5 μg/ml

So-69
37.5 μg/ml

Naïve group

Free uptake group

So-70
3.75 μg/ml

So-70
12.5 μg/ml

So-70
37.5 μg/ml

Naïve group

Free uptake group

So-71
37.5 μg/ml

Naïve group

Free uptake group

So-72

3.75 μg/ml

So-72
12.5 μg/ml

So-72
37.5 μg/ml

So-73
3.75 μg/ml

So-73
12.5 μg/ml

So-73
37.5 μg/ml

Naïve group

Free uptake group

**So-74
3.75µg/ ml**

So-74
12.5μg/ml

So-74
37.5μg/ml

Naïve group

Free uptake group

So-75
3.75µg/ ml

So-75
12.5µg/ ml

So-75
37.5μg/ml

Naïve group

Free uptake

No.41+ No.38+ So-1

Naïve group

Free uptake

No.41+ No.38+ So-2

Naïve group

Free uptake

No.41+ No.38+ So-3

Naïve group

Free uptake

No.41+ No.38+ So-4

Naïve group

Free uptake

No.41+ No.38+ So-5

Naïve group

Free uptake

No.41+ No.38+ So-6

Naïve group

Free uptake

No.41+ No.38+ So-7

Naïve group

Free uptake

No.41+ No.38+ So-8

Naïve group

Free uptake

No.41+ No.38+ So-9

Naïve group

Free uptake

No.41+ No.38+ So-10

Naïve group

Free uptake

No.41+ No.38+ So-11

Naïve group

Free uptake

No.41+ No.38+ So-12

Naïve group

Free uptake

No.41+ No.38+ So-13

Naïve group

Free uptake

No.41+ No.38+ So-14

Naïve group

Free uptake

No.41+ No.38+ So-15

Naïve group

Free uptake

No.41+ No.38+ So-45

Naïve group

Free uptake

No.41+ No.38+ So-46

Naïve group

Free uptake

No.41+ No.38+ So-47

Naïve group

Free uptake

No.41+ No.38+ So-48

Naïve group

Free uptake

Naïve group

Free uptake

No.41+ No.38+ So-50

Naïve group

Free uptake

No.41+ No.38+ So-51

Naïve group

Free uptake

No.41+ No.38+ So-52

Naïve group

Free uptake

Naïve group

Free uptake

No.41+ No.38+ So-54

Naïve group

Free uptake

No.41+ No.38+ So-55

Naïve group

Free uptake

No.41+ No.38+ So-56

Naïve group

Free uptake

No.41+ No.38+ So-57

Naïve group

Free uptake

No.41+ No.38+ So-58

Naïve group

Free uptake

No.41+ No.38+ So-59

Naïve group

Free uptake

No.41+ No.38+ So-60

Naïve group

Free uptake

Naïve group

Free uptake

No.41+ No.38+ So-62

Naïve group

Free uptake

No.41+ No.38+ So-63

Naïve group

Free uptake

No.41+ No.38+ So-64

Naïve group

Free uptake

No.41+ No.38+ So-65

Naïve group

Naïve group

Free uptake

Naïve group

Naïve group

Free uptake

No.41+ No.38+ So-69

Naïve group

Free uptake

No.41+ No.38+ So-70

Naïve group

Free uptake

No.41+ No.38+ So-71

Naïve group

Free uptake

No.41+ No.38+ So-72

Naïve group

Free uptake

No.41+ No.38+ So-73

Naïve group

Free uptake

No.41+ No.38+ So-74

Naïve group

Free uptake

No.41+ No.38+ So-75

Naïve group

Naïve group

Free uptake

Naïve group

Naïve group

Free uptake

Naïve group

Free uptake

NO.41+38+48+46

Naïve group

Free uptake

Naïve group

Free uptake

NO.41+38+48+52

Naïve group

Free uptake

Naïve group

Naïve group

Free uptake

Naïve group

Free uptake

NO.41+38+48+59

Naïve group

Free uptake

Naïve group

Free uptake

NO.41+38+48+61

Naïve group

Free uptake

Naïve group

Free uptake

Naïve group

Naïve group

Free uptake

Naïve group

Naïve group

Free uptake

```
                        SEQUENCE LISTING

<160> NUMBER OF SEQ ID NOS: 7

<210> SEQ ID NO 1
<211> LENGTH: 21
<212> TYPE: DNA
<213> ORGANISM: Artificial Sequence
<220> FEATURE:
<223> OTHER INFORMATION: Synthetic

<400> SEQUENCE: 1
gttcagagtt ctacagtccg a                                             21

<210> SEQ ID NO 2
<211> LENGTH: 53
<212> TYPE: DNA
<213> ORGANISM: Artificial Sequence
<220> FEATURE:
<223> OTHER INFORMATION: Synthetic

<400> SEQUENCE: 2
gtcgtatcca gtgcagggtc cgaggtattc gcactggata cgacaaaaat atg          53

<210> SEQ ID NO 3
<211> LENGTH: 50
<212> TYPE: DNA
<213> ORGANISM: Artificial Sequence
<220> FEATURE:
<223> OTHER INFORMATION: Synthetic

<400> SEQUENCE: 3
gtcgtatcca gtgcacgctc cgaggtattc gcactggata cgactcggac              50

<210> SEQ ID NO 4
<211> LENGTH: 18
<212> TYPE: DNA
<213> ORGANISM: Artificial Sequence
<220> FEATURE:
<223> OTHER INFORMATION: Synthetic

<400> SEQUENCE: 4
gcgcgtcgtg aagcgttc                                                 18

<210> SEQ ID NO 5
<211> LENGTH: 16
<212> TYPE: DNA
<213> ORGANISM: Artificial Sequence
<220> FEATURE:
<223> OTHER INFORMATION: Synthetic

<400> SEQUENCE: 5
gtgcagggtc cgaggt                                                   16

<210> SEQ ID NO 6
<211> LENGTH: 17
<212> TYPE: DNA
<213> ORGANISM: Artificial Sequence
<220> FEATURE:
<223> OTHER INFORMATION: Synthetic

<400> SEQUENCE: 6
```

```
tcgcgcgttc agagttc                                              17

<210> SEQ ID NO 7
<211> LENGTH: 16
<212> TYPE: DNA
<213> ORGANISM: Artificial Sequence
<220> FEATURE:
<223> OTHER INFORMATION: Synthetic

<400> SEQUENCE: 7
gtgcacgctc cgaggt                                               16
```

ARTIFICIALLY SYNTHESIZED SPHINGOSINE DERIVATIVE LIPOID MONOMER AND USE OF SAME FOR DELIVERING NUCLEIC ACID

SEQUENCE LISTING

A copy of the Sequence Listing is submitted with the specification electronically via EFS-Web as an ASCII formatted sequence listing with a file name of "074844-8006US01-SL-20201208 ST25", a creation date of Dec. 8, 2020, and a size of 1,601 bytes. The sequence listing contained in this ASCII formatted document is part of the specification and is herein incorporated by reference in its entirety.

CROSS REFERENCE TO RELATED APPLICATIONS

This application claims priority to PCT Application No. PCT/CN2018/081155, titled "Application of compound or traditional Chinese medicine extract in preparation of nucleic acid delivery agent and related products thereof" filed on Mar. 29, 2018, the entirety of which is incorporated herein by reference.

TECHNICAL FIELD

The present application generally relates to a delivery means of nucleic acid therapy, more particularly, relates to a more efficient delivery carrier and delivery means.

BACKGROUND

Nucleic acid, as the main genetic material of living organisms, also has its unique potential for drug development. Currently, there are 6 types of nucleic acid drugs approved by the FDA, including Formavirsen (ISIS PHARMS INC, NDA: 20-961), mainly for the treatment of cytomegalovirus retinitis; Pagatanib (VALEANT PHARMS LLC, NDA: 21-756), mainly for neovascular age-related macular degeneration; Mipomethan (KASTLE THERAPS LLC, NDA: 203458), commonly for Homozygous familial hypercholesterolemia; Exondys 51 (SAREPTA THERAPS INC, NDA: 206488), for Duchenne muscular dystrophy; defibrotide-sodium (JAZZ PHAEMS INC, NDA: 208114), for the treatment of hepatic vein occlusive disease with renal or pulmonary dysfunction after hematopoiesis; Nusinersen (BIOGEN IDEC, NDA: 209531), for the treatment of spinal muscular atrophy; Patisiran (ALNYLAM PHARMS INC, NDA: 210922), for amyloidosis related to hereditary hyperthyroidism protein. These drugs are all administered by injection, and the drug delivery efficiency is relatively low.

From our previous research, there are hundreds of single lipids in the herbal decoctosome. In the further experiments of the present application, it was found that sphingosine lipids had better efficiency in the delivery process. Therefore, a series of sphingosine lipids and related derivatives had been artificially synthesized to specifically explore the delivery effect of sphingosine lipids. It was concluded that sphingosines and derivative lipids thereof could effectively deliver small RNAs.

SUMMARY OF INVENTION

The present application is partly based on the inventors' discovery of a series of single sphingosine lipid. It was found that single sphingosine can be used as a carrier to efficiently deliver small RNA into cells.

The present application discovered that single sphingosine lipids can efficiently deliver small RNAs as drugs into cells without any toxicity to the body and significantly improve the delivery efficiency and medicinal value of nucleic acid drugs.

The sphingosine lipids and its single derivative can effectively deliver sRNA into cells. Functional small RNA with fluorescent FAM label (sRNA-PGY6) was used as a marker to detect the fluorescence shift after delivery to cells. Compared with free uptake, the experimental group of sphingosine lipid and its single derivative delivering small RNA had significant fluorescence shift, indicating that bencaosome formed by the sphingosine lipid and its single derivative can more effectively deliver small RNAs into cells to perform corresponding functions.

The present application provides the following contents:
1. Use or method for delivering a nucleic acid to a cell or a subject using a compound of Formula (I), a stereoisomer or a pharmaceutical acceptable salt thereof, or a combination comprising a compound of Formula (I), a stereoisomer or a pharmaceutical acceptable salt thereof,

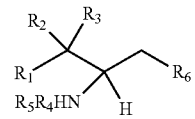

I wherein:
R1 is selected from $C_{1-20}$ alkyl or $C_{2-20}$ alkenyl, which is optionally substituted by one to three hydroxyl groups;
R2 is hydrogen and R3 is hydroxyl; or
R2 and R3 together form oxo (=O);
R4 and R5 are independently selected from the group consisting of hydrogen, $C_{1-20}$ alkyl, $C_{1-30}$ alkylacyl and $C_{1-30}$ alkenylacyl, said $C_{1-30}$ alkylacyl and $C_{1-30}$ alkenylacyl are optionally substituted by one to three groups selected from biotin acyl or hydroxyl;
or —NR4R5 group is a quaternary ammonium cation;
R6 is selected from the group consisting of hydrogen, hydroxyl, phosphate ester group, —O-glycosyl, Ganglioside, and aminoethoxyphosphonate ester group ($NH_2$—$CH_2$—$CH_2$—O—P(O)OH—).
2. The use or method of item 1, wherein:
R1 is selected from $C_{14-20}$ alkyl or $C_{14-20}$ alkenyl containing one double bond;
R4 and R5 are independently selected from the group consisting of hydrogen, $C_{1-6}$ alkyl, $C_{6-30}$ alkylacyl and $C_{6-30}$ alkenylacyl, said $C_{6-30}$ alkylacyl and the $C_{6-30}$ alkenylacyl are optionally substituted at the terminal by one group selected from biotin acyl or hydroxyl, or optionally substituted at the α-carbon of the acyl by a hydroxyl.
3. The use or method of item 1 or 2, wherein R4 and R5 are independently selected from methyl.
4. The use or method of item 1 or 2, wherein at least one of R4 and R5 is hydrogen and the other is straight-chain $C_{6-30}$ alkylacyl or straight-chain $C_{6-30}$ alkenylacyl.
5. The use or method of any one of items 1-4, wherein at least one of R4 and R5 is hydrogen and the other is a straight-chain $C_{7-14}$ alkyl; or both R4 and R5 are $C_{1-6}$ alkyl.

6. The use or method of any one of items 1-5, wherein R1 is selected from a straight-chain $C_{14-20}$ alkyl or a straight-chain $C_{14-20}$ alkenyl containing one double bond.
7. The use or method of any one of items 1-6, wherein the glycosyl is glucosyl, lactosyl, or galactosyl.
8. The use or method of any one of items 1-7, wherein the —NR4R5 group is —$NH_3^+$ or $N(CH_3)_3^+$.
9. The use or method of any one of items 1-8, wherein the glycosyl is 113-D-glucosyl;
R2 is hydrogen, and R3 is hydroxyl;
R1 is selected from $C_{14-20}$ alkenyl containing one double bond, and the alkenyl is immediately adjacent to the carbon atom to which R2 and R3 are attached.
10. The use or method of any one of the preceding items, wherein the compound has the following Formula (Ia):

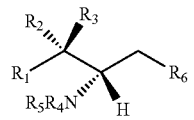

11. Use or method of delivering a nucleic acid to a cell or a subject using a compound selected from the following group, a stereoisomer or a pharmaceutically acceptable salt thereof, or a combination comprising the compound, a stereoisomer or a pharmaceutically acceptable salt thereof:

| No. | Structure |
|---|---|
| So-1 | 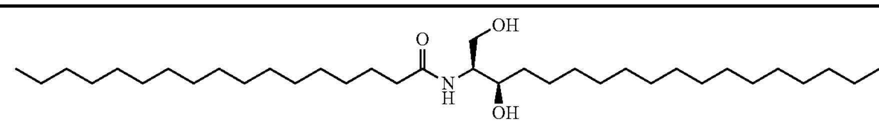 |
| So-2 | 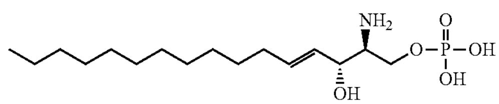 [SMILES: CCCCCCCCCCC/C=C/[C@@H](O)[C@@H](N)COP(=O)(O)O] |
| So-3 | 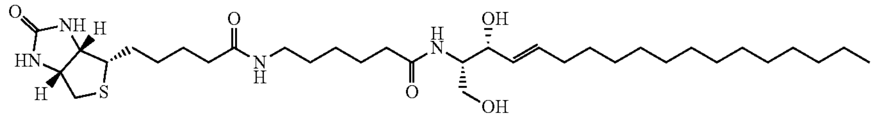 [SMILES: CCCCCCCCCCCCC/C=C/[C@@H](O)[C@H](CO)NC(=O)CCCCCNC(=O)CCCC[C@@H]1SC[C@@H]2NC(=O)N[C@@H]21] |
| So-4 | 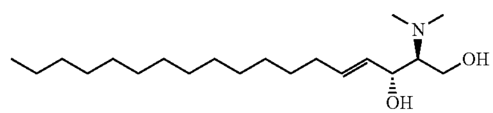 [SMILES: CCCCCCCCCCCCC/C=C/[C@@H](O)[C@H](CO)N(C)C] |
| So-5 | 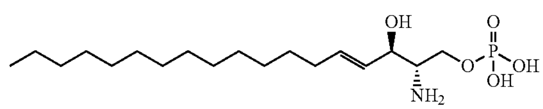 |
| So-6 | 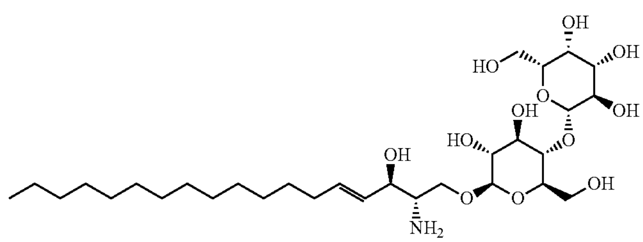 [SMILES: CCCCCCCCCCCCC/C=C/[C@@H](O)[C@@H](N)CO[C@@H]1O[C@H](CO)[C@@H](O[C@@H]2O[C@H](CO)[C@H](O)[C@H](O)[C@H]2O)[C@H](O)[C@H]1O] |
| So-7 | 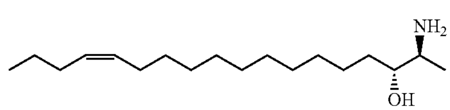 [SMILES: CCC/C=C\CCCCCCCCCC[C@@H](O)[C@H](C)N] |
| So-8 | 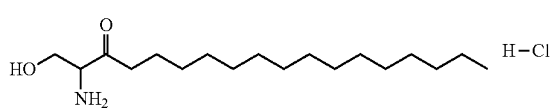 |
| So-9 | 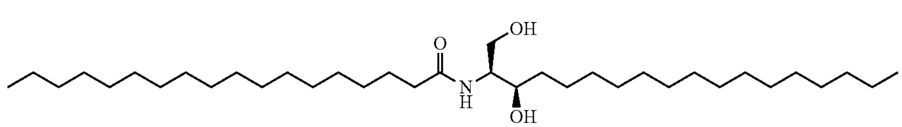 [SMILES: CCCCCCCCCCCCCCCCCC(=O)N[C@@H](CO)[C@H](O)CCCCCCCCCCCCCCC] |

-continued

| No. | Structure |
|---|---|
| So-10 | 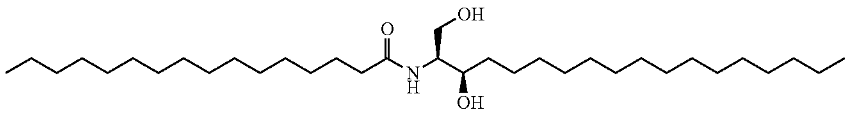 |
| So-11 | 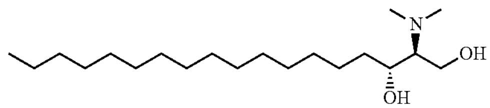 [SMILES: CCCCCCCCCCCCCCC[C@@H](O)[C@H](CO)N(C)C] |
| So-12 | 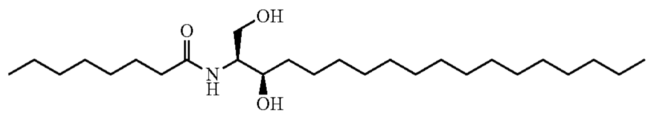 [SMILES: CCCCCCCCCCCCCCC[C@@H](O)[C@H](CO)NC(=O)CCCCCCC] |
| So-13 | 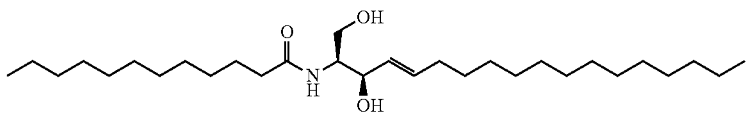 [SMILES: CCCCCCCCCCCCC/C=C/[C@@H](O)[C@H](CO)NC(=O)CCCCCCCCCCC] |
| So-14 | 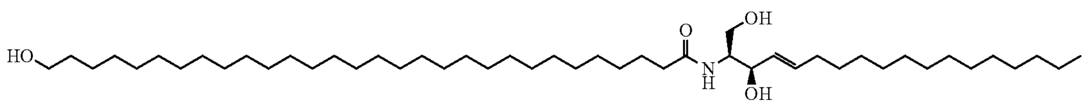 [SMILES: CCCCCCCCCCCCC/C=C/[C@@H](O)[C@H](CO)NC(=O)CCCCCCCCCCCCCCCCCCCCCCCCCCCCCO] |
| So-15 | 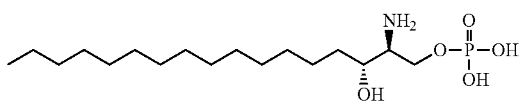 [SMILES: CCCCCCCCCCCCCC[C@@H](O)[C@@H](N)COP(=O)(O)O] |
| So-16 | 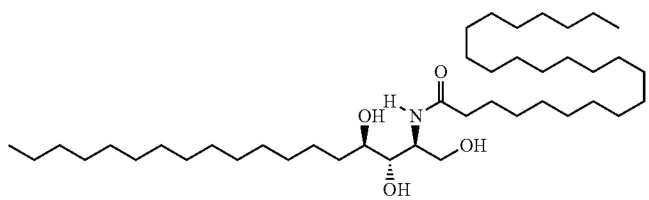 [SMILES: CCCCCCCCCCCCCCCCCCCCCCCC(=O)N[C@@H](CO)[C@H](O)[C@H](O)CCCCCCCCCCCCCC] |
| So-17 | 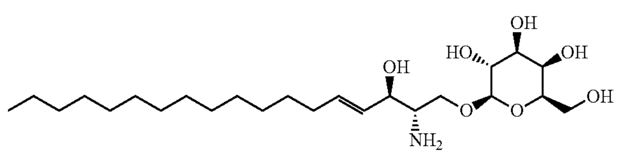 [SMILES: CCCCCCCCCCCCC/C=C/[C@@H](O)[C@@H](N)CO[C@@H]1O[C@H](CO)[C@H](O)[C@H](O)[C@H]1O] |
| So-18 | 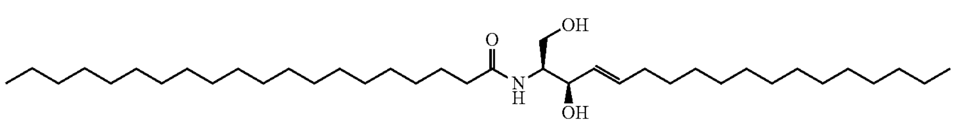 [SMILES: CCCCCCCCCCCCC/C=C/[C@@H](O)[C@H](CO)NC(=O)CCCCCCCCCCCCCCCCCCC] |
| So-19 | 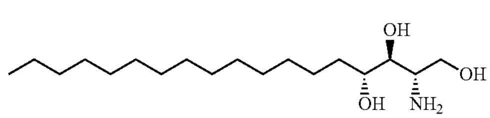 [SMILES: CCCCCCCCCCCCCC[C@@H](O)[C@@H](O)[C@@H](N)CO] |
| So-20 | 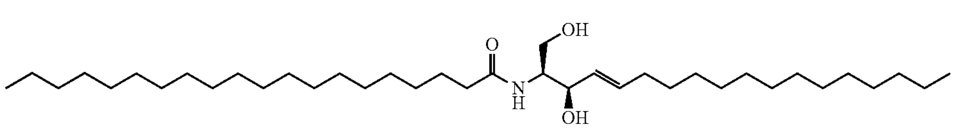 [SMILES: CCCCCCCCCCCCC/C=C/[C@@H](O)[C@H](CO)NC(=O)CCCCCCCCCCCCCCCCCCC] |
| So-21 | 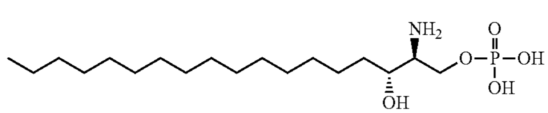 [SMILES: CCCCCCCCCCCCCCC[C@@H](O)[C@@H](N)COP(=O)(O)O] |

-continued
| No. | Structure |
|---|---|
| So-23 | 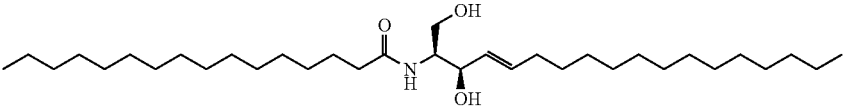 [SMILES: CCCCCCCCCCCCC/C=C/[C@@H](O)[C@H](CO)NC(=O)CCCCCCCCCCCCCCC] |
| So-25 | 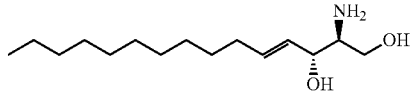 [SMILES: CCCCCCCCCC/C=C/[C@@H](O)[C@@H](N)CO] |
| So-26 | 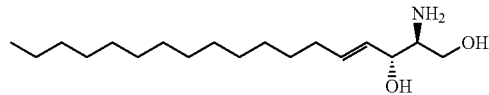 [SMILES: CCCCCCCCCCCCC/C=C/[C@@H](O)[C@@H](N)CO] |
| So-27 | 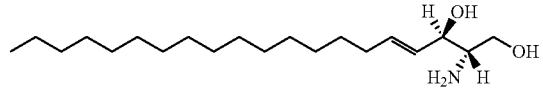 [SMILES: CCCCCCCCCCCCCCC/C=C/[C@@H](O)[C@@H](N)CO] |
| So-29 | 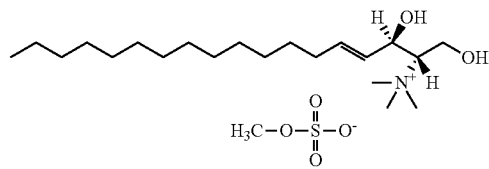 |
| So-30 | 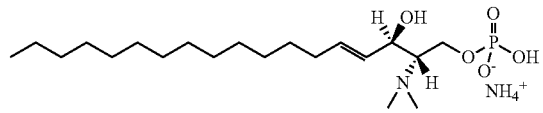 [SMILES: CCCCCCCCCCCCC/C=C/[C@@H](O)[C@H](COP(=O)([O-])O)N(C)C ; [NH4+]] |
| So-31 | 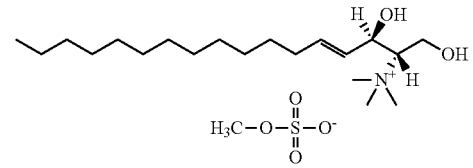 |
| So-32 | 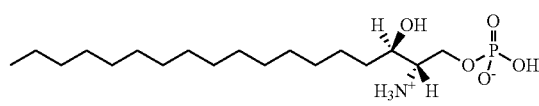 |
| So-33 | 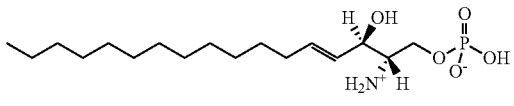 |
| So-34 | 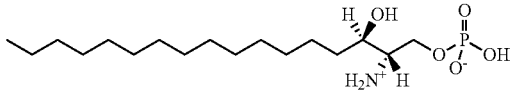 |
| So-35 | 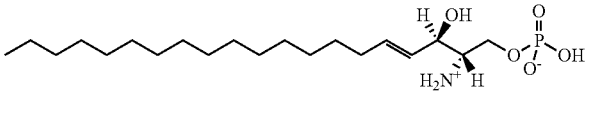 |
| So-36 | 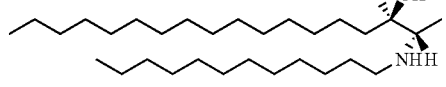 |
| So-37 | L-threo- 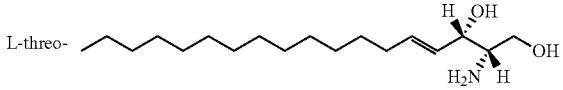 |

| No. | Structure |
|---|---|
| So-38 | (structure) |
| So-40 | (structure) |
| So-41 | (structure) |
| So-42 | (structure) |
| So-43 | (structure) |
| So-44 | (structure) |
| So-45 | (structure) |
| So-46 | (structure) |
| So-47 | (structure) |
| So-48 | (structure) |
| So-49 | (structure) |

-continued
| No. | Structure |
|---|---|
| So-50 | 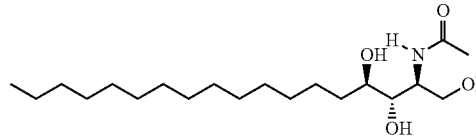 |
| So-51 | 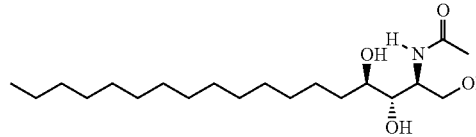 |
| So-52 | 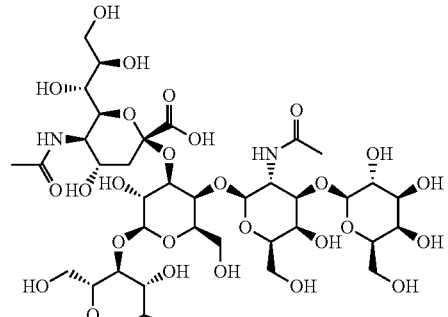 |
| So-53 | 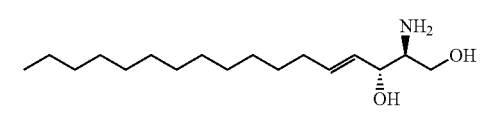 [SMILES: CCCCCCCCCCCC/C=C/[C@@H](O)[C@@H](N)CO] |
| So-54 | 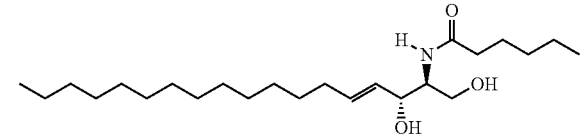 [SMILES: CCCCCCCCCCCCC/C=C/[C@@H](O)[C@H](CO)NC(=O)CCCCC] |
| So-55 | 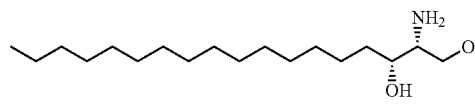 |
| So-56 | 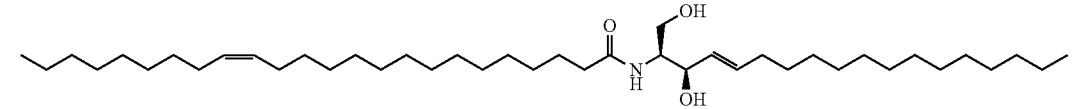 [SMILES: CCCCCCCC/C=C\CCCCCCCCCCCCCC(=O)N[C@@H](CO)[C@H](O)/C=C/CCCCCCCCCCCCC] |
| So-57 | 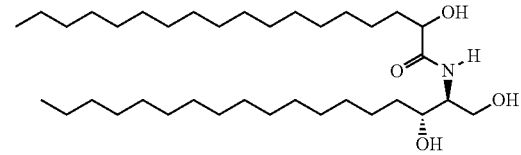 [SMILES: CCCCCCCCCCCCCCCCC(O)C(=O)N[C@@H](CO)[C@H](O)CCCCCCCCCCCCCCC] |
| So-58 | 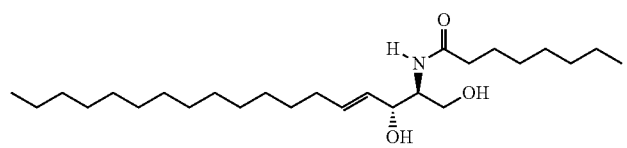 [SMILES: CCCCCCCCCCCCC/C=C/[C@@H](O)[C@H](CO)NC(=O)CCCCCCC] |

-continued

| No. | Structure |
|---|---|
| So-59 | *(chemical structure)* |
| So-60 | *(chemical structure)* |
| So-61 | *(chemical structure)* |
| So-62 | *(chemical structure)* |
| So-63 | *(chemical structure)* |
| So-64 | *(chemical structure)* |
| So-65 | *(chemical structure)* |
| So-66 | *(chemical structure)* |
| So-67 | *(chemical structure)* |
| So-68 | *(chemical structure)* |

| No. | Structure |
|---|---|
| So-69 | 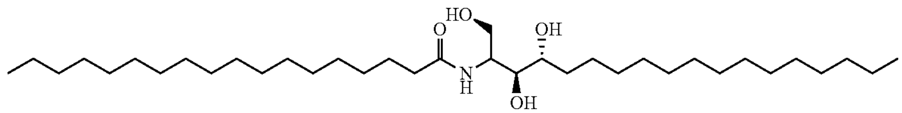 |
| So-70 | 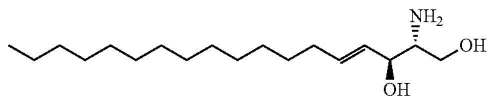 [SMILES: CCCCCCCCCCCCC/C=C/[C@H](O)[C@H](N)CO] |
| So-71 | 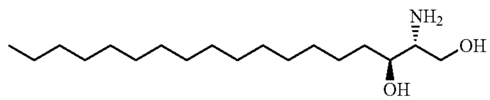 [SMILES: CCCCCCCCCCCCCCC[C@H](O)[C@H](N)CO] |
| So-72 | 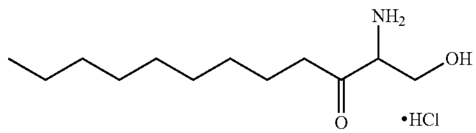 |
| So-73 | 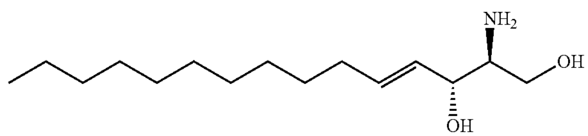 [SMILES: CCCCCCCCCC/C=C/[C@@H](O)[C@@H](N)CO] |
| So-74 | 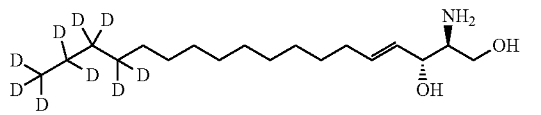 [SMILES: [2H]C([2H])([2H])C([2H])([2H])C([2H])([2H])C([2H])([2H])CCCCCCCCC/C=C/[C@@H](O)[C@@H](N)CO] |
| So-75 | 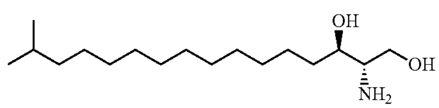 [SMILES: CC(C)CCCCCCCCCCC[C@@H](O)[C@@H](N)CO] |
| No. 41 | 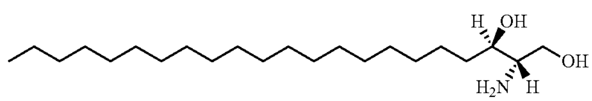 [SMILES: CCCCCCCCCCCCCCCCCCC[C@@H](O)[C@@H](N)CO] |
| No. 38 | 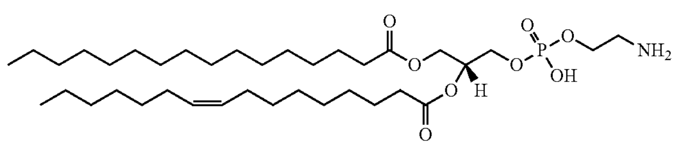 [SMILES: CCCCCC/C=C\CCCCCCCC(=O)O[C@H](COC(=O)CCCCCCCCCCCCCCC)COP(=O)(O)OCCN] |
| No. 48 | 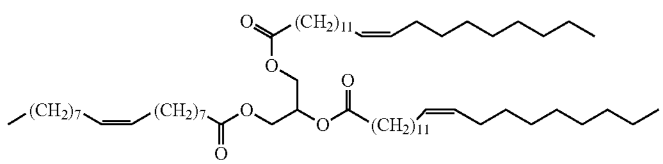 |

12. The use or method of any one of the preceding items, wherein the combination is a combination comprising any one or more of No. 41, No. 38, No. 48, a combination comprising any one or more of No. 41, No. 38, No. 48 and any one or more of the compound selecting from item 11, a combination comprising the following: No. 41+No. 38+sphingosine derivative So-1; No. 41+No. 38+sphingosine derivative So-2; No. 41+No. 38+sphingosine derivative So-3; No. 41+No. 38+sphingosine derivative So-4; No. 41+No. 38+sphingosine derivative So-5; No. 41+No. 38+sphingosine derivative So-6; No. 41+No. 38+sphingosine derivative So-7; No. 41+No. 38+sphingosine derivative So-8; No. 41+No. 38+sphingosine derivative So-9; No. 41+No. 38+sphingosine derivative So-10; No. 41+No. 38+sphingosine derivative So-11; No. 41+No. 38+sphingosine derivative So-12; No. 41+No. 38+sphingosine derivative So-13; No. 41+No. 38+sphingosine derivative So-14; No. 41+No. 38+sphingosine derivative So-15; No. 41+No. 38+sphingosine derivative So-45; No. 41+No.

38+sphingosine derivative So-46; No. 41+No.
38+sphingosine derivative So-47; No. 41+No.
38+sphingosine derivative So-48; No. 41+No.
38+sphingosine derivative So-49; No. 41+No.
38+sphingosine derivative So-50; No. 41+No.
38+sphingosine derivative So-51; No. 41+No.
38+sphingosine derivative So-52; No. 41+No.
38+sphingosine derivative So-53; No. 41+No.
38+sphingosine derivative So-54; No. 41+No.
38+sphingosine derivative So-55; No. 41+No.
38+sphingosine derivative So-56; No. 41+No.
38+sphingosine derivative So-57; No. 41+No.
38+sphingosine derivative So-58; No. 41+No.
38+sphingosine derivative So-59; No. 41+No.
38+sphingosine derivative So-60; No. 41+No.
38+sphingosine derivative So-61; No. 41+No.
38+sphingosine derivative So-62; No. 41+No.
38+sphingosine derivative So-63; No. 41+No.
38+sphingosine derivative So-64; No. 41+No.
38+sphingosine derivative So-65; No. 41+No.
38+sphingosine derivative So-66; No. 41+No.
38+sphingosine derivative So-67; No. 41+No.
38+sphingosine derivative So-68; No. 41+No.
38+sphingosine derivative So-69; No. 41+No.
38+sphingosine derivative So-70; No. 41+No.
38+sphingosine derivative So-71; No. 41+No.
38+sphingosine derivative So-72; No. 41+No.
38+sphingosine derivative So-73; No. 41+No.
38+sphingosine derivative So-74; No. 41+No.
38+sphingosine derivative So-75; No. 41+No. 38+No.
48+sphingosine derivative So-42; No. 41+No. 38+No.
48+sphingosine derivative So-43;
No. 41+No. 38+No. 48+sphingosine derivative So-44;
No. 41+No. 38+No. 48+sphingosine derivative So-45;
No. 41+No. 38+No. 48+sphingosine derivative So-46;
No. 41+No. 38+No. 48+sphingosine derivative So-47;
No. 41+No. 38+No. 48+sphingosine derivative So-52;
No. 41+No. 38+No. 48+sphingosine derivative So-56;
No. 41+No. 38+No. 48+sphingosine derivative So-57;
No. 41+No. 38+No. 48+sphingosine derivative So-58;
No. 41+No. 38+No. 48+sphingosine derivative So-59;
No. 41+No. 38+No. 48+sphingosine derivative So-60;
No. 41+No. 38+No. 48+sphingosine derivative So-61;
No. 41+No. 38+No. 48+sphingosine derivative So-62;
No. 41+No. 38+No. 48+sphingosine derivative So-63;
No. 41+No. 38+No. 48+sphingosine derivative So-64;
No. 41+No. 38+No. 48+sphingosine derivative So-67;
No. 41+No. 38+No. 48+sphingosine derivative So-68;
No. 41+No. 38+No. 48+sphingosine derivative So-69;
No. 41+No. 38+No. 48+sphingosine derivative So-70; No. 41+No. 38+any one or more of sphingosine derivative So-23, 25, 26, 27, 29, 30, 31, 32, 33, 34, 35, 36, 37, 38, 40, 41, 42, 43, 44, 70, 71 or 73; preferably, the compounds above are used at concentrations as shown in Table 1; preferably, the ratio of the compounds above is 0.1-10:0.1-10, 0.2-9:0.2-9, 0.3-8:0.3-8, 0.4-7:0.4-7, 0.5-6:0.5-6, 0.6-5:0.6-5, 0.7-4:0.7-4, 0.8-3:0.8-3, 0.9-2:0.9-2; more preferably 1:1.

13. The use or method of any one of the preceding items, wherein the nucleic acid is synthetic or purified, therapeutic or non-therapeutic, and/or diagnostic or non-diagnostic, for example selected from RNA or DNA, for example selected from single-stranded or double-stranded or partially double-stranded RNA or DNA; preferably, when the nucleic acid is therapeutic or diagnostic, the nucleic acid is used to treat or diagnose a disease selected from the group consisting of: inflammatory diseases, pneumonia, myocarditis, acute and chronic gastritis, acute and chronic enteritis, acute and chronic hepatitis, acute and chronic nephritis, dermatitis, encephalitis, lymphitis, conjunctivitis, keratitis, iridocyclitis, otitis media, allergic rhinitis, asthma, pulmonary fibrosis, chronic obstructive pulmonary disease, allergic dermatitis, sickle cell disease, multiple sclerosis, systemic lupus erythematosus, lupus nephritis, lung cancer, gastric cancer, colorectal cancer, liver cancer, pancreatic cancer, cervical cancer, breast cancer, leukemia, multiple myeloma, diabetes, and gout.

14. The use or method of item 13, wherein the RNA is selected from the group consisting of messenger RNA (mRNA), rRNA (ribosomal RNA), tRNA (transfer RNA), heterogeneous nuclear RNA (hnRNA), small nuclear RNA (snRNA), small nucleolar RNA (snoRNA), small cytoplasmic RNA, small RNA, transfer-messenger RNA (tmRNA), telomerase RNA and antisense RNA, preferably small RNA.

15. The use or method of item 14, wherein the length of the small RNA is 14-32 bp, 16-28 bp, or 18-24 bp.

16. The use or method of item 15, wherein the small RNA comprises the sequence of GTTCAGAGTTCTACAGTCCGA (SEQ ID NO: 1).

17. The use or method of any one of the preceding items, wherein the delivery comprises treating the compound, a stereoisomer or a pharmaceutically acceptable salt or a combination comprising the compound of Formula (I), a stereoisomer or a pharmaceutically acceptable salt thereof or combination thereof, by heating method, reverse evaporation method, direct mixing, repeated freeze-thaw and/or thin film dispersion.

18. The use or method of item 17, wherein the heating method is conducted at a temperature of about 0° C. to about 100° C., about 25° C. to about 100° C., preferably about 80° C. to about 100° C., for example 4° C., 37° C., 60° C., 80° C. or 100° C.; the reverse evaporation method is conducted at a temperature of about 25° C. to about 70° C., preferably about 55° C. for a heating time of about 0 minutes to about 24 hours, about minutes to about 20 hours, about 5 minutes to about 16 hours, about 5 minutes to about 10 hours, about 5 minutes to about 4 hours, or about 10 hours to about 1 hour, preferably 15 minutes.

19. The use of item 17, wherein the delivery comprises in vitro cell delivery or in vivo subject delivery.

20. The use or method of item 19, wherein the in vivo subject delivery comprises oral administration, intravenous administration such as injection or infusion, subcutaneous administration, intramuscular administration, intraarterial administration, intraperitoneal administration, intrapulmonary administration, intracerebral and intraspinal administration, intra-articular administration, intrasynovial administration, intrathecal administration, intra-trauma administration, and/or administration via inhalation paths such as intranasal, typically intravenous or subcutaneous administration.

21. Use of a compound of Formula (I), a stereoisomer or a pharmaceutically acceptable salt thereof, or a combination comprising a compound of Formula (I), a stereoisomer or a pharmaceutically acceptable salt thereof for the manufacture of a reagent for nucleic acid delivery,

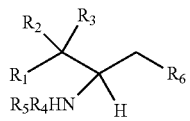

wherein:
R1 is selected from $C_{1-20}$ alkyl or $C_{2-20}$ alkenyl, which is optionally substituted by one to three hydroxyl groups;
R2 is hydrogen and R3 is hydroxyl; or
R2 and R3 together form oxo (=O);
R4 and R5 are independently selected from the group consisting of hydrogen, $C_{1-20}$ alkyl, $C_{1-30}$ alkylacyl and $C_{1-30}$ alkenylacyl, said $C_{1-30}$ alkylacyl and $C_{1-30}$ alkenylacyl are optionally substituted by one to three groups selected from biotin acyl or hydroxyl;
or —NR4R5 group is a quaternary ammonium cation;
R6 is selected from the group consisting of hydrogen, hydroxyl, phosphate ester group, —O-glycosyl, Ganglioside, and aminoethoxyphosphonate ester group ($NH_2$—$CH_2$—$CH_2$—O—P(O)OH—).

22. The use of item 21, wherein:
R1 is selected from $C_{14-20}$ alkyl or $C_{14-20}$ alkenyl containing one double bond;
R4 and R5 are independently selected from the group consisting of hydrogen, $C_{1-6}$ alkyl, $C_{6-30}$ alkylacyl and $C_{6-30}$ alkenylacyl, said $C_{6-30}$ alkylacyl and the $C_{6-30}$ alkenylacyl are optionally substituted at the terminal by one group selected from biotin acyl or hydroxyl, or optionally substituted at the α-carbon of the acyl by one hydroxyl.

23. The use of item 21 or 22, wherein R4 and R5 are independently selected from methyl.

24. The use of item 21 or 22, wherein at least one of R4 and R5 is hydrogen and the other is straight-chain $C_{6-30}$ alkylacyl or straight-chain $C_{6-30}$ alkenylacyl.

25. The use of any one of items 21-24, wherein at least one of R4 and R5 is hydrogen and the other is a straight-chain $C_{7-14}$ alkyl; or both R4 and R5 are $C_{1-6}$ alkyl.

26. The use of any one of items 21-25, wherein R1 is selected from a straight-chain $C_{14-20}$ alkyl or a straight-chain $C_{14-20}$ alkenyl containing one double bond.

27. The use of any one of items 21-26, wherein the glycosyl is glucosyl, lactosyl, or galactosyl.

28. The use of any one of items 21-27, wherein the glycosyl is 1-β-D-glucosyl;
R2 is hydrogen, and R3 is hydroxyl;
R1 is selected from $C_{14-20}$ alkenyl containing one double bond, and the alkenyl is immediately adjacent to the carbon atom to which R2 and R3 are attached.

29. The use of any one of items 21-28, wherein the compound has the following Formula (Ia):

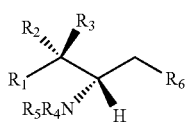

30. The use of any one of items 21-29, wherein the compound of Formula (I) is selected from one or more compounds of item 11.

31. The use of any one of items 21-30, wherein the combination is a combination comprising any one or more of No. 41, No. 38, No. 48, a combination comprising any one or more of No. 41, No. 38, No. 48 and any one or more of the compound selecting from item 7, a combination comprising the following: No. 41+No. 38+sphingosine derivative So-1; No. 41+No. 38+sphingosine derivative So-2; No. 41+No. 38+sphingosine derivative So-3; No. 41+No. 38+sphingosine derivative So-4; No. 41+No. 38+sphingosine derivative So-5; No. 41+No. 38+sphingosine derivative So-6; No. 41+No. 38+sphingosine derivative So-7; No. 41+No. 38+sphingosine derivative So-8; No. 41+No. 38+sphingosine derivative So-9; No. 41+No. 38+sphingosine derivative So-10; No. 41+No. 38+sphingosine derivative So-11; No. 41+No. 38+sphingosine derivative So-12; No. 41+No. 38+sphingosine derivative So-13; No. 41+No. 38+sphingosine derivative So-14; No. 41+No. 38+sphingosine derivative So-15; No. 41+No. 38+sphingosine derivative So-45; No. 41+No. 38+sphingosine derivative So-46; No. 41+No. 38+sphingosine derivative So-47; No. 41+No. 38+sphingosine derivative So-48; No. 41+No. 38+sphingosine derivative So-49; No. 41+No. 38+sphingosine derivative So-50; No. 41+No. 38+sphingosine derivative So-51; No. 41+No. 38+sphingosine derivative So-52; No. 41+No. 38+sphingosine derivative So-53; No. 41+No. 38+sphingosine derivative So-54; No. 41+No. 38+sphingosine derivative So-55; No. 41+No. 38+sphingosine derivative So-56; No. 41+No. 38+sphingosine derivative So-57; No. 41+No. 38+sphingosine derivative So-58;
No. 41+No. 38+sphingosine derivative So-59; No. 41+No. 38+sphingosine derivative So-60; No. 41+No. 38+sphingosine derivative So-61; No. 41+No. 38+sphingosine derivative So-62; No. 41+No. 38+sphingosine derivative So-63; No. 41+No. 38+sphingosine derivative So-64; No. 41+No. 38+sphingosine derivative
So-65; No. 41+No. 38+sphingosine derivative So-66; No. 41+No. 38+sphingosine derivative So-67; No. 41+No. 38+sphingosine derivative So-68;
No. 41+No. 38+sphingosine derivative So-69; No. 41+No. 38+sphingosine derivative So-70; No. 41+No. 38+sphingosine derivative So-71; No. 41+No. 38+sphingosine derivative So-72; No. 41+No. 38+sphingosine derivative So-73;
No. 41+No. 38+sphingosine derivative So-74; No. 41+No. 38+sphingosine derivative So-75; No. 41+No. 48+sphingosine derivative So-42;
No. 41+No. 38+No. 48+sphingosine derivative So-43;
No. 41+No. 38+No. 48+sphingosine derivative So-44;
No. 41+No. 38+No. 48+sphingosine derivative So-45;
No. 41+No. 38+No. 48+sphingosine derivative So-46;
No. 41+No. 38+No. 48+sphingosine derivative So-47;
No. 41+No. 38+No. 48+sphingosine derivative So-52;
No. 41+No. 38+No. 48+sphingosine derivative So-56;
No. 41+No. 38+No. 48+sphingosine derivative So-57;
No. 41+No. 38+No. 48+sphingosine derivative So-58;
No. 41+No. 38+No. 48+sphingosine derivative So-59;
No. 41+No. 38+No. 48+sphingosine derivative So-60;
No. 41+No. 38+No. 48+sphingosine derivative So-61;
No. 41+No. 38+No. 48+sphingosine derivative So-62;
No. 41+No. 38+No. 48+sphingosine derivative So-63;
No. 41+No. 38+No. 48+sphingosine derivative So-64;

No. 41+No. 38+No. 48+sphingosine derivative So-67;
No. 41+No. 38+No. 48+sphingosine derivative So-68;
No. 41+No. 38+No. 48+sphingosine derivative So-69;
No. 41+No. 38+No. 48+sphingosine derivative So-70; No. 41+No. 38+any one or more of sphingosine derivative So-23, 25, 26, 27, 29, 30, 31, 32, 33, 34, 35, 36, 37, 38, 40, 41, 42, 43, 44, 70, 71 or 73; preferably, the compounds above are used at concentrations as shown in Table 1; preferably, the ratio of the compounds above is 0.2-9:0.2-9, 0.3-8:0.3-8, 0.4-7:0.4-7, 0.5-6:0.5-6, 0.6-5:0.6-5, 0.7-4:0.7-4, 0.8-3:0.8-3, 0.9-2:0.9-2; more preferably 1:1.

32. The use of any one of items 21-31, wherein the nucleic acid is synthetic or purified, therapeutic or non-therapeutic, and/or diagnostic or non-diagnostic, for example selected from RNA or DNA, for example selected from single-stranded or double-stranded or partially double-stranded RNA or DNA;

preferably, when the nucleic acid is therapeutic or diagnostic, the nucleic acid is used to treat or diagnose a disease selected from the group consisting of: inflammatory diseases, pneumonia, myocarditis, acute and chronic gastritis, acute and chronic enteritis, acute and chronic hepatitis, acute and chronic nephritis, dermatitis, encephalitis, lymphitis, conjunctivitis, keratitis, iridocyclitis, otitis media, allergic rhinitis, asthma, pulmonary fibrosis, chronic obstructive pulmonary disease, allergic dermatitis, sickle cell disease, multiple sclerosis, systemic lupus erythematosus, lupus nephritis, lung cancer, gastric cancer, colorectal cancer, liver cancer, pancreatic cancer, cervical cancer, breast cancer, leukemia, multiple myeloma, diabetes, and gout.

33. The use of item 32, wherein the RNA is selected from the group consisting of messenger RNA (mRNA), rRNA (ribosomal RNA), tRNA (transfer RNA), heterogeneous nuclear RNA (hnRNA), small nuclear RNA (snRNA), small nucleolar RNA (snoRNA), small cytoplasmic RNA, small RNA, transfer-messenger RNA (tmRNA), telomerase RNA and antisense RNA, preferably small RNA.

34. The use of item 33, wherein the length of the small RNA is 14-32 bp, 16-28 bp, or 18-24 bp.

The use of item 34, wherein the small RNA comprises the sequence of GTTCAGAGTTCTACAGTCCGA (SEQ ID NO: 1).

36. The use of any one of items 21-35, wherein the delivery comprises treating the compound, a stereoisomer or a pharmaceutically acceptable salt or a combination comprising the compound of Formula (I), a stereoisomer or a pharmaceutically acceptable salt thereof or combination thereof with the nucleic acid, by heating method, reverse evaporation method, direct mixing, repeated freeze-thaw and/or thin film dispersion.

37. The use of item 36, wherein the heating method is conducted at a temperature of about 0° C. to about 100° C., about 25° C. to about 100° C., preferably about 80° C. to about 100° C., for example 4° C., 37° C., 60° C., 80° C. or 100° C.; the reverse evaporation method is conducted at a temperature of about 25° C. to about 70° C., preferably about for a heating time of about 0 minutes to about 24 hours, about 5 minutes to about 20 hours, about 5 minutes to about 16 hours, about 5 minutes to about 10 hours, about 5 minutes to about 4 hours, or about 10 hours to about 1 hour, preferably 15 minutes.

38. The use of item 36, wherein the delivery comprises in vitro cell delivery or in vivo subject delivery.

39. The use of item 38, wherein the in vivo subject delivery comprises oral administration, intravenous administration such as injection or infusion, subcutaneous administration, intramuscular administration, intraarterial administration, intraperitoneal administration, intrapulmonary administration, intracerebral and intraspinal administration, intra-articular administration, intrasynovial administration, intrathecal administration, intra-trauma administration, and/or administration via inhalation paths such as intranasal, typically intravenous or subcutaneous administration.

40. A composition or a combination of compounds, comprising the compound of items 1-12, a stereoisomer or a pharmaceutically acceptable salt thereof, or a combination thereof 41. The composition or the combination of compounds of item 40 for use in delivering a nucleic acid to a cell or a subject.

42. The composition or the combination of compounds of item 41, wherein the nucleic acid is synthetic or purified, therapeutic or non-therapeutic, and/or diagnostic or non-diagnostic, for example selected from RNA or DNA, for example selected from single-stranded or double-stranded or partially double-stranded RNA and DNA;

preferably, when the nucleic acid is therapeutic or diagnostic, the nucleic acid is used to treat or diagnose a disease selected from the group consisting of: inflammatory diseases, pneumonia, myocarditis, acute and chronic gastritis, acute and chronic enteritis, acute and chronic hepatitis, acute and chronic nephritis, dermatitis, encephalitis, lymphitis, conjunctivitis, keratitis, iridocyclitis, otitis media, allergic rhinitis, asthma, pulmonary fibrosis chronic obstructive pulmonary disease, allergic dermatitis, sickle cell disease, multiple sclerosis, systemic lupus erythematosus, lupus nephritis, lung cancer, gastric cancer, colorectal cancer, liver cancer, pancreatic cancer, cervical cancer, breast cancer, leukemia, multiple myeloma, diabetes, and gout.

43. The composition or the combination of compounds of item 42, wherein the RNA is selected from the group consisting of messenger RNA (mRNA), rRNA (ribosomal RNA), tRNA (transfer RNA), heterogeneous nuclear RNA (hnRNA), small nuclear RNA (snRNA), small nucleolar RNA (snoRNA), small cytoplasmic RNA, small RNA, transfer-messenger RNA (tmRNA), telomerase RNA and antisense RNA, preferably small RNA.

44. The composition or the combination of compounds of item 43, wherein the length of the small RNA is 14-32 bp, 16-28 bp, or 18-24 bp.

45. The composition or the combination of compounds of item 44, wherein the small RNA comprises the sequence of GTTCAGAGTTCTACAGTCCGA (SEQ ID NO: 1).

46. The composition or the combination of compounds of any one of items 40-45 wherein the delivery comprises treating the compound, a stereoisomer or a pharmaceutically acceptable salt or a combination comprising the compound of Formula (I), a stereoisomer or a pharmaceutically acceptable salt thereof, with nucleic acid by heating method, reverse evaporation method, direct mixing, repeated freeze-thaw and/or thin film dispersion.

47. The composition or the combination of compounds of item 46, wherein the heating method is conducted at a temperature of about 0° C. to about 100° C., about to about 100° C., preferably about 80° C. to about 100° C., for example 4° C., 37° C., 80° C. or 100° C.; the reverse evaporation method is conducted at a temperature of about 25° C. to about 70° C., preferably about 55° C. for a heating time of about 0 minutes to about 24 hours, about 5 minutes to about 20 hours, about 5 minutes to about 16 hours, about 5 minutes to about 10 hours, about 5 minutes to about 4 hours, or about 10 hours to about 1 hour, preferably 15 minutes.

48. The composition or the combination of compounds of item 46, wherein the delivery comprises in vitro cell delivery or in vivo subject delivery.
49. The composition or the combination of compounds of item 48, wherein the in vivo subject delivery comprises oral administration, intravenous administration such as injection or infusion, subcutaneous administration, intramuscular administration, intraarterial administration, intraperitoneal administration, intrapulmonary administration, intracerebral and intraspinal administration, intra-articular administration, intrasynovial administration, intrathecal administration, intra-trauma administration, and/or administration via inhalation paths such as intranasal, typically intravenous or subcutaneous administration.
50. A kit comprising the compound of items 1-12, a stereoisomer or a pharmaceutically acceptable salt thereof or a combination thereof; preferably, the kit is used for any one of the use above.

BRIEF DESCRIPTIONS OF THE DRAWINGS

Figure 34A:
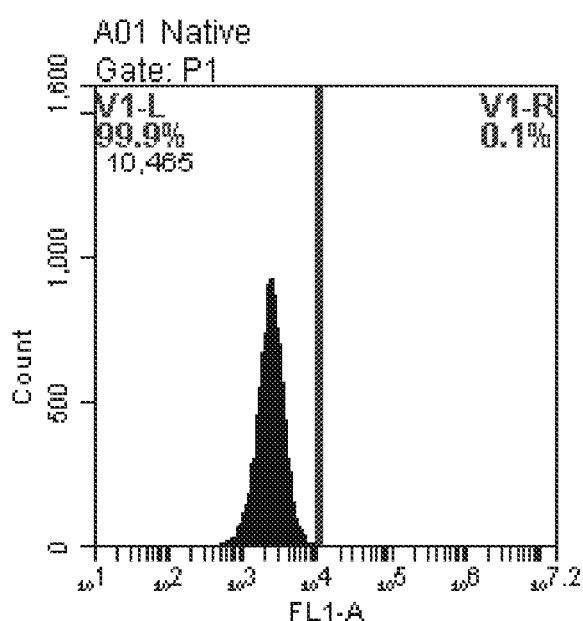
Figure 34B:
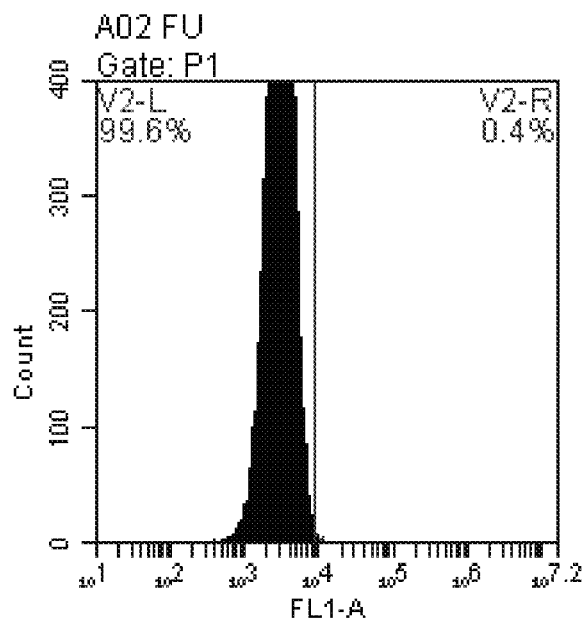
Figure 34C:
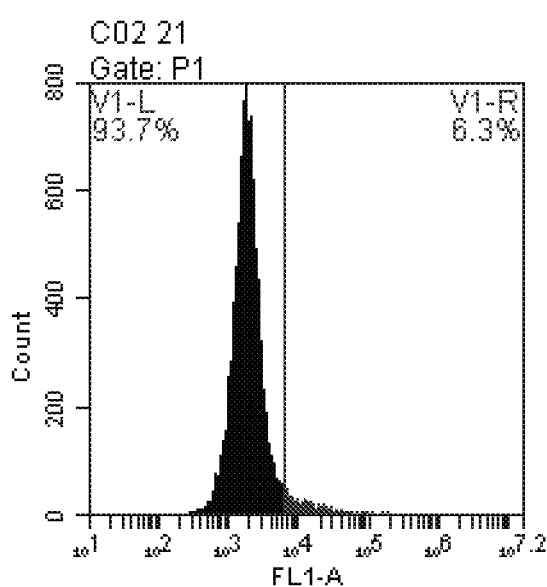
Figure 35A:
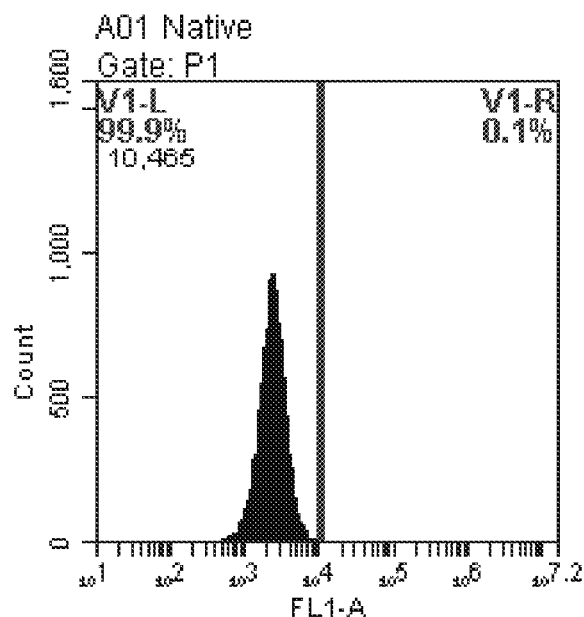
Figure 35B:
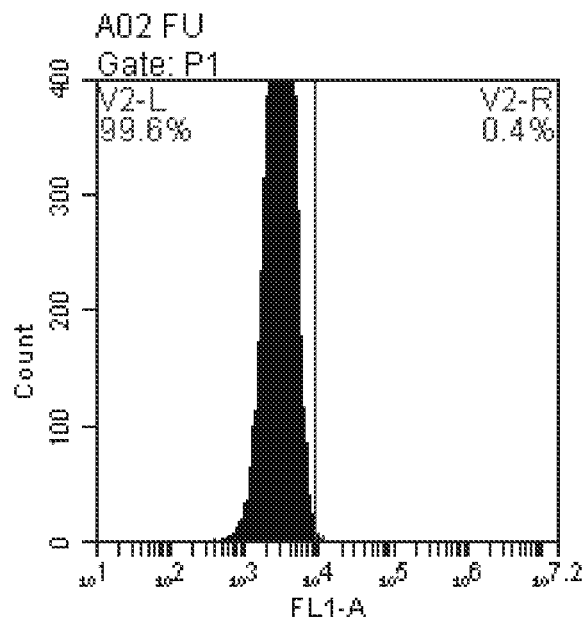
Figure 35C:
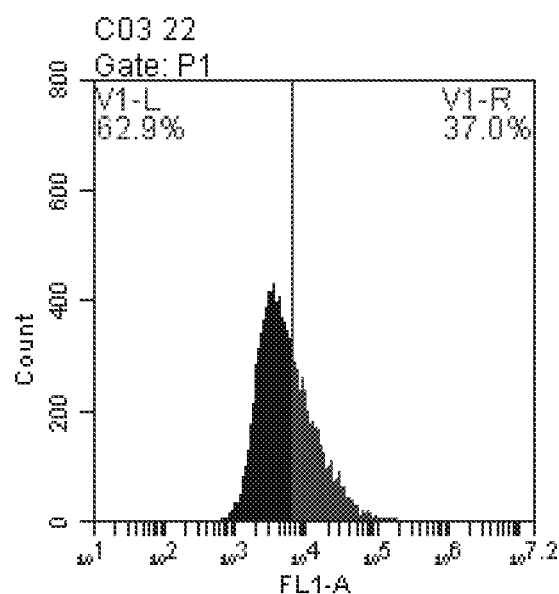
Figure 36A:
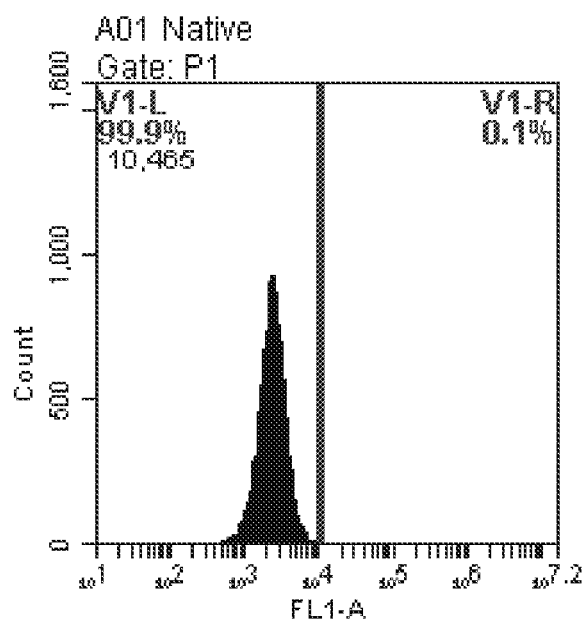
Figure 36B:
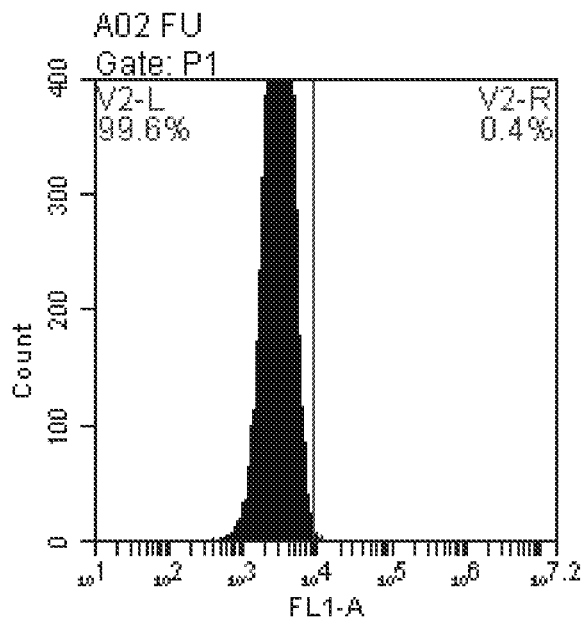
Figure 36C:
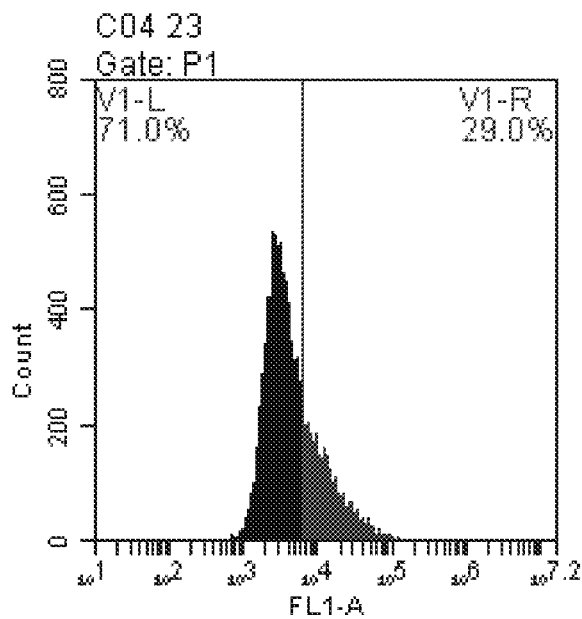
Figure 37A:
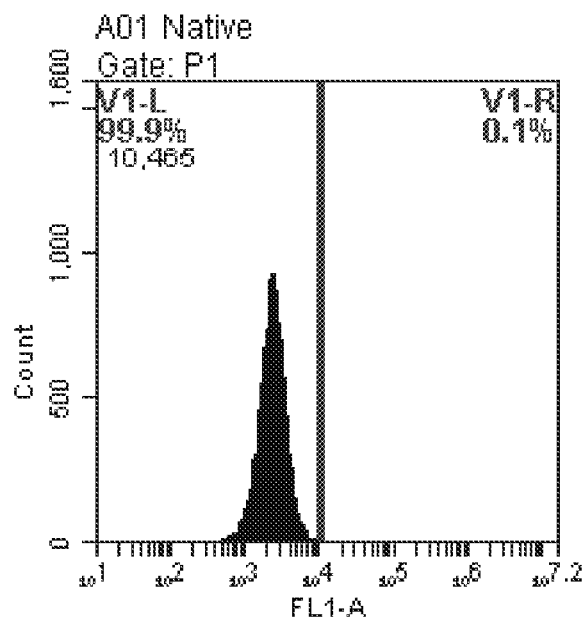
Figure 37B:
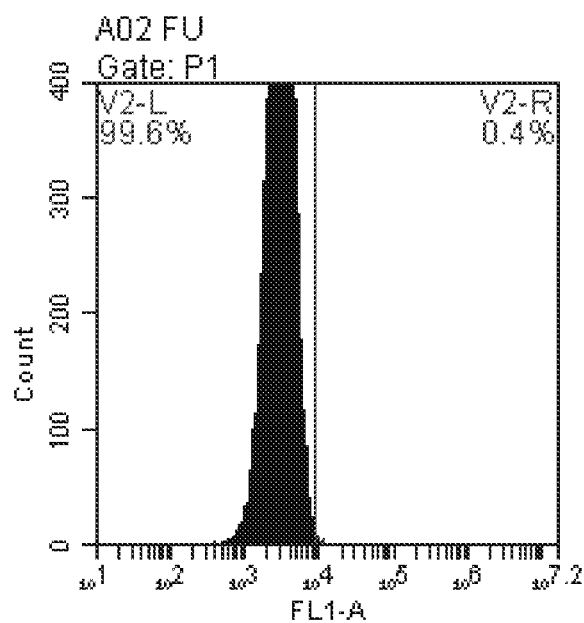
Figure 37C:
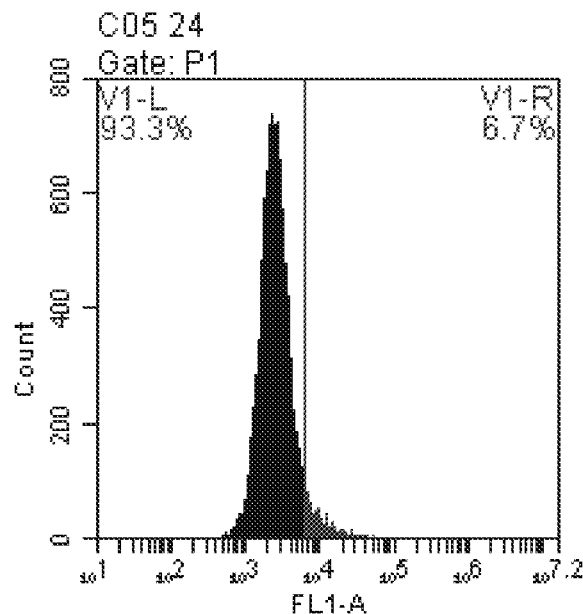
Figure 38A:
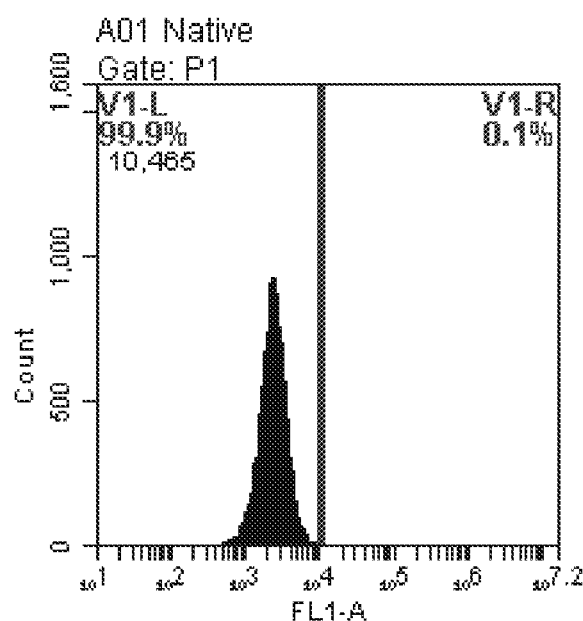
Figure 38B:
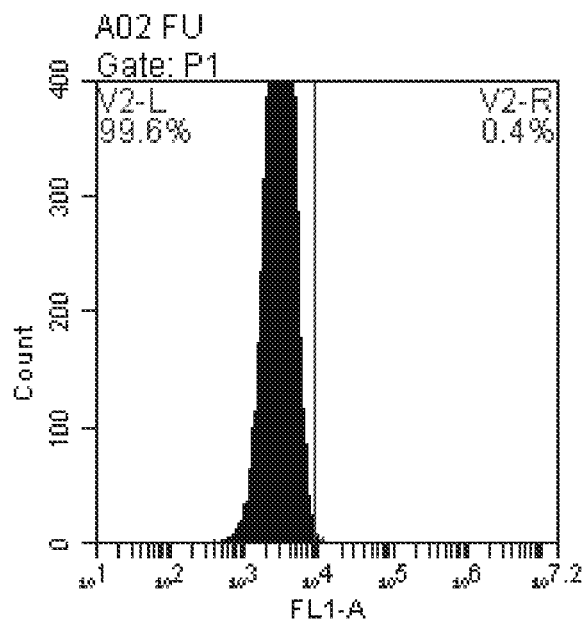
Figure 38C:
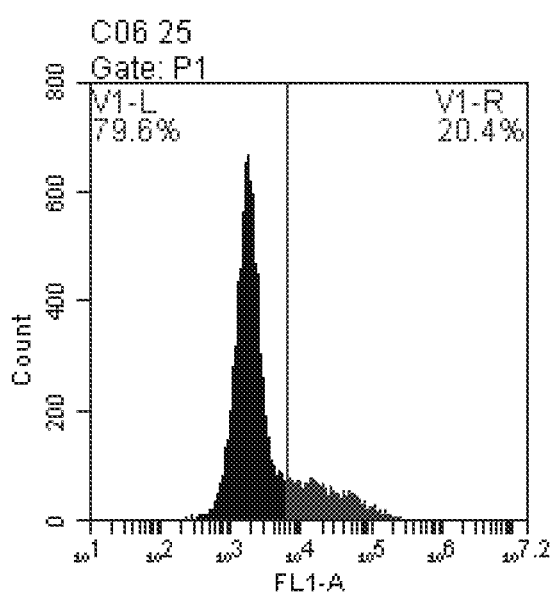
Figure 39A:
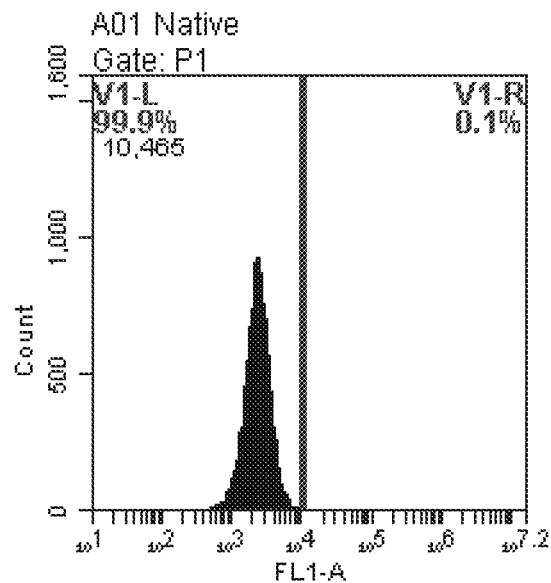
Figure 39B:
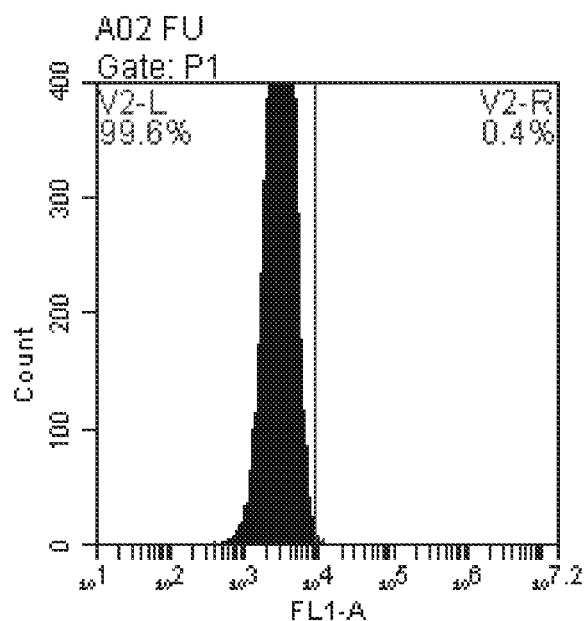
Figure 39C:
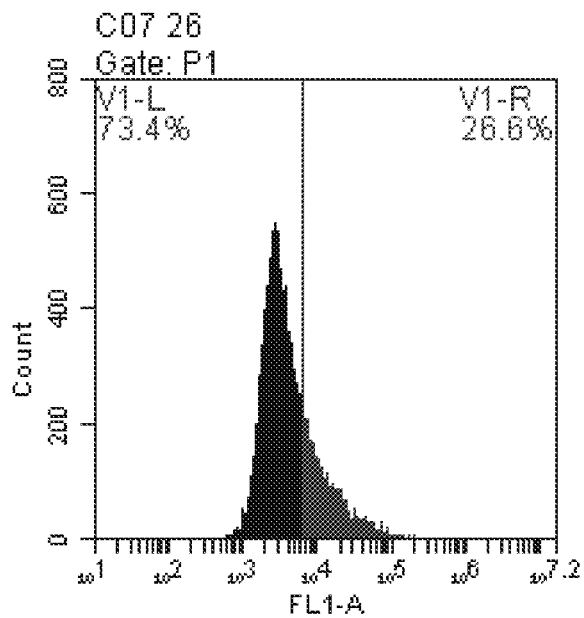
Figure 40A:
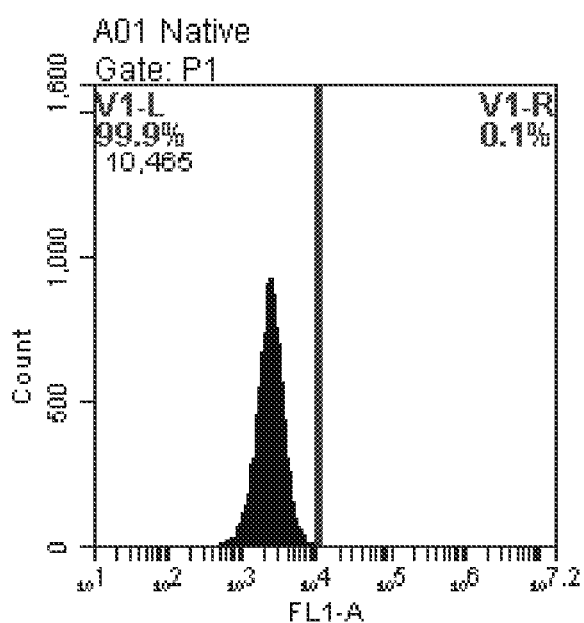
Figure 40B:
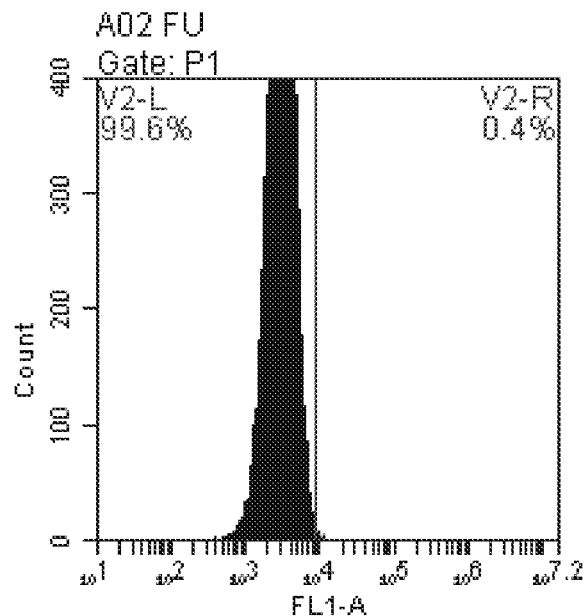
Figure 40C:
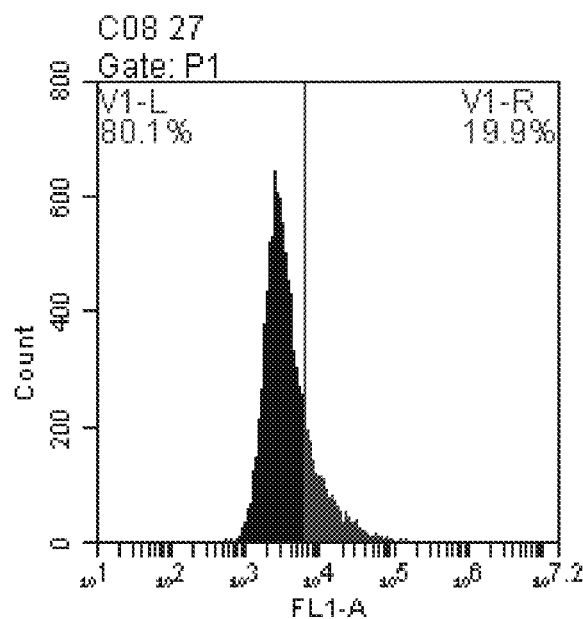
Figure 41A:
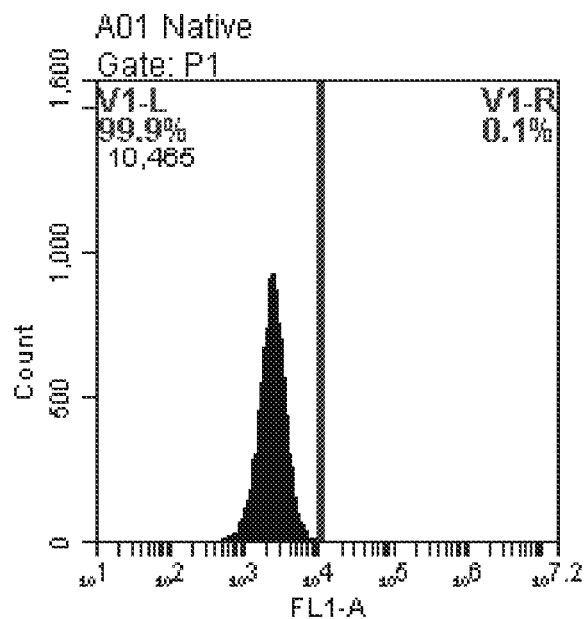
Figure 41B:
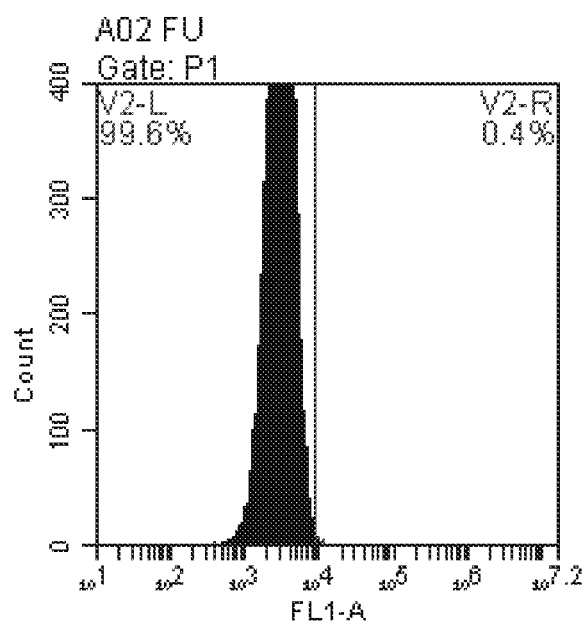
Figure 41C:
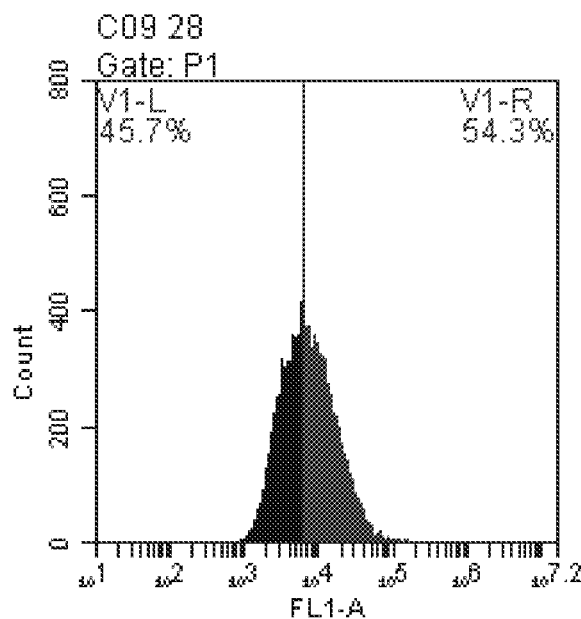
Figure 42A:
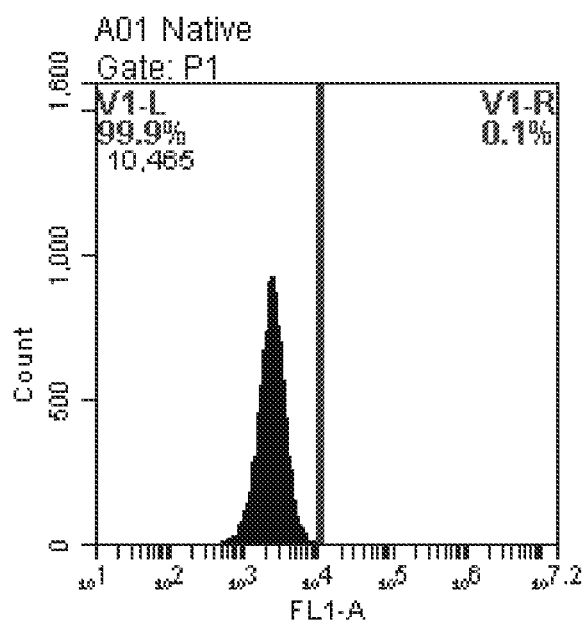
Figure 42B:
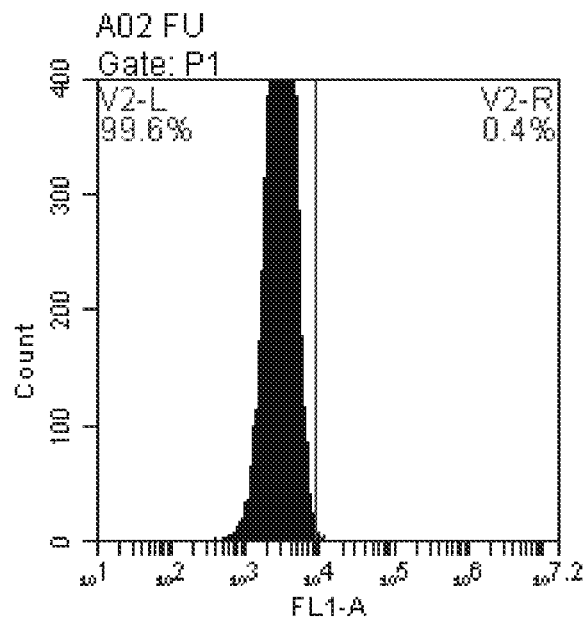
Figure 42C:
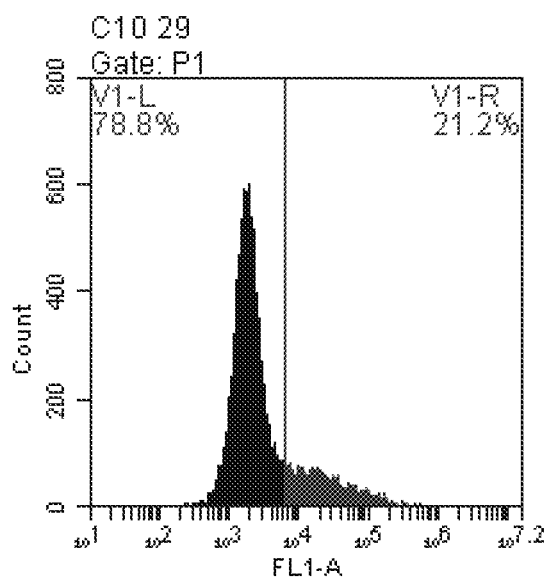
Figure 43A:
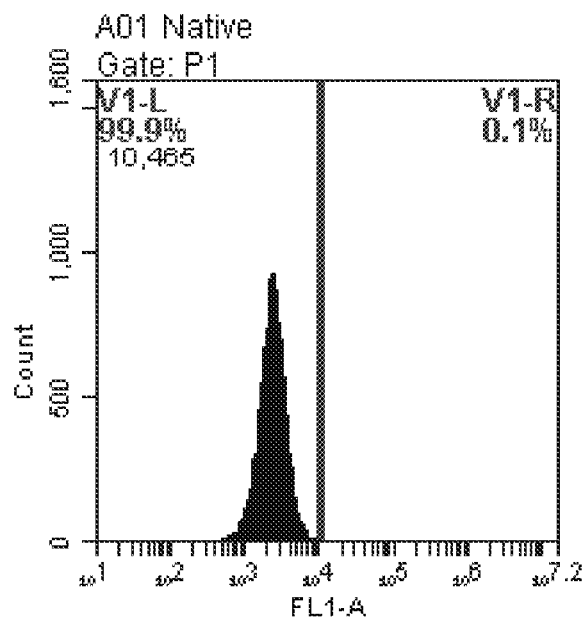
Figure 43B:
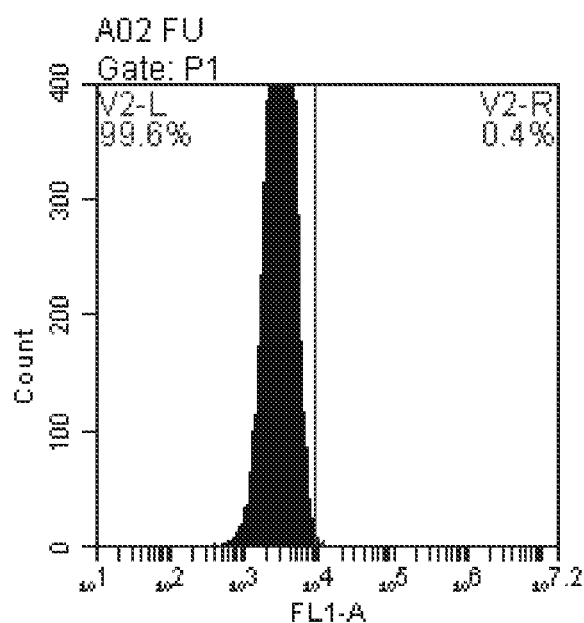
Figure 43C:
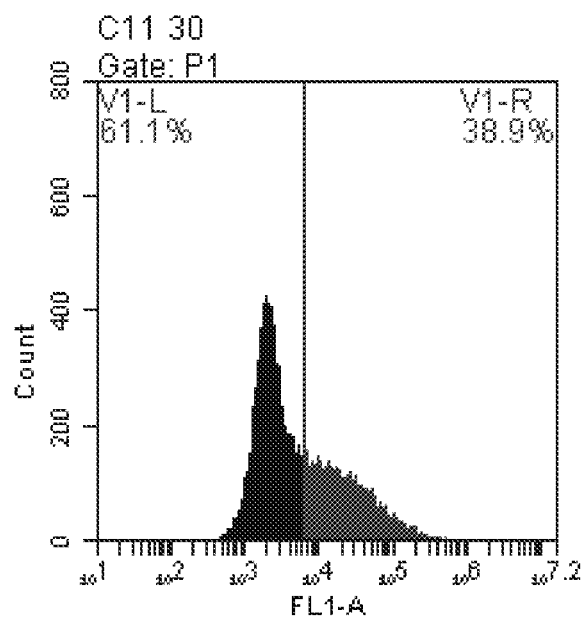
Figure 44A:
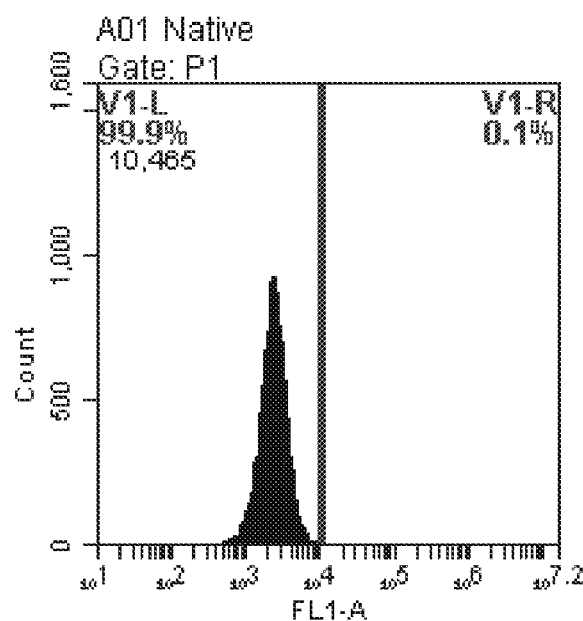
Figure 44B:
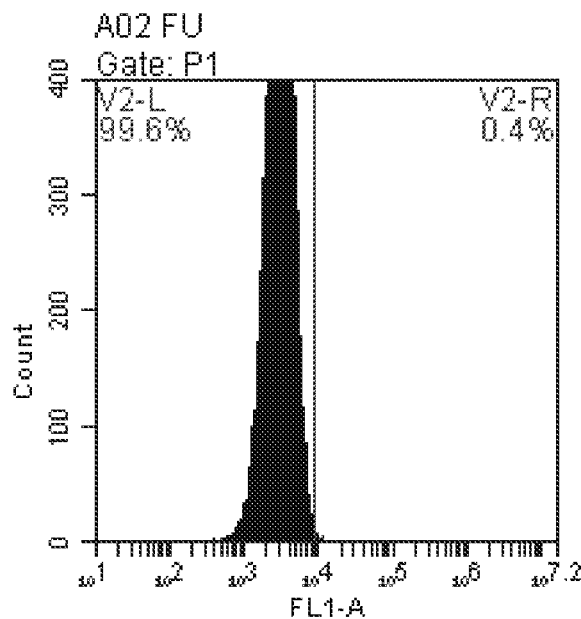
Figure 44C:
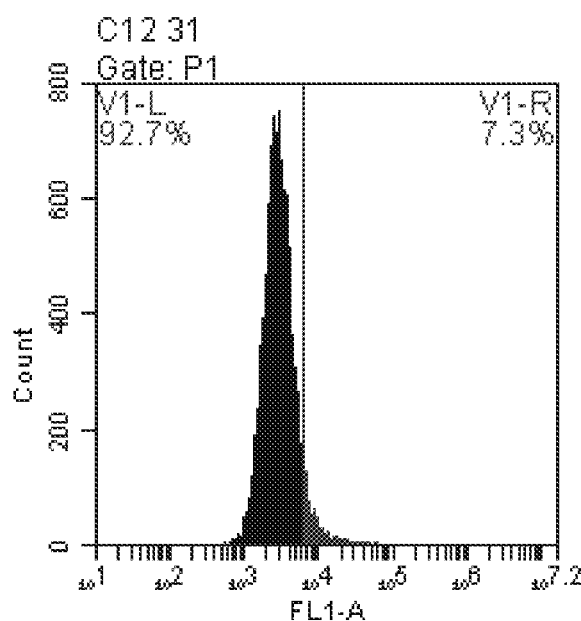
Figure 45A:
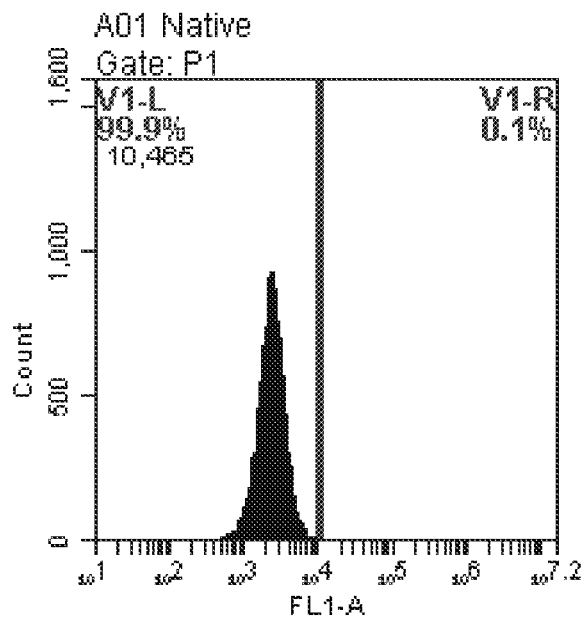
Figure 45B:
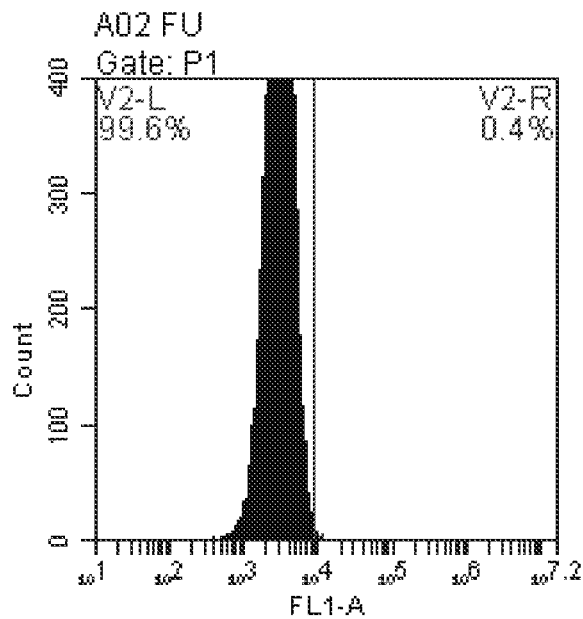
Figure 45C:
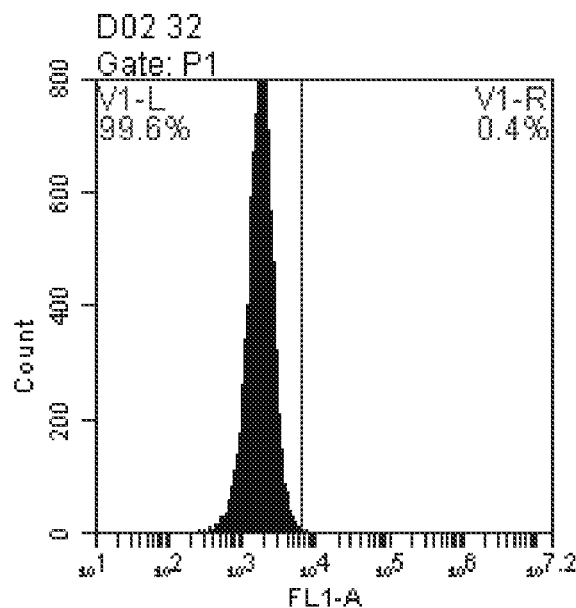
Figure 46A:
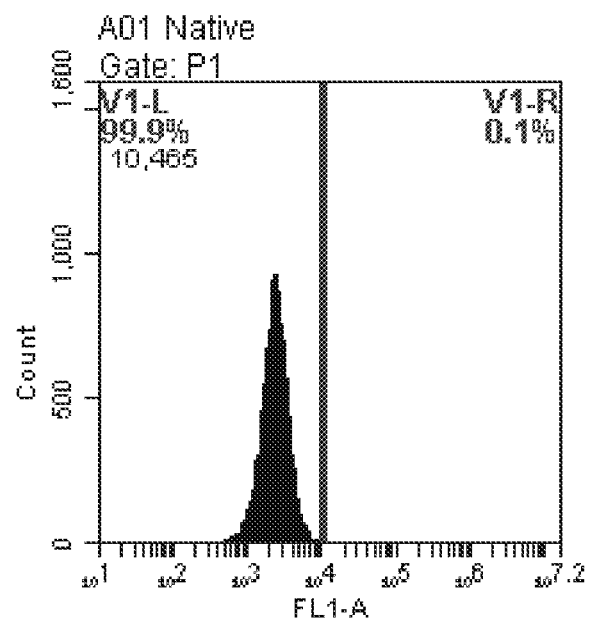
Figure 46B:
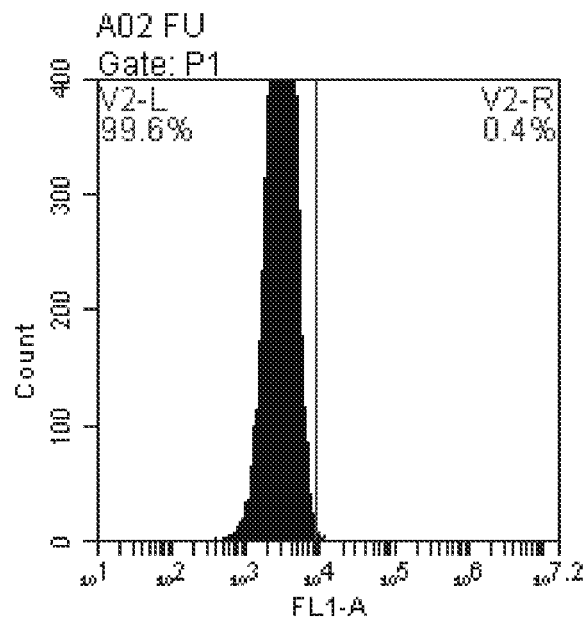
Figure 46C:
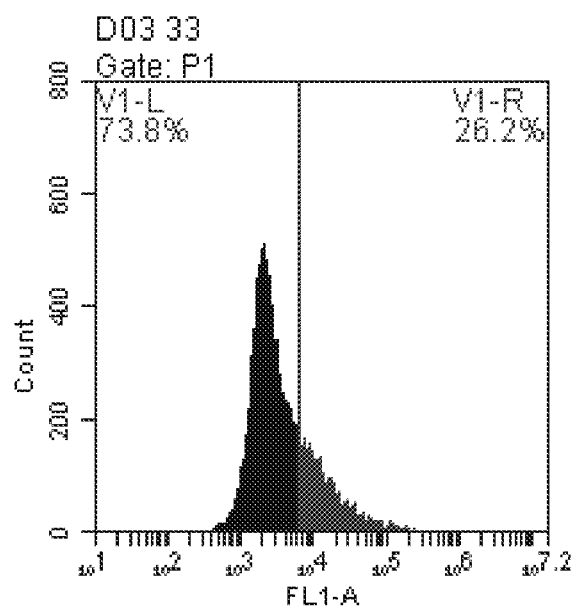
Figure 47A:
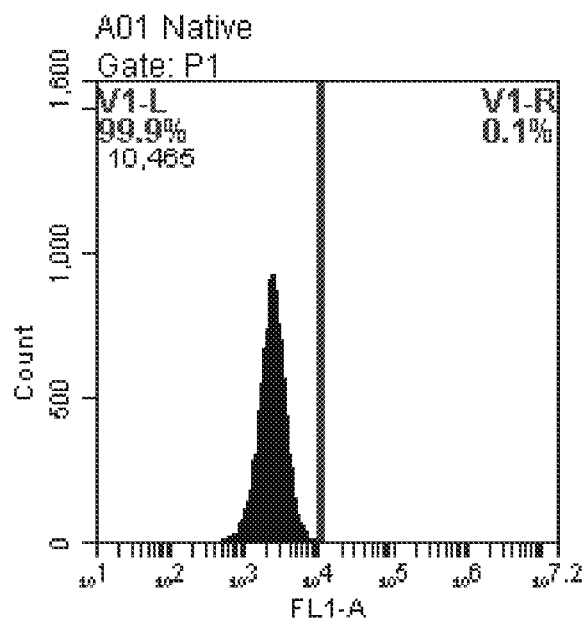
Figure 47B:
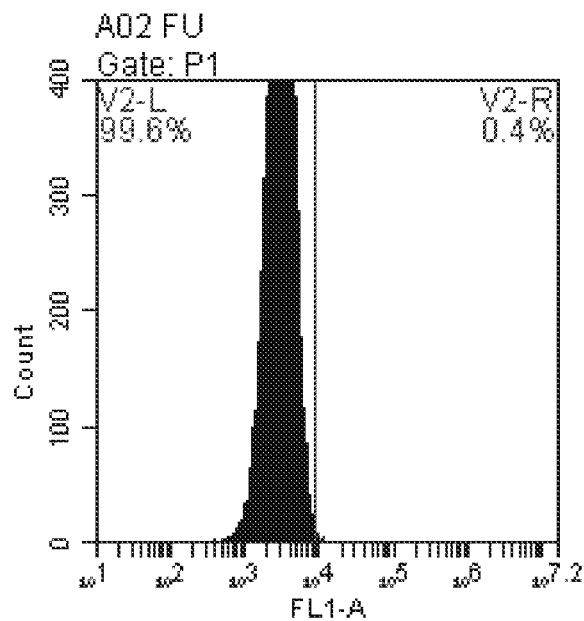
Figure 47C:
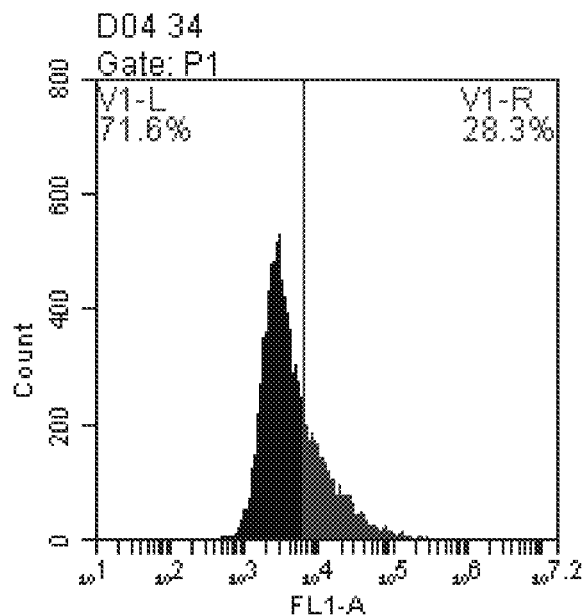
Figure 48A:
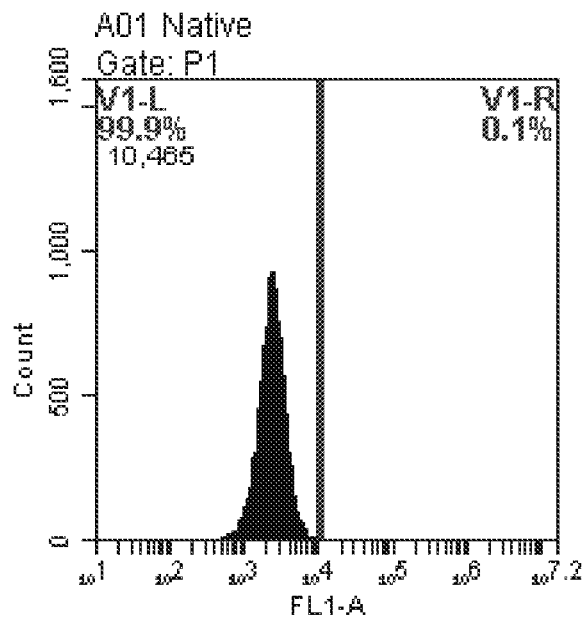
Figure 48B:
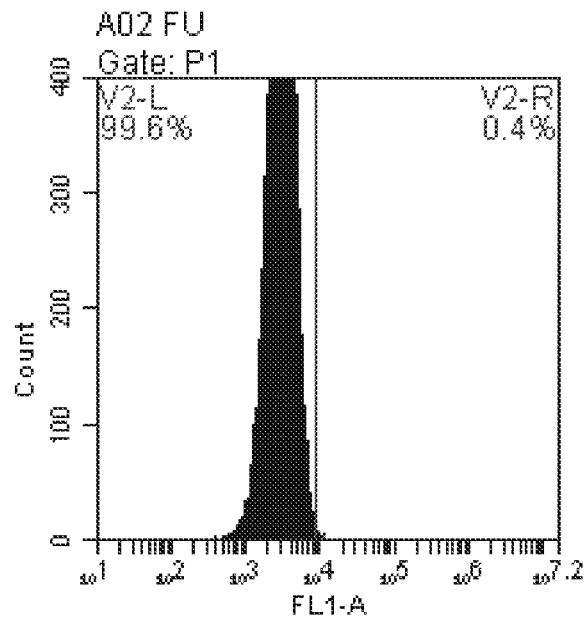
Figure 48C:
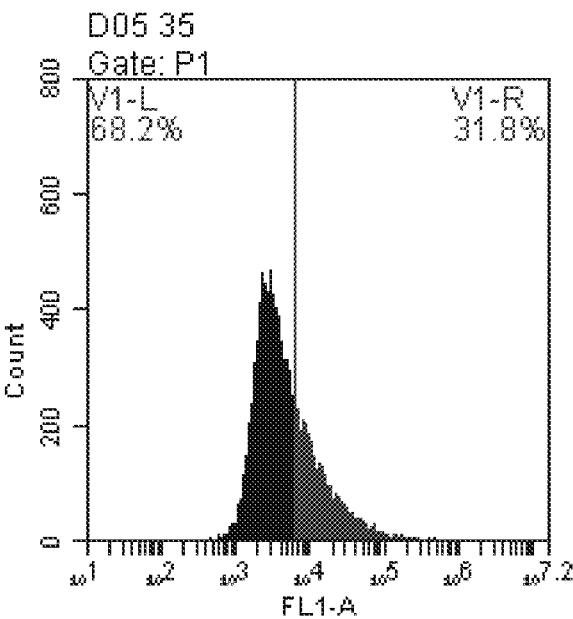
Figure 49A:
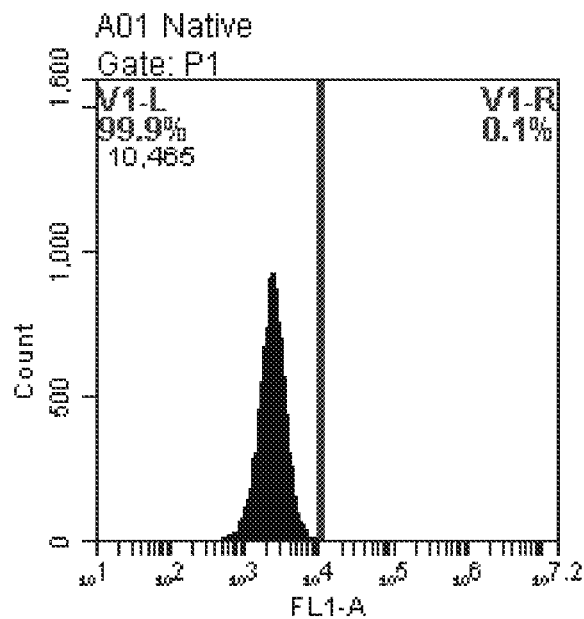
Figure 49B:
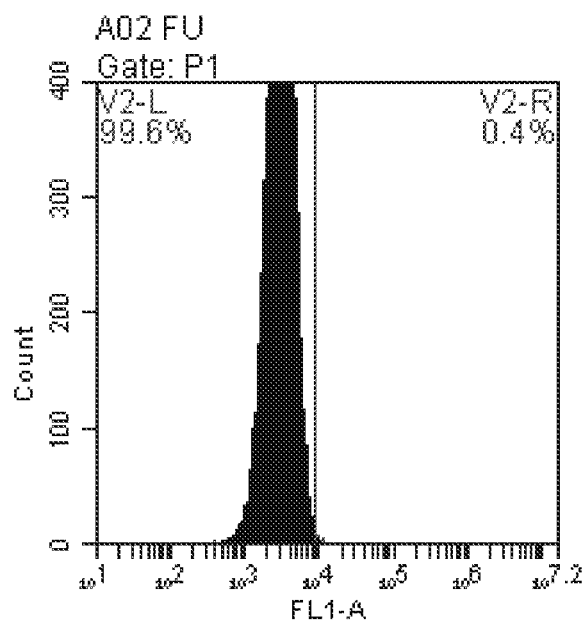
Figure 49C:
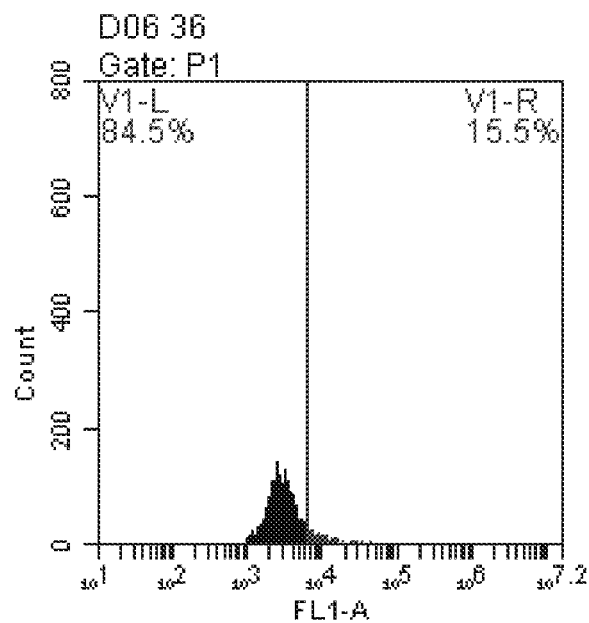
Figure 50A:
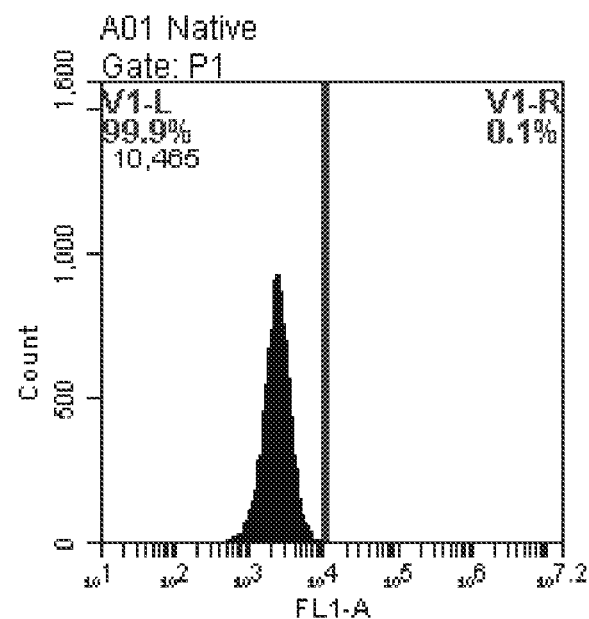
Figure 50B:
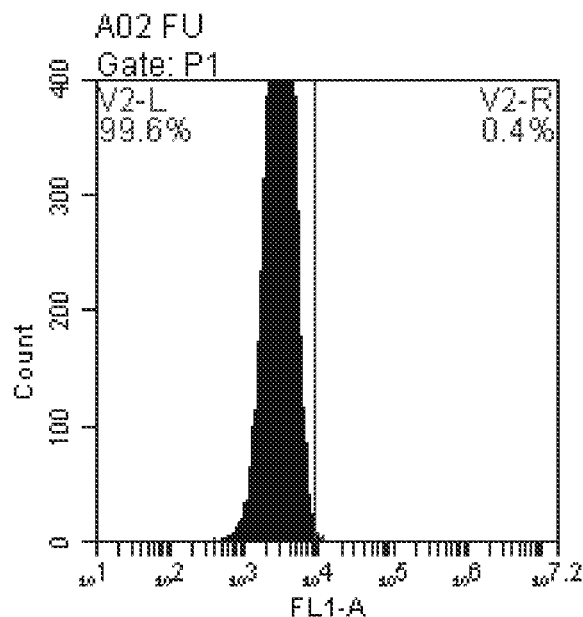
Figure 50C:
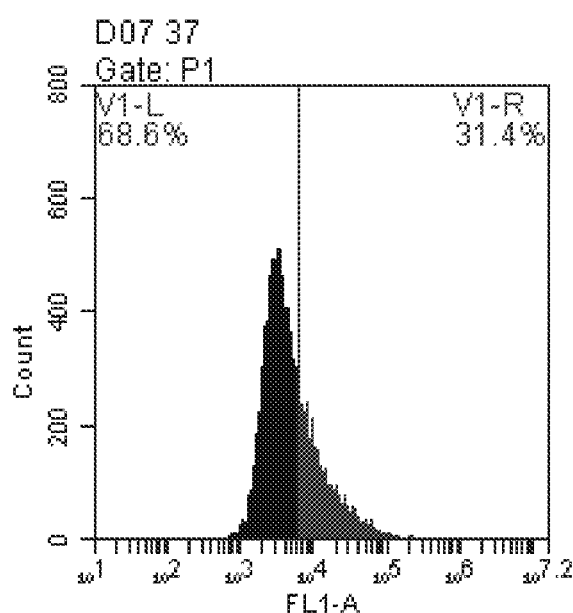
Figure 51A:
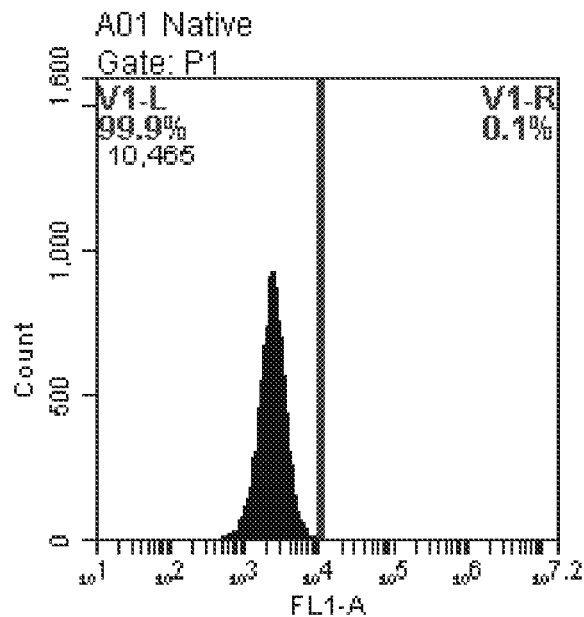
Figure 51B:
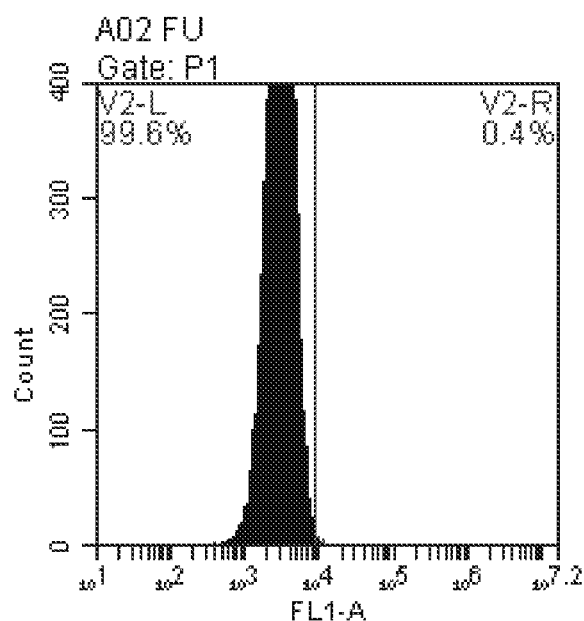
Figure 51C:
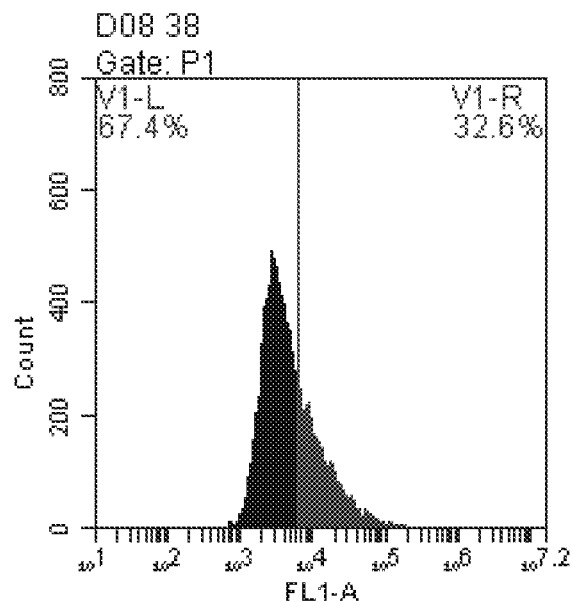
Figure 52A:
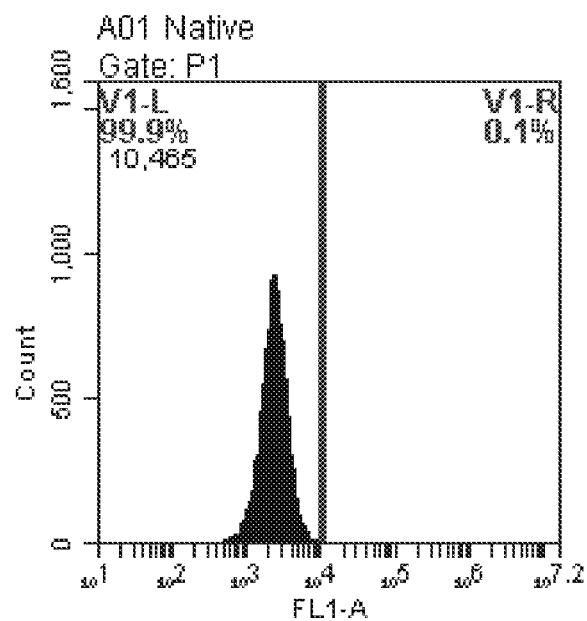
Figure 52B:
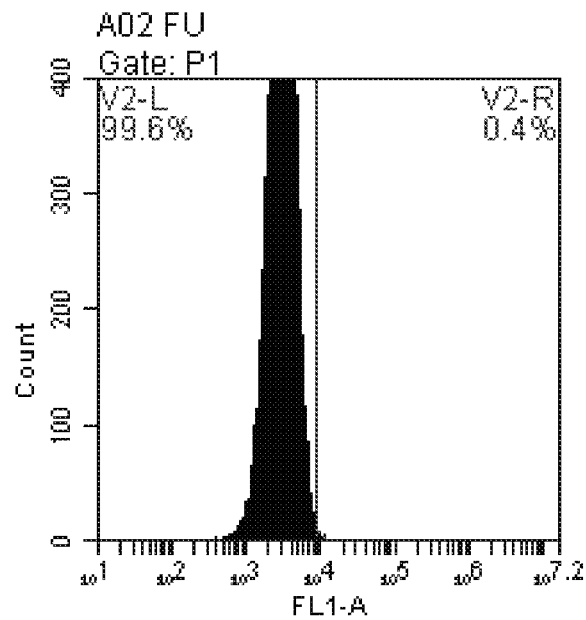
Figure 52C:
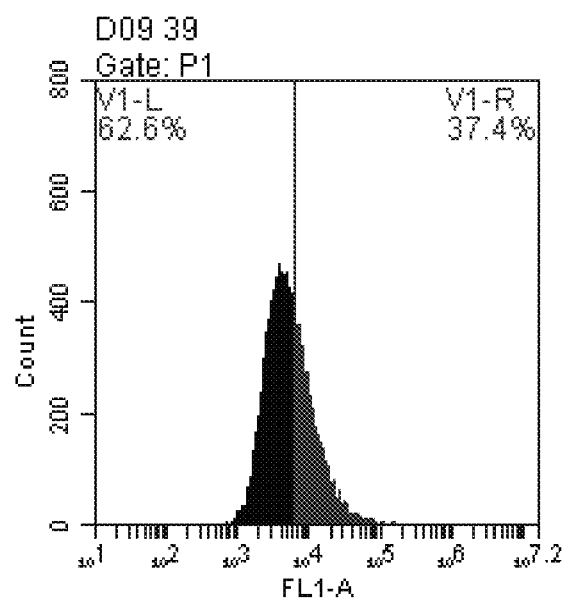
Figure 53A:
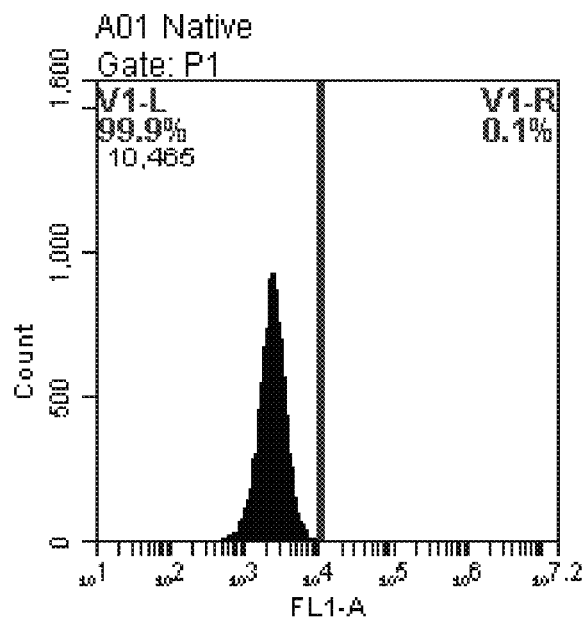
Figure 53B:
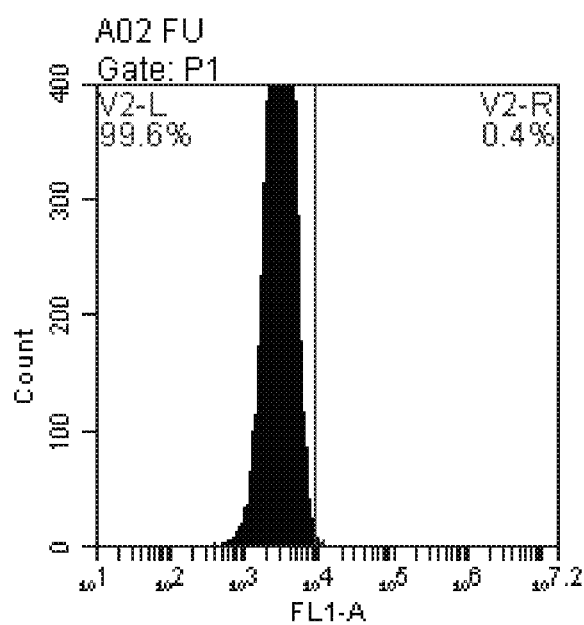
Figure 53C:
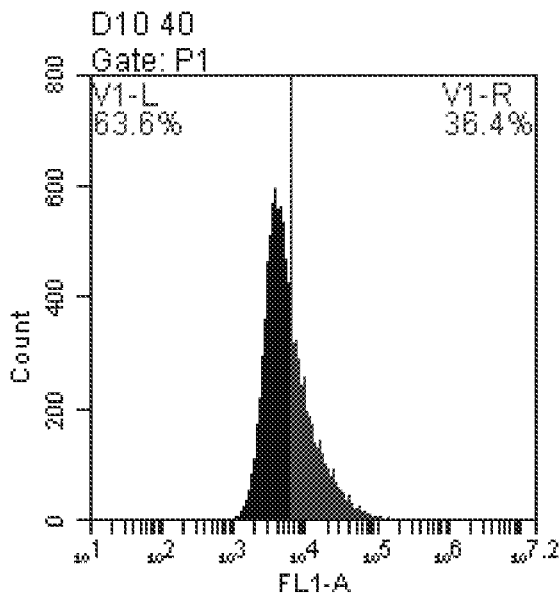
Figure 54A:
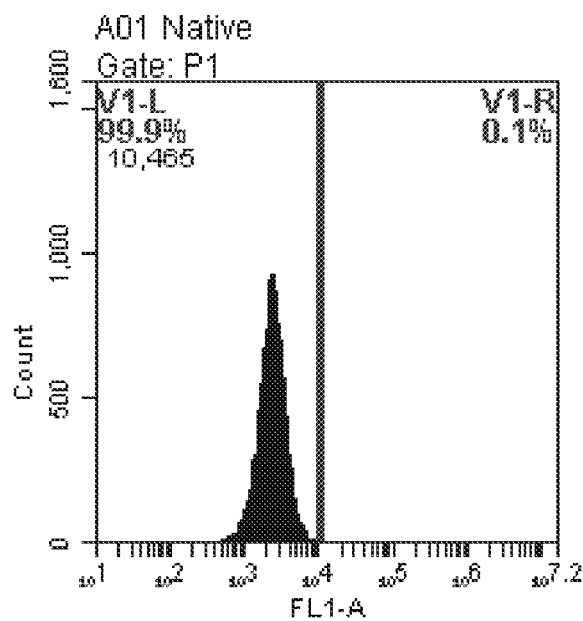
Figure 54B:
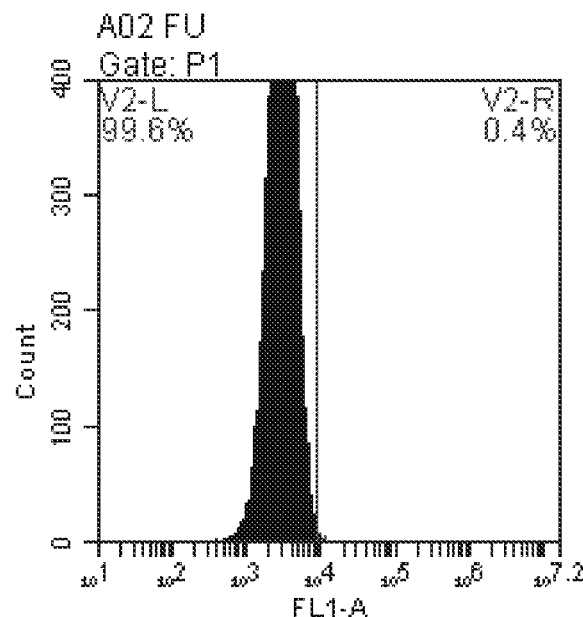
Figure 54C:
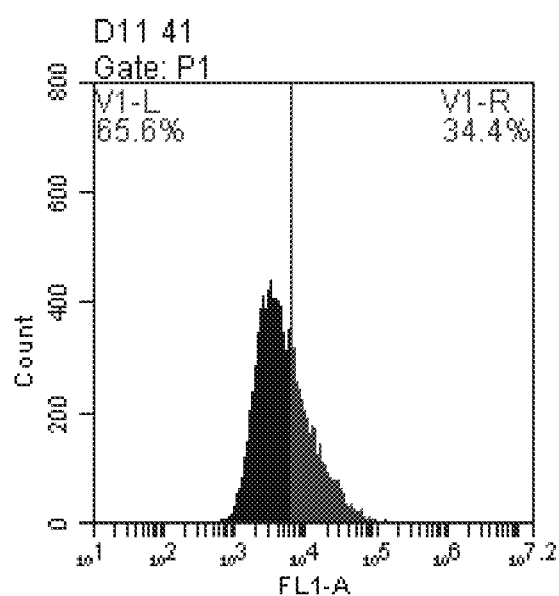
Figure 55A:
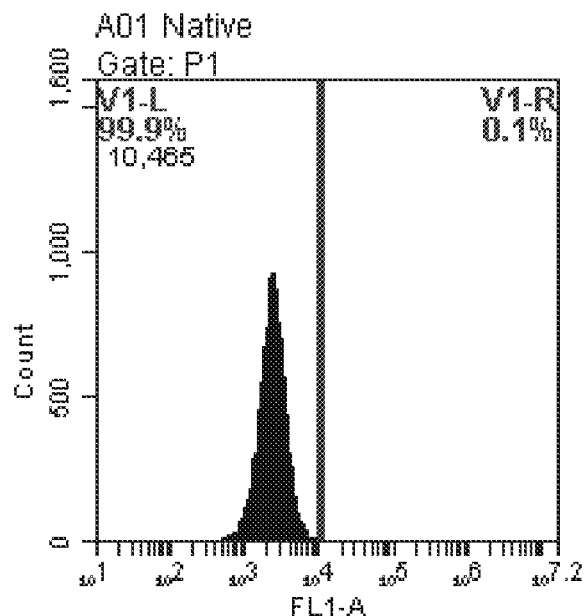
Figure 55B:
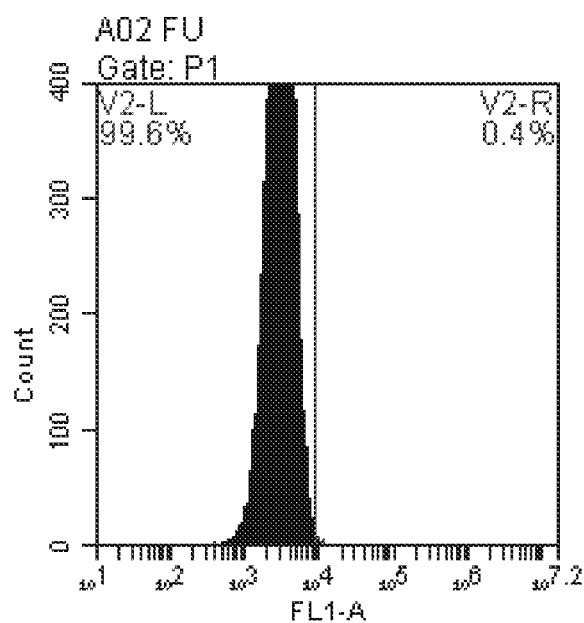
Figure 55C:
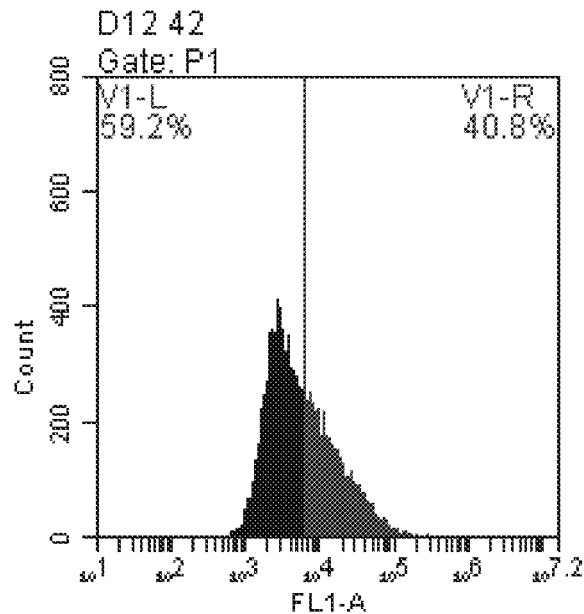
Figure 56A:
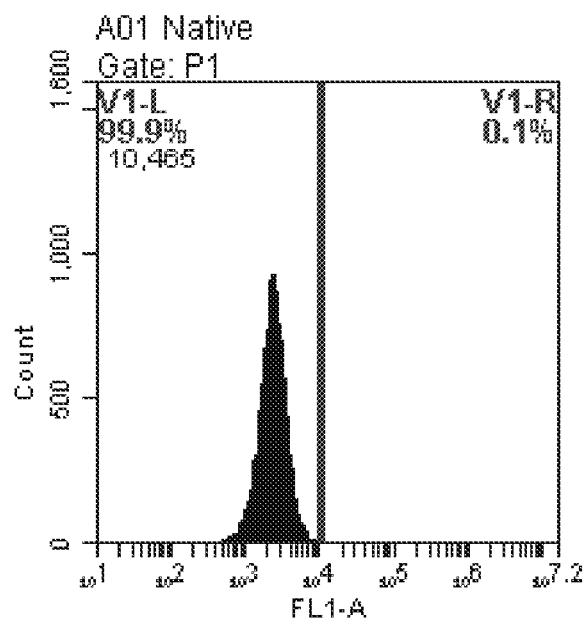
Figure 56B:
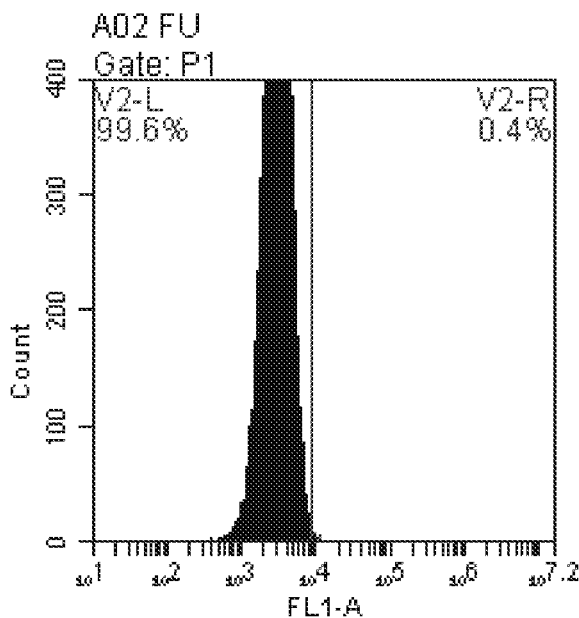
Figure 56C:
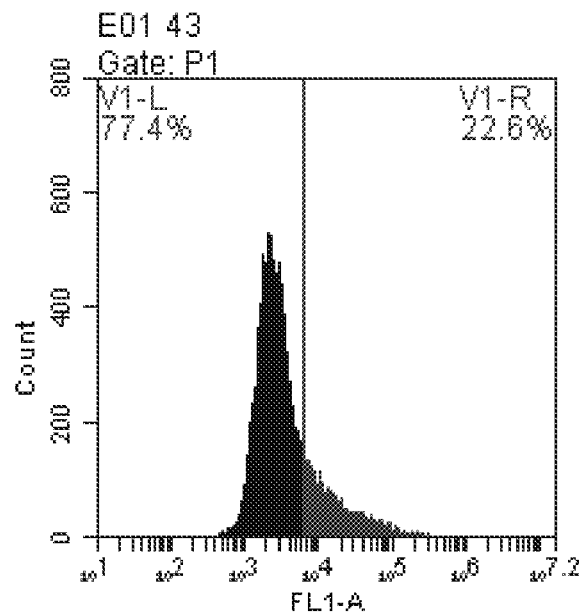
Figure 57A:
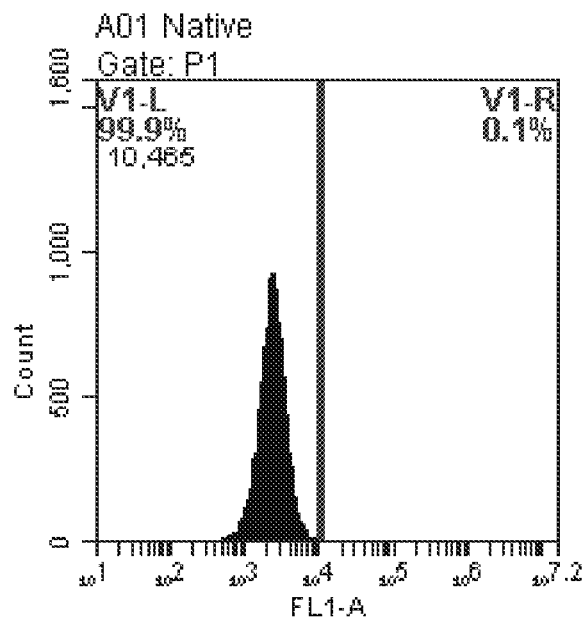
Figure 57B:
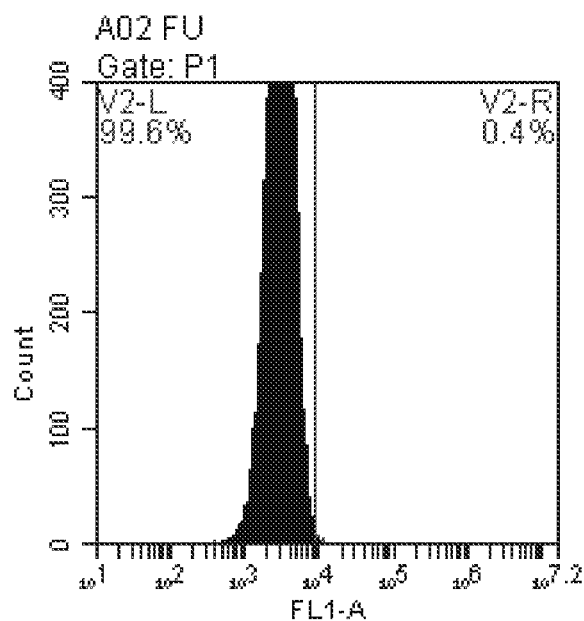
Figure 57C:
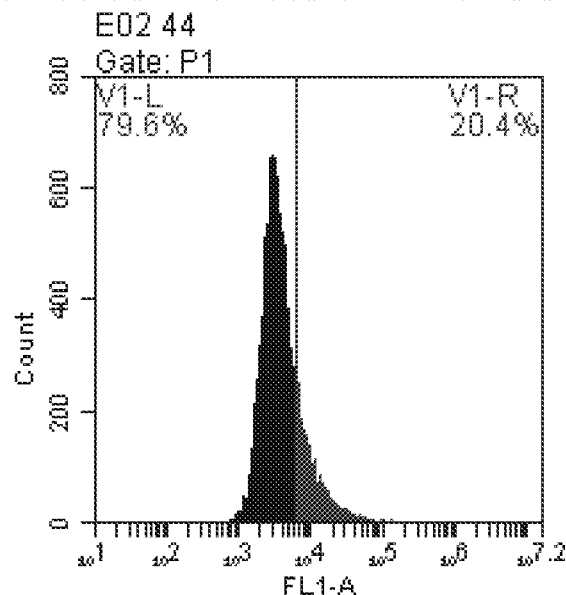
Figure 58A:
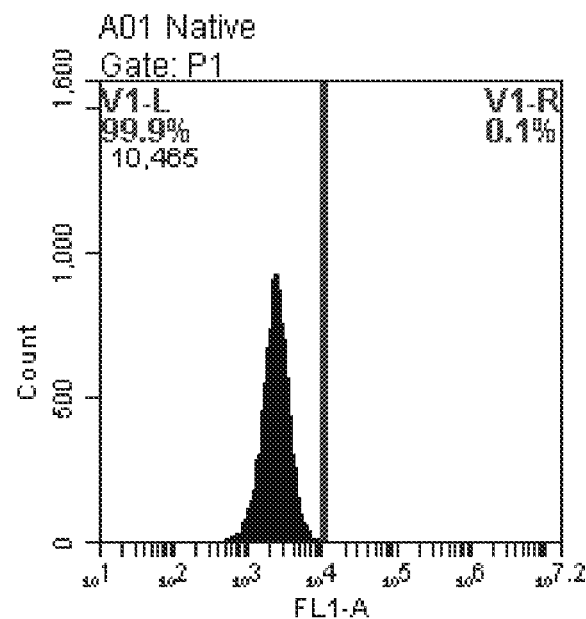
Figure 58B:
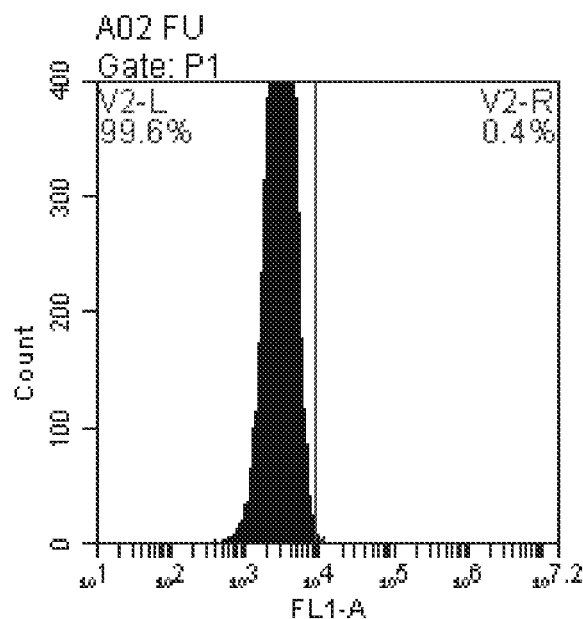
Figure 58C:
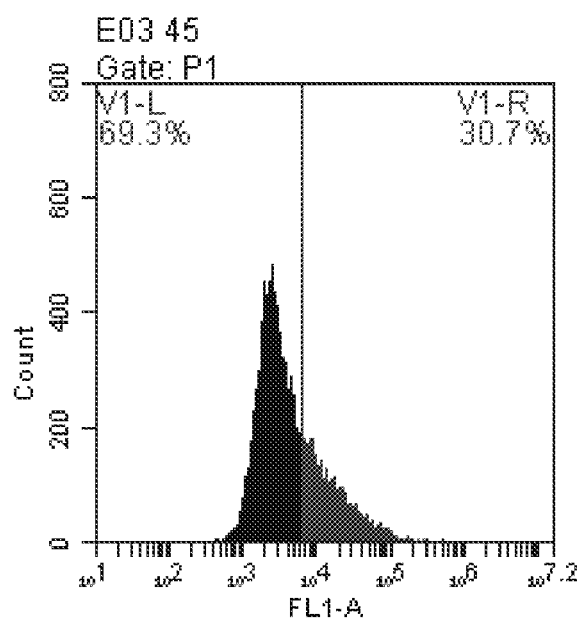
Figure 59A:
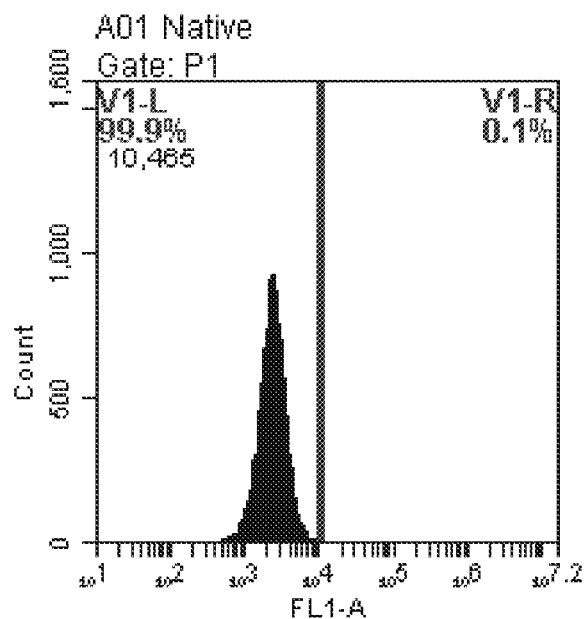
Figure 59B:
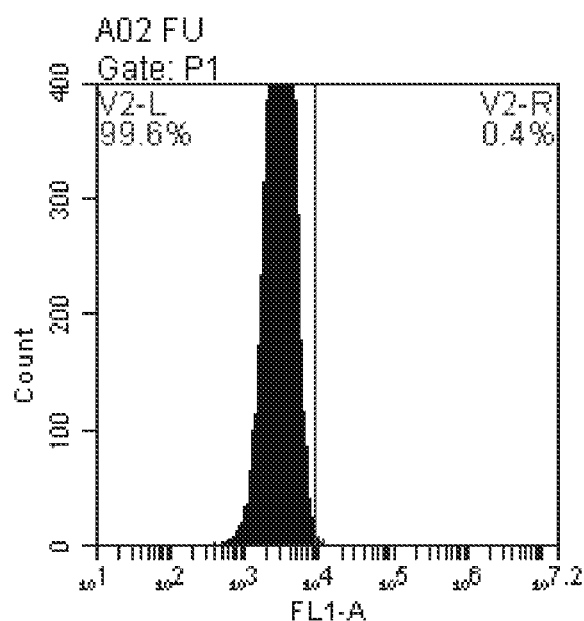
Figure 59C:
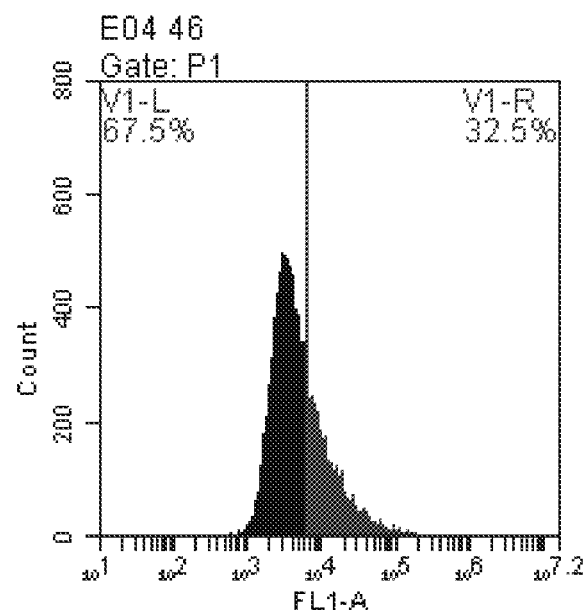
Figure 60A:
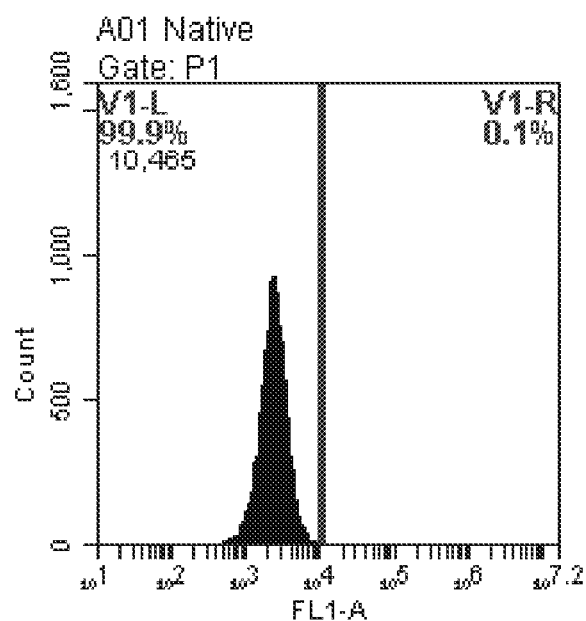
Figure 60B:
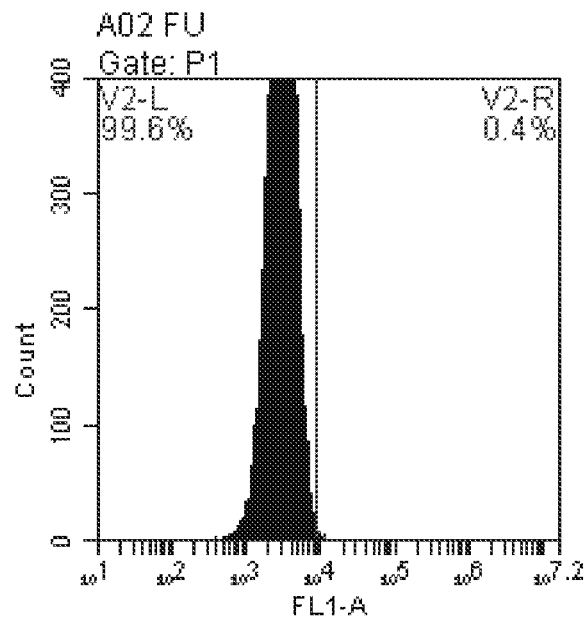
Figure 60C:
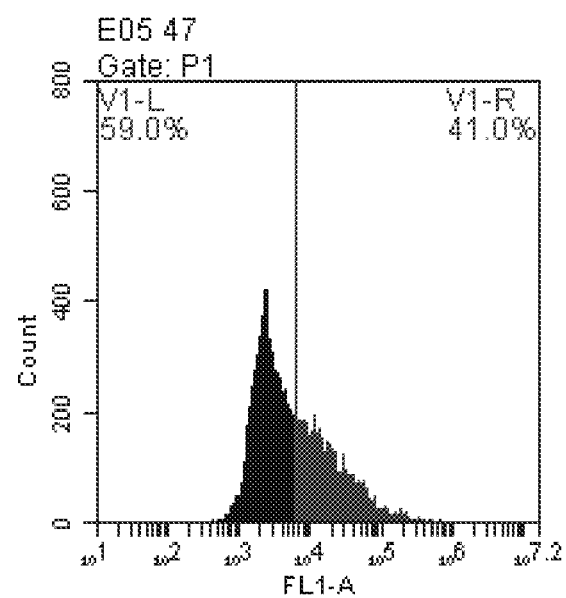
Figure 61A:
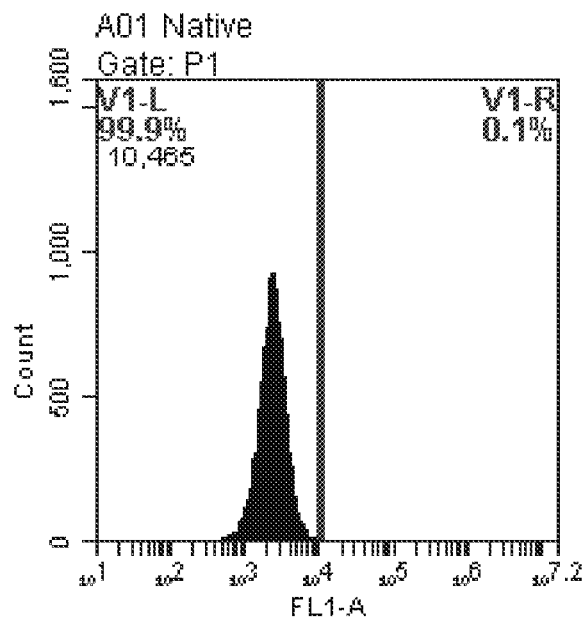
Figure 61B:
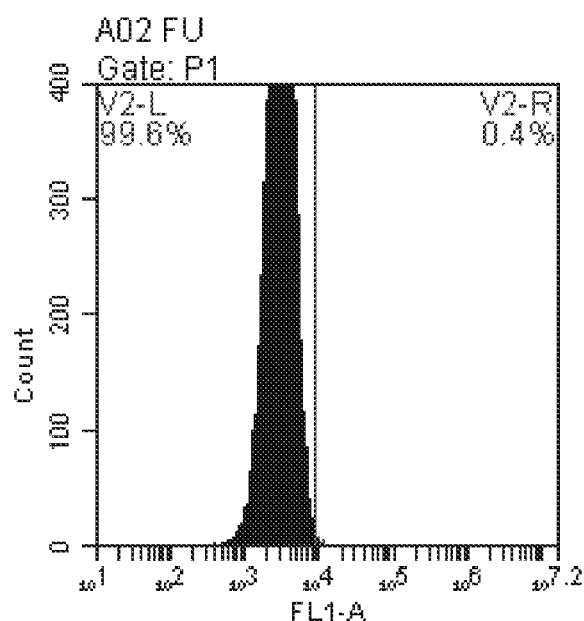
Figure 61C:
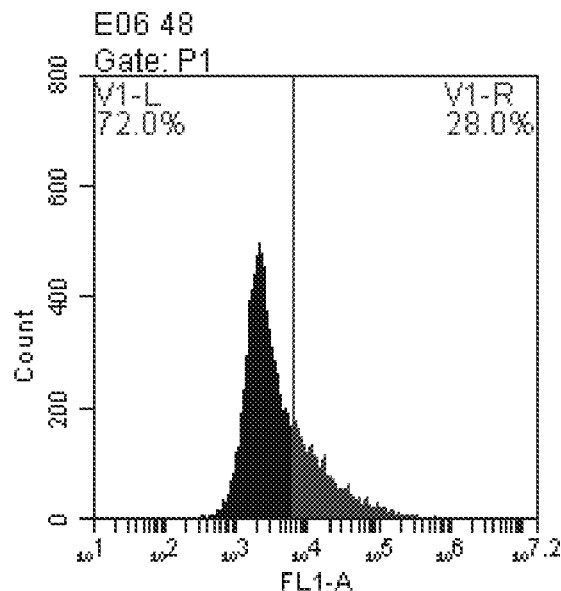
Figure 62A:
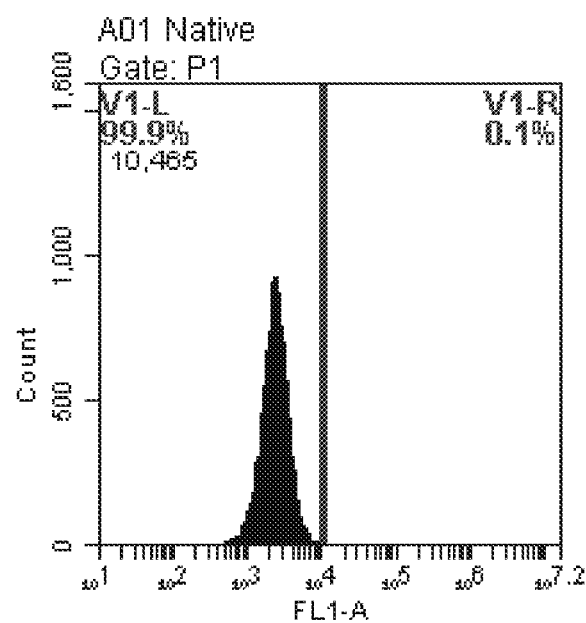
Figure 62B:
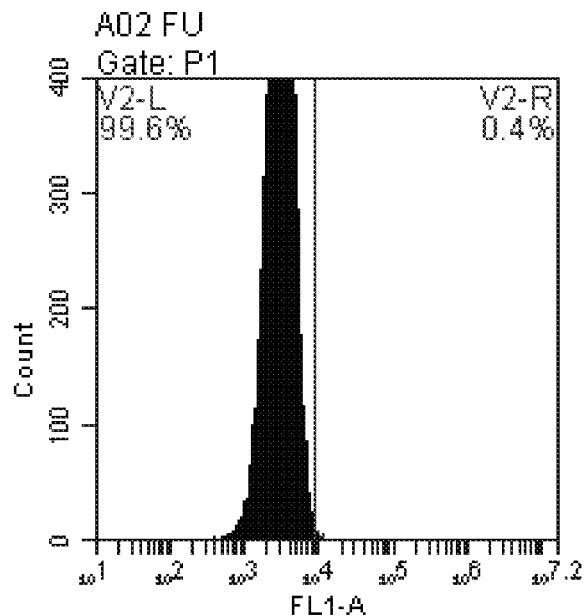
Figure 62C:
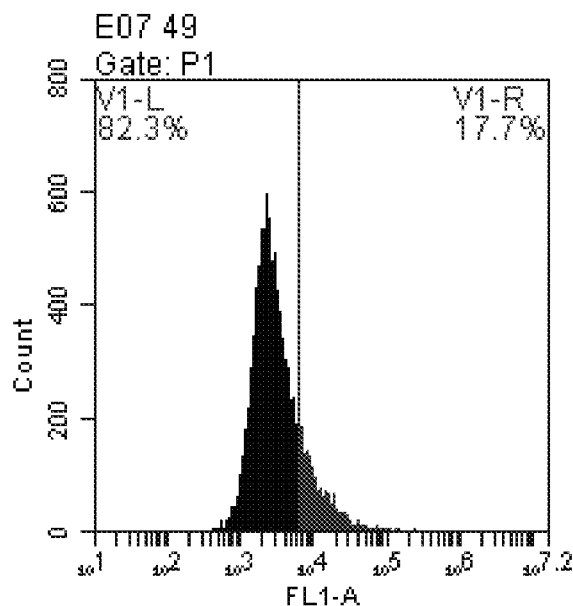
Figure 63A:
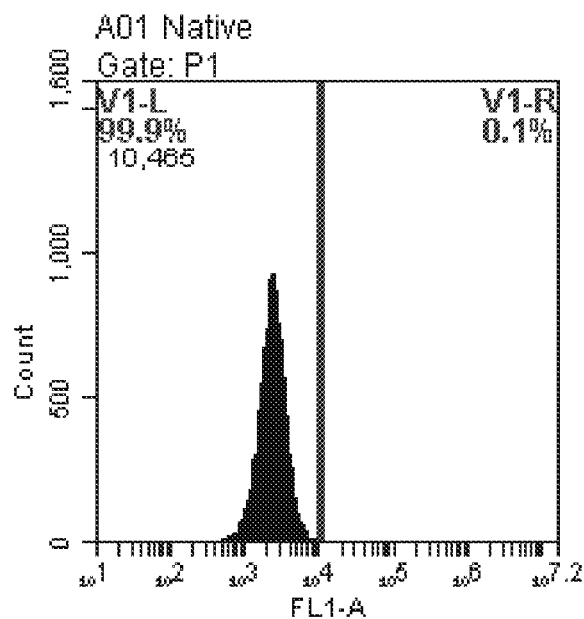
Figure 63B:
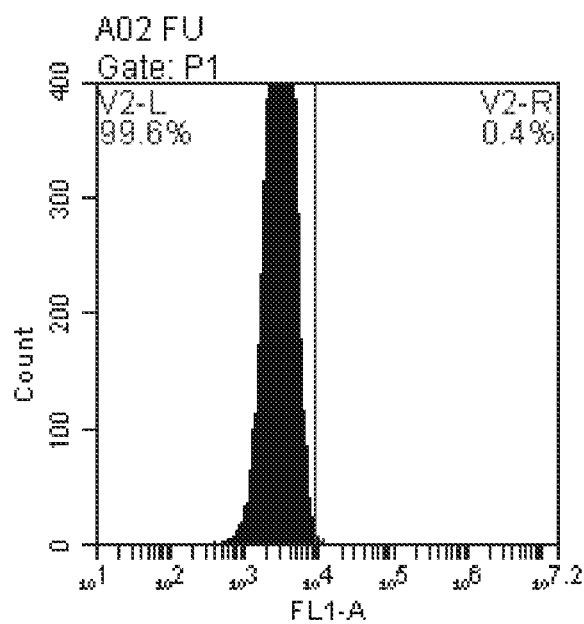
Figure 63C:
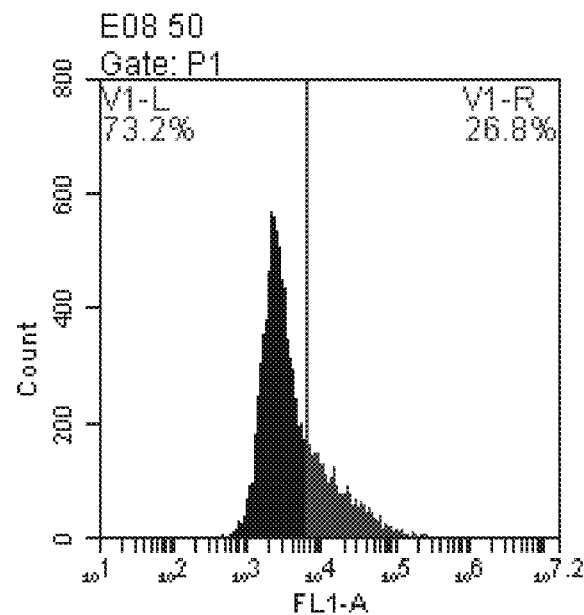
Figure 64A:
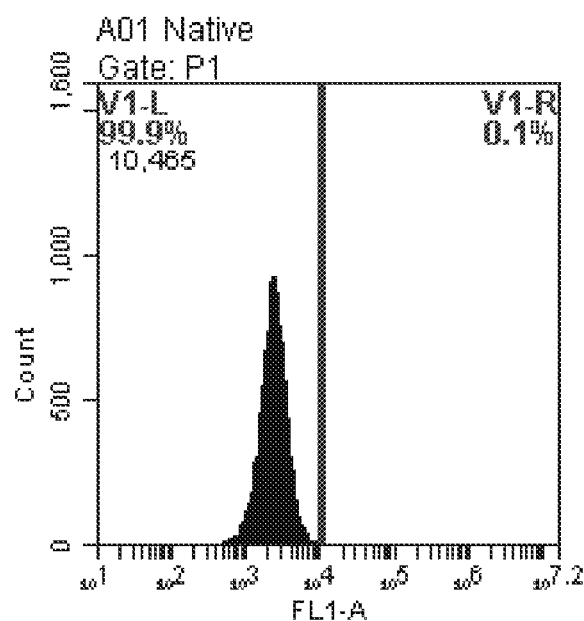
Figure 64B:
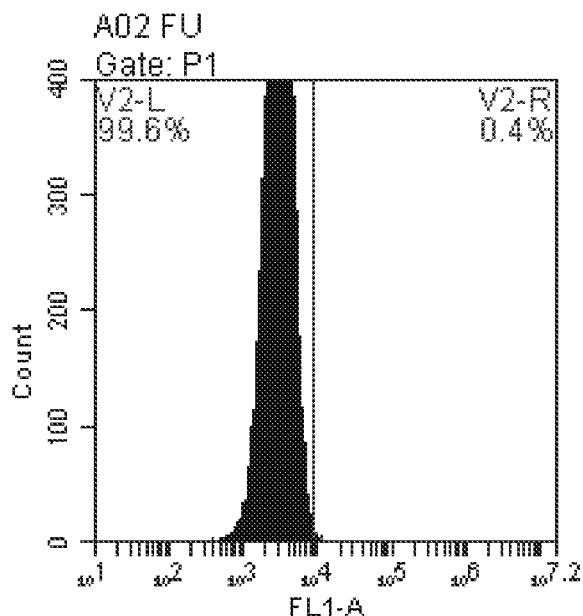
Figure 64C:
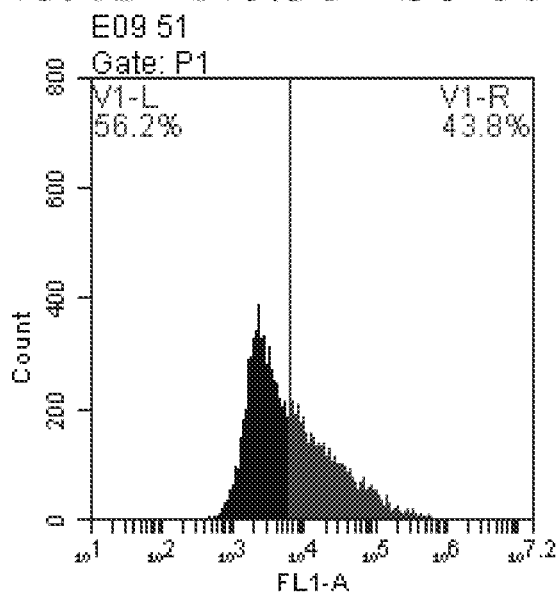
Figure 65A:
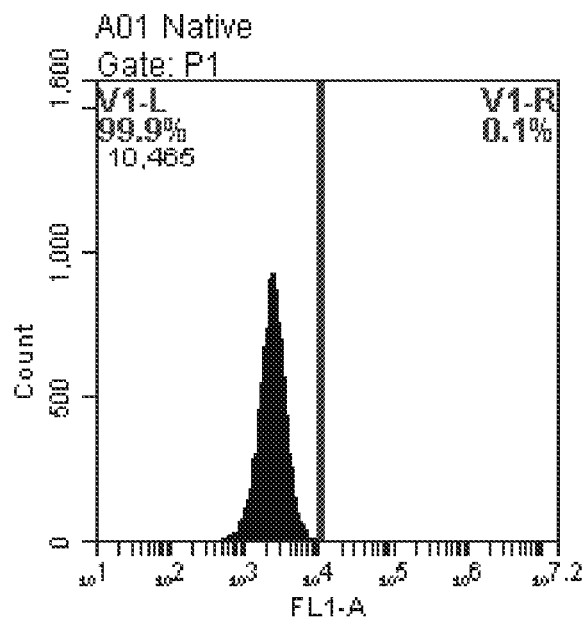
Figure 65B:
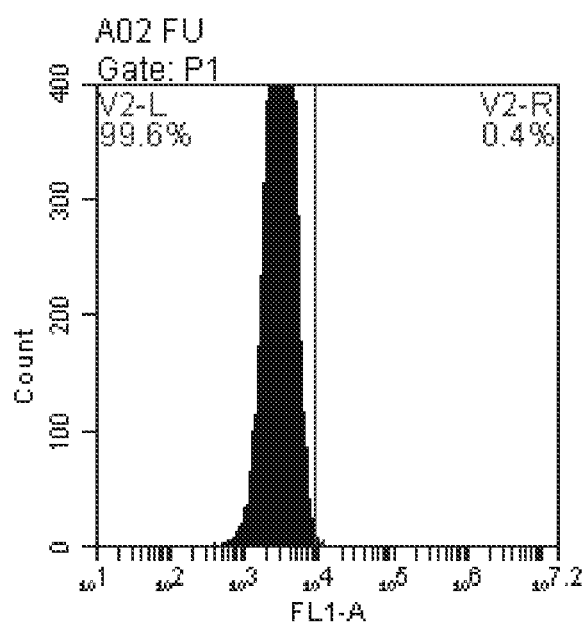
Figure 65C:
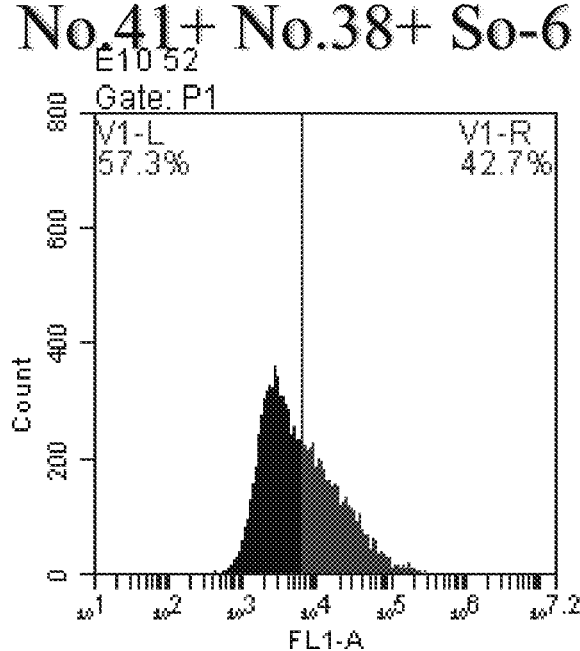
Figure 66A:
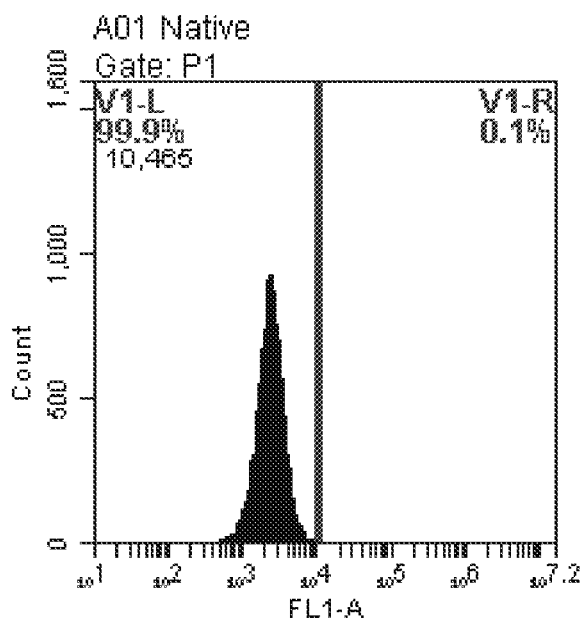
Figure 66B:
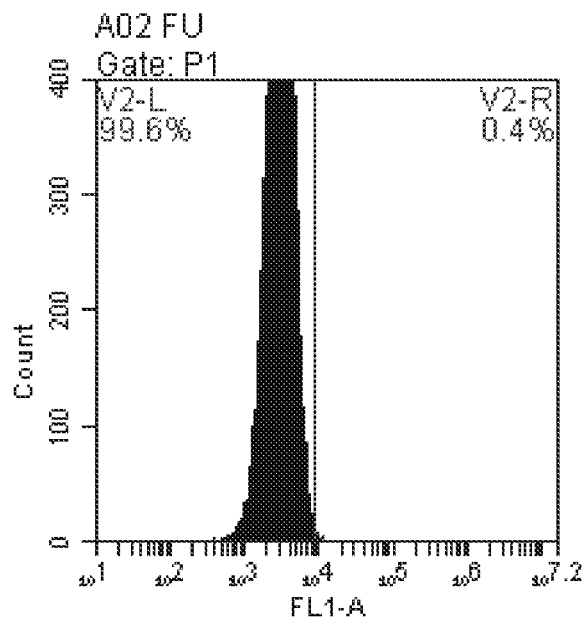
Figure 66C:
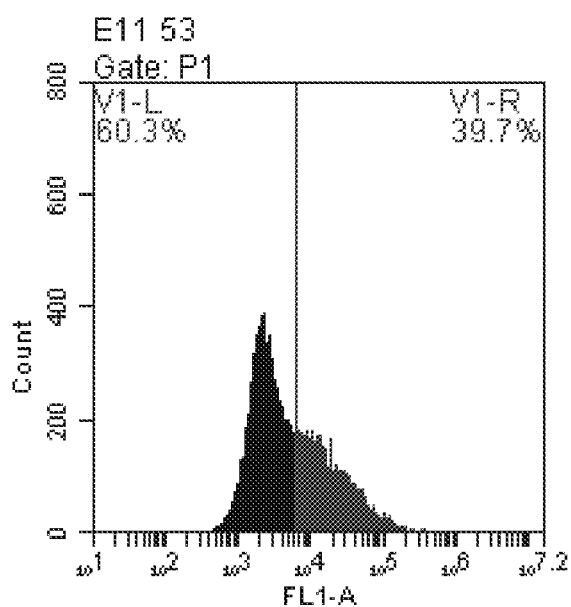
Figure 67A:
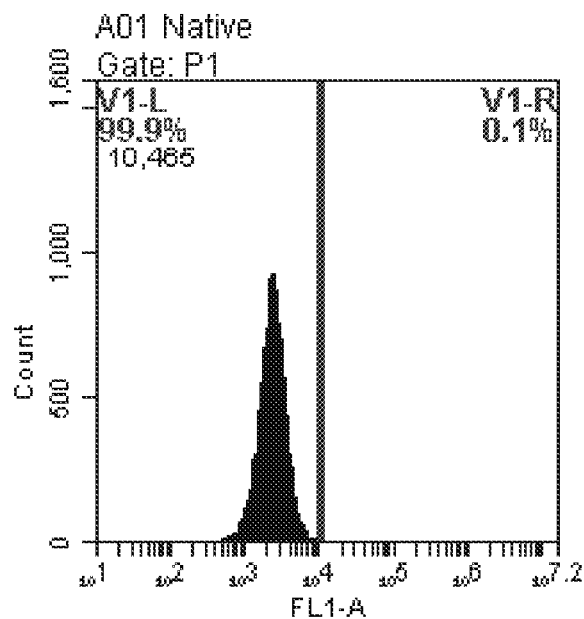
Figure 67B:
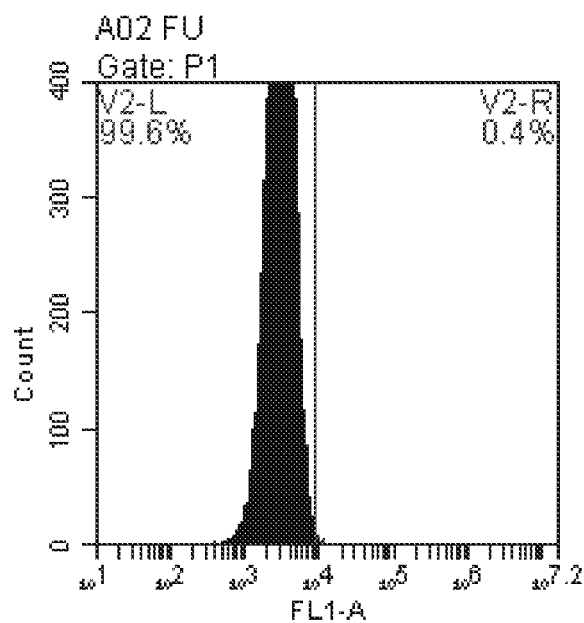
Figure 67C:
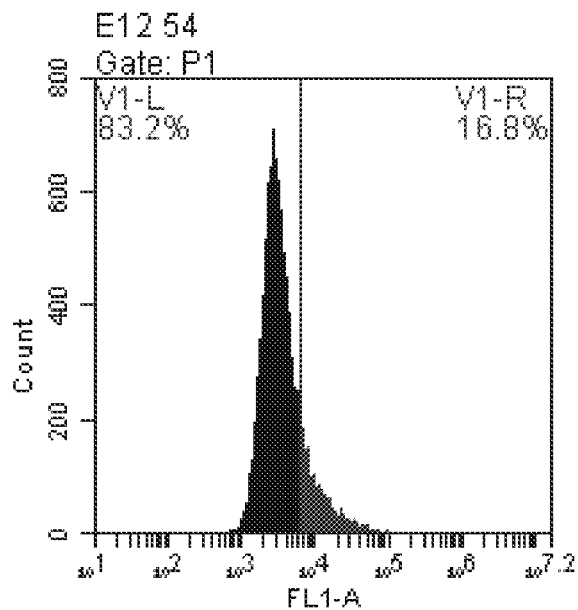
Figure 68A:
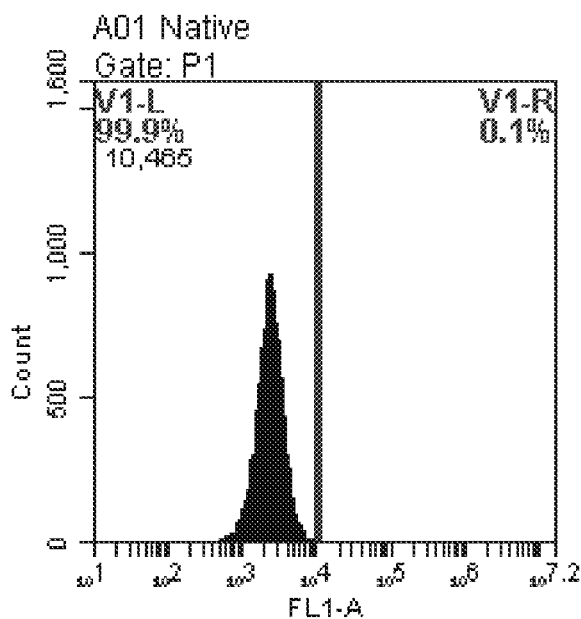
Figure 68B:
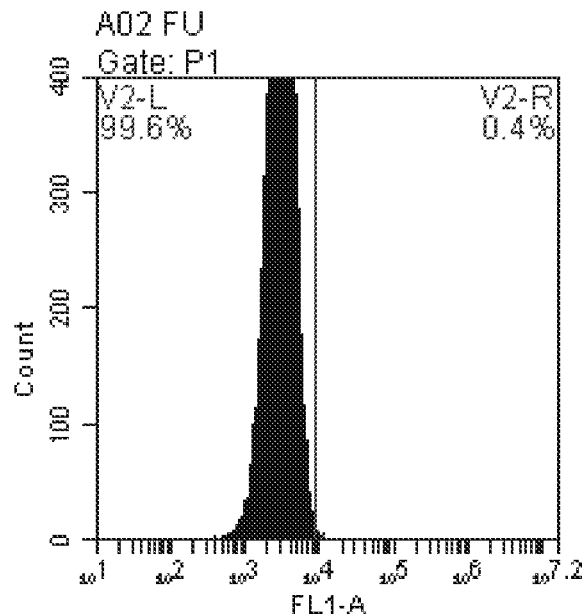
Figure 68C:
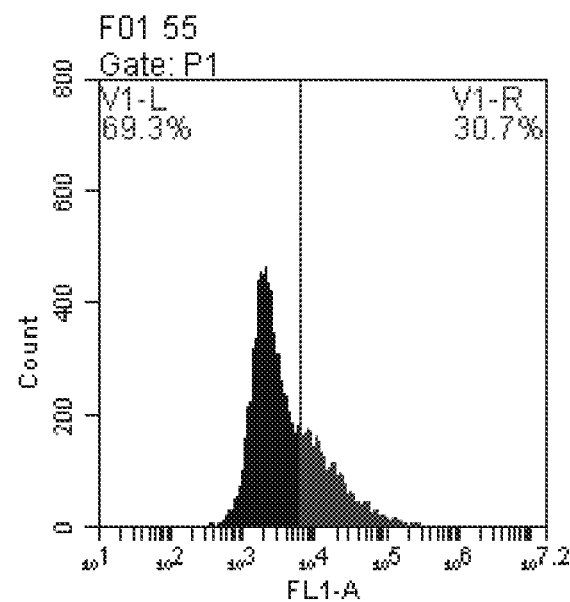
Figure 69A:
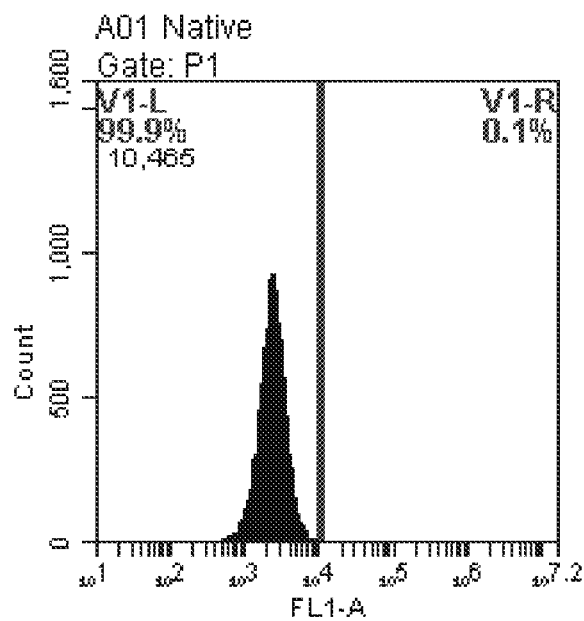
Figure 69B:
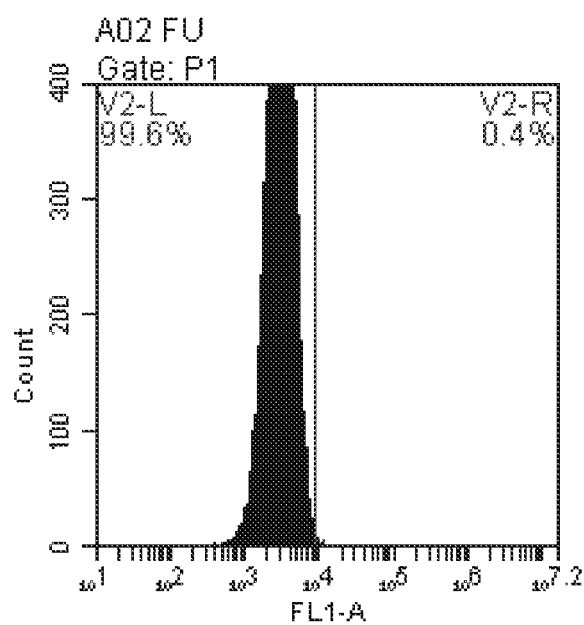
Figure 69C:
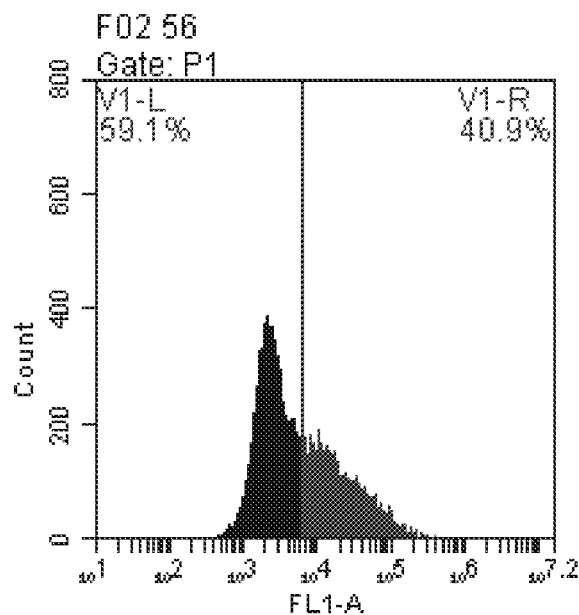
Figure 70A:
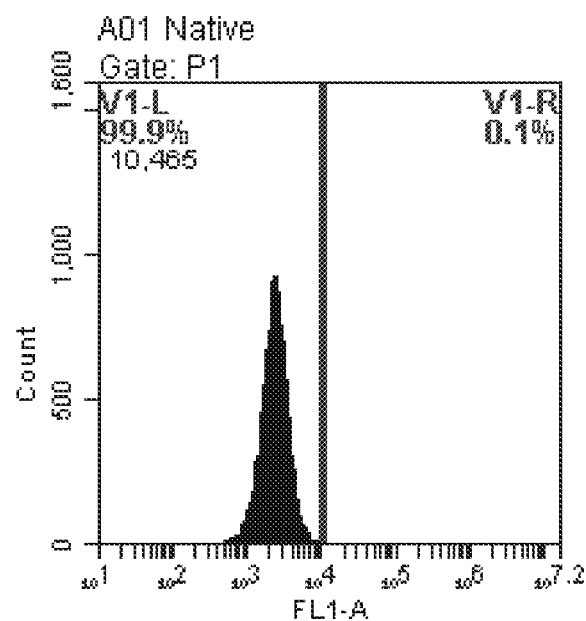
Figure 70B:
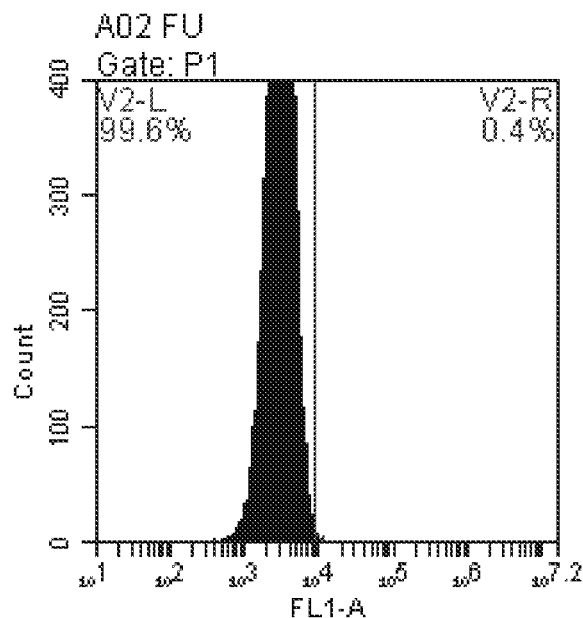
Figure 70C:
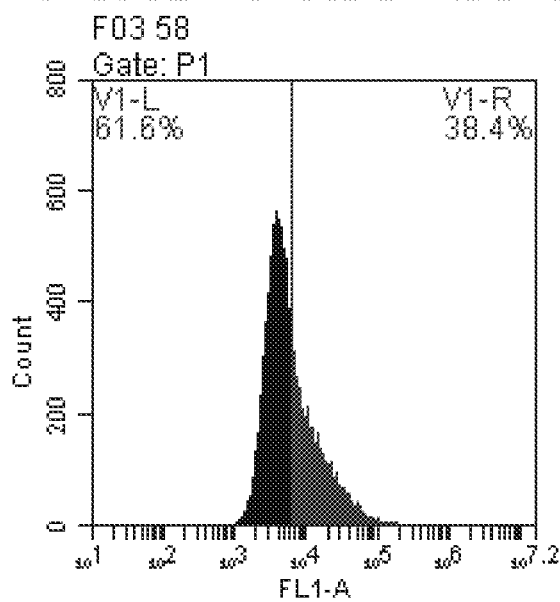
Figure 71A:
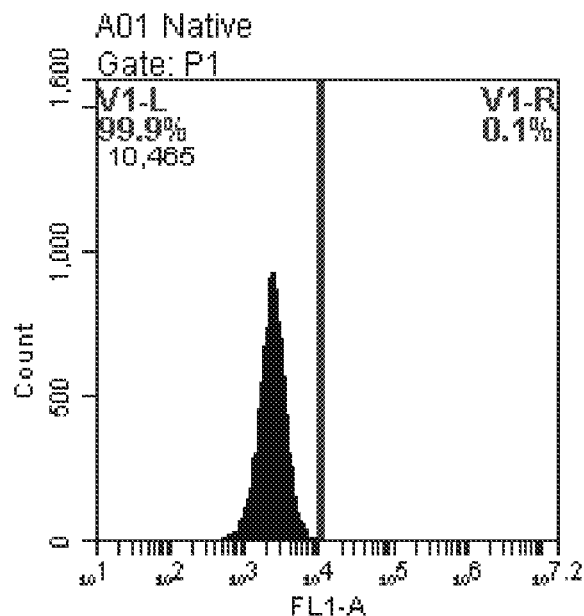
Figure 71B:
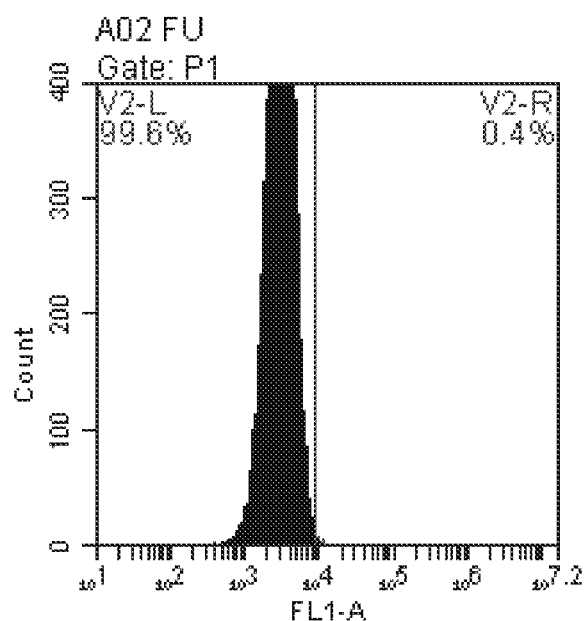
Figure 71C:
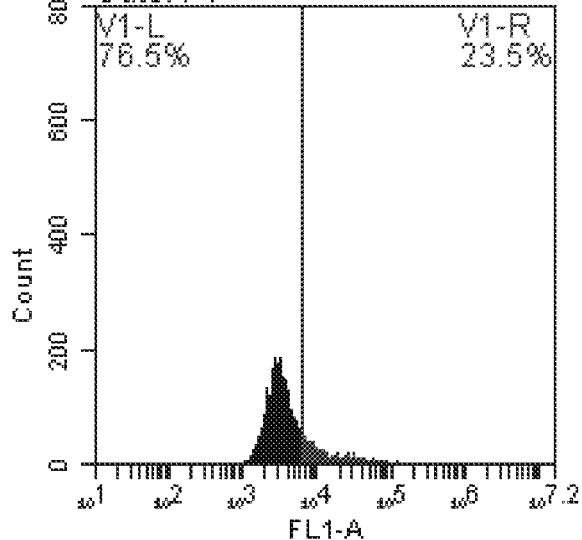
Figure 72A:
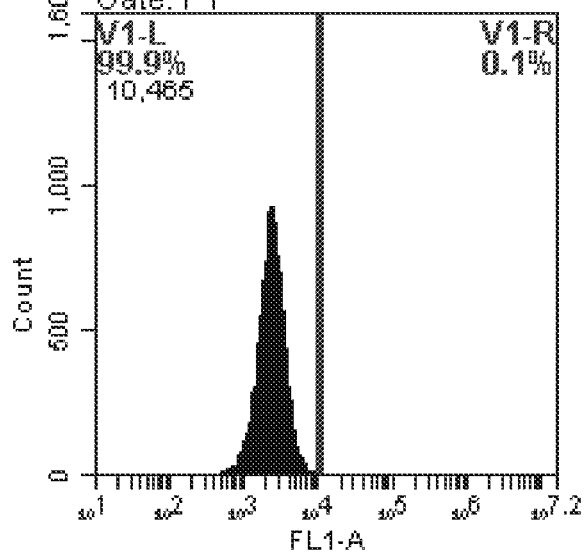
Figure 72B:
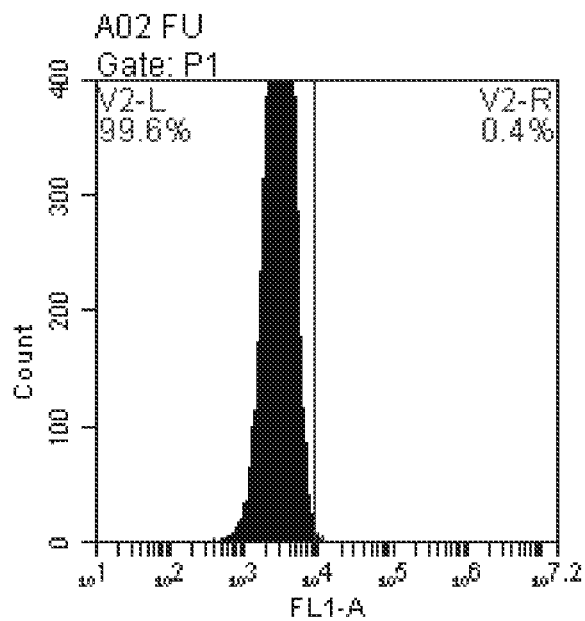
Figure 72C:
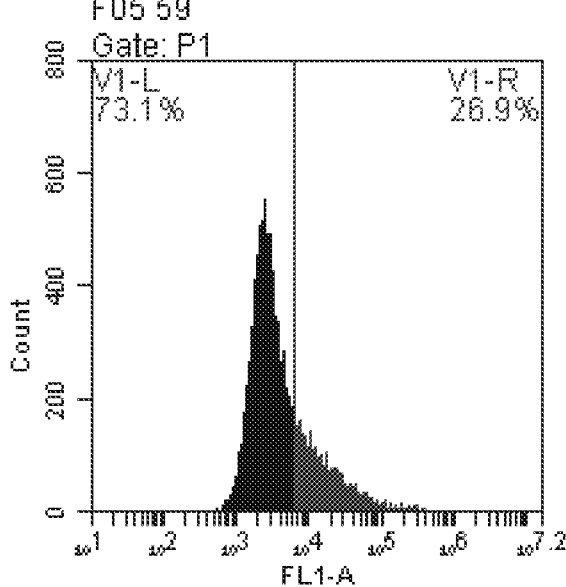
Figure 73A:
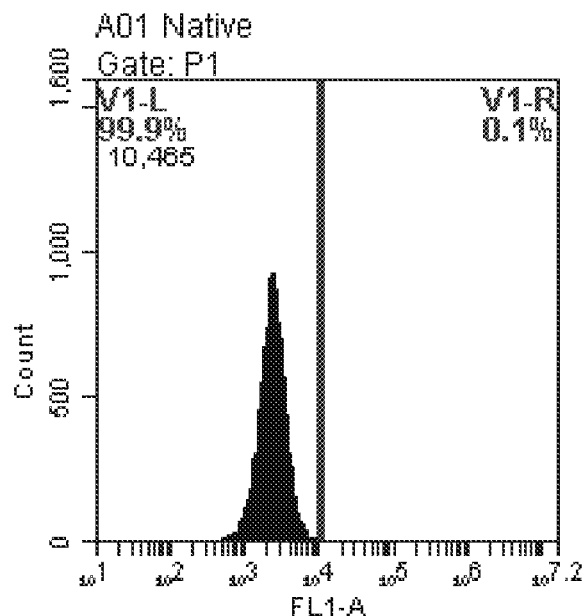
Figure 73B:
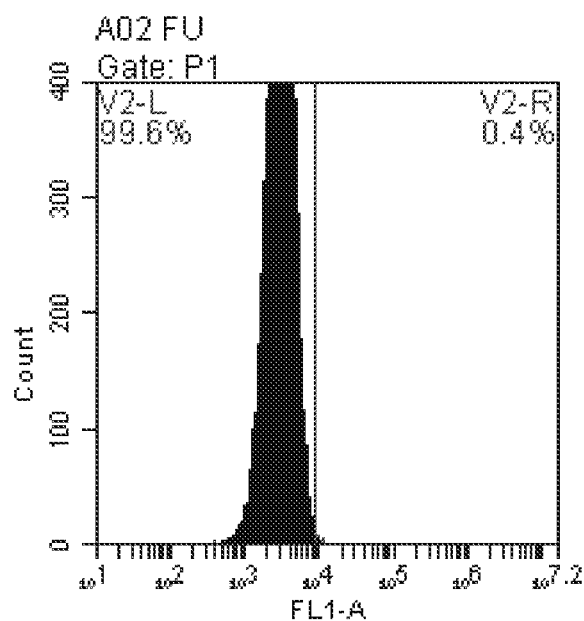
Figure 73C:
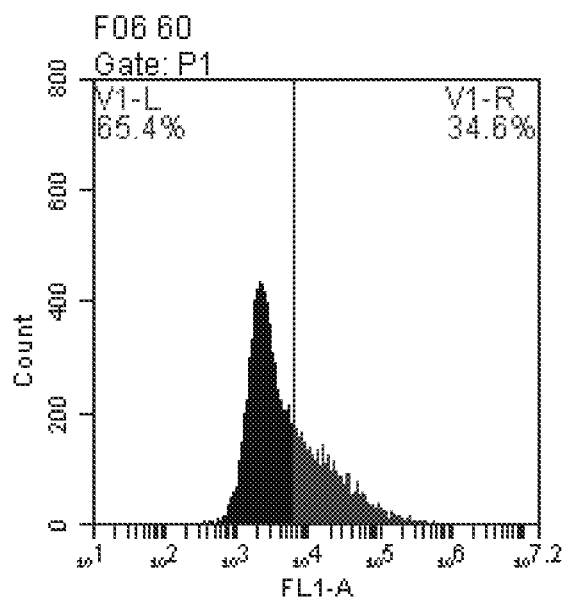
Figure 74A:
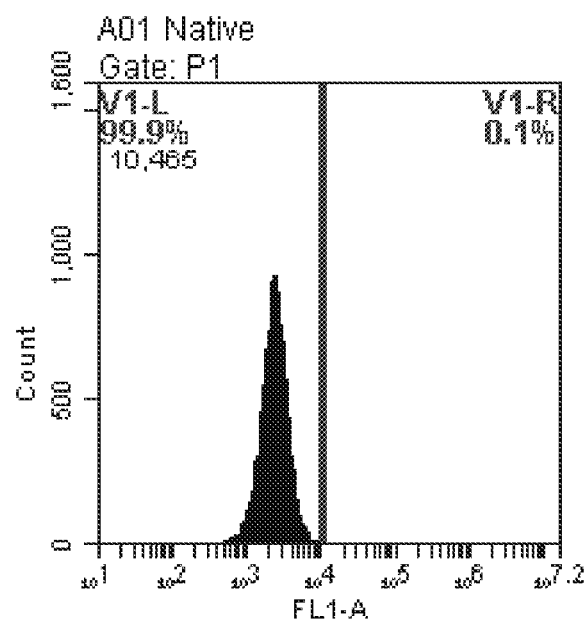
Figure 74B:
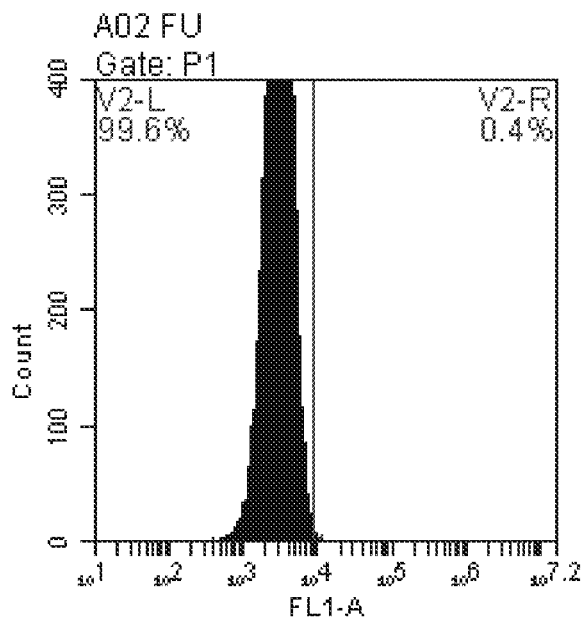
Figure 74C:
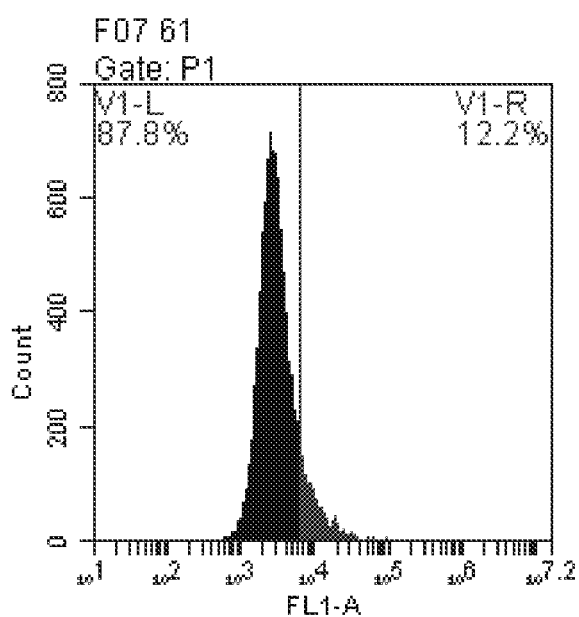
Figure 75A:
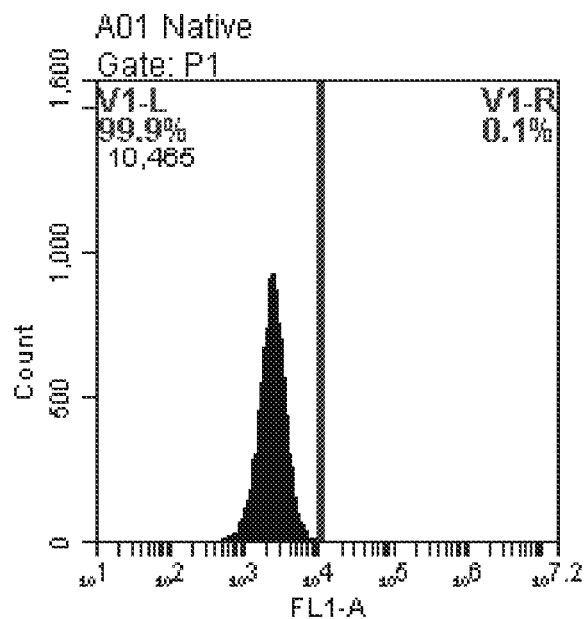
Figure 75B:
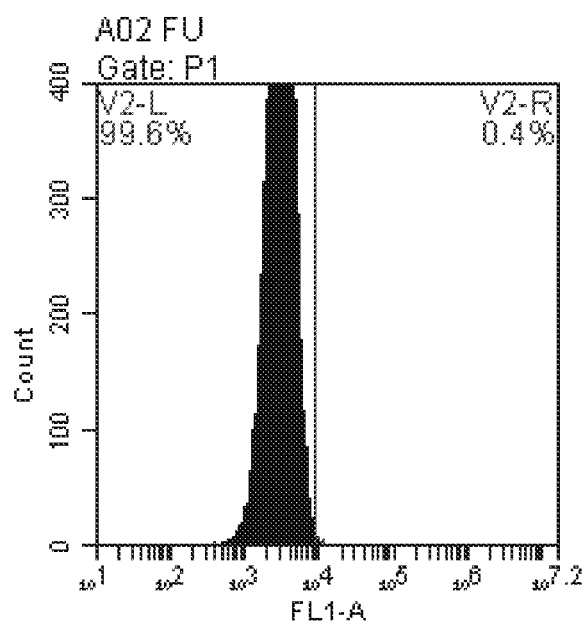
Figure 75C:
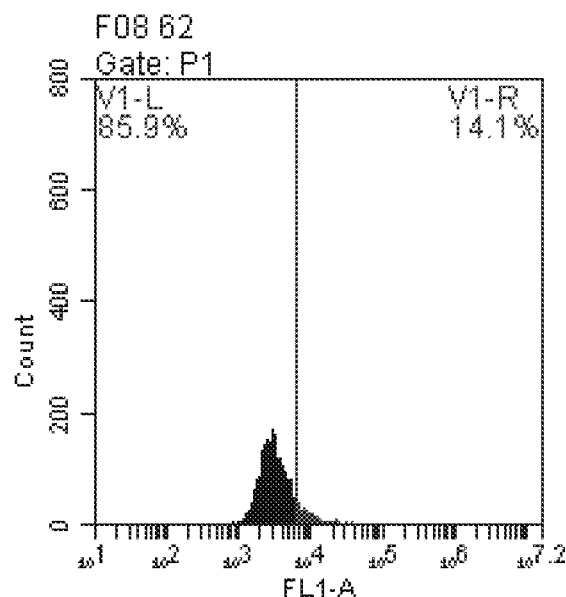
Figure 76A:
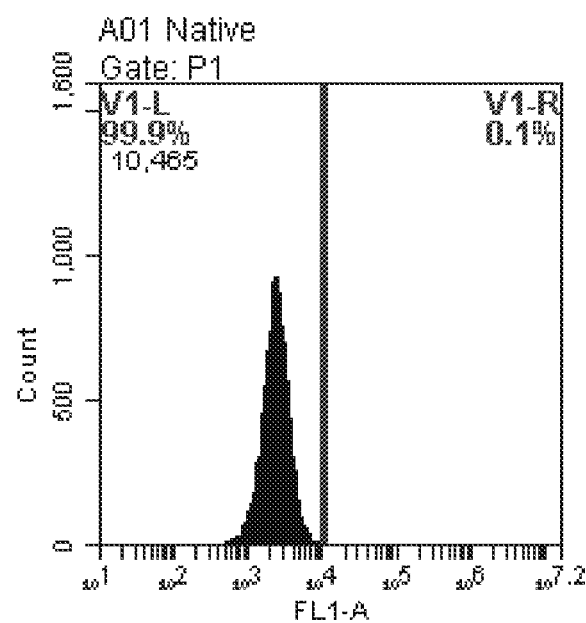
Figure 76B:
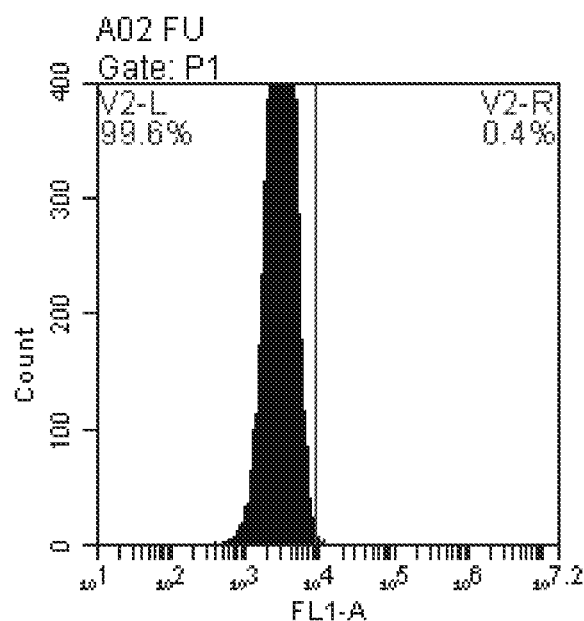
Figure 76C:
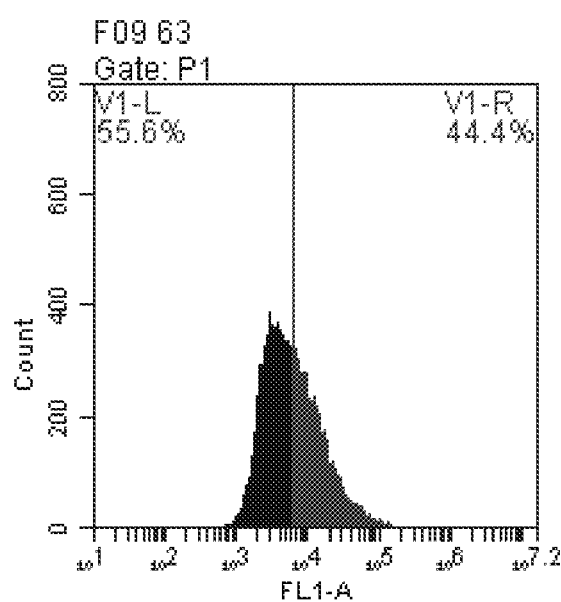
Figure 77A:
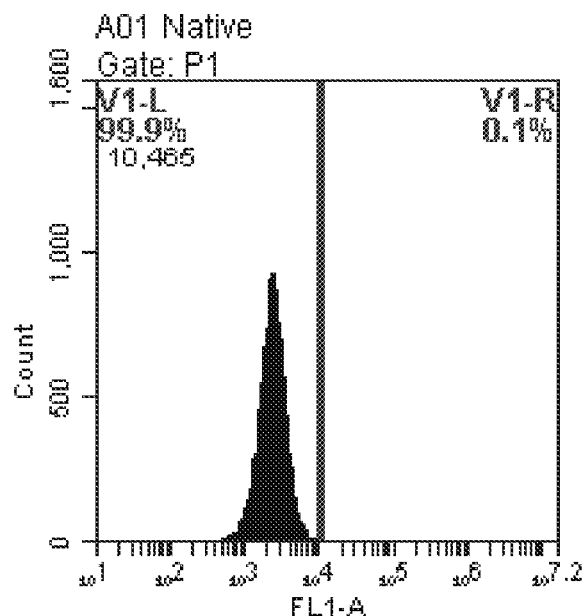
Figure 77B:
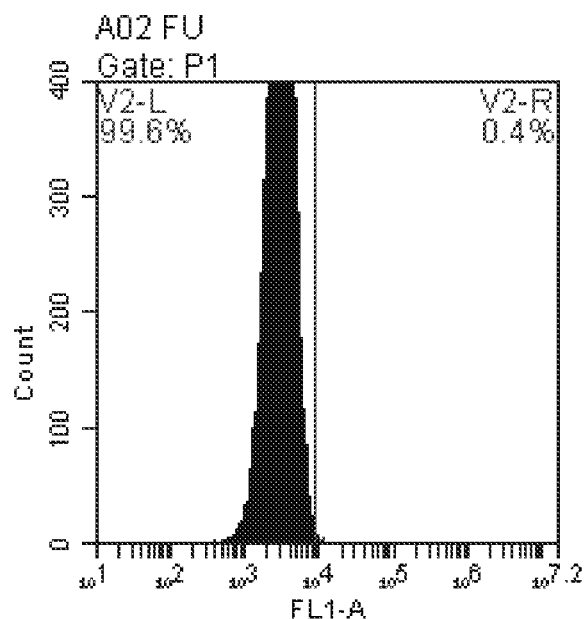
Figure 77C:
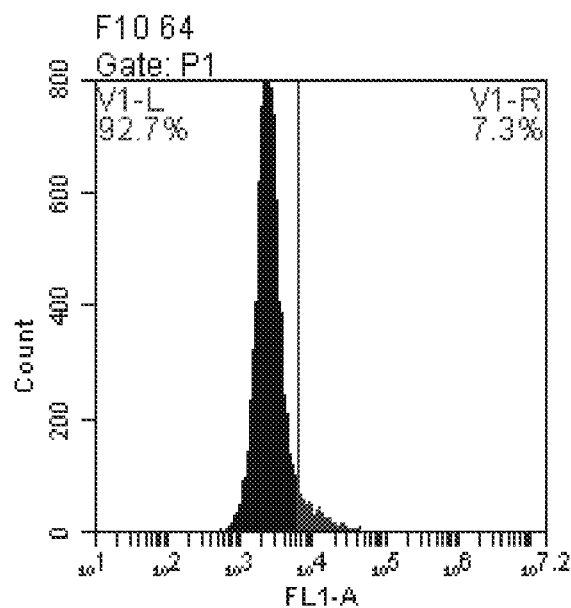
Figure 78A:
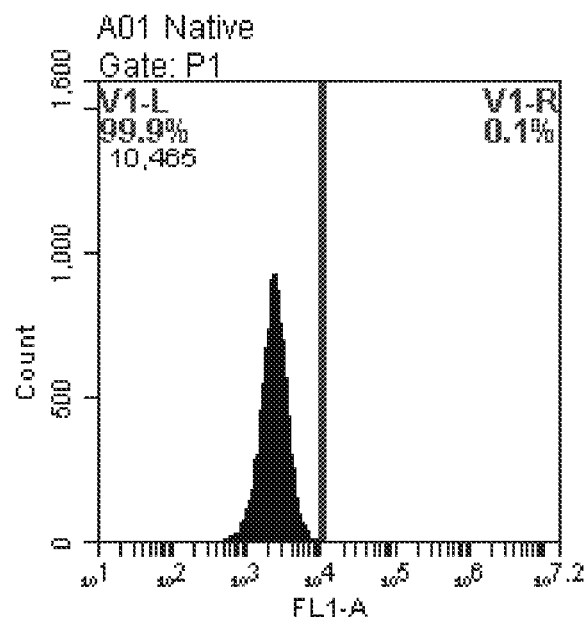
Figure 78B:
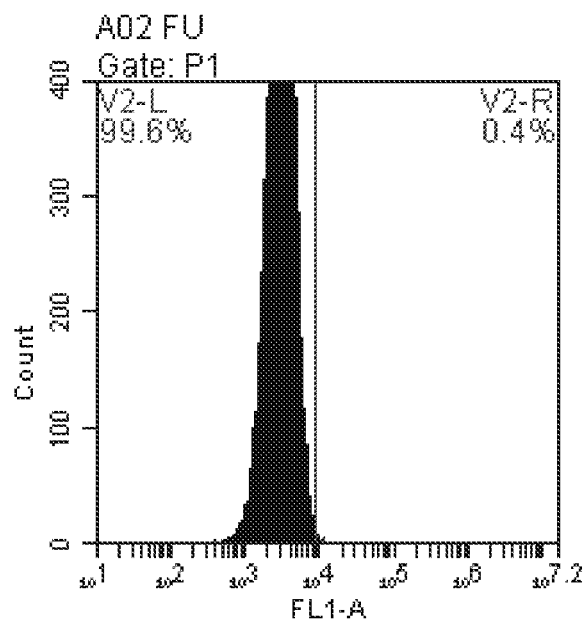
Figure 78C:
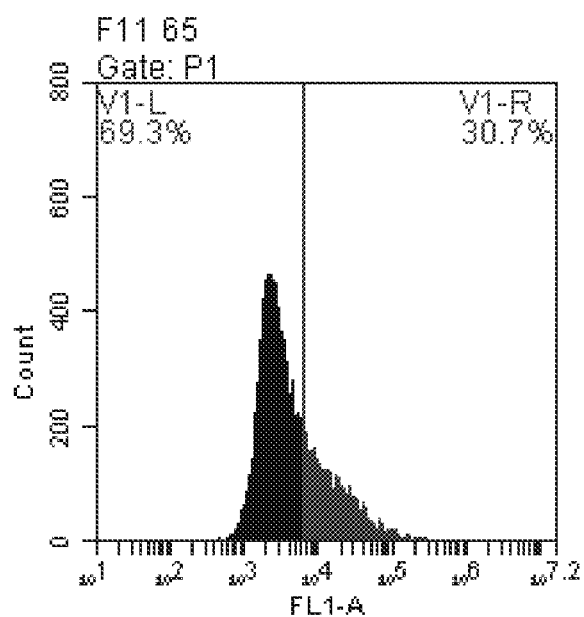
Figure 79A:
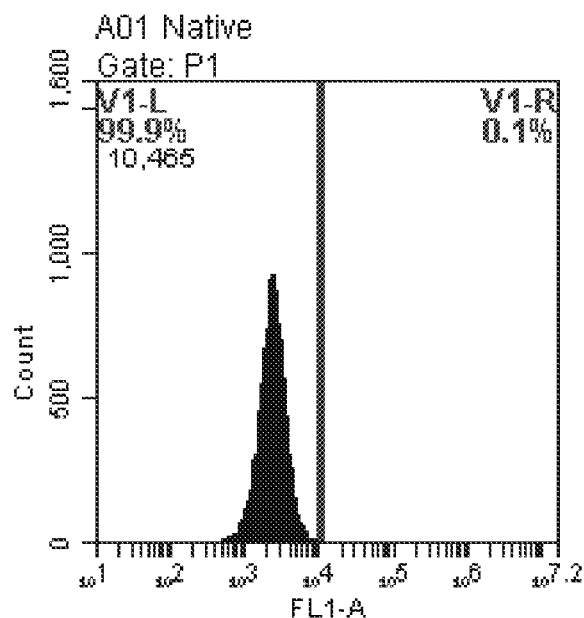
Figure 79B:
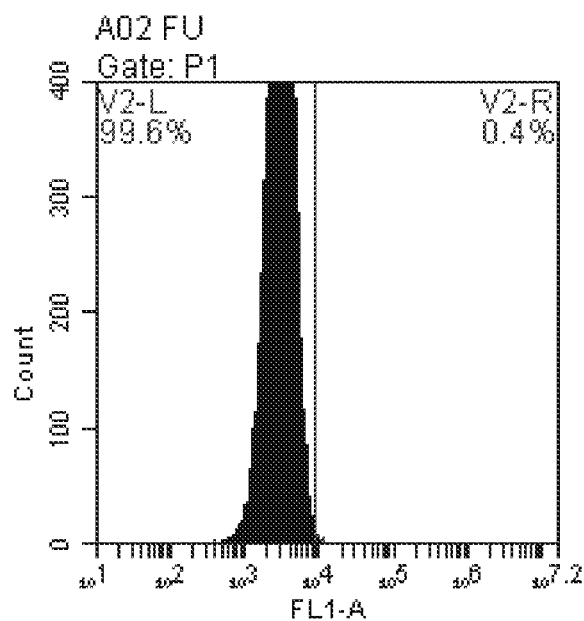
Figure 79C:
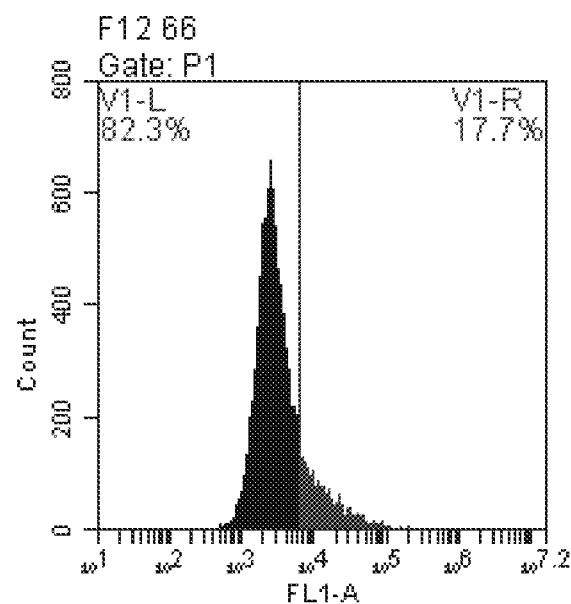
Figure 80A:
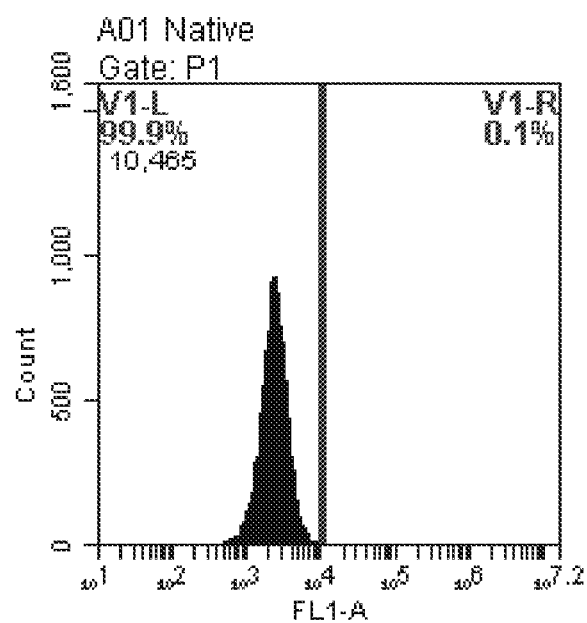
Figure 80B:
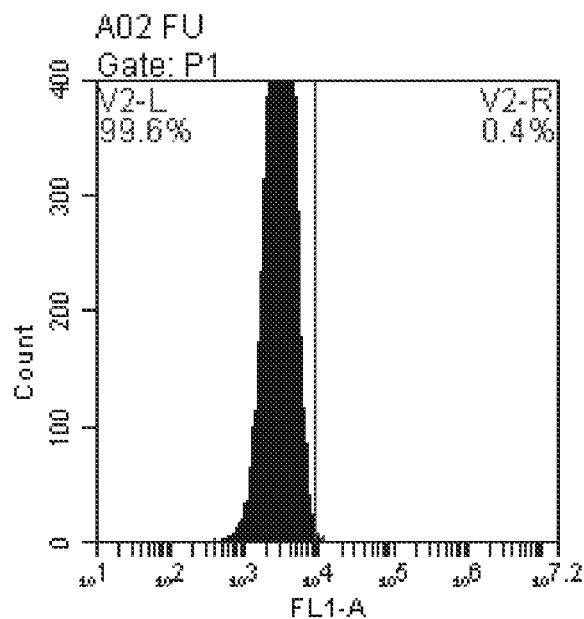
Figure 80C:
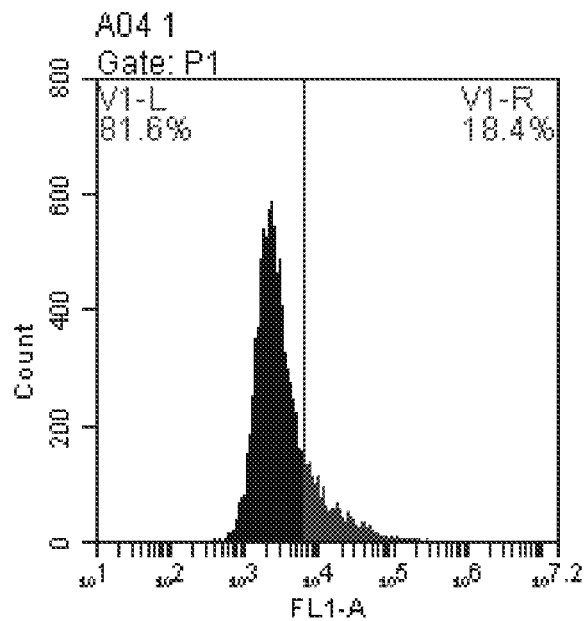
Figure 81A:
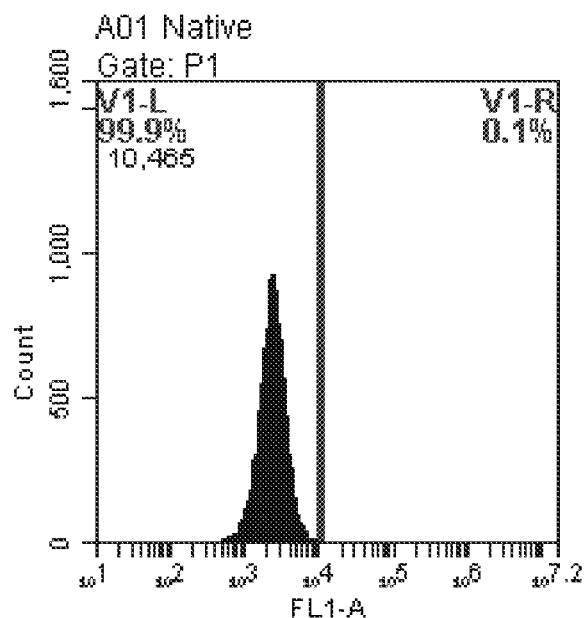
Figure 81B:
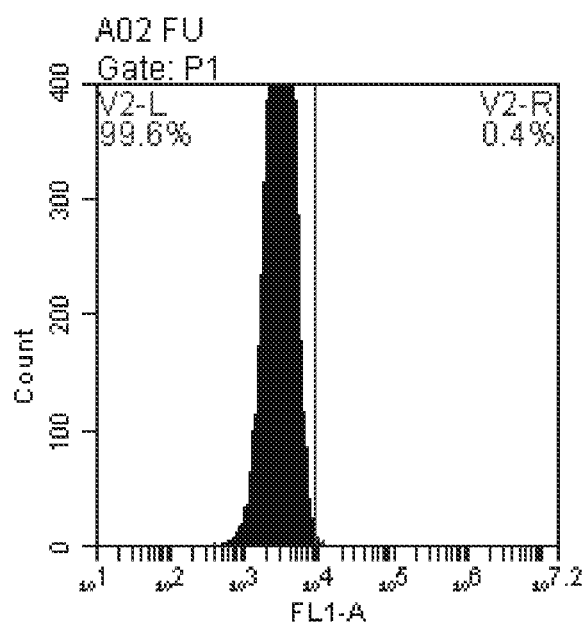
Figure 81C:
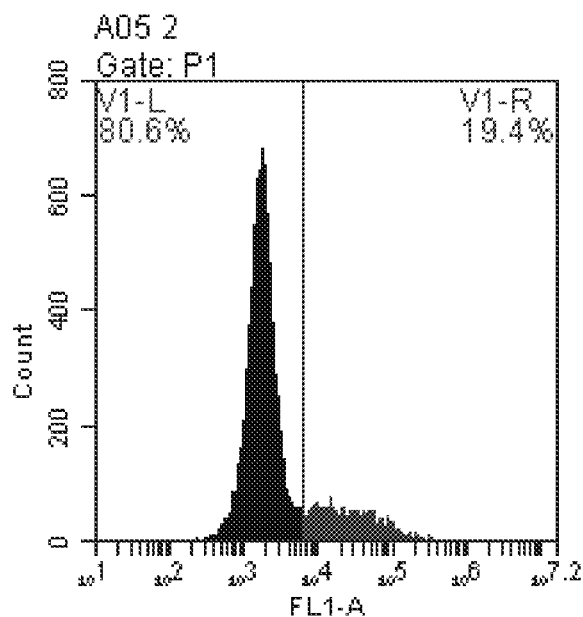
Figure 82A:
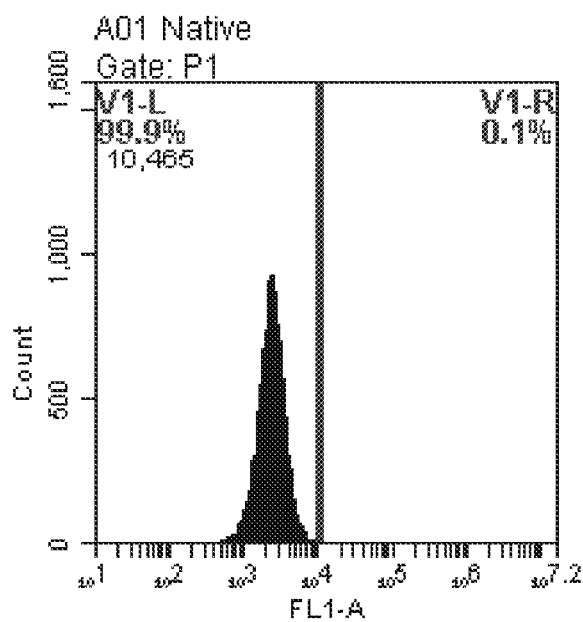
Figure 82B:
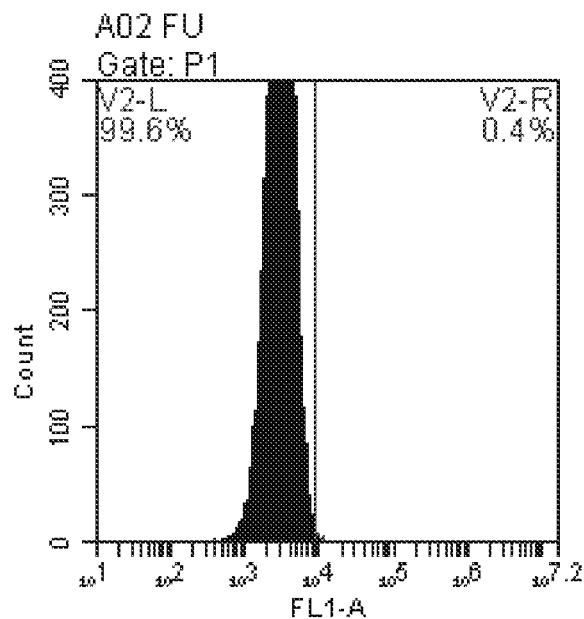
Figure 82C:
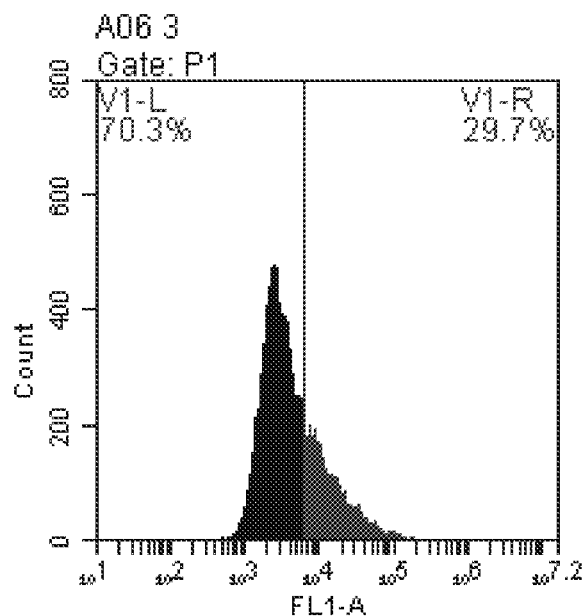
Figure 83A:
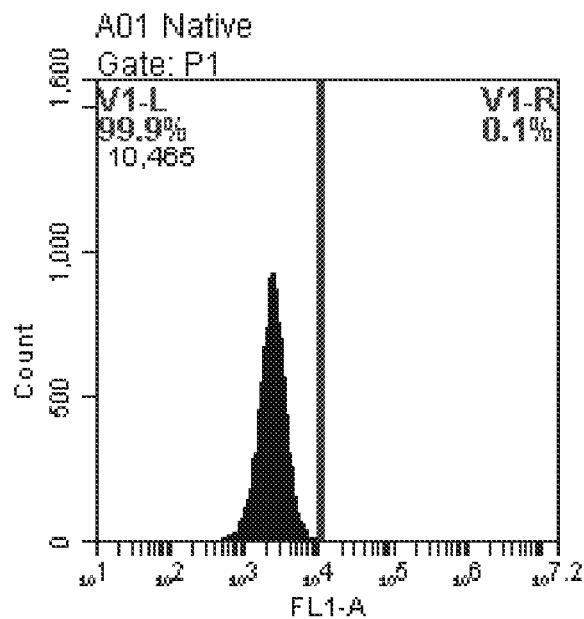
Figure 83B:
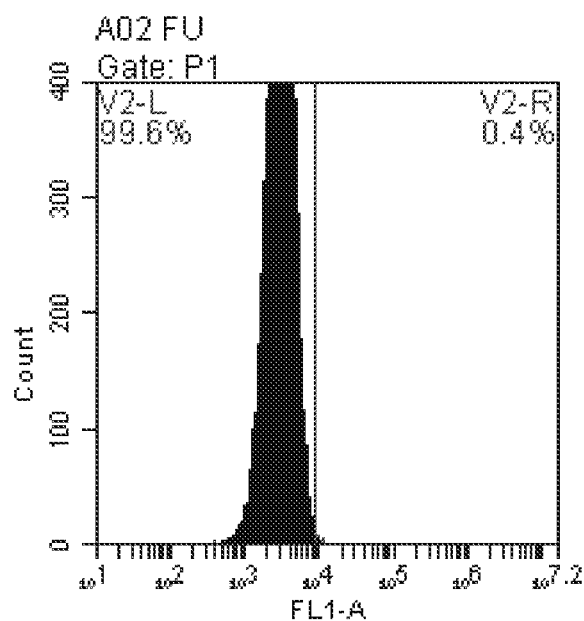
Figure 83C:
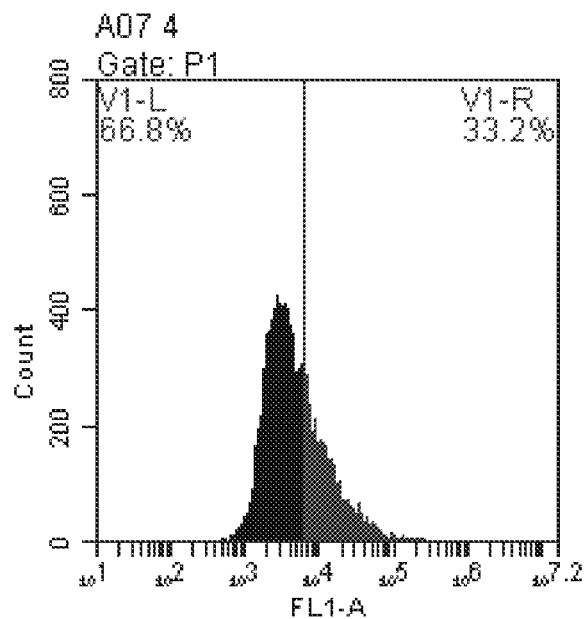
Figure 84A:
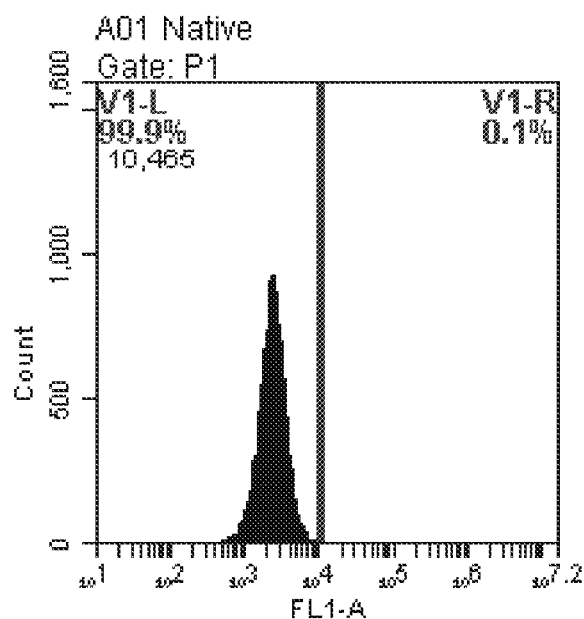
Figure 84B:
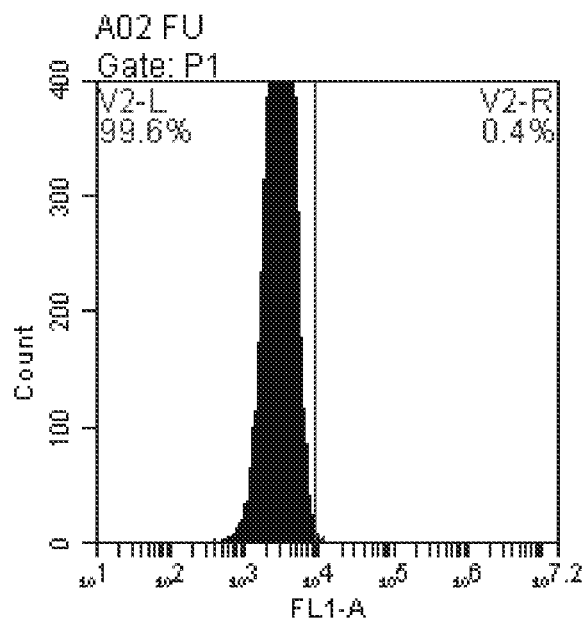
Figure 84C:
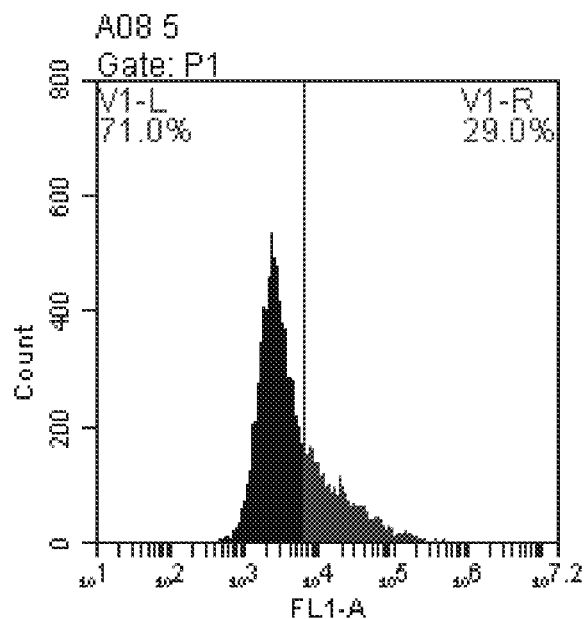
Figure 85A:
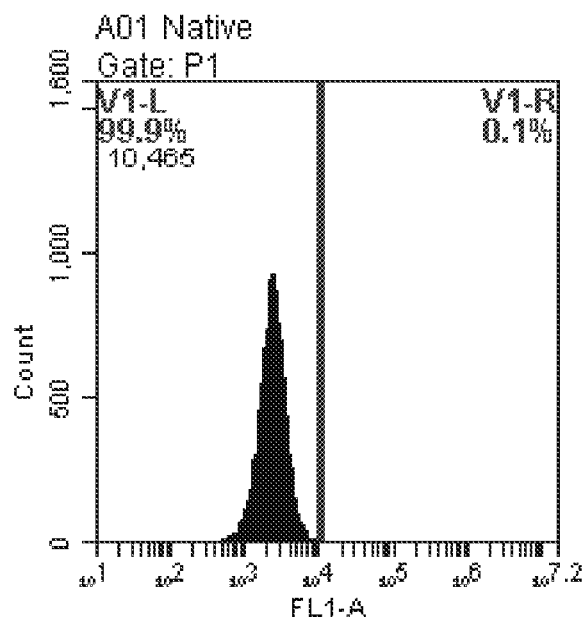
Figure 85B:
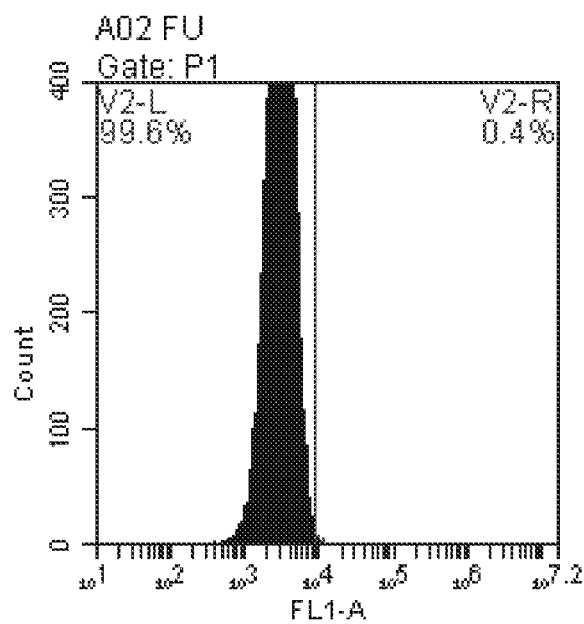
Figure 85C:
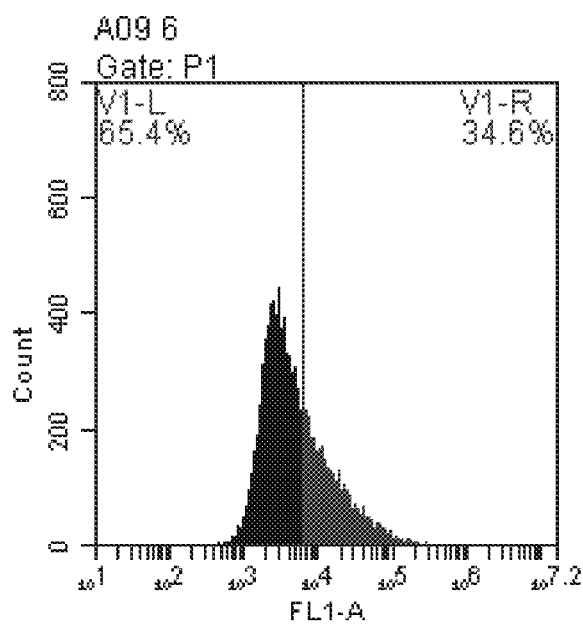
Figure 86A:
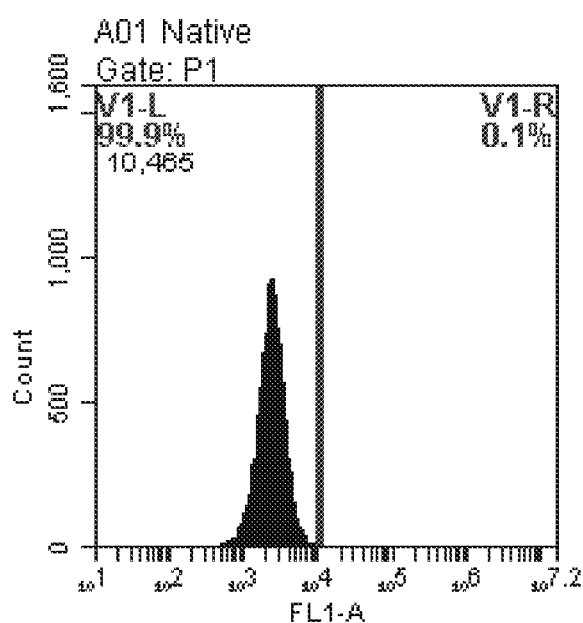
Figure 86B:
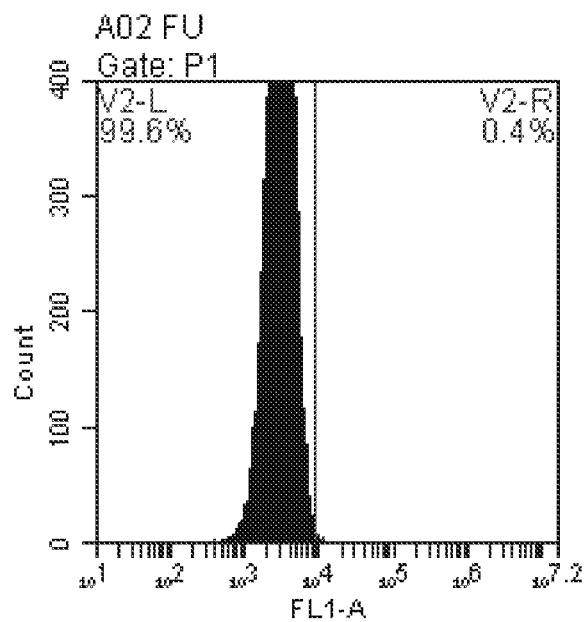
Figure 86C:
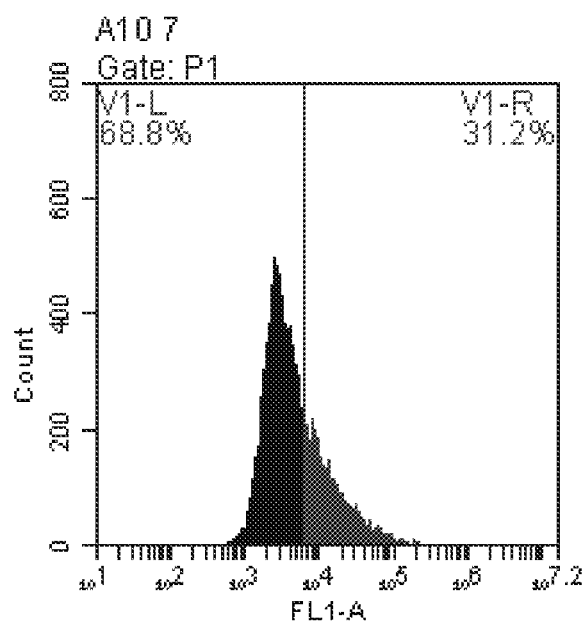
Figure 87A:
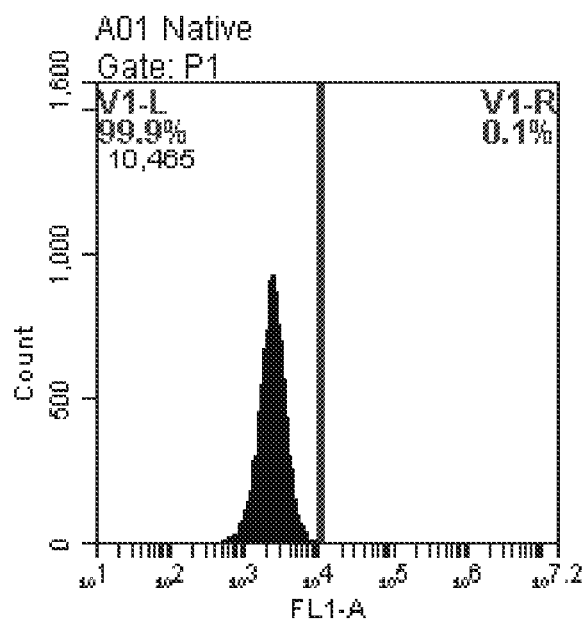
Figure 87B:
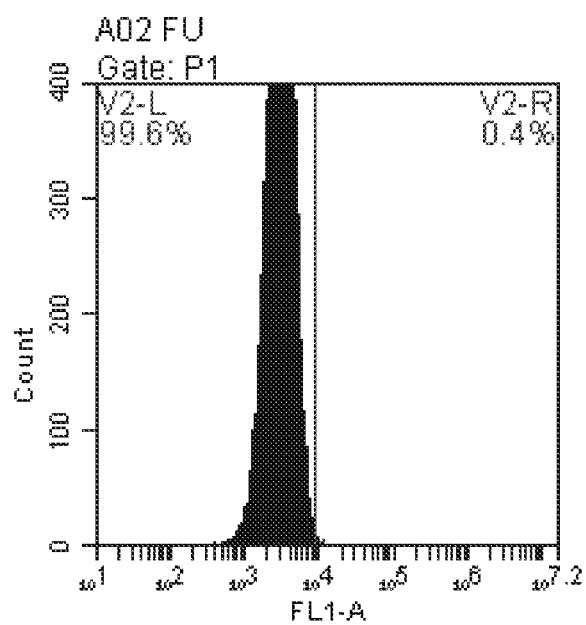
Figure 87C:
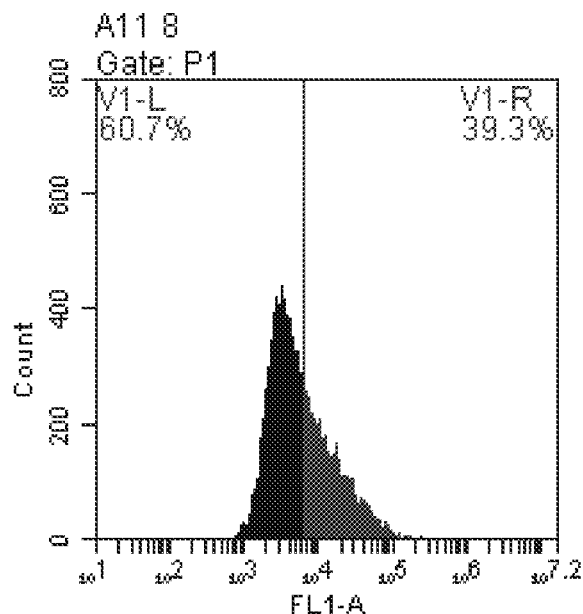
Figure 88A:
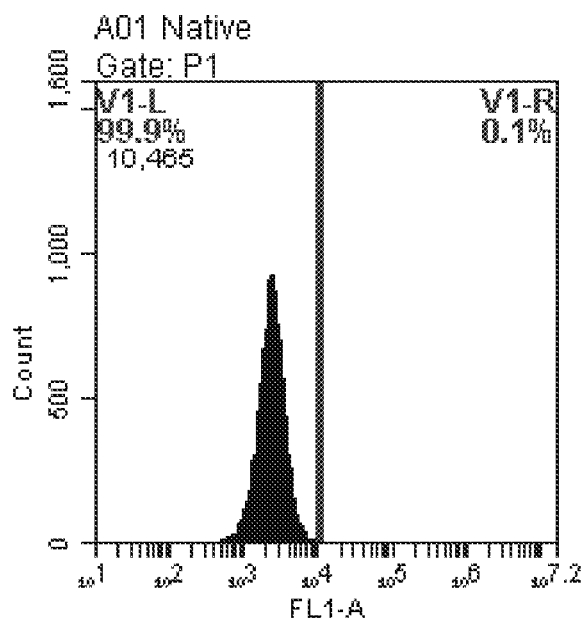
Figure 88B:
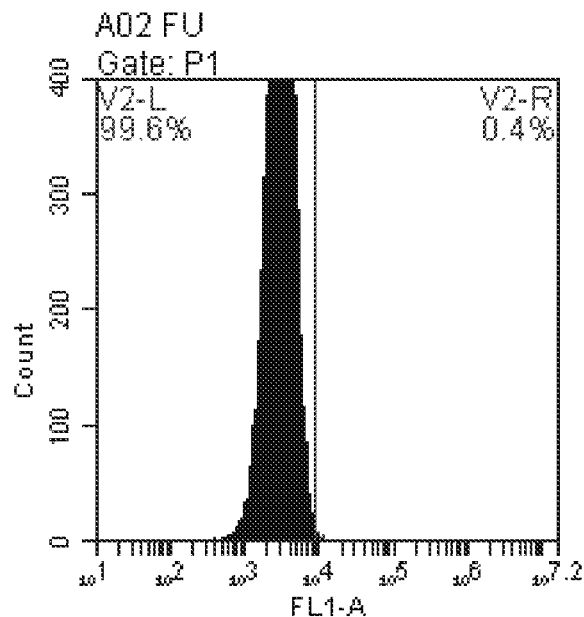
Figure 88C:
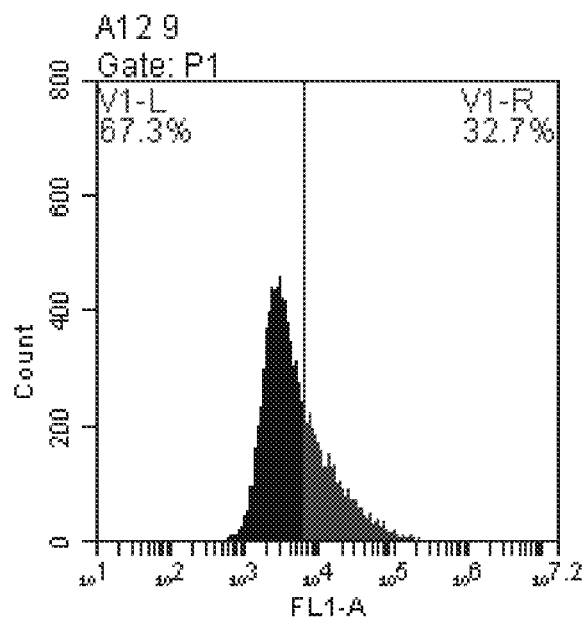
Figure 89A:
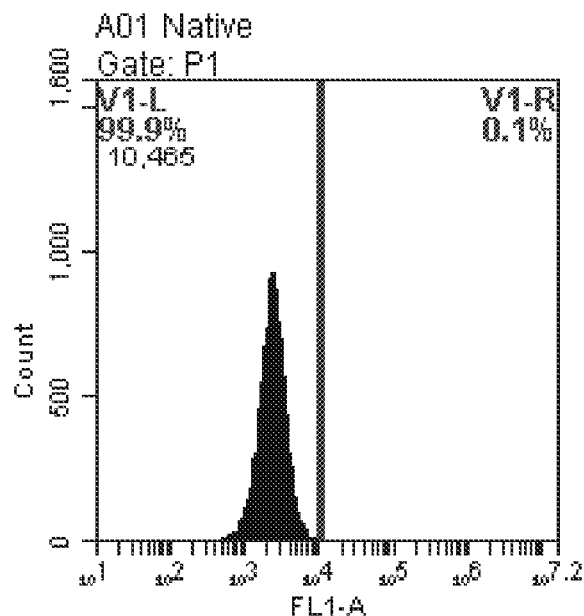
Figure 89B:
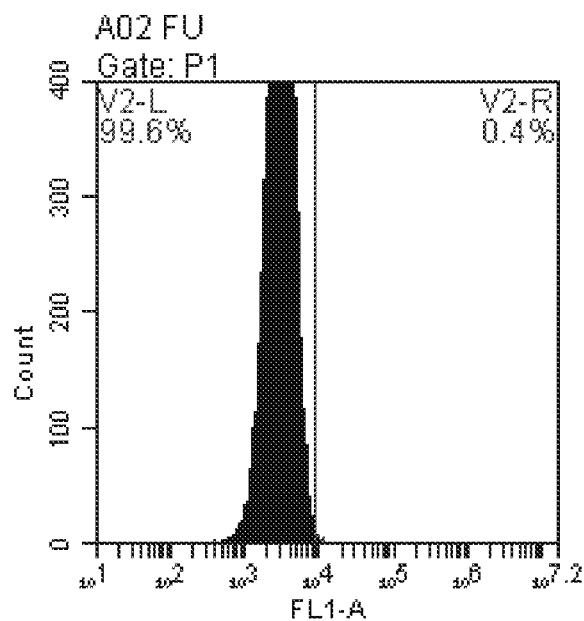
Figure 89C:
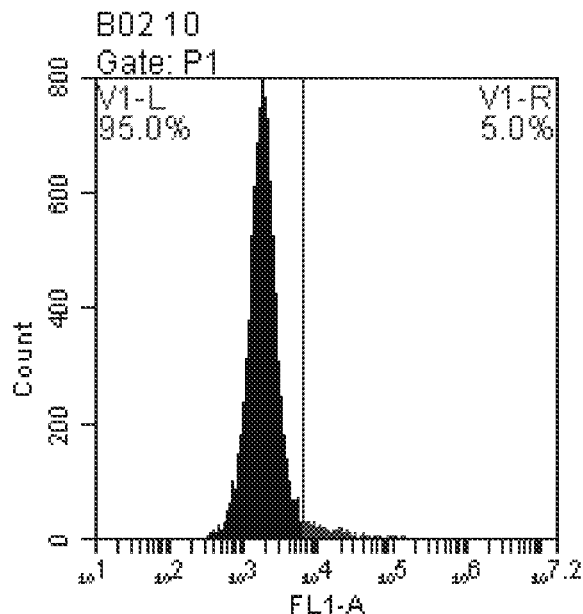
Figure 90A:
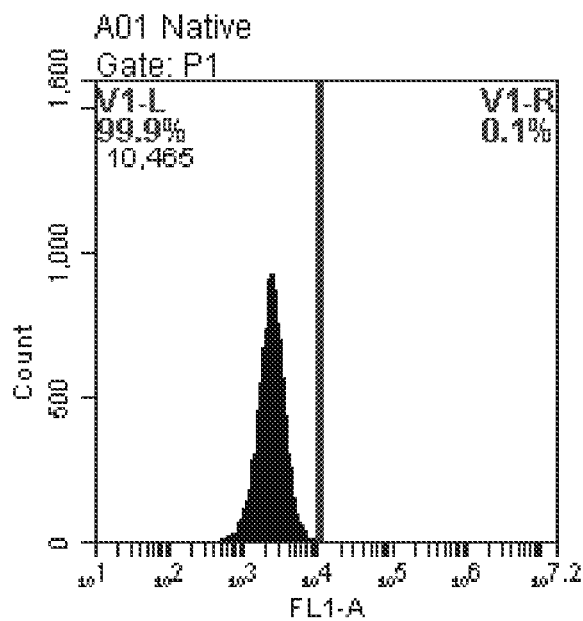
Figure 90B:
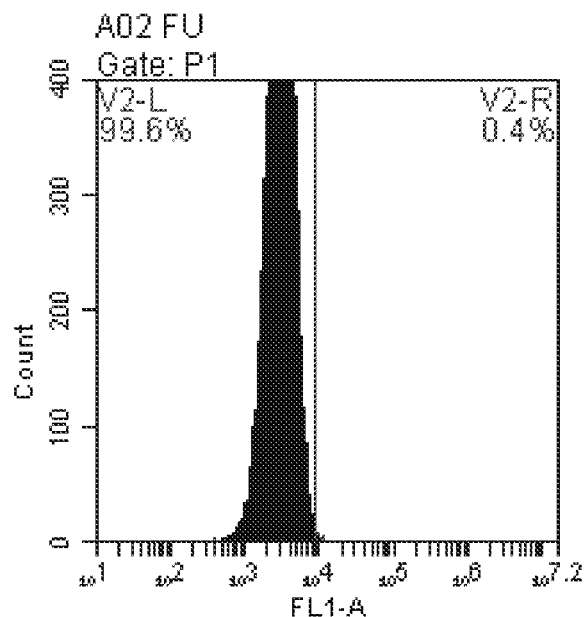
Figure 90C:
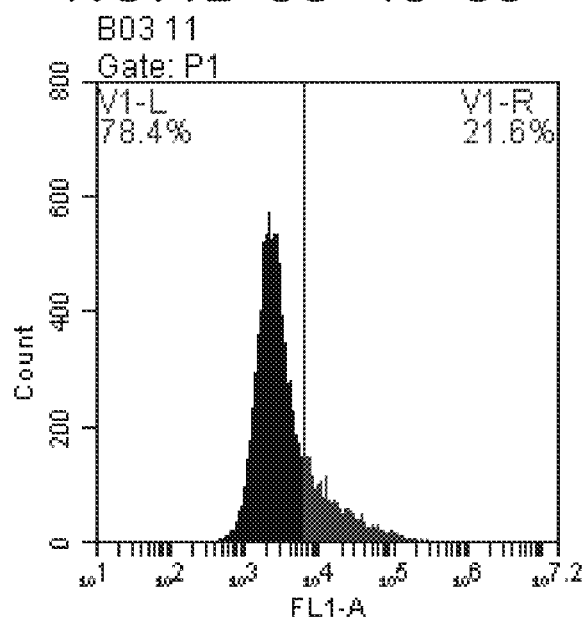
Figure 91A:
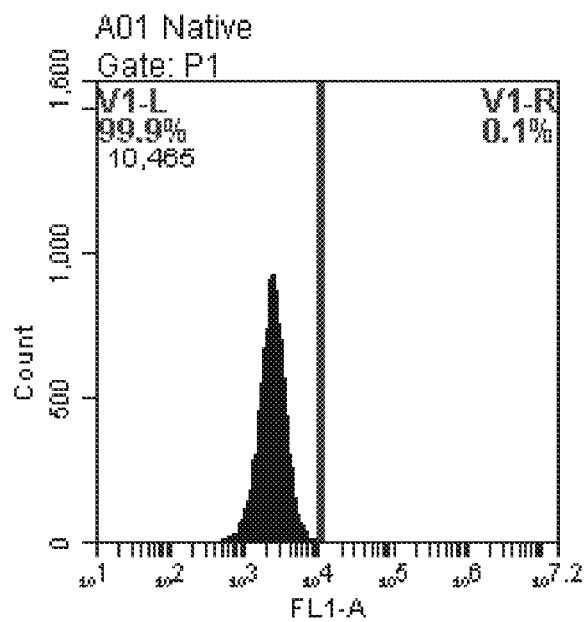
Figure 91B:
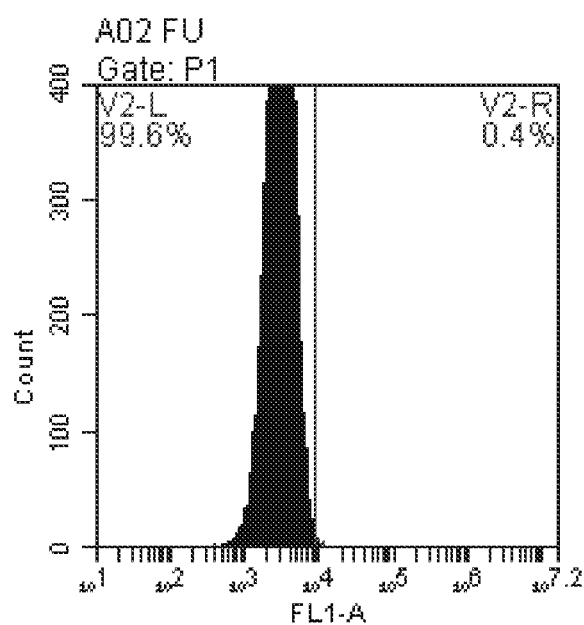
Figure 91C:
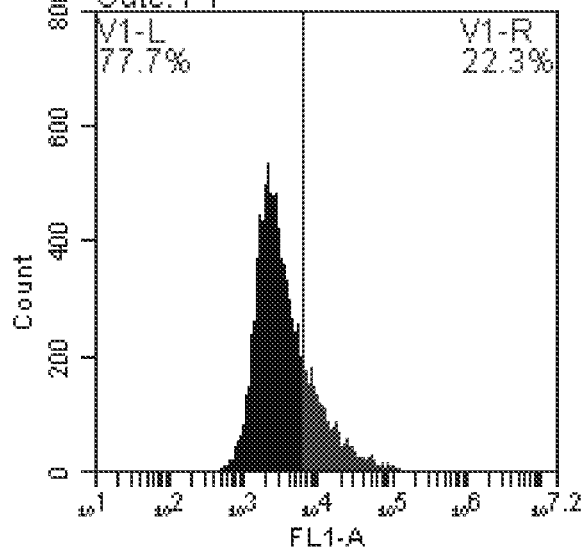
Figure 92A:
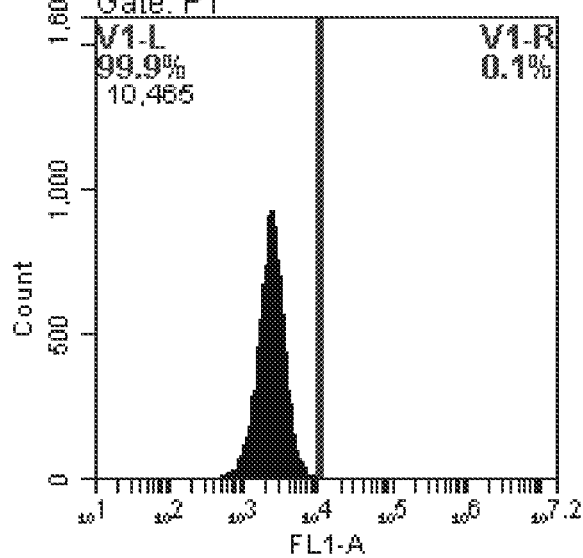
Figure 92B:
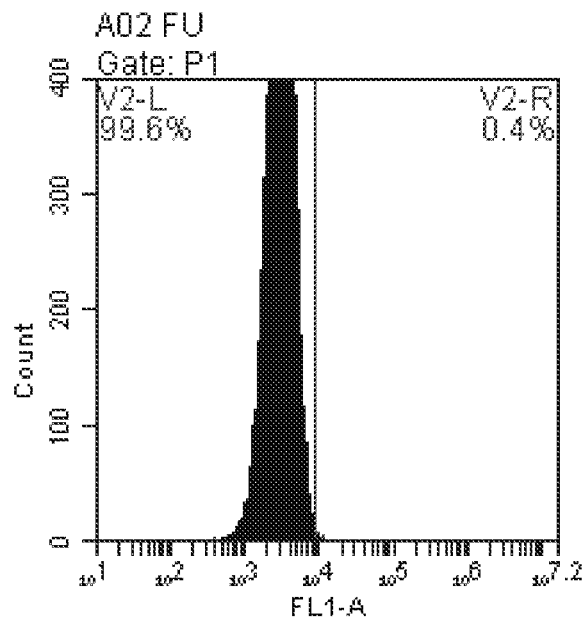
Figure 92C:
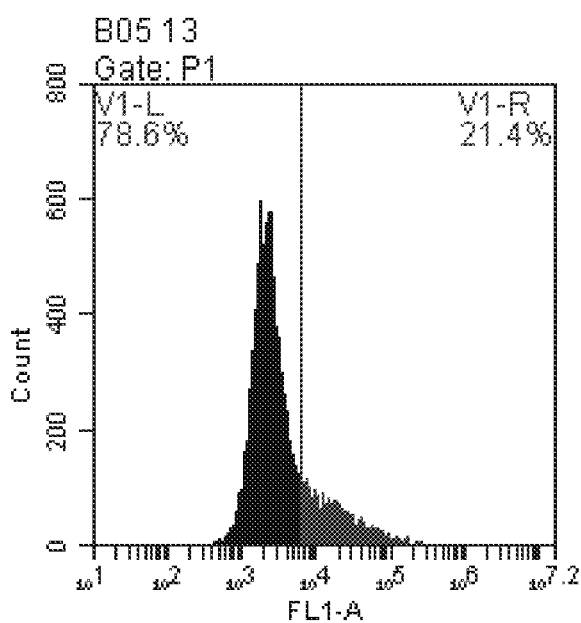
Figure 93A:
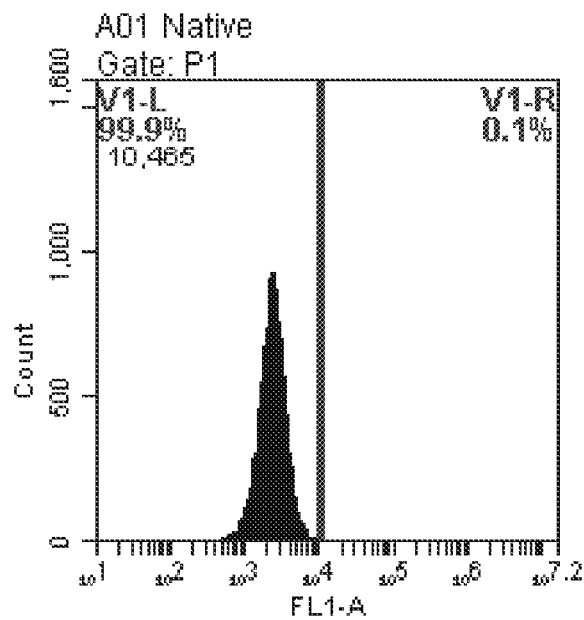
Figure 93B:
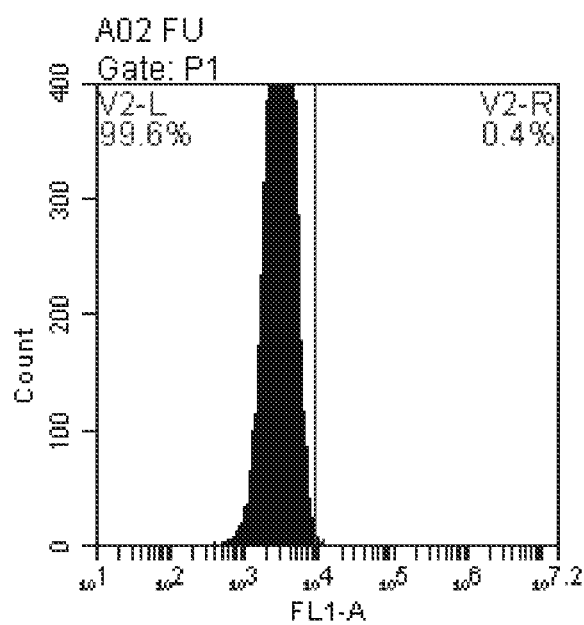
Figure 93C:
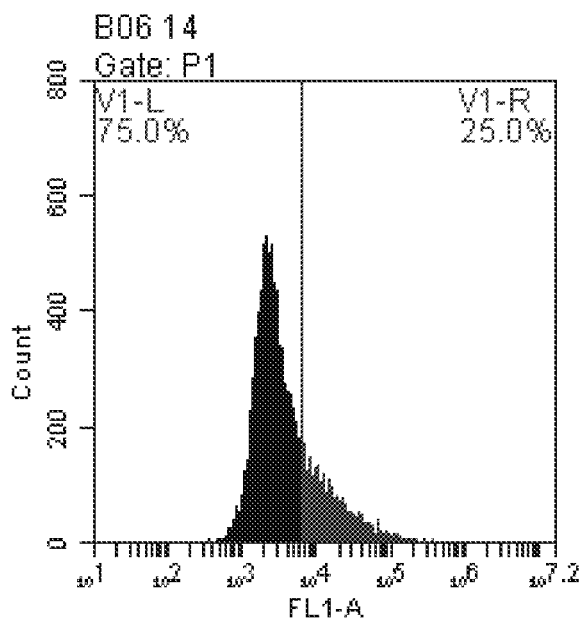
Figure 94A:
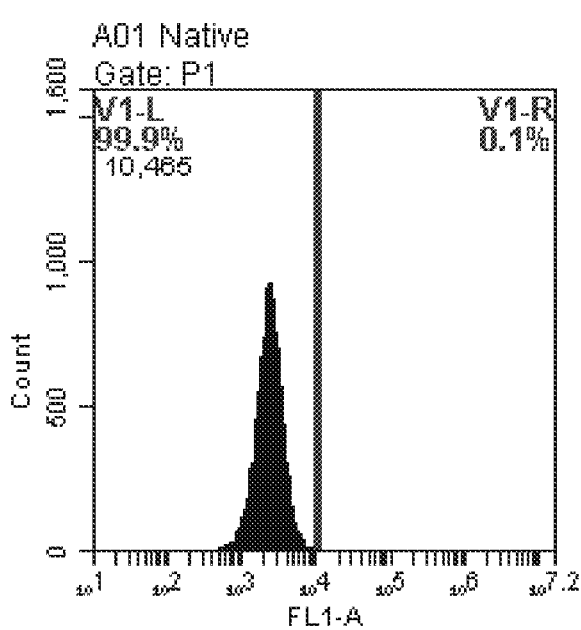
Figure 94B:
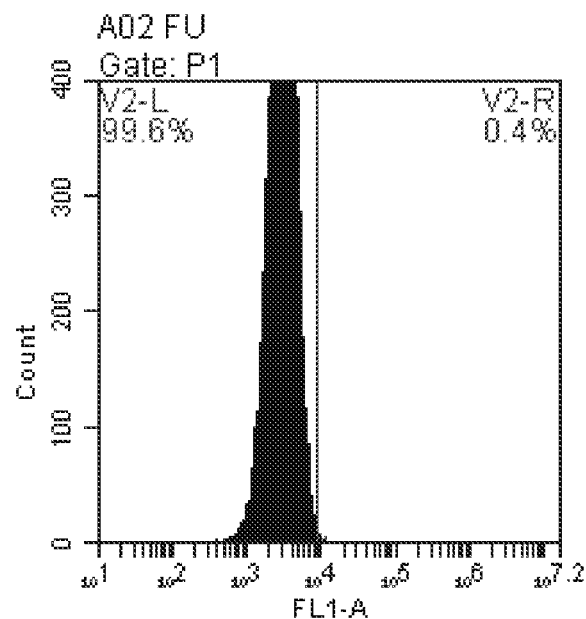
Figure 94C:
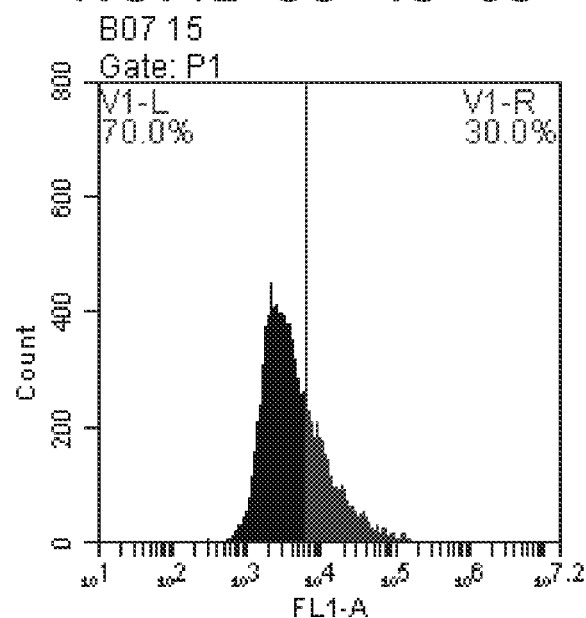
Figure 95A:
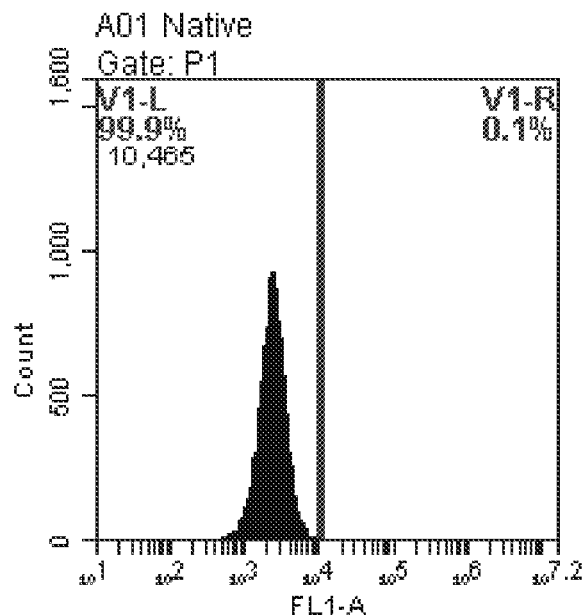
Figure 95B:
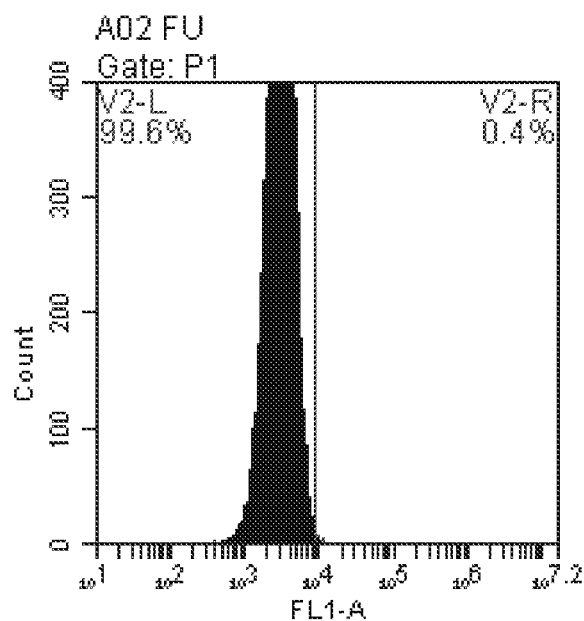
Figure 95C:
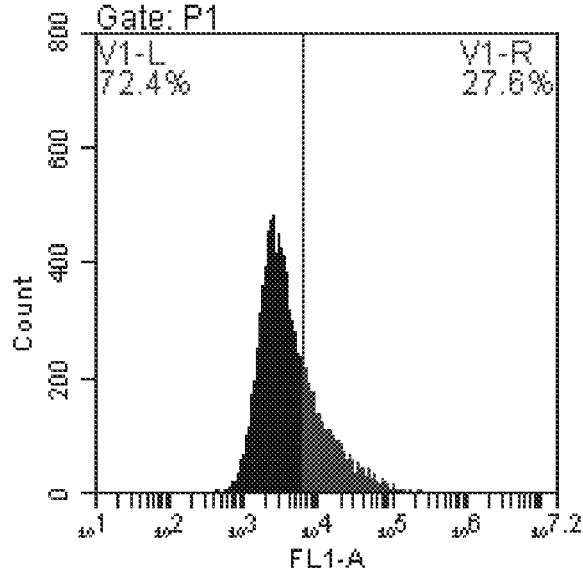
Figure 96A:
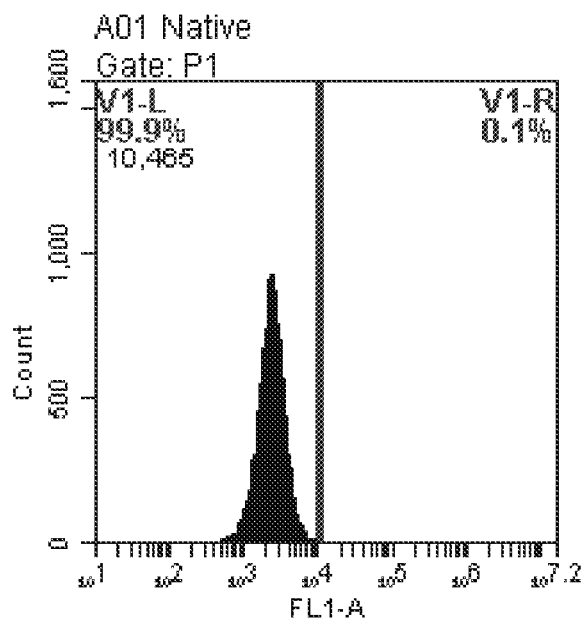
Figure 96B:
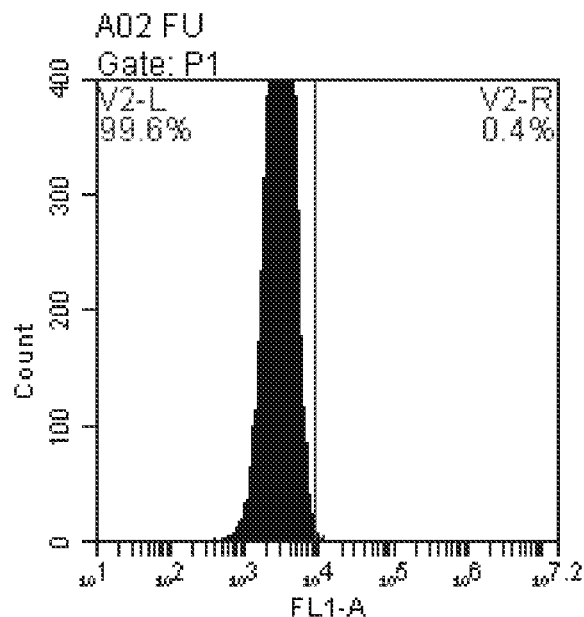
Figure 96C:
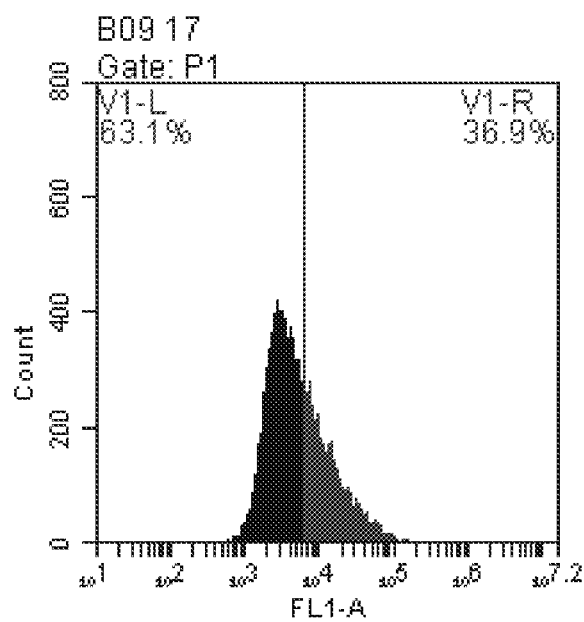
Figure 97A:
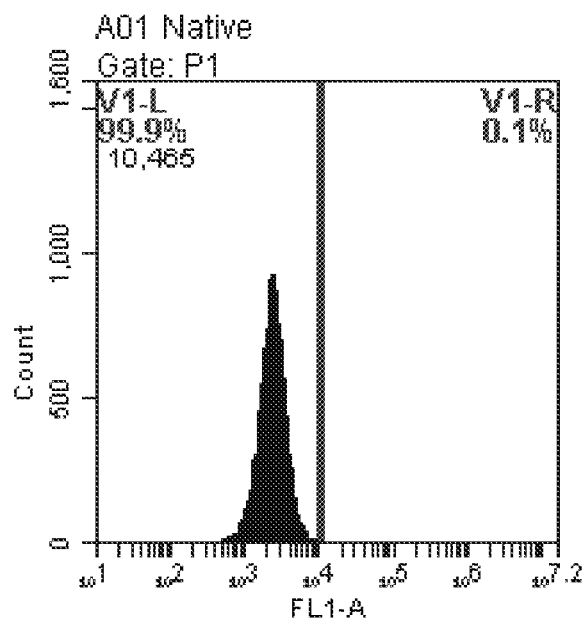
Figure 97B:
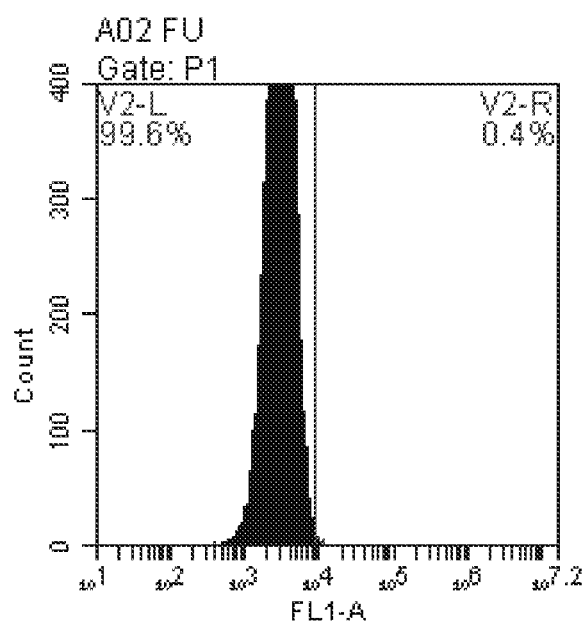
Figure 97C:
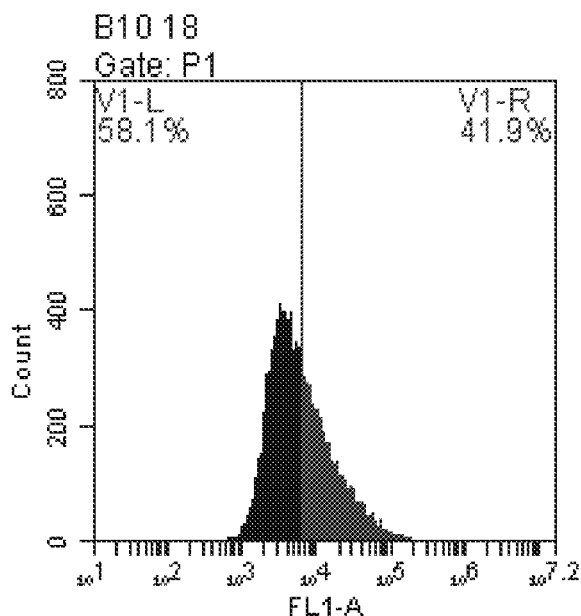
Figure 98A:
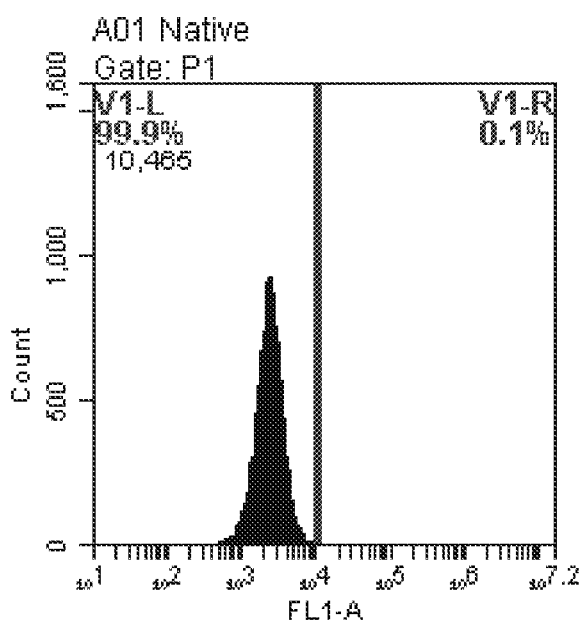
Figure 98B:
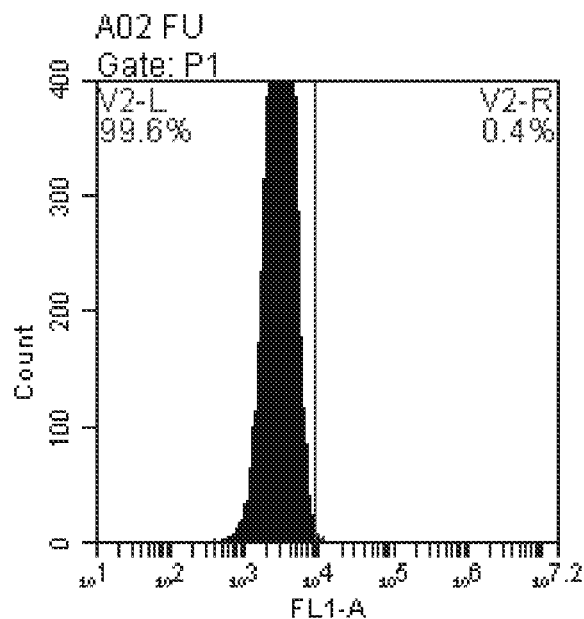
Figure 98C:
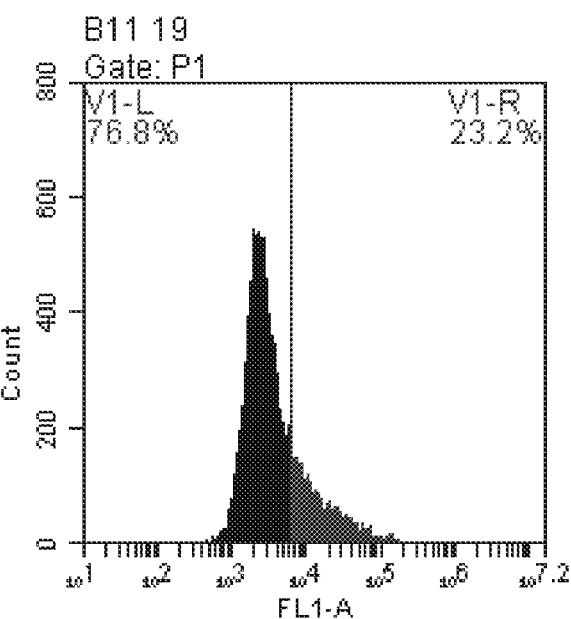
Figure 99A:
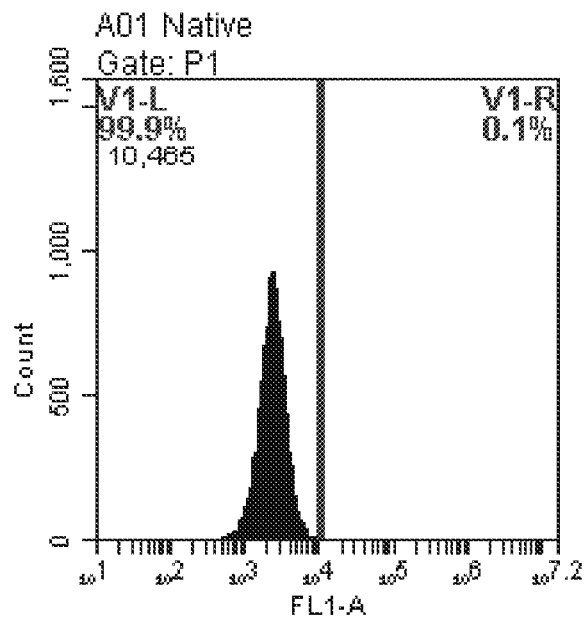
Figure 99B:
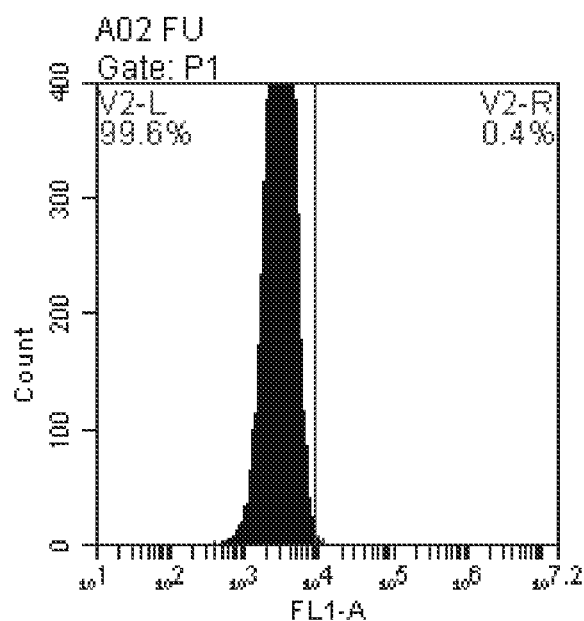
Figure 99C:
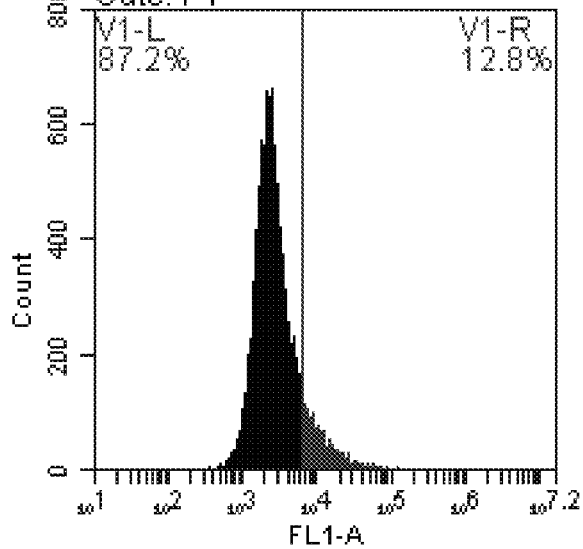
Figure 100:
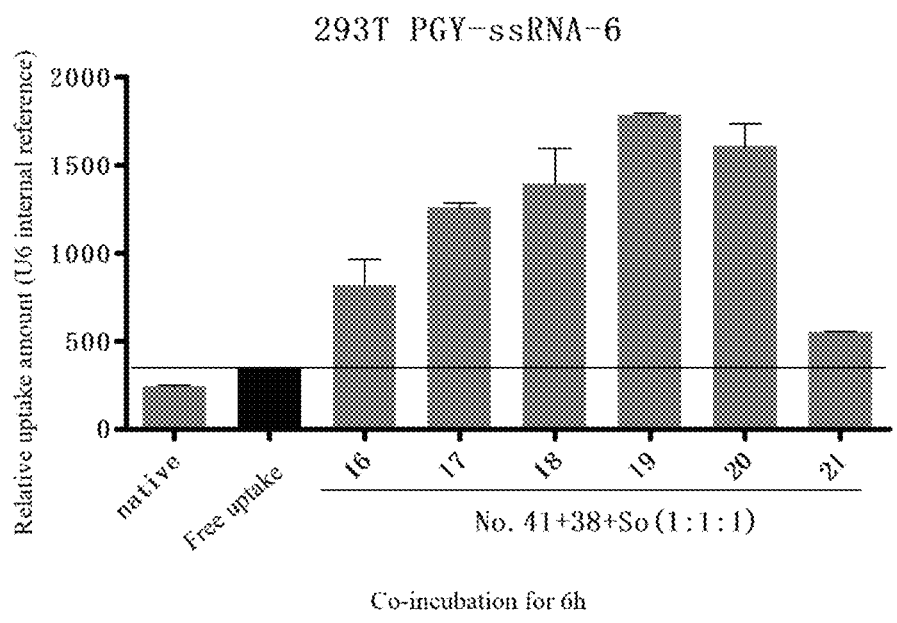
Figure 101:
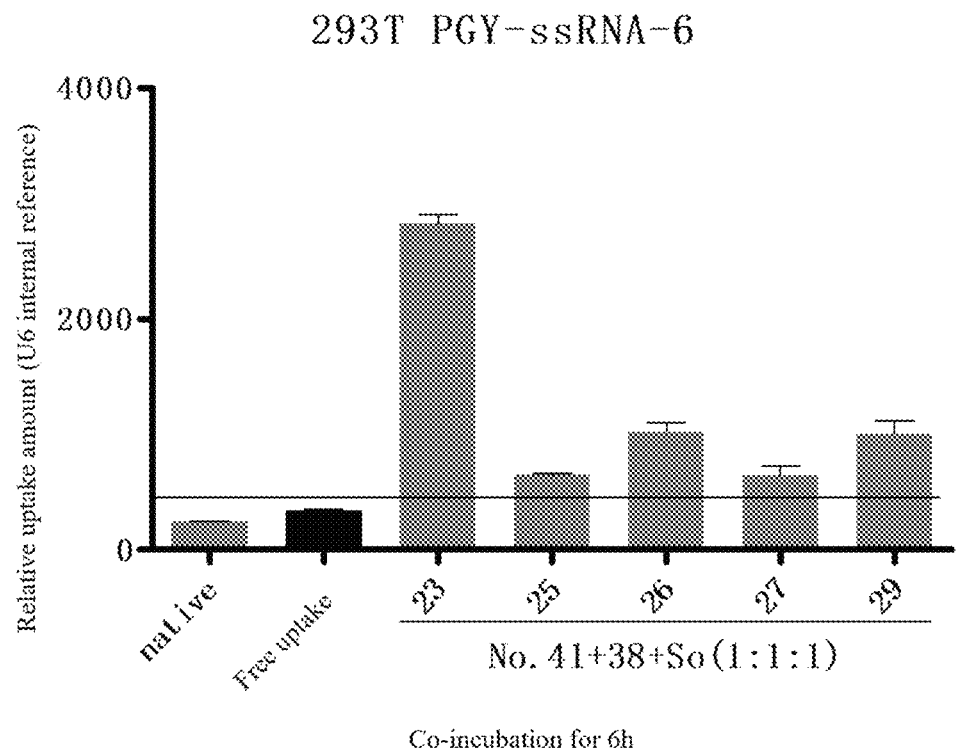
Figure 102:
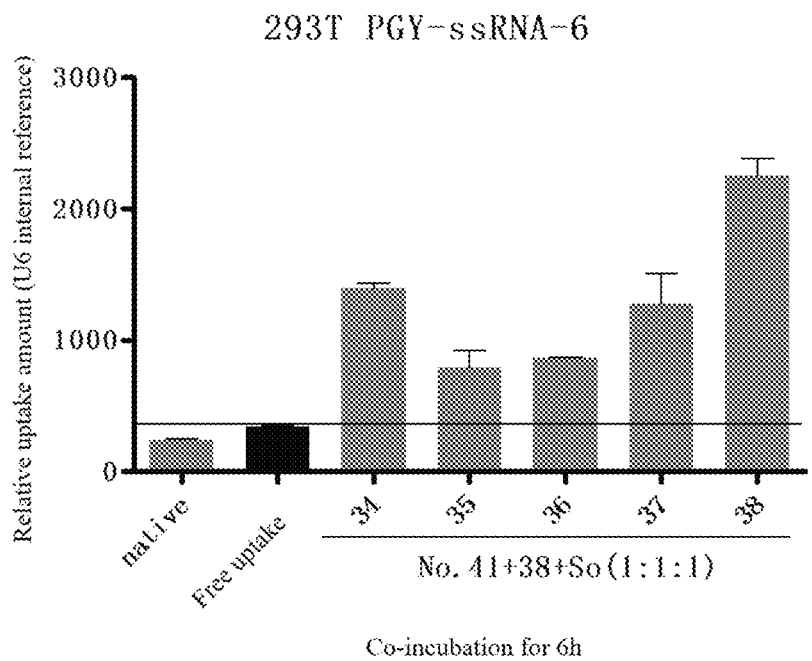
Figure 103:
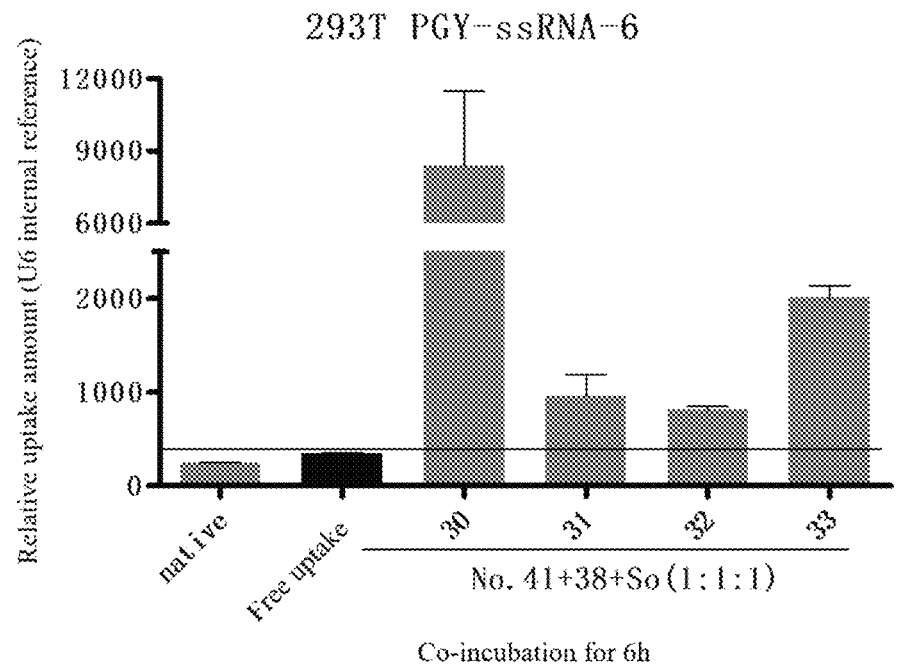
Figure 104:
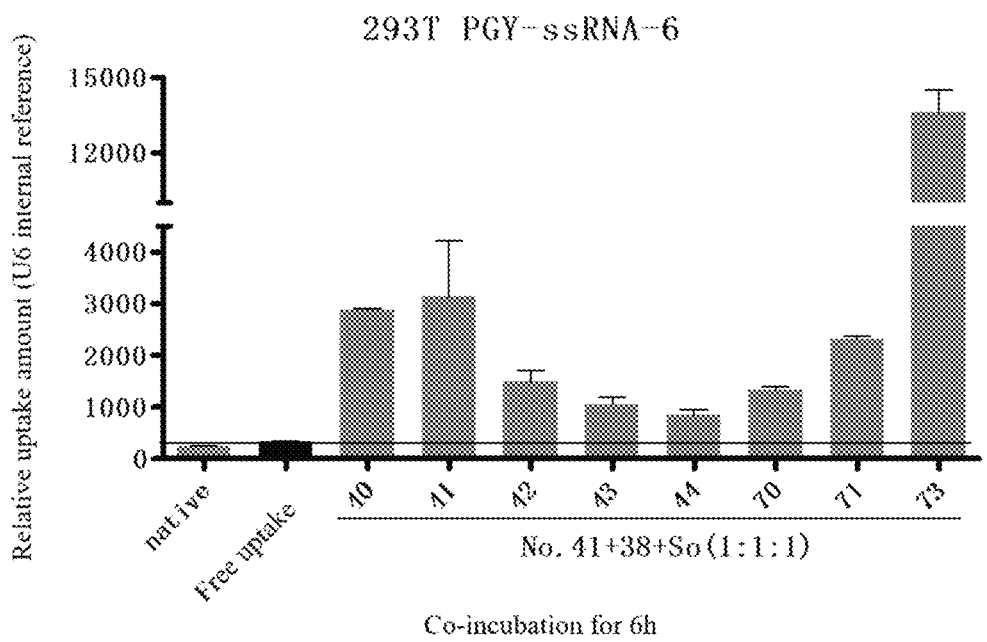

FIG. 1a-e: Different concentrations of sphingosine derivative So-1 deliver single-stranded PGY-sRNA-6 into 293T cells;

FIG. 2a-e: Different concentrations of sphingosine derivative So-3 deliver single-stranded PGY-sRNA-6 into 293T cells;

FIG. 3a-e: Different concentrations of sphingosine derivative So-4 deliver single-stranded PGY-sRNA-6 into 293T cells;

FIG. 4a-e: Different concentrations of sphingosine derivative So-5 deliver single-stranded PGY-sRNA-6 into 293T cells;

FIG. 5a-e: Different concentrations of sphingosine derivative So-7 deliver single-stranded PGY-sRNA-6 into 293T cells;

FIG. 6a-e: Different concentrations of sphingosine derivative So-8 deliver single-stranded PGY-sRNA-6 into 293T cells;

FIG. 7a-e: Different concentrations of sphingosine derivative So-9 deliver single-stranded PGY-sRNA-6 into 293T cells;

FIG. 8a-e: Different concentrations of sphingosine derivative So-10 deliver single-stranded PGY-sRNA-6 into 293T cells;

FIG. 9a-e: Different concentrations of sphingosine derivative So-11 deliver single-stranded PGY-sRNA-6 into 293T cells;

FIG. 10a-e: Different concentrations of sphingosine derivative So-12 deliver single-stranded PGY-sRNA-6 into 293T cells;

FIG. 11a-e: Different concentrations of sphingosine derivative So-13 deliver single-stranded PGY-sRNA-6 into 293T cells;

FIG. 12a-e: Different concentrations of sphingosine derivative So-14 deliver single-stranded PGY-sRNA-6 into 293T cells;

FIG. 13a-e: Different concentrations of sphingosine derivative So-15 deliver single-stranded PGY-sRNA-6 into 293T cells;

FIG. 14a-e: Different concentrations of sphingosine derivative So-26 deliver single-stranded PGY-sRNA-6 into 293T cells;

FIG. 15a-e: Different concentrations of sphingosine derivative So-46 deliver single-stranded PGY-sRNA-6 into 293T cells;

FIG. 16a-e: Different concentrations of sphingosine derivative So-49 deliver single-stranded PGY-sRNA-6 into 293T cells;

FIG. 17a-e: Different concentrations of sphingosine derivative So-53 deliver single-stranded PGY-sRNA-6 into 293T cells;

FIG. 18a-e: Different concentrations of sphingosine derivative So-60 deliver single-stranded PGY-sRNA-6 into 293T cells;

FIG. 19a-e: Different concentrations of sphingosine derivative So-61 deliver single-stranded PGY-sRNA-6 into 293T cells;

FIG. 20a-e: Different concentrations of sphingosine derivative So-62 deliver single-stranded PGY-sRNA-6 into 293T cells;

FIG. 21a-e: Different concentrations of sphingosine derivative So-63 deliver single-stranded PGY-sRNA-6 into 293T cells;

FIG. 22a-e: Different concentrations of sphingosine derivative So-64 deliver single-stranded PGY-sRNA-6 into 293T cells;

FIG. 23a-e: Different concentrations of sphingosine derivative So-65 deliver single-stranded PGY-sRNA-6 into 293T cells;

FIG. 24a-e: Different concentrations of sphingosine derivative So-66 deliver single-stranded PGY-sRNA-6 into 293T cells;

FIG. 25a-e: Different concentrations of sphingosine derivative So-67 deliver single-stranded PGY-sRNA-6 into 293T cells;

FIG. 26a-e: Different concentrations of sphingosine derivative So-68 deliver single-stranded PGY-sRNA-6 into 293T cells;

FIG. 27a-e: Different concentrations of sphingosine derivative So-69 deliver single-stranded PGY-sRNA-6 into 293T cells;

FIG. 28a-e: Different concentrations of sphingosine derivative So-70 deliver single-stranded PGY-sRNA-6 into 293T cells;

FIG. 29a-e: Different concentrations of sphingosine derivative So-71 deliver single-stranded PGY-sRNA-6 into 293T cells;

FIG. 30a-e: Different concentrations of sphingosine derivative So-72 deliver single-stranded PGY-sRNA-6 into 293T cells;

FIG. 31a-e: Different concentrations of sphingosine derivative So-73 deliver single-stranded PGY-sRNA-6 into 293T cells;

FIG. 32a-e: Different concentrations of sphingosine derivative So-74 deliver single-stranded PGY-sRNA-6 into 293T cells;

FIG. 33a-e: Different concentrations of sphingosine derivative So-75 deliver single-stranded PGY-sRNA-6 into 293T cells;

FIG. 34a-c: No. 41+No. 38+sphingosine derivative So-1 mixture delivers single-stranded PGY-sRNA-6 into THP-1 cells;

FIG. 35a-c: No. 41+No. 38+sphingosine derivative So-2 mixture delivers single-stranded PGY-sRNA-6 into THP-1 cells;

FIG. 36a-c: No. 41+No. 38+sphingosine derivative So-3 mixture delivers single-stranded PGY-sRNA-6 into THP-1 cells;

FIG. 37a-c: No. 41+No. 38+sphingosine derivative So-4 mixture delivers single-stranded PGY-sRNA-6 into THP-1 cells;

FIG. 38a-c: No. 41+No. 38+sphingosine derivative So-5 mixture delivers single-stranded PGY-sRNA-6 into THP-1 cells;

FIG. 39a-c: No. 41+No. 38+sphingosine derivative So-6 mixture delivers single-stranded PGY-sRNA-6 into THP-1 cells;

FIG. 40a-c: No. 41+No. 38+sphingosine derivative So-7 mixture delivers single-stranded PGY-sRNA-6 into THP-1 cells;

FIG. 41a-c: No. 41+No. 38+sphingosine derivative So-8 mixture delivers single-stranded PGY-sRNA-6 into THP-1 cells;

FIG. 42a-c: No. 41+No. 38+sphingosine derivative So-9 mixture delivers single-stranded PGY-sRNA-6 into THP-1 cells;

FIG. 43a-c: No. 41+No. 38+sphingosine derivative So-10 mixture delivers single-stranded PGY-sRNA-6 into THP-1 cells;

FIG. 44a-c: No. 41+No. 38+sphingosine derivative So-11 mixture delivers single-stranded PGY-sRNA-6 into THP-1 cells;

FIG. 45a-c: No. 41+No. 38+sphingosine derivative So-12 mixture delivers single-stranded PGY-sRNA-6 into THP-1 cells;

FIG. 46a-c: No. 41+No. 38+sphingosine derivative So-13 mixture delivers single-stranded PGY-sRNA-6 into THP-1 cells;

FIG. 47a-c: No. 41+No. 38+sphingosine derivative So-14 mixture delivers single-stranded PGY-sRNA-6 into THP-1 cells;

FIG. 48a-c: No. 41+No. 38+sphingosine derivative So-15 mixture delivers single-stranded PGY-sRNA-6 into THP-1 cells;

FIG. 49a-c: No. 41+No. 38+sphingosine derivative So-45 mixture delivers single-stranded PGY-sRNA-6 into THP-1 cells;

FIG. 50a-c: No. 41+No. 38+sphingosine derivative So-46 mixture delivers single-stranded PGY-sRNA-6 into THP-1 cells;

FIG. 51a-c: No. 41+No. 38+sphingosine derivative So-47 mixture delivers single-stranded PGY-sRNA-6 into THP-1 cells;

FIG. 52a-c: No. 41+No. 38+sphingosine derivative So-48 mixture delivers single-stranded PGY-sRNA-6 into THP-1 cells;

FIG. 53a-c: No. 41+No. 38+sphingosine derivative So-49 mixture delivers single-stranded PGY-sRNA-6 into THP-1 cells;

FIG. 54a-c: No. 41+No. 38+sphingosine derivative So-50 mixture delivers single-stranded PGY-sRNA-6 into THP-1 cells;

FIG. 55a-c: No. 41+No. 38+sphingosine derivative So-51 mixture delivers single-stranded PGY-sRNA-6 into THP-1 cells;

FIG. 56a-c: No. 41+No. 38+sphingosine derivative So-52 mixture delivers single-stranded PGY-sRNA-6 into THP-1 cells;

FIG. 57a-c: No. 41+No. 38+sphingosine derivative So-53 mixture delivers single-stranded PGY-sRNA-6 into THP-1 cells;

FIG. 58a-c: No. 41+No. 38+sphingosine derivative So-54 mixture delivers single-stranded PGY-sRNA-6 into THP-1 cells;

FIG. 59a-c: No. 41+No. 38+sphingosine derivative So-55 mixture delivers single-stranded PGY-sRNA-6 into THP-1 cells;

FIG. 60a-c: No. 41+No. 38+sphingosine derivative So-56 mixture delivers single-stranded PGY-sRNA-6 into THP-1 cells;

FIG. 61a-c: No. 41+No. 38+sphingosine derivative So-57 mixture delivers single-stranded PGY-sRNA-6 into THP-1 cells;

FIG. 62a-c: No. 41+No. 38+sphingosine derivative So-58 mixture delivers single-stranded PGY-sRNA-6 into THP-1 cells;

FIG. 63a-c: No. 41+No. 38+sphingosine derivative So-59 mixture delivers single-stranded PGY-sRNA-6 into THP-1 cells;

FIG. 64a-c: No. 41+No. 38+sphingosine derivative So-60 mixture delivers single-stranded PGY-sRNA-6 into THP-1 cells;

FIG. 65a-c: No. 41+No. 38+sphingosine derivative So-61 mixture delivers single-stranded PGY-sRNA-6 into THP-1 cells;

FIG. 66a-c: No. 41+No. 38+sphingosine derivative So-62 mixture delivers single-stranded PGY-sRNA-6 into THP-1 cells;

FIG. 67a-c: No. 41+No. 38+sphingosine derivative So-63 mixture delivers single-stranded PGY-sRNA-6 into THP-1 cells;

FIG. 68a-c: No. 41+No. 38+sphingosine derivative So-64 mixture delivers single-stranded PGY-sRNA-6 into THP-1 cells;

FIG. 69a-c: No. 41+No. 38+sphingosine derivative So-65 mixture delivers single-stranded PGY-sRNA-6 into THP-1 cells;

FIG. 70a-c: No. 41+No. 38+sphingosine derivative So-66 mixture delivers single-stranded PGY-sRNA-6 into THP-1 cells;

FIG. 71a-c: No. 41+No. 38+sphingosine derivative So-67 mixture delivers single-stranded PGY-sRNA-6 into THP-1 cells;

FIG. 72a-c: No. 41+No. 38+sphingosine derivative So-68 mixture delivers single-stranded PGY-sRNA-6 into THP-1 cells;

FIG. 73a-c: No. 41+No. 38+sphingosine derivative So-69 mixture delivers single-stranded PGY-sRNA-6 into THP-1 cells;

FIG. 74a-c: No. 41+No. 38+sphingosine derivative So-70 mixture delivers single-stranded PGY-sRNA-6 into THP-1 cells;

FIG. 75a-c: No. 41+No. 38+sphingosine derivative So-71 mixture delivers single-stranded PGY-sRNA-6 into THP-1 cells;

FIG. 76a-c: No. 41+No. 38+sphingosine derivative So-72 mixture delivers single-stranded PGY-sRNA-6 into THP-1 cells;

FIG. 77a-c: No. 41+No. 38+sphingosine derivative So-73 mixture delivers single-stranded PGY-sRNA-6 into THP-1 cells;

FIG. 78a-c: No. 41+No. 38+sphingosine derivative So-74 mixture delivers single-stranded PGY-sRNA-6 into THP-1 cells;

FIG. 79a-c: No. 41+No. 38+sphingosine derivative So-75 mixture delivers single-stranded PGY-sRNA-6 into THP-1 cells;

FIG. 80a-c: No. 41+No. 38+No. 48+sphingosine derivative So-42 mixture delivers single-stranded PGY-sRNA-6 into THP-1 cells;

FIG. 81a-c: No. 41+No. 38+No. 48+sphingosine derivative So-43 mixture delivers single-stranded PGY-sRNA-6 into THP-1 cells;

FIG. 82a-c: No. 41+No. 38+No. 48+sphingosine derivative So-44 mixture delivers single-stranded PGY-sRNA-6 into THP-1 cells;

FIG. 83a-c: No. 41+No. 38+No. 48+sphingosine derivative So-45 mixture delivers single-stranded PGY-sRNA-6 into THP-1 cells;

FIG. 84a-c: No. 41+No. 38+No. 48+sphingosine derivative So-46 mixture delivers single-stranded PGY-sRNA-6 into THP-1 cells;

FIG. 85a-c: No. 41+No. 38+No. 48+sphingosine derivative So-47 mixture delivers single-stranded PGY-sRNA-6 into THP-1 cells;

FIG. 86a-c: No. 41+No. 38+No. 48+sphingosine derivative So-52 mixture delivers single-stranded PGY-sRNA-6 into THP-1 cells;

FIG. 87a-c: No. 41+No. 38+No. 48+sphingosine derivative So-56 mixture delivers single-stranded PGY-sRNA-6 into THP-1 cells;

FIG. 88a-c: No. 41+No. 38+No. 48+sphingosine derivative So-57 mixture delivers single-stranded PGY-sRNA-6 into THP-1 cells;

FIG. 89a-c: No. 41+No. 38+No. 48+sphingosine derivative So-58 mixture delivers single-stranded PGY-sRNA-6 into THP-1 cells;

FIG. 90a-c: No. 41+No. 38+No. 48+sphingosine derivative So-59 mixture delivers single-stranded PGY-sRNA-6 into THP-1 cells;

FIG. 91a-c: No. 41+No. 38+No. 48+sphingosine derivative So-60 mixture delivers single-stranded PGY-sRNA-6 into THP-1 cells;

FIG. 92a-c: No. 41+No. 38+No. 48+sphingosine derivative So-61 mixture delivers single-stranded PGY-sRNA-6 into THP-1 cells;

FIG. 93a-c: No. 41+No. 38+No. 48+sphingosine derivative So-62 mixture delivers single-stranded PGY-sRNA-6 into THP-1 cells;

FIG. 94a-c: No. 41+No. 38+No. 48+sphingosine derivative So-63 mixture delivers single-stranded PGY-sRNA-6 into THP-1 cells;

FIG. 95a-c: No. 41+No. 38+No. 48+sphingosine derivative So-64 mixture delivers single-stranded PGY-sRNA-6 into THP-1 cells;

FIG. 96a-c: No. 41+No. 38+No. 48+sphingosine derivative So-67 mixture delivers single-stranded PGY-sRNA-6 into THP-1 cells;

FIG. 97a-c: No. 41+No. 38+No. 48+sphingosine derivative So-68 mixture delivers single-stranded PGY-sRNA-6 into THP-1 cells;

FIG. 98a-c: No. 41+No. 38+No. 48+sphingosine derivative So-69 mixture delivers single-stranded PGY-sRNA-6 into THP-1 cells;

FIG. 99a-c: No. 41+No. 38+No. 48+sphingosine derivative So-70 mixture delivers single-stranded PGY-sRNA-6 into THP-1 cells;

FIG. 100: Results of lipid combination delivering single-stranded PGY-sRNA-6 into 293T;

FIG. 101: Results of lipid combination delivering single-stranded PGY-sRNA-6 into 293T;

FIG. 102: Results of lipid combination delivering single-stranded PGY-sRNA-6 into 293T;

FIG. 103: Results of lipid combination delivering single-stranded PGY-sRNA-6 into 293T;

FIG. 104: Results of lipid combination delivering single-stranded PGY-sRNA-6 into 293T.

DETAILED DESCRIPTION OF THE INVENTION

Definition of Terms

The term as used herein may have a single dash "-" (or horizontal line) or a double dash "=" in front of and/or behind it to indicate the bond level of the bond between the mentioned substituent and its parent moiety; a single dash "-" (or horizontal line) refers to a single bond, and a double dash refers to a double bond; in the absence of single or double dash, it is understood that a single bond is formed between the substituent and its parent moiety; in addition, the substituent is to be construed "from left to right" unless otherwise indicated.

A dashed line ("-") that is not between two letters or symbols is used to represent the linking points of substituents. For example, —C(O)NH$_2$ is linked through a carbon atom. The dashed line before or after a chemical group is for convenience. The chemical group can be depicted with or without one or more dashed lines without losing its usual meaning. The wavy line drawn through the lines in the structure represents the linking points of the groups.

When a range of values is listed, it is intended to include every value and subrange within the range. For example, "$C_{1-6}$ alkyl" is intended to include $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$ and $C_{5-6}$ alkyl groups.

The term "alkyl" as used herein refers to a straight or branched saturated hydrocarbon chain. As described herein, an alkyl group has 1 to 24 carbon atoms (i.e., $C_{1-24}$ alkyl), 1 to 20 carbon atoms (i.e., $C_{1-20}$ alkyl), 1 to 8 carbon atoms (i.e., $C_{1-8}$ alkyl), 1 to 6 carbon atoms (i.e., $C_{1-6}$ alkyl), or 1 to 4 carbon atoms (i.e., $C_{1-4}$ alkyl). In one embodiment, the alkyl group is a $C_{1-6}$ alkyl group. In one embodiment, the alkyl group is a $C_{14-20}$ alkyl group. In one embodiment, the alkyl group is a straight $C_{14}$, $C_{15}$, $C_{16}$, $C_{17}$, $C_{18}$, $C_{19}$, $C_{20}$ alkyl group.

The term "alkenyl" as used herein refers to an aliphatic hydrocarbon chain having specified number of carbon atoms and containing at least one carbon-carbon double bond. As described herein, an alkenyl group has 2 to 24 carbon atoms (i.e., $C_{2-24}$ alkenyl), 2 to 20 carbon atoms (i.e., $C_{2-20}$ alkenyl), 2 to 8 carbon atoms (i.e., $C_{2-8}$ alkenyl), 2 to 6 carbon atoms (i.e., $C_{2-6}$ alkenyl), or 2 to 4 carbon atoms (i.e., $C_{2-4}$ alkenyl). In one embodiment, the alkenyl group is a $C_{14-20}$ alkenyl group. In one embodiment, the alkenyl group is a $C_{14}$, $C_{15}$, $C_{16}$, $C_{17}$, $C_{18}$, $C_{19}$, $C_{20}$ alkenyl group.

As used herein, the term "acyl" refers to group —CO—.

As used herein, the term "phosphate ester" refers to group

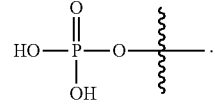

As used herein, the term "biotin acyl" refers to group

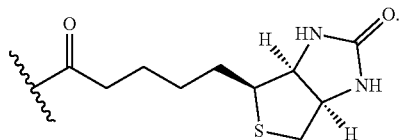 [SMILES: *C(=O)CCCC[C@@H]1SC[C@@H]2NC(=O)N[C@@H]21]

As used herein, the term "glycosyl" refers to a monovalent substituent obtained by removing the hemiacetal hydroxyl group from the cyclic form of a monosaccharide. For example, the term "1-β-D-glucosyl" refers to group

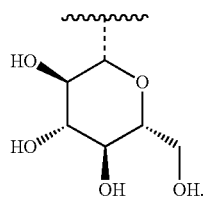 [SMILES: *[C@@H]1O[C@H](CO)[C@@H](O)[C@H](O)[C@H]1O]

Examples of glycosyl include, but are not limited to, glucosyl, lactosyl, galactosyl, mannosyl, fructosyl, and sorbosyl. In one embodiment, the glycosyl is β-D-glucosyl.

The term "pharmaceutically acceptable salt" refers to the salt, within the scope of reasonable medical judgment, suitable for use in contact with tissues of human and lower animals without improper toxicity, stimulation, allergic reactions, etc. and commensurate with a reasonable benefit/risk ratio. Pharmaceutically acceptable salts are well known in the art. For example, Berge et al. described pharmaceutically acceptable salts in detail in J. Pharmaceutical Sciences, 1977, 66, pages 1-19, which is incorporated herein by reference. Pharmaceutically acceptable salts of the compounds of the present application include those derived from suitable inorganic and organic acids and bases. Examples of pharmaceutically acceptable non-toxic acid addition salts are salts formed from amino with inorganic acids (such as hydrochloric acid, hydrobromic acid, phosphoric acid, sulfuric acid, and perchloric acid) or with organic acids (such as acetic acid, oxalic acid, maleic acid, tartaric acid, citric acid, succinic acid, or malonic acid), or salts formed by using other methods known in the art (for example, ion exchange methods). Other pharmaceutically acceptable salts include adipate, alginate, ascorbate, aspartate, benzenesulfonate, benzoate, bisulfate, borate, butyrate, camphorate, camphor sulfonate, citrate, cyclopentane propionate, digluconate, lauryl sulfate, ethane sulfonate, formate, fumarate, gluceptate, glycerophosphate, gluconate, hemisulfate, enanthate, caproate, hydroiodide, 2-hydroxy-ethane sulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectate, persulfate, 3-phenylpropionate, phosphate, picrate, pivalate, propionate, stearate, succinate, sulfate, methyl sulfate, tartrate, thiocyanate, p-toluenesulfonate, undecanoate, valerate, etc. Salts derived from appropriate bases include alkali metal salts, alkaline-earth metal salts, ammonium salts, and $N^+(C_{1-4}alkyl)_4^-$ salts. Representative alkali metal or alkaline-earth metal salts include sodium salt, lithium salt, potassium salt, calcium salt, magnesium salt and the like. Where appropriate, other pharmaceutically acceptable salts include non-toxic ammonium, quaternary ammonium, and amine cations formed using counterions such as halogen, hydroxide, carboxylate, sulfate, phosphate, nitrate, lower alkylsulfonate and arylsulphonate.

The term reverse evaporation method as described herein refers to adding an aqueous solution of nucleic acid to a solution of lipid in an organic solvent, ultrasonicating, evaporating to remove the organic solvent, and then hydrating to obtain a lipid nucleic acid mixture.

The term "boiling method" (also refers to "heating method") as described herein refers to adding an organic solvent solution of lipid to an aqueous solution of nucleic acid and boiling at about 100° C. for 30 minutes to obtain a lipid nucleic acid mixture. The method is not limited to heating by boiling, and other means of heating or raising temperature known in the art can also be used.

Reverse evaporation method and boiling method are carried out under controlled temperature and mixing conditions. Suitable processing times, and temperatures can be readily determined by a person skilled in the art. For example, the temperature of reverse evaporation method is ranged preferably from about 25° C. to about 70° C., more preferably from about 30° C. to about 65° C., and more preferably from about 40° C. to about 60° C., especially about 55° C. The temperature of boiling method is ranged preferably from about 25° C. to about 100° C., more preferably from about 50° C. to about 100° C., and more preferably from about 95° C. to about 100° C., especially preferably from about 80° C. to 100° C.

The nucleic acid as described herein comprises DNA and RNA, preferably small RNA, for example, the small RNA having a length of 14-32 bp, 16-28 bp, 18-24 bp, and particularly, a length of 14, 15, 16, 17, 18, 19, 20, 21, 22, 23, 24, 25, 26, 27, 28, 29, 31, 32 bp.

In the present application, a nucleic acid can be delivered to a cell or a subject by mixing compounds or combination or composition containing one or more of the compounds and the nucleic acid. In one embodiment, the compound has a structure of Formula (I), a stereoisomer thereof or a pharmaceutical acceptable salt thereof,

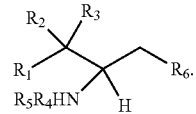

I

In one embodiment, the substituents of Formula (I) are as defined above. The compound may be a compound in Table 1. The combination or composition comprising the compound may include any one or more of the compounds in Table 1. Those skilled in the art can add or delete one or more compounds in the combination or composition as needed.

In one embodiment, the combination or composition herein is a combination comprising any one or more of No. 41, No. 38, No. 48. In one embodiment, a combination comprising any one or more of No. 41, No. 38, No. 48 and any one or more of the compound selecting from item 11. In one embodiment, a combination comprising the following: No. 41+No. 38+sphingosine derivative So-1; No. 41+No. 38+sphingosine derivative So-2; No. 41+No. 38+sphingosine derivative So-3; No. 41+No. 38+sphingosine derivative So-4; No. 41+No. 38+sphingosine derivative So-5; No. 41+No. 38+sphingosine derivative So-6; No. 41+No. 38+sphingosine derivative So-7; No. 41+No. 38+sphingosine derivative So-8; No. 41+No. 38+sphingosine derivative So-9; No. 41+No. 38+sphingosine derivative So-10; No. 41+No. 38+sphingosine derivative So-11; No. 41+No. 38+sphingosine derivative So-12; No. 41+No. 38+sphingosine derivative So-13; No. 41+No. 38+sphingosine derivative So-14; No. 41+No. 38+sphingosine derivative So-15; No. 41+No. 38+sphingosine derivative So-45; No. 41+No. 38+sphingosine derivative So-46; No. 41+No. 38+sphingosine derivative So-47; No. 41+No. 38+sphingosine derivative So-48; No. 41+No. 38+sphingosine derivative So-49; No. 41+No. 38+sphingosine derivative So-50; No. 41+No. 38+sphingosine derivative So-51; No. 41+No. 38+sphingosine derivative So-52; No. 41+No. 38+sphingosine derivative So-53; No. 41+No. 38+sphingosine derivative So-54; No. 41+No. 38+sphingosine derivative So-55; No. 41+No. 38+sphingosine derivative So-56; No. 41+No. 38+sphingosine derivative So-57; No. 41+No. 38+sphingosine derivative So-58; No. 41+No. 38+sphingosine derivative So-59; No. 41+No. 38+sphingosine derivative So-60; No. 41+No. 38+sphingosine derivative So-61; No. 41+No. 38+sphingosine derivative So-62; No. 41+No. 38+sphingosine derivative So-63; No. 41+No. 38+sphingosine derivative So-64; No. 41+No. 38+sphingosine derivative So-65; No. 41+No. 38+sphingosine derivative So-66; No. 41+No. 38+sphingosine derivative So-67; No. 41+No. 38+sphingosine derivative So-68; No. 41+No. 38+sphingosine derivative So-69; No. 41+No. 38+sphingosine derivative So-70; No. 41+No. 38+sphingosine derivative So-71; No. 41+No. 38+sphingosine derivative So-72; No. 41+No. 38+sphingosine derivative So-73; No. 41+No. 38+sphingosine derivative So-74; No. 41+No. 38+sphingosine derivative So-75; No. 41+No. 38+No. 48+sphingosine derivative So-42; No. 41+No. 38+No. 48+sphingosine derivative So-43;

No. 41+No. 38+No. 48+sphingosine derivative So-44;
No. 41+No. 38+No. 48+sphingosine derivative So-45;
No. 41+No. 38+No. 48+sphingosine derivative So-46;
No. 41+No. 38+No. 48+sphingosine derivative So-47;
No. 41+No. 38+No. 48+sphingosine derivative So-52;
No. 41+No. 38+No. 48+sphingosine derivative So-56;
No. 41+No. 38+No. 48+sphingosine derivative So-57;
No. 41+No. 38+No. 48+sphingosine derivative So-58;
No. 41+No. 38+No. 48+sphingosine derivative So-59;
No. 41+No. 38+No. 48+sphingosine derivative So-60;
No. 41+No. 38+No. 48+sphingosine derivative So-61;
No. 41+No. 38+No. 48+sphingosine derivative So-62;
No. 41+No. 38+No. 48+sphingosine derivative So-63;
No. 41+No. 38+No. 48+sphingosine derivative So-64;
No. 41+No. 38+No. 48+sphingosine derivative So-67;
No. 41+No. 38+No. 48+sphingosine derivative So-68;
No. 41+No. 38+No. 48+sphingosine derivative So-69;
No. 41+No. 38+No. 48+sphingosine derivative So-70; No. 41+No. 38+any one or more of sphingosine derivative So-23, 25, 26, 27, 29, 30, 31, 32, 33, 34, 35, 36, 37, 38, 40, 41, 42, 43, 44, 70, 71 or 73. Those skilled in the art can select the appropriate concentration and use volume. Preferably, the compounds above are used at concentrations as shown in Table 1. The ratio of the compounds above is 0.1-10:0.1-10, 0.2-9:0.2-9, 0.3-8:0.3-8, 0.4-7:0.4-7, 0.5-6:0.5-6, 0.6-5:0.6-5, 0.7-4:0.7-4, 0.8-3:0.8-3, 0.9-2:0.9-2; more preferably 1:1, or any ratio between them. Those skilled in the art can appropriately adjust the ratio of various compounds according to the concentration of the mother liquor of the compounds. In addition, the present application proved that a specific lipid combination can effectively promote the delivery of nucleic acids, and the effect is better than that of a single lipid.

In one embodiment, the nucleic acid is synthetic or purified, therapeutic or non-therapeutic, and/or diagnostic or non-diagnostic, for example selected from RNA or DNA, for example selected from single-stranded or double-stranded or partially double-stranded RNA or DNA. When the nucleic acid is therapeutic or diagnostic, the nucleic acid is used to treat or diagnose a disease selected from the group consisting of: inflammatory diseases, pneumonia, myocarditis, acute and chronic gastritis, acute and chronic enteritis, acute and chronic hepatitis, acute and chronic nephritis, dermatitis, encephalitis, lymphitis, conjunctivitis, keratitis, iridocyclitis, otitis media, allergic rhinitis, asthma, pulmonary fibrosis, chronic obstructive pulmonary disease, allergic dermatitis, sickle cell disease, multiple sclerosis, systemic lupus erythematosus, lupus nephritis, lung cancer, gastric cancer, colorectal cancer, liver cancer, pancreatic cancer, cervical cancer, breast cancer, leukemia, multiple myeloma, diabetes, and gout. Those skilled in the art can select a suitable nucleic acid according to the specific situation. For example, the RNA can be messenger RNA (mRNA), rRNA (ribosomal RNA), tRNA (transfer RNA), heterogeneous nuclear RNA (hnRNA), small nuclear RNA (snRNA), small nucleolar RNA (snoRNA), small cytoplasmic RNA, small RNA, transfer-messenger RNA (tmRNA), telomerase RNA and antisense RNA, preferably small RNA.

In one embodiment, the delivery comprises treating the compound, a stereoisomer thereof or a pharmaceutically acceptable salt thereof or a combination comprising them by heating method, reverse evaporation method, direct mixing, repeated freeze-thaw and/or thin film dispersion. Those skilled in the art can select a suitable method for delivery. In one embodiment, the heating method is conducted at a temperature of about 0° C. to about 100° C., about 25° C. to about 100° C., preferably about 80° C. to about 100° C., for example 4° C., 37° C., 60° C., 80° C. or 100° C.; the reverse evaporation method is conducted at a temperature of about 25° C. to about 70° C., preferably about 55° C. for a heating time of about 0 minutes to about 24 hours, about 5 minutes to about 20 hours, about 5 minutes to about 16 hours, about 5 minutes to about 10 hours, about 5 minutes to about 4 hours, or about 10 hours to about 1 hour, preferably 15 minutes.

In one embodiment, the nucleic acid is treated with the compound, and the treated mixture can be directly administered to the subject via oral administration. In addition, the subject can also be administered by other means, for example, intravenous administration such as injection or infusion, subcutaneous administration, intramuscular administration, intraarterial administration, intraperitoneal administration, intrapulmonary administration, intracerebral and intraspinal administration, intra-articular administration, intrasynovial administration, intrathecal administration, intra-trauma administration, and/or administration via inhalation paths such as intranasal, typically intravenous or subcutaneous administration.

The invention also provides combinations, compositions or kits of compounds, which comprise any compound described herein, such as any one or more of the compounds in Table 1. Those skilled in the art can add other compounds to the combinations, compositions or kits of compounds as needed, as long as the function of delivering nucleic acid is retained.

TABLE 1

Molecular structure information of single lipid

| No. | Brand | Catalog No. | Abbreviation | IUPAC Name | Molecular structure | Concentration in chloroform solution/ (mg/mL) |
|---|---|---|---|---|---|---|
| So-1 | Cayman | CAC-24427-5 | C17 dihydro Ceramide (d18:0/17:0) | CAS No 1388156-40-8 N-heptadecanoyl-D-erythro-Dihydrosphingosine | 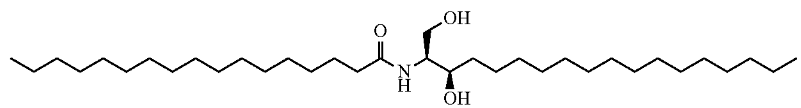 [SMILES: CCCCCCCCCCCCCCCCC(=O)N[C@@H](CO)[C@H](O)CCCCCCCCCCCCCCC] | 5 |
| So-2 | Cayman | CAC-9002921-5 | Sphingosine-1-phosphate (d16:1) | CAS No 709026-60-8 C16 Sphingosine-1-phosphate | 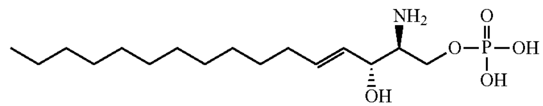 [SMILES: CCCCCCCCCCC/C=C/[C@@H](O)[C@@H](N)COP(=O)(O)O] | 5 |
| So-3 | Cayman | CAC-9000415-5 | C6 Biotin Ceramide (d18:1/6:0) | N-hexanoyl-biotin-D-erythro-Sphingosine | 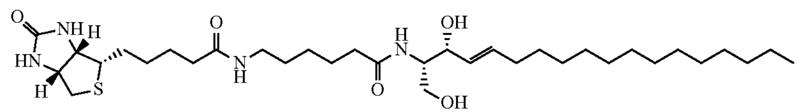 [SMILES: CCCCCCCCCCCCC/C=C/[C@@H](O)[C@H](CO)NC(=O)CCCCCNC(=O)CCCC[C@@H]1SC[C@@H]2NC(=O)N[C@@H]21] | 5 |
| So-4 | Cayman | CAC-62575-5 | N,N-Dimethylsphingosine (d18:1) | CAS No 119567-63-4 | 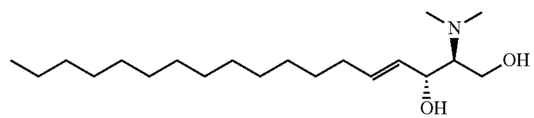 [SMILES: CCCCCCCCCCCCC/C=C/[C@@H](O)[C@H](CO)N(C)C] | 5 |
| So-5 | Cayman | CAC-62570-5 | Sphingosine-1-phosphate (d18:1) | CAS No 26993-30-6 Sphingosine-1-Phosphoric Acid | 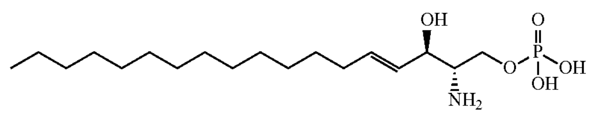 | 5 |
| So-6 | Cayman | CAC-24867-1 | Lactosylsphingosine (d18:1) (synthetic) | CAS No 109785-20-8 Lyso-Lactosylceramide (synthetic) | 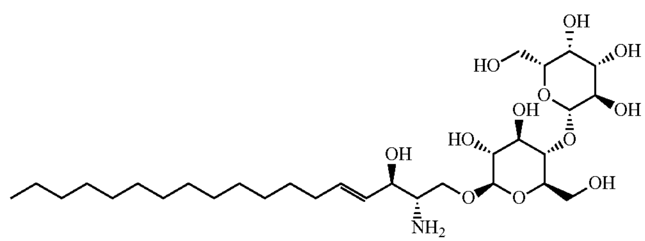 [SMILES: CCCCCCCCCCCCC/C=C/[C@@H](O)[C@@H](N)CO[C@@H]1O[C@H](CO)[C@@H](O[C@@H]2O[C@H](CO)[C@H](O)[C@H](O)[C@H]2O)[C@H](O)[C@H]1O] | 1 |

TABLE 1-continued

Molecular structure information of single lipid

| No. | Brand | Catalog No. | Abbreviation | IUPAC Name | Molecular structure | Concentration in chloroform solution (mg/mL) |
|---|---|---|---|---|---|---|
| So-7 | Cayman | CAC-24515-1 | 1-Deoxysphingosine (m18:1(14Z)) | CAS No 2190487-94-4 1Z-1-Deoxysphingosine (d18:1) | 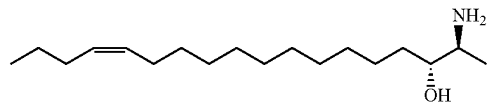 | 5 |
| So-8 | Cayman | CAC-24380-5 | 3-keto Sphinganine (d18:0) (hydrochloride) | CAS No 35299-94-6 3-keto Dihydrosphingosine | 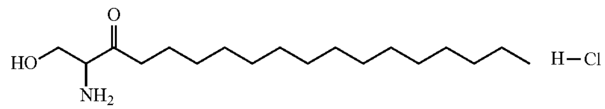 | 5 |
| So-9 | Cayman | CAC-24379-10 | C18 dihydro Ceramide (d18:0/18:0) | CAS No 2304-80-5 N-octadecanoyl-D-erythro-Dihydrosphingosine | 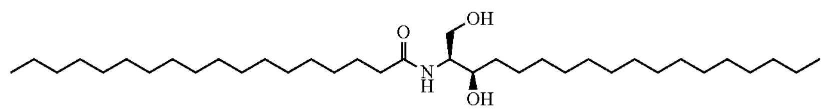 | 10 |
| So-10 | Cayman | CAC-24369-5 | C16 dihydro Ceramide (d18:0/16:0) | CAS No 5966-29-0 N-hexadecanoyl-D-erythro-Dihydrosphingosine | 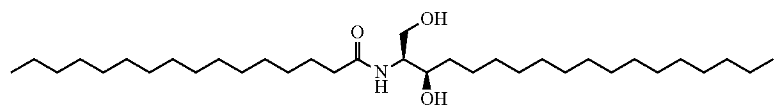 | 5 |
| So-11 | Cayman | CAC-22504-5 | N,N-dimethyl Sphinganine (d18:0) | CAS No 17267-46-8 N,N-dimethyl-D-erythro-Dihydrosphingosine | 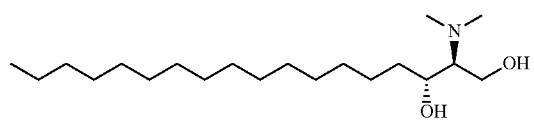 [SMILES: CCCCCCCCCCCCCCC[C@@H](O)[C@H](CO)N(C)C] | 5 |
| So-12 | Cayman | CAC-24358-5 | C8 dihydro Ceramide (d18:0/8:0) | CAS No 145774-33-0 N-octanoyl-D-erythro-Dihydrosphingosine | 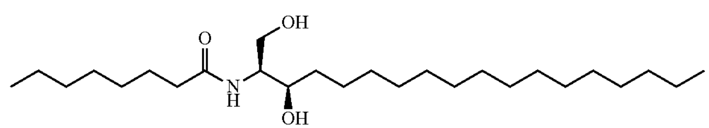 [SMILES: CCCCCCCCCCCCCCC[C@@H](O)[C@H](CO)NC(=O)CCCCCCC] | 5 |
| So-13 | Cayman | CAC-22530-5 | C12 Ceramide (d18:1/12:0) | CAS No 74713-60-3 N-Lauroyl-D-erythro-Sphingosine | 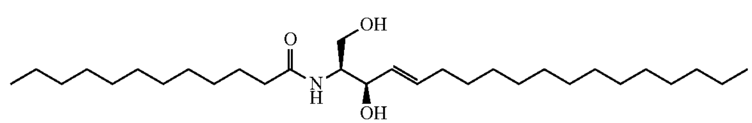 [SMILES: CCCCCCCCCCCCC/C=C/[C@@H](O)[C@H](CO)NC(=O)CCCCCCCCCCC] | 5 |

TABLE 1-continued

Molecular structure information of single lipid

| No. | Brand | Catalog No. | Abbreviation | IUPAC Name | Molecular structure | Concentration in chloroform solution (mg/mL) |
|---|---|---|---|---|---|---|
| So-14 | Cayman | CAC-22688-5 | C30(ω-hydroxy) Ceramide (d18:1/30:0) | CAS No 457100-08-2 ω-hydroxy-C30 Sphingosine (d18:1/30:0) | 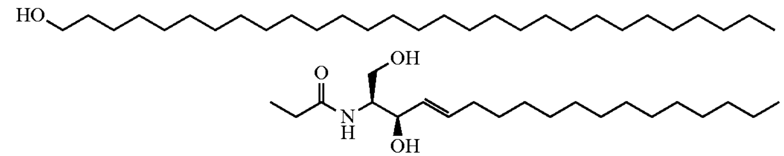 | 5 |
| So-15 | Cayman | CAC-22501-5 | C17 Sphinganine-1-phosphate (d17:0) | CAS No 474923-29-0 dihydro-D-erythro-Sphingosine-C17-1-phosphate | 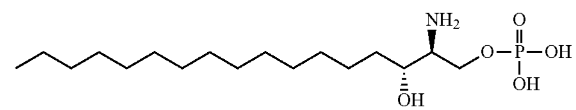 [SMILES: CCCCCCCCCCCCCC[C@@H](O)[C@@H](N)COP(=O)(O)O] | 5 |
| So-16 | Cayman | CAC-22827-5 | C24 Phytosphingosine (t18:0/24:0) | CAS No 34437-74-6 N-Tetracosanoyl Phytosphingosine | 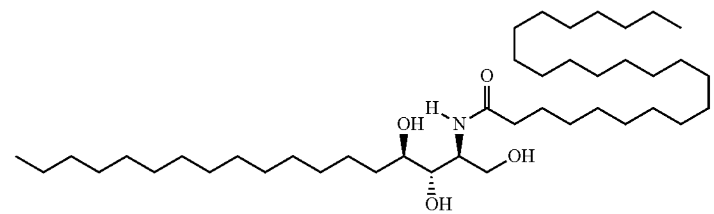 [SMILES: CCCCCCCCCCCCCCCCCCCCCCCC(=O)N[C@@H](CO)[C@H](O)[C@H](O)CCCCCCCCCCCCCC] | 5 |
| So-17 | Cayman | CAC-20338-5 | Galactosylsphingosine (d18:1) | CAS No 2238-90-6 Galactosylsphingosine | 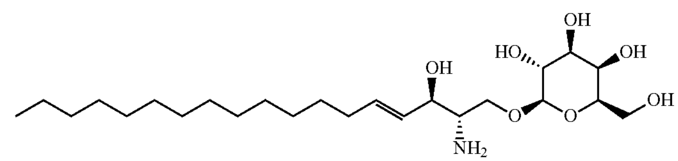 | 5 |
| So-18 | Cayman | CAC-19556-5 | C18 Ceramide (d18:1/18:0) | CAS No 2304-81-6 N-Stearoyl-D-Sphingosine | 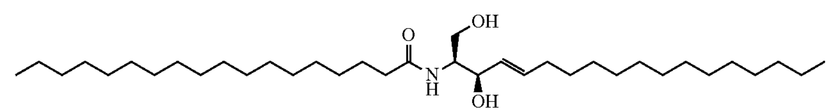 [SMILES: CCCCCCCCCCCCC/C=C/[C@@H](O)[C@H](CO)NC(=O)CCCCCCCCCCCCCCCCC] | 5 |
| So-19 | Cayman | CAC-20217-5 | Phytosphingosine | CAS No 554-62-1 D-ribo Phytosphingosine | 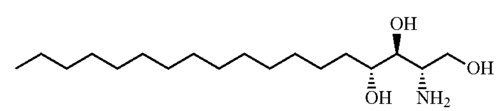 | 5 |

TABLE 1-continued

Molecular structure information of single lipid

| No. | Brand | Catalog No. | Abbreviation | IUPAC Name | Molecular structure | Concentration in chloroform solution (mg/mL) |
|---|---|---|---|---|---|---|
| So-20 | Cayman | CAC-10724-5 | C20 Ceramide (d18:1/20:0) | CAS No 7344-02-7 N-arachidoyl-D-erythro-Sphingosine | 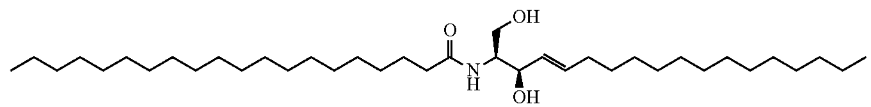 [SMILES: CCCCCCCCCCCCC/C=C/[C@@H](O)[C@H](CO)NC(=O)CCCCCCCCCCCCCCCCCCC] | 5 |
| So-21 | Cayman | CAC-22500-5 | Sphinganine-1-phosphate (d18:0) | CAS No 19794-97-9 dihydro-D-erythro-Sphingosine-1-phosphate | 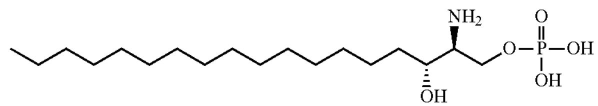 [SMILES: CCCCCCCCCCCCCCC[C@@H](O)[C@@H](N)COP(=O)(O)O] | 5 |
| So-23 | Cayman | CAC-10681-5 | C16 Ceramide (d18:1/16:0) | CAS No 24696-26-2 N-Palmitoyl-D-erythro-Sphingosine | 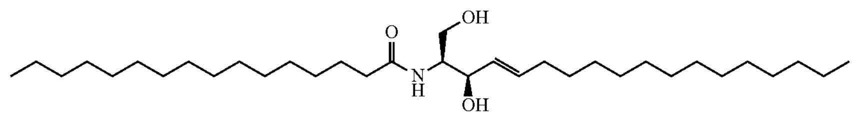 [SMILES: CCCCCCCCCCCCC/C=C/[C@@H](O)[C@H](CO)NC(=O)CCCCCCCCCCCCCCC] | 5 |
| So-25 | Cayman | CAC-10007901-5 | Sphingosine (d15:1) | CAS No 86555-28-4 D-erythro-Sphingosine C-15 | 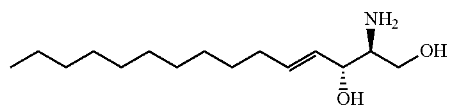 [SMILES: CCCCCCCCCC/C=C/[C@@H](O)[C@@H](N)CO] | 5 |
| So-26 | Cayman | CAC-10007907-10 | Sphingosine (d18:1) | CAS No 123-78-4 D-erythro-Sphingosine C-18 | 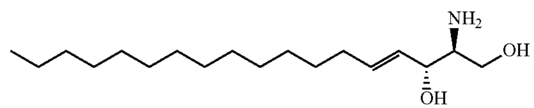 [SMILES: CCCCCCCCCCCCC/C=C/[C@@H](O)[C@@H](N)CO] | 10 |
| So-27 | Avanti | 860660P-5MG | Sphingosine (D20:1) | CAS: 6918-49-6 D-erythro-sphingosine (C20 base) | 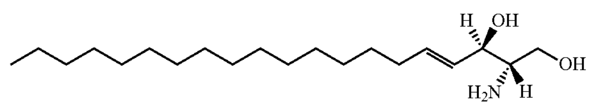 | 5 |
| So-29 | Avanti | 860497P-5MG | TRIMETHYL SPHINGOSINE (D18:1) | CAS: 133561-52-1 N,N,N-trimethyl-D-erythro-sphingosine (methyl sulfate salt) | 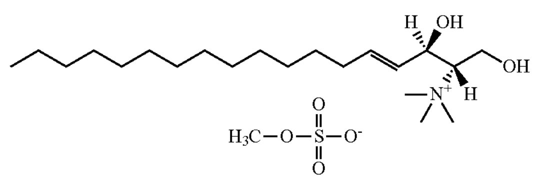 | 5 |

TABLE 1-continued

Molecular structure information of single lipid

| No. | Brand | Catalog No. | Abbreviation | IUPAC Name | Molecular structure | Concentration in chloroform solution (mg/mL) |
|---|---|---|---|---|---|---|
| So-30 | Avanti | 860601P-5MG | DIMETHYL SPHINGOSINE-1-PHOSPHATE (D18:1) | CAS: 474943-83-4 N,N-dimethyl-D-erythro-sphingosine-1-phosphate (ammonium salt) | 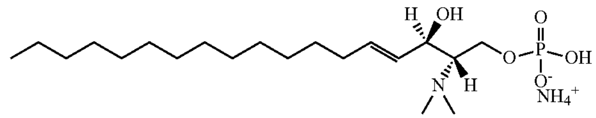 [SMILES: CCCCCCCCCCCCC/C=C/[C@@H](O)[C@H](COP(=O)([O-])O)N(C)C ; [NH4+]] | 5 |
| So-31 | Avanti | 860643P-5MG | TRIMETHYL SPHINGOSINE (D17:1) | CAS: 474943-94-7 N,N,N-trimethyl-D-erythro-sphingosine (C17 base) (methyl sulfate salt) | 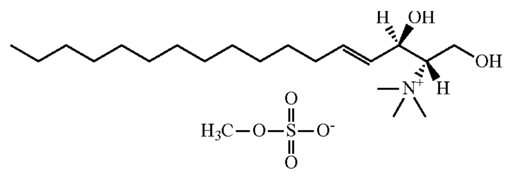 | 5 |
| So-32 | Avanti | 860536P-5MG | SPHINGANINE-1-PHOSPHATE (D18:0) | CAS: 19794-97-9 D-erythro-sphinganine-1-phosphate | 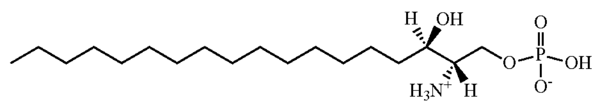 | 5 |
| So-33 | Avanti | 860641P-5MG | SPHINGANINE-1-PHOSPHATE (D17:1) | CAS: 474923-27-8 D-erythro-sphingosine-1-phosphate (C17 base) | 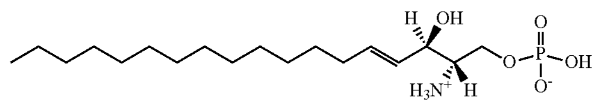 | 5 |
| So-34 | Avanti | 860655P-1MG | SPHINGANINE-1-PHOSPHATE (D17:0) | CAS: 474923-29-0 D-erythro-sphinganine-1-phosphate (C17 base) | 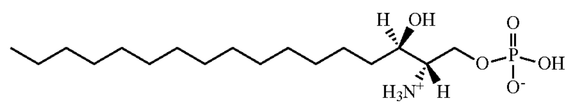 | 5 |
| So-35 | Avanti | 860662P-1MG | SPHINGOSINE-1-PHOSPHATE (D20:1) | CAS: 799812-75-2 D-erythro-sphingosine-1-phosphate (C20 base) | 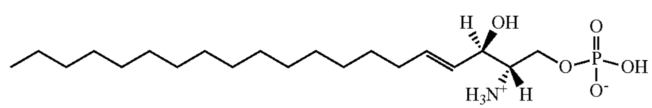 | 5 |
| So-36 | Avanti | 860481P-1MG | N-12:0-1-DEOXYSPHINGANINE | CAS: 1246298-40-7 N-dodecanoyl-1-deoxysphinganine | 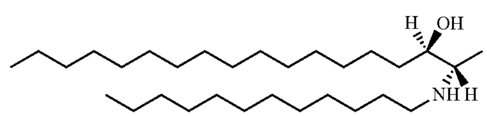 [SMILES: CCCCCCCCCCCCCCC[C@@H](O)[C@H](C)NCCCCCCCCCCCC] | 5 |

TABLE 1-continued

Molecular structure information of single lipid

| No. | Brand | Catalog No. | Abbreviation | IUPAC Name | Molecular structure | Concentration in chloroform solution (mg/mL) |
|---|---|---|---|---|---|---|
| So-37 | Avanti | 860489P-5MG | L-THREO-SPHINGOSINE (D18:1) | CAS: 25695-95-8 (2S,3S,4E)-2-aminooctadec-4-ene-1,3-diol | L-threo- | 5 |
| So-38 | Avanti | 860665P-1MG | 4E 14Z-SPHINGADIENE | CAS: 25696-03-1 (2S,3R,4E,14Z)-2-aminooctadec-4,14-diene-1,3-diol | 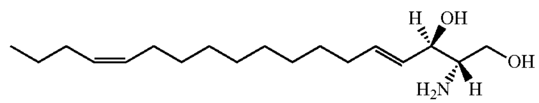 | 5 |
| So-40 | Avanti | 860675P-1mg | Sphinganine-1-Phosphate (d20:0) | CAS: 436846-91-2 D-erythro-sphinganine-1-phosphate (C20 base) | 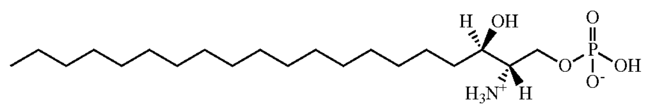 | 5 |
| So-41 | Avanti | 860640P-5MG | Sphingosine (d17:1) | D-erythro-sphingosine (C17 base) | 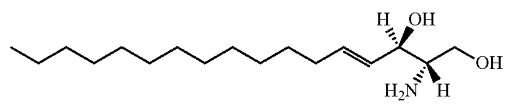 [SMILES: CCCCCCCCCCCC/C=C/[C@@H](O)[C@@H](N)CO] | 5 |
| So-42 | Cayman | 22532 | C17 Ceramide (d18:1/17:0) | CAS No 67492-16-4 N-heptadecanoyl-D-erythro-Sphingosine | 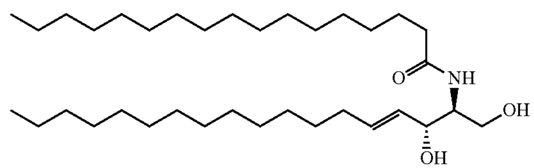 [SMILES: CCCCCCCCCCCCC/C=C/[C@@H](O)[C@H](CO)NC(=O)CCCCCCCCCCCCCCCC] | 5 |
| So-43 | Cayman | 22531 | C14 Ceramide (d18:1/14:0) | CAS No 34227-72-0 Ceramide (d18:1/14:0) | 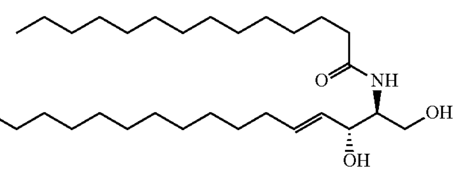 | 5 |
| So-44 | Cayman | 24357 | C8 Phytoceramide (t18:0/8:0) | CAS No 249728-93-6 N-Octanoyl Phytosphingosine | 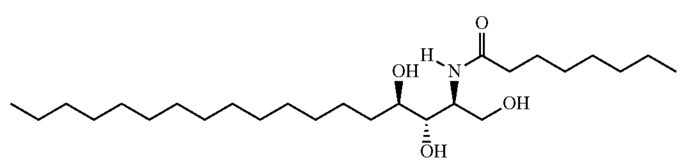 [SMILES: CCCCCCCCCCCCCC[C@@H](O)[C@@H](O)[C@H](CO)NC(=O)CCCCCCC] | 5 |

TABLE 1-continued

Molecular structure information of single lipid

| No. | Brand | Catalog No. | Abbreviation | IUPAC Name | Molecular structure | Concentration in chloroform solution/ (mg/mL) |
|---|---|---|---|---|---|---|
| So-45 | Cayman | 24367 | DL-erythro/threo Sphinganine (d18:0) | CAS No 3102-56-5 DL-erythro Sphinganine (d18:0) | 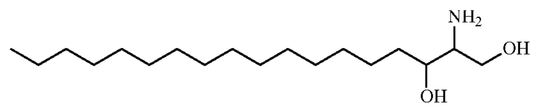 [SMILES: CCCCCCCCCCCCCCCC(O)C(N)CO] | 5 |
| So-46 | Cayman | 24374 | L-erythro Sphinganine (d18:0) | CAS No 6036-76-6 C18 L-erythro Sphinganine (d18:0) | 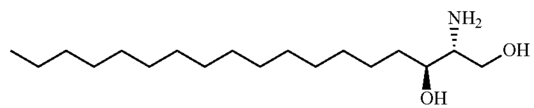 | 5 |
| So-47 | Cayman | 24372 | L-erythro Sphingosine (d18:1) | CAS No 6036-75-5 L-erythro-C18-Sphingosine | 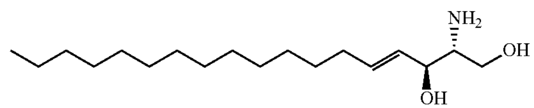 [SMILES: CCCCCCCCCCCCC/C=C/[C@H](O)[C@H](N)CO] | 5 |
| So-48 | Cayman | 24385 | N,N-dihexyl Sphingosine (d18:1/6:0/6:0) | N,N-dihexyl-D-erythro-Sphingosine | 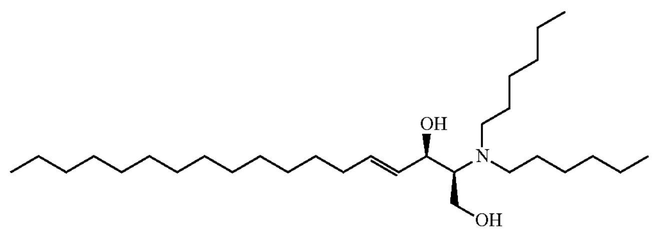 [SMILES: CCCCCCCCCCCCC/C=C/[C@@H](O)[C@H](CO)N(CCCCCC)CCCCCC] | 5 |
| So-49 | Cayman | 23211 | 1-β-D-Glucosylsphingosine (d18:1) | CAS No 52050-17-6 1-β-D-Glucosylsphingosine (synthetic) | 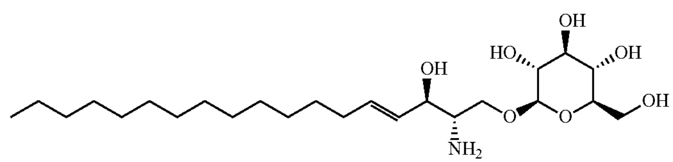 [SMILES: CCCCCCCCCCCCC/C=C/[C@@H](O)[C@@H](N)CO[C@@H]1O[C@H](CO)[C@@H](O)[C@H](O)[C@H]1O] | 5 |
| So-50 | Cayman | 24435 | C12(±)-2-hydroxy) dihydro Ceramide (d18:0/12:0) | N-(R,S)-α-hydroxy-dodecanoyl-D-erythro-Dihydrosphingosine | 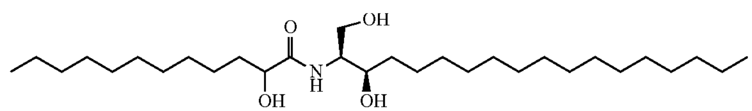 [SMILES: CCCCCCCCCCCCCCC[C@@H](O)[C@H](CO)NC(=O)C(O)CCCCCCCCCC] | 5 |

TABLE 1-continued

Molecular structure information of single lipid

| No. | Brand | Catalog No. | Abbreviation | IUPAC Name | Molecular structure | Concentration in chloroform solution (mg/mL) |
|---|---|---|---|---|---|---|
| So-51 | Cayman | 22823 | C2 Phytoceramide (t18:0/2:0) | Ceramide (t18:0/2:0) | 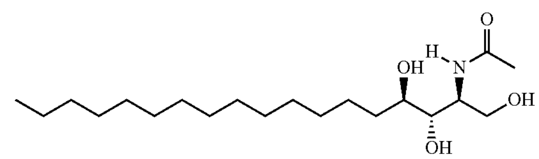 [SMILES: CCCCCCCCCCCCCC[C@@H](O)[C@@H](O)[C@H](CO)NC(C)=O] | 5 |
| So-52 | Cayman | 19579 | Ganglioside GM1 Mixture | CAS No 37758-47-7 Monosialoganglioside GM1 Mixture | 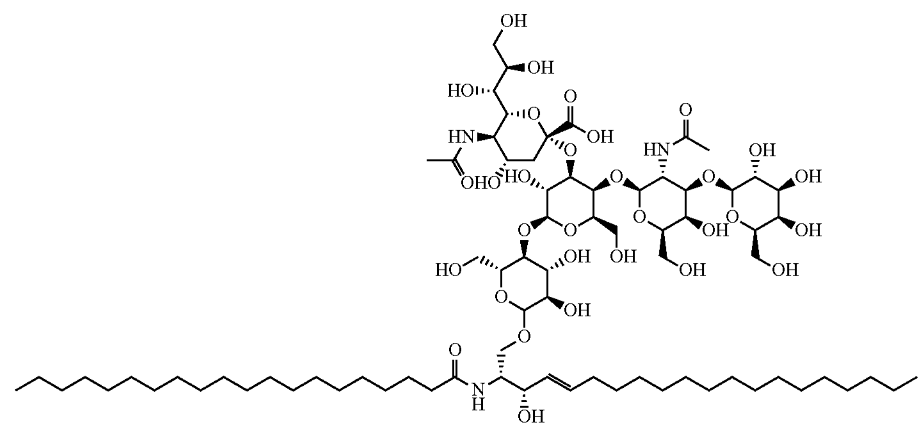 [SMILES: CCCCCCCCCCCCCCC/C=C/[C@H](O)[C@@H](COC1O[C@H](CO)[C@@H](O[C@@H]2O[C@H](CO)[C@H](O[C@@H]3O[C@H](CO)[C@H](O)[C@H](O[C@@H]4O[C@H](CO)[C@H](O)[C@H](O)[C@H]4O)[C@H]3NC(C)=O)[C@H](O[C@]3(C(=O)O)C[C@H](O)[C@@H](NC(C)=O)[C@H]([C@H](O)[C@H](O)CO)O3)[C@H]2O)[C@H](O)[C@H]1O)NC(=O)CCCCCCCCCCCCCCCCCCC] | 5 |
| So-53 | Cayman | 10007902 | Sphingosine (d17:1) | CAS No 6918-48-5 D-erythro-Sphingosine C-17 | 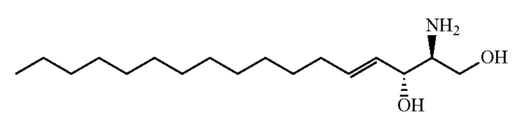 | 5 |
| So-54 | Cayman | 62525 | C6 Ceramide (d18:1/6:0) | CAS No 124753-97-5 N-hexanoyl-D-erythro-sphingosine | 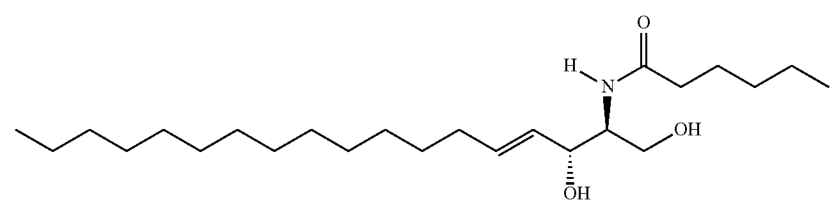 [SMILES: CCCCCCCCCCCCC/C=C/[C@@H](O)[C@H](CO)NC(=O)CCCCC] | 5 |

TABLE 1-continued

Molecular structure information of single lipid

| No. | Brand | Catalog No. | Abbreviation | IUPAC Name | Molecular structure | Concentration in chloroform solution (mg/mL) |
|---|---|---|---|---|---|---|
| So-55 | Cayman | 24375 | D-threo Sphinganine (d18:0) | CAS No 6036-86-8 D-threo-Dihydrosphingosine | 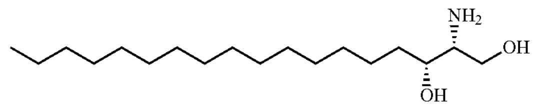 [SMILES: CCCCCCCCCCCCCCC[C@@H](O)[C@H](N)CO] | 5 |
| So-56 | Cayman | 62530 | C24:1 Ceramide (d18:1/24:1(15Z)) | CAS No 54164-50-0 N-Nervonoyl-D-erythro-Sphingosine | 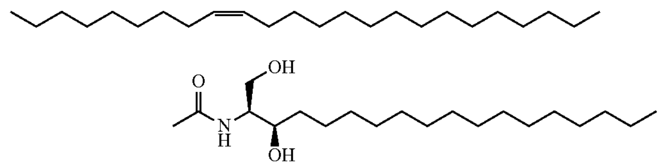 | 5 |
| So-57 | Cayman | 24437 | C18((±)-2'-hydroxy) dihydro Ceramide (d18:0/18:0) | CAS No 215528-91-9 N-(2'-(R,S)-hydroxy stearoyl)-D-erythro-Dihydrosphingosine | 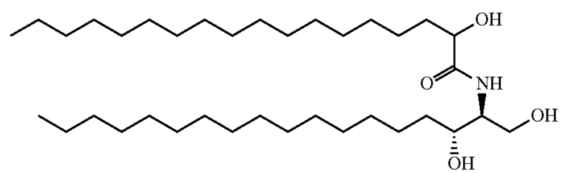 [SMILES: CCCCCCCCCCCCCCCCC(O)C(=O)N[C@@H](CO)[C@H](O)CCCCCCCCCCCCCCC] | 5 |
| So-58 | Cayman | 62540 | C8 Ceramide (d18:1/8:0) | CAS No 74713-59-0 N-octanoyl-D-erythro-Sphingosine | 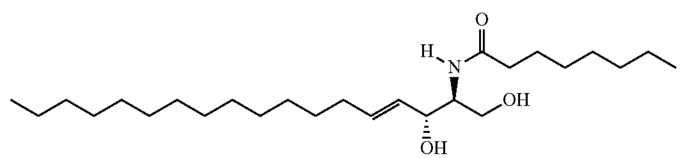 [SMILES: CCCCCCCCCCCCC/C=C/[C@@H](O)[C@H](CO)NC(=O)CCCCCCC] | 5 |
| So-59 | Cayman | 62510 | C2 Ceramide (d18:1/2:0) | CAS No 3102-57-6 N-acetyl-D-erythro-sphingosine | 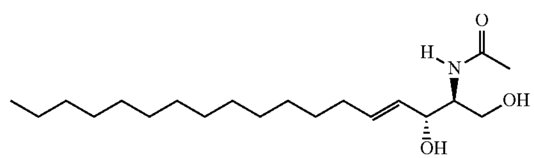 [SMILES: CCCCCCCCCCCCC/C=C/[C@@H](O)[C@H](CO)NC(C)=O] | 5 |
| So-60 | Larodan | 56-1095-4 | N-Acetyl-Sphingosylphosphoryl-ethanolamine CPEs | N-Acetyl-Sphingosylphosphoryl-ethanolamine | 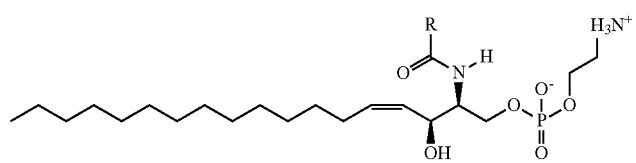 | 5 |

TABLE 1-continued

Molecular structure information of single lipid

| No. | Brand | Catalog No. | Abbreviation | IUPAC Name | Molecular structure | Concentration in chloroform solution (mg/mL) |
|---|---|---|---|---|---|---|
| So-61 | Larodan | 56-1096-4 | N-Pentadecanoyl-Psychosine | N-[(1S,2R,3E)-1-[(β-D-galactopyranosyloxy)methyl]-2-hydroxy-3-heptadecen-1-yl]-pentadecanamide | 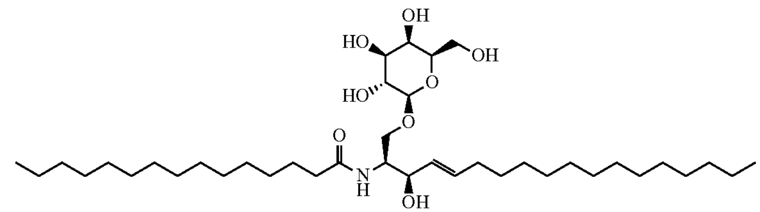 [SMILES: CCCCCCCCCCCCC/C=C/[C@@H](O)[C@H](CO[C@@H]1O[C@H](CO)[C@H](O)[C@H](O)[C@H]1O)NC(=O)CCCCCCCCCCCCCC] | 5 |
| So-62 | Larodan | 56-1120-5 | N-Lauroyl-D-Sphingosine | N-[(1S,2R,3E)-2-hydroxy-1-(hydroxymethyl)-3-heptadecen-1-yl]-dodecanamide | 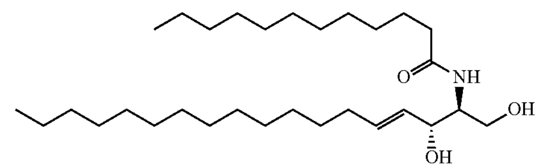 [SMILES: CCCCCCCCCCCCC/C=C/[C@@H](O)[C@H](CO)NC(=O)CCCCCCCCCCC] | 5 |
| So-63 | Larodan | 56-1125-5 | Phytosphingosine | 2S-amino-1,3S,4R-octadecanetriol | 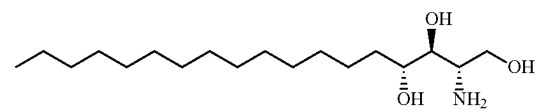 | 5 |
| So-64 | Larodan | 56-1135-5 | N-Pentadecanoyl-D-Sphingosine | N-[(1S,2R,3E)-2-hydroxy-1-(hydroxymethyl)-3-heptadecen-1-yl]-pentadecanamide | 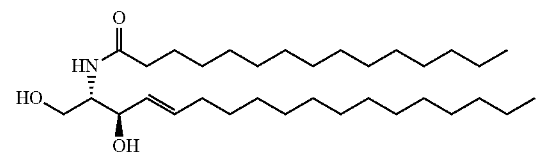 [SMILES: CCCCCCCCCCCCC/C=C/[C@@H](O)[C@H](CO)NC(=O)CCCCCCCCCCCCCC] | 5 |
| So-65 | Larodan | 56-1137-5 | N-Nonadecanoyl-D-Sphingosine | N-[(1S,2R,3E)-2-hydroxy-1-(hydroxymethyl)-3-heptadecen-1-yl]-nonadecanamide | 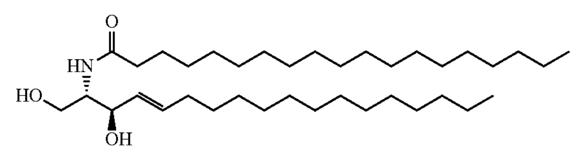 [SMILES: CCCCCCCCCCCCC/C=C/[C@@H](O)[C@H](CO)NC(=O)CCCCCCCCCCCCCCCCCC] | 5 |
| So-66 | Larodan | 56-1141-4 | Glucosylsphingosine (d18:1) | D-glucosyl-β1-1'-D-erythro-sphingosine, | 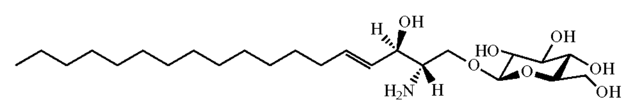 | 5 |

TABLE 1-continued

Molecular structure information of single lipid

| No. | Brand | Catalog No. | Abbreviation | IUPAC Name | Molecular structure | Concentration in chloroform solution (mg/mL) |
|---|---|---|---|---|---|---|
| So-67 | Larodan | 56-1161-4 | N-Hexanoyl-Phytosphingosine, Cer(t18:0/6:0) | N-[(1S,2S,3R)-2,3-dihydroxy-1-(hydroxymethyl)heptadecyl]-hexanamide | 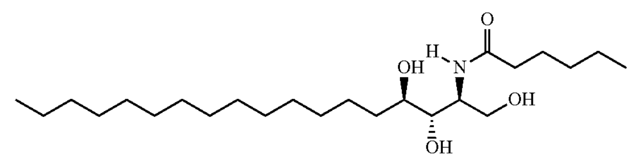 [SMILES: CCCCCCCCCCCCCC[C@@H](O)[C@@H](O)[C@H](CO)NC(=O)CCCCC] | 5 |
| So-68 | Larodan | 56-1163-4 | N-Palmitoyl-Phytosphingosine, Cer(t18:0/16:0) | N-[(1S,2S,3R)-2,3-dihydroxy-1-(hydroxymethyl)heptadecyl]-hexadecanamide | 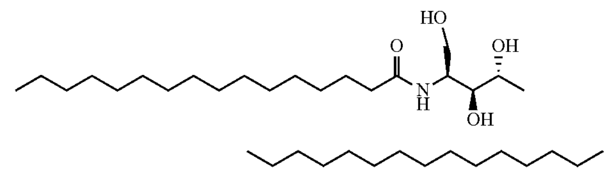 | 5 |
| So-69 | Larodan | 56-1164-4 | N-Stearoyl-Phytosphingosine, Cer(t18:0/18:0) | N-[(1S,2S,3R)-2,3-dihydroxy-1-(hydroxymethyl)heptadecyl]-octadecanamide | 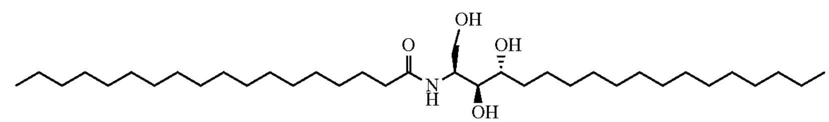 [SMILES: CCCCCCCCCCCCCCCCCC(=O)N[C@@H](CO)[C@H](O)[C@H](O)CCCCCCCCCCCCCC] | 5 |
| So-70 | Larodan | 56-1304-4 | trans L-erythro-Sphingosine (synthetic) | (2R,3S,4E)-2-amino-4-octadecene-1,3-diol | 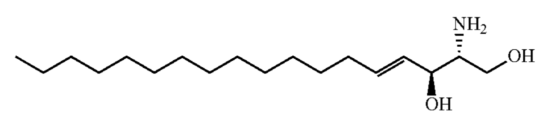 | 5 |
| So-71 | Larodan | 56-1306-5 | DL-erythro/threo Sphinganine (d18:0) | (2S,3R)-2-amino-1,3-Octadecanediol | 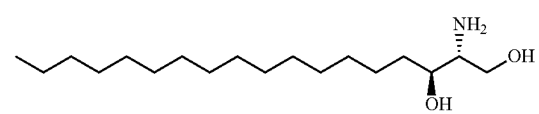 [SMILES: CCCCCCCCCCCCC/C=C/[C@H](O)[C@H](N)CO] | 5 |
| So-72 | Larodan | 56-1315-5 | 3-keto Sphinganine (d12:0) | 2-amino-1-hydroxy-3-dodecanone, monohydrochloride | 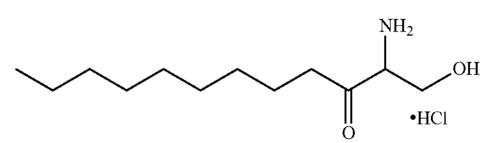 | 5 |
| So-73 | Larodan | 56-1326-4 | C15-D-erythro-Sphingosine | 2S-amino-4E-pentadecene-1,3R-diol | 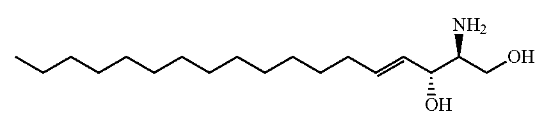 [SMILES: CCCCCCCCCCCCC/C=C/[C@@H](O)[C@@H](N)CO] | 5 |

TABLE 1-continued

Molecular structure information of single lipid

| No. | Brand | Catalog No. | Abbreviation | IUPAC Name | Molecular structure | Concentration in chloroform solution (mg/mL) |
|---|---|---|---|---|---|---|
| So-74 | Larodan | 71-1302-1 | D-erythro-Sphingosine, D9 | (2S,3R,E)-aminooctadec-4-ene-15,15,16,16,17,17,18,18,18-d9-1,3-diol | 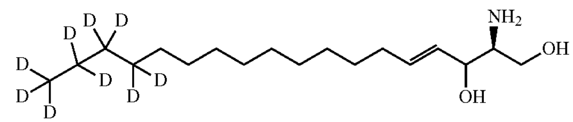 [SMILES: [2H]C([2H])([2H])C([2H])([2H])C([2H])([2H])C([2H])([2H])CCCCCCCCC/C=C/C(O)[C@@H](N)CO] | 5 |
| So-75 | Larodan | 56-1615-4 | 15-Methylhexadeca Sphinganine | 1,3-Hexadecanediol, 2-amino-15-methyl-, D-erythro- | 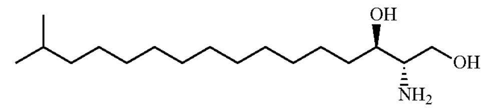 | 5 |
| No.41 | avanti | 792079P | Sphinganine(d22:0) | | 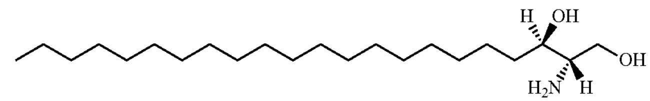 | 10 |
| No.38 | avanti | 791016 | PE(16:0/16:1) | (2-aminoethoxy)[(2R)-2-[(9Z)-hexadec-9-enoyloxy]-3-(hexadecanoyloxy)propoxy] phosphinic acid | 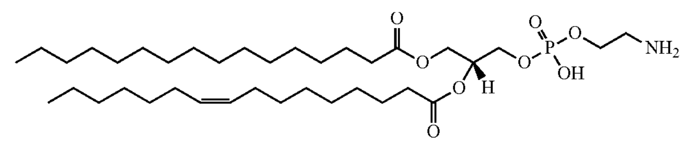 [SMILES: CCCCCC/C=C\CCCCCCCC(=O)O[C@H](COC(=O)CCCCCCCCCCCCCCC)COP(=O)(O)OCCN] | 10 |
| No.48 | Larodan | 34-2230 | TG(18:1/22:1/22:1) | 1,2-Eucin(13Z)-3-Olein | 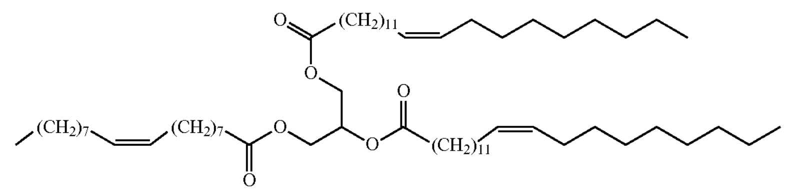 | 10 |

TABLE 2

Synthesis information of small RNA (purchased from Guangzhou RiboBio Co., LTD, Ribobio)

| Title | Single-/double-stranded | Sequence | Concentration |
|---|---|---|---|
| PGY-ssRNA-6 | single-stranded | GTTCAGAGTTCTACAGTCCGA (SEQ ID NO: 1) | 20 μM |

TABLE 3

PBS formulation having a total system of 2 Liters (reagents purchased from Beijing Chemical Works)

| PBS total system | 2 liters |
|---|---|
| NaCl | 16 g |
| Na2HPO4•12H2O | 7.16 g |
| KH2PO4 | 0.48 g |
| KCl | 0.4 g |

EXAMPLES

Experimental Methods

1. Cell Culture

The human embryonic kidney cell line HEK293T and human monocyte THP-1 used in the experiment were purchased from the Cell Culture Center of Peking Union Medical College. The cells were cultured in a 37° C., 5% $CO_2$ incubator, wherein HEK293T cells were cultured in DMEM medium (HyClone) and THP-1 cells were cultured in RPMI-1640 medium (HyClone), each medium containing 10% fetal bovine serum and a certain proportion of antibiotics (penicillin 100 U/ml & streptomycin 100 mg/ml). The cells were cultured to logarithmic growth phase, and the cell density was $6 \times 10^5/1$ mL medium/well. The 12-well plate (1 mL medium/well) was incubated overnight (12 h) at 37° C., followed by subsequent experiments.

2. Preparation of System of Sphingosine Lipid for Delivering Small RNA 2.1 5 μl of small RNA (Ribobio, 20 μM, as shown in Table 2) and 95 μL of DEPC (Sigma) treated water were added into a 1.5 ml EP tube and mixed well. Then a certain amount of single lipid or lipid composition in chloroform solution (as shown in Table 1) was added and fully mixed by sucking and blowing;

2.2 The system was fully mixed and was heated in a water bath at 90° C. for 15 minutes;

2.3 The system was taken out and cooled down to room temperature.

3. Real-Time Quantitative PCR (RT-qPCR) Detection of Intracellular

Expression of Nucleic Acids Delivered by Lipid 3.1 The human embryonic kidney cell line HEK293T used in the experiment was cultured to logarithmic growth phase, and then plated on a 12-well plate with a cell density of $6 \times 10^5/1$ mL medium/well. The 12-well plate (1 mL medium/well) was incubated overnight (12 h) at 37° C., followed by subsequent experiments.

3.2 Experimental groups were as follows:
1) Naïve group: untreated cells. This group served as a blank control group;
2) Free uptake group: small RNA solution was directly added (the storage concentration was 20 μM). This group served as a negative control group;
3) Lipid nucleic acid mixture: the mixture of lipid and small RNA prepared from the step 2 was added into cells and mixed, and the final concentration of small RNA was 100 nM.

3.3 After co-incubation with cells for a specific period of time, the cells were washed three times with PBS. The cells were harvested with TRIzol lysis buffer (purchased from Sigma-Aldrich), and total RNA was extracted. The abundance of small RNA that entered the cells was detected by RT-qPCR; the protocols were as follows:

1) Extraction of total cellular RNA:

To the cells cultured in a 12-well plate (about $1 \times 10^6$ cells/well) was added 1 mL TRIzol lysis buffer in each well, and then placed on ice. After all the samples were added TRIzol, they were allowed to stand at room temperature for 5 min to be fully lysed.

Centrifugation was conducted at 4° C., 12,000 rpm for 5 min. The precipitates were discarded and TRIzol was transferred to a fresh centrifuge tube;

Chloroform was added at a ratio of 200 μL chloroform/mL TRIzol, shaken well and mixed. The mixture was placed at room temperature for 5 min;

Centrifugation was conducted at 4° C., 12,000 rpm for 15 min;

The upper aqueous phase was pipetted into another centrifuge tube, and isopropanol was added at a ratio of 0.5 mL isopropanol/mL TRIzol. The mixture was placed at room temperature for 5-10 min;

Centrifugation was conducted at 4° C., 12,000 rpm for 15 min. The supernatant was discarded, and the RNA precipitates to the bottom of the tube;

The tube was added 1 mL 75% ethanol and gently shaken to suspend the precipitates;

Centrifugation was conducted at 4° C., 12,000 rpm for 10 min. The supernatant was discarded. The tube was added 1 mL 75% ethanol and gently shaken to suspend the precipitate;

Centrifugation was conducted at 4° C., 12,000 rpm for 10 min, and the supernatant was discarded. The DNA sample was dried at room temperature and dissolved with 50 μL RNase-free $H_2O$. The RNA concentration was quantified by measuring the OD value.

2) Total RNA was reverse transcribed to cDNA: Reverse Transcription Kit (High-Capacity cDNA Reverse Transcription Kits, Applied Biosystems, cat. no. 4368813) was used to reverse transcribe sRNA to cDNA by stem-loop method (see, e.g. Real-time quantification of microRNAs by stem-loop RT-PCR, Nucleic Acids Res. 2005 Nov. 27; 33(20): e179, incorporated by reference herein). The reverse transcription system was as follows: template RNA (150 ng/μL) 10 μL, 10×RT buffer 2.0 μL, 25×dNTP Mix (100 mM) 0.8 μL, U6 RT stem-loop primer 2.0 μL, HJT-sRNA-m7 RT stem-Loop primer 2.0 μL, Multi Scribe™ reverse transcriptase 1.0 μL, RNase inhibitor 1.0 μL, nuclease-free $H_2O$ 1.2 μL. The sample was loaded into a PCR reactor after short spin. The reaction conditions were as follows: (1) 25° C., 10 min; (2) 37° C., 120 min; (3) 85° C., 5 min; (4) 4° C., termination of reaction. 20 μl RNase-free dd$H_2O$ was added to make up the final volume to 40 μl after the reaction. The stem-loop primer used in the reverse transcription process was synthesized by Beijing Tsingke Biotechnology Co., Ltd. (U6 RT primer, because the quantification of small RNA by RT-qPCR reaction can only be relative, so U6 was used as a standard reference gene for calculating the relative expression level): GTCGTATCCAGTGCAGGGTCCGAGGTAT-TCGCACTGGATACGACAAAAAT ATG (SEQ ID NO: 2); PGY-sRNA-m7 RT stem-loop primer:

GTCGTATCCAGTGCACGCTCCGAGGTATTCGCACTGGATACGACTCGGAC (SEQ ID NO: 3)).

3) Quantitative PCR amplification reaction: the qPCR reaction system had a total volume of 10 μl, containing: 5 μL 2×SYBR Green Master Mix, 0.5 μl forward primer (10 μM), 0.5 μl reverse primer (10 μM), 1 μl cDNA obtained by reverse transcription, 3 μl RNase-free dH$_2$O. LightCycler 480 fluorescence quantitative PCR instrument was used, and the PCR reaction conditions were: 95° C., pre-denaturation for 5 min, followed by PCR amplification cycle: (1) 95° C., 10 s; (2) 55° C., 10 s; (3) 72° C., 20 s; a total of 40 cycles; 40° C. for 10 s in the end to cool down. Both the forward and reverse primers of the amplification reaction were designed and synthesized by Beijing Tsingke Biotechnology Co., Ltd. (U6 forward primer: GCGCGTCGTGAAGCGTTC (SEQ ID NO: 4), U6 reverse primer: GTGCAGGGTCCGAGGT (SEQ ID NO: 5), PGY-sRNA-m7 forward primer: TCGCGCGTTCAGAGTTC (SEQ ID NO: 6), PGY-sRNA-m7 reverse primer: GTGCACGCTCCGAGGT (SEQ ID NO: 7)).

4) 2-ΔCt method (relative gene expression level=2-(Ct target gene-Ct internal reference gene)) was used to calculate the relative amount of entry (single or double stranded RNA).

4. Flow Cytometry Technology (CFlow) Determined the Uptake Amount of Nucleic Acid that is Delivered into Cells by Lipid.

4.1 Main experimental instruments and equipment:
10 cm cell culture dishes, 12-well cell culture plates, pipettor, pipette, optical microscopes, flow cytometer Accuri® C6 instrument (purchased from BD, USA);

4.2 Main experimental reagents:
Model building and transfection: artificially synthesized single lipid shown in Table 1, artificially synthesized 5'-FAM labeled sRNAs (single-stranded, Ribobio) shown in Table 2;

4.3 The human embryonic kidney cell line HEK293T and human monocyte THP-1 cells used in the experiment were cultured to logarithmic growth phase, and then plated into 12-well plates with a cell density of 6×10$^5$/1 mL medium/well. The 12-well plate (1 mL medium/well) was incubated overnight (12 h) at 37° C., followed by subsequent experiments.

4.4 The experiment groups were as follows:
1) Naïve group: untreated cells. This group served as a blank control group.
2) Free uptake group: 5 mL of 5'-FAM labeled small RNA solution (storage concentration is 20 μM) was directly added. This group served as a negative control group;
3) Lipid nucleic acid mixture treatment group: The mixture of the lipid prepared in step 2 and the 5'-FAM-labeled small RNA was added into the cells and mixed well. The final concentration of small RNA is 100 nM.

4.5 After co-incubation with cells for 6 h/9 h, the cells were washed three times with PBS. The cells were re-suspended with PBS (self-prepared). The flow cytometer Accuri® C6 instrument (purchased from BD, US) was used to detect the fluorescence intensity of the cells in the sample wells. Implementation method: the software CFlow Plus used in the flow cytometer Accuri® C6 instrument detection was opened, the instrument was washed with cleaning solution for 3 minutes, and then washed with double-distilled water for 5 minutes. The injection of blank group samples was started while setting the number of cells unlimited. The injection of Naïve group samples was stopped when the number of cells detected was 10000 events. The live cell group in the fluorescence spectrum (abscissa: FSC-A, ordinate: SSC-A) was circled as gate P1. With the number of cells set as limited, the detection was stopped when the number of cells in gate P1 reached 10000 events. The fluorescence shift value was obtained in the fluorescence spectrum (abscissa: fluorescence channel FLA-1, ordinate: SSC-A).

Example 1: Delivery of Small RNA into HEK293T Cell by Different Concentrations of Single Sphingosine Derivative (1) Experimental Groups:
A: Naïve group: untreated cells. This group served as a blank control group;
B: Free uptake group: the solvent CHCl$_3$ of sphingosine was used as a carrier to deliver FAM-labeled small RNA, and the final concentration of nucleic acid was 100 nM. This group served as a negative control group;
C: 0.1 nmol FAM-labeled single-stranded PGY-sRNA-6 was delivered into the cell by 3.75 μg of the single sphingosine derivative solution shown in Table 4, and the final concentration of nucleic acid was 100 nM;
D: 0.1 nmol FAM-labeled single-stranded PGY-sRNA-6 was delivered into the cell by 12.5 μg of the single sphingosine derivative solution shown in Table 4, and the final concentration of nucleic acid was 100 nM;
E: 0.1 nmol FAM-labeled single-stranded PGY-sRNA-6 was delivered into the cell by 37.5 μg of the single sphingosine derivative solution shown in Table 4, and the final concentration of nucleic acid was 100 nM;

(2) Experimental Procedures
1) Conditions of the boiling method: to 100 μL FAM-labeled single-stranded PGY-sRNA-6 solution was added corresponding amount of lipid solution, and heated at 90° C. for 15 min;
2) Experimental conditions: the final concentration of small RNA was 100 nM. 9 hours after being added to the cells, the amount of single-stranded PGY-sRNA-6 that entered into the cells was compared by detecting the fluorescence shift using flow cytometry technology. For the detailed protocols, see "Flow cytometry technology (CFlow) determined the uptake amount of nucleic acid that is delivered into cells by lipid". All experiments were performed in triplicates.

Conclusions: The results indicated that as compared to the free uptake group, the fluorescence value showed significant shift in the experimental group after delivery of fluorescently labeled nucleic acids by sphingosine lipids, indicating that different single sphingosine lipid derivatives were effective in delivering single-stranded small RNA into cells (see FIG. 1a-e to FIG. 33a-e). The effectiveness of single sphingosine lipid derivative for nucleic acid delivery, and the efficiency of sphingosine derivative to deliver sRNA were concentration dependent. Herein, the delivery by high-concentration sphingosine derivative (0.1 nmol small RNA was delivered into the cell by 37.5 us of the single sphingosine derivative solution) had a more significant effect (see Table 4).

Example 2: Delivery of Single-Stranded PGY-sRNA-6 into THP-1 Cell by Mixtures of Different Single Sphingosine Derivatives, Sphingosine (So) and Phosphatidyl Ethanolamine (PE)

(1) Experimental Groups:
A: Naïve group: untreated cells. This group served as a blank control group;
B: Free uptake group: the solvent CHCl$_3$ of sphingosine was used as a carrier to deliver FAM-labeled small RNA, and the final concentration of nucleic acid was 100 nM. This group served as a negative control group;

C: Lipid mixture delivery group: 0.1 nmol FAM-labeled single-stranded PGY-sRNA-6 was delivered into the cell by 12.5 µg of the lipid mixture of sphingosine derivative (No. 41: No. 38: So=1:1:1, wherein the specific lipid mixture is shown in FIG. 34a-c to FIG. 79a-c and Table 4). The final concentration of nucleic acid was 100 nM.

(2) Experimental Procedures

1) Conditions of the boiling method: to 100 µL FAM-labeled small RNA solution was added 12.5 µg of lipid mixture solution, and heated at 90° C. for 15 min;

2) Experimental conditions: the final concentration of small RNA was 100 nM. 6 hours after being added to the cells, the amount of small RNA that entered into the cells was compared by detecting the fluorescence shift using flow cytometry technology. For the detailed protocols, see "Flow cytometry technology (CFlow) determined the uptake amount of nucleic acid that is delivered into cells by lipid". All experiments were performed in triplicates.

Conclusions: The results indicated that as compared to the free uptake group, the fluorescence value showed significant shift in the experimental group after delivery of nucleic acids by sphingosine lipids (see FIG. 34a-c to FIG. 79a-c, Table 4), indicating that 12.5 µg of lipid mixture was effective in delivering small RNA into cells. The effectiveness of lipid mixture (No. 41: No. 38: So=1:1:1) for nucleic acid delivery (see Table 4). Delivery of small RNA by lipid mixture had the potential of improving the efficiency of the delivery of nucleic acid drug in clinical settings.

Example 3: Delivery of Single-Stranded PGY-sRNA-6 into THP-1 Cell by Mixtures of Different Single Sphingosine Derivatives, Sphingosine (So), Phosphatidyl Ethanolamine (PE) and Triglyceride (TG)

(1) Experimental Groups:

A: Naïve group: untreated cells. This group served as a blank control group;

B: Free uptake group: the solvent $CHCl_3$ of sphingosine was used as a carrier to deliver FAM-labeled small RNA, and the final concentration of nucleic acid was 100 nM. This group served as a negative control group;

C: Lipid mixture delivery group: 0.1 nmol FAM-labeled single-stranded PGY-sRNA-6 was delivered into the cell by 12.5 µg of the lipid mixture of sphingosine derivative (No. 41: No. 38: So=2:2:1:2, wherein the specific lipid mixture was shown in FIG. 80a-c to FIG. 99a-c and Table 4), the final concentration of nucleic acid was 100 nM.

(2) Experimental Procedures

1) Conditions of the boiling method: to 100 µL FAM-labeled small RNA solution was added 12.5 µg of lipid mixture solution, and heated at 90° C. for 15 min;

2) Experimental conditions: the final concentration of small RNA was 100 nM. 6 hours after being added to the cells, the amount of small RNA that entered into the cells was compared by detecting the fluorescence shift using flow cytometry technology. For the detailed protocols, see "Flow cytometry technology (CFlow) determined the uptake amount of nucleic acid that is delivered into cells by lipid". All experiments were performed in triplicates.

Conclusions: The results indicated that as compared to the free uptake group, the fluorescence value showed significant shift in the experimental group after delivery of nucleic acids by sphingosine lipids (see FIG. 80a-c to FIG. 80a-c, Table 4), indicating that 12.5 µg of lipid mixture (No. 41: No. 38: No. 48: So=2:2:1:2) was effective in delivering small RNA into cells. The effectiveness of lipid mixture (No. 41: No. 38: No. 48: So=2:2:1:2) for nucleic acid delivery (see Table 4). Delivery of small RNA by lipid mixture had the potential of improving the efficiency of the delivery of nucleic acid drug in clinical settings.

Example 4: Delivery of Single-Stranded PGY-sRNA-6 into HEK293T Cell by Mixtures of Different Single Sphingosine Derivatives, Sphingosine (So) and Phosphatidyl Ethanolamine (PE)

(1) Experimental Groups:

A: Naïve group: untreated cells. This group served as a blank control group;

B: Free uptake group: the solvent $CHCl_3$ of sphingosine was used as a carrier to deliver small RNA, and the final concentration of nucleic acid was 100 nM. This group served as a negative control group;

C: Lipid mixture delivery group: 0.1 nmol single-stranded PGY-sRNA-6 was delivered into the cell by 12.5 µg of the lipid mixture of sphingosine derivative (No. 41: No. 38: So=1:1:1, wherein the specific lipid mixture was shown in FIG. 100-104), the final concentration of nucleic acid was 100 nM.

(2) Experimental Procedures

1) Conditions of the boiling method: to 100 µL small RNA solution was added corresponding amount of lipid solution, and heated at 90° C. for 15 min;

2) Experimental conditions: the final concentration of small RNA was 100 nM. 6 hours after being added to the cells, the amount of small RNA that entered into the cells was compared by RT-qPCR detection. For the detailed protocols, see "Real-time quantitative PCR (RT-qPCR) detection of intracellular expression of nucleic acids delivered by lipid". All experiments were performed in triplicates.

Conclusions: The results indicated that as compared to the Naïve group and the negative control group, a significant increase in relative uptake amount of small RNA in cells was detected after delivery of 0.1 nmol nucleic acids by 12.5 µg of the lipid combination (No. 41: No. 38: So=1:1:1) containing sphingosine derivative in the experimental group, indicating that the addition of multiple single sphingosine lipid derivatives could greatly improve the efficiency of the delivery of lipid combinations.

TABLE 4

| FIGS. | Name of the lipid | Naïve group | Free uptake group | Lipid delivery group (different concentrations of lipids) | | | Delivery sequence | Cell line |
|---|---|---|---|---|---|---|---|---|
| | | | | 3.75 µg/mL | 12.5 µg/mL | 37.5 µg/mL | | |
| FIG. 1a-e | sphingosine derivative So-1 | 0.00% | 0.20% | 1.60% | 1.50% | 1.40% | PGY-ssRNA-6 | 293T |

TABLE 4-continued

| FIGS. | Name of the lipid | Naïve group | Free uptake group | Lipid delivery group (different concentrations of lipids) | | | Delivery sequence | Cell line |
|---|---|---|---|---|---|---|---|---|
| | | | | 3.75 µg/mL | 12.5 µg/mL | 37.5 µg/mL | | |
| FIG. 2a-e | sphingosine derivative So-3 | 0.00% | 0.20% | 1.40% | 2.10% | 3.40% | PGY-ssRNA-6 | 293T |
| FIG. 3a-e | sphingosine derivative So-4 | 0.00% | 0.20% | 1.70% | 2.20% | 0.00% | PGY-ssRNA-6 | 293T |
| FIG. 4a-e | sphingosine derivative So-5 | 0.00% | 0.20% | 2.80% | 1.60% | 2.40% | PGY-ssRNA-6 | 293T |
| FIG. 5a-e | sphingosine derivative So-7 | 0.00% | 0.20% | 1.20% | 0.20% | 4.30% | PGY-ssRNA-6 | 293T |
| FIG. 6a-e | sphingosine derivative So-8 | 0.00% | 0.20% | 3.60% | 4.50% | 1.90% | PGY-ssRNA-6 | 293T |
| FIG. 7a-e | sphingosine derivative So-9 | 0.00% | 0.10% | 3.30% | 2.60% | 2.70% | PGY-ssRNA-6 | 293T |
| FIG. 8a-e | sphingosine derivative So-10 | 0.00% | 0.10% | 2.10% | 3.40% | 2.50% | PGY-ssRNA-6 | 293T |
| FIG. 9a-e | sphingosine derivative So-11 | 0.00% | 0.10% | 3.60% | 7.40% | 12.70% | PGY-ssRNA-6 | 293T |
| FIG. 10a-e | sphingosine derivative So-12 | 0.00% | 0.10% | 5.60% | 2.30% | 1.60% | PGY-ssRNA-6 | 293T |
| FIG. 11a-e | sphingosine derivative So-13 | 0.00% | 0.10% | 3.40% | 3.20% | 5.20% | PGY-ssRNA-6 | 293T |
| FIG. 12a-e | sphingosine derivative So-14 | 0.00% | 0.10% | 4.40% | 3.30% | 4.30% | PGY-ssRNA-6 | 293T |
| FIG. 13a-e | sphingosine derivative So-15 | 0.00% | 0.10% | 4.70% | 1.90% | 2.40% | PGY-ssRNA-6 | 293T |
| FIG. 14a-e | sphingosine derivative So-26 | 0.10% | 0.20% | 0.20% | 3.80% | 0.50% | PGY-ssRNA-6 | 293T |
| FIG. 15a-e | sphingosine derivative So-46 | 0.10% | 0.20% | 0.20% | 0.30% | 6.90% | PGY-ssRNA-6 | 293T |
| FIG. 16a-e | sphingosine derivative So-49 | 0.10% | 0.20% | 0.50% | 1.70% | 7.40% | PGY-ssRNA-6 | 293T |
| FIG. 17a-e | sphingosine derivative So-53 | 0.10% | 0.20% | 0.20% | 0.30% | 6.70% | PGY-ssRNA-6 | 293T |
| FIG. 18a-e | sphingosine derivative So-60 | 0.00% | 0.60% | 7.10% | 7.10% | 6.20% | PGY-ssRNA-6 | 293T |
| FIG. 19a-e | sphingosine derivative So-61 | 0.00% | 0.60% | 7.40% | 8.10% | 7.00% | PGY-ssRNA-6 | 293T |
| FIG. 20a-e | sphingosine derivative So-62 | 0.00% | 0.60% | 6.60% | 6.50% | 7.10% | PGY-ssRNA-6 | 293T |
| FIG. 21a-e | sphingosine derivative So-63 | 0.00% | 0.60% | 5.60% | 7.70% | 6.50% | PGY-ssRNA-6 | 293T |
| FIG. 22a-e | sphingosine derivative So-64 | 0.00% | 0.60% | 7.40% | 6.20% | 8.70% | PGY-ssRNA-6 | 293T |
| FIG. 23a-e | sphingosine derivative So-65 | 0.00% | 0.60% | 7.60% | 7.50% | 6.80% | PGY-ssRNA-6 | 293T |
| FIG. 24a-e | sphingosine derivative So-66 | 0.00% | 0.60% | 7.10% | 18.10% | 29.50% | PGY-ssRNA-6 | 293T |
| FIG. 25a-e | sphingosine derivative So-67 | 0.00% | 0.60% | 6.30% | 5.30% | 2.80% | PGY-ssRNA-6 | 293T |

TABLE 4-continued

| FIGS. | Name of the lipid | Naïve group | Free uptake group | Lipid delivery group (different concentrations of lipids) | | | Delivery sequence | Cell line |
|---|---|---|---|---|---|---|---|---|
| | | | | 3.75 μg/mL | 12.5 μg/mL | 37.5 μg/mL | | |
| FIG. 26a-e | sphingosine derivative So-68 | 0.00% | 0.60% | 4.80% | 3.80% | 3.90% | PGY-ssRNA-6 | 293T |
| FIG. 27a-e | sphingosine derivative So-69 | 0.00% | 0.60% | 4.60% | 3.80% | 3.30% | PGY-ssRNA-6 | 293T |
| FIG. 28a-e | sphingosine derivative So-70 | 0.00% | 0.60% | 4.70% | 10.10% | 11.40% | PGY-ssRNA-6 | 293T |
| FIG. 29a-e | sphingosine derivative So-71 | 0.00% | 0.60% | 3.60% | 6.20% | 8.80% | PGY-ssRNA-6 | 293T |
| FIG. 30a-e | sphingosine derivative So-72 | 0.00% | 0.60% | 2.40% | 3.40% | 14.10% | PGY-ssRNA-6 | 293T |
| FIG. 31a-e | sphingosine derivative So-73 | 0.00% | 0.60% | 3.20% | 4.60% | 9.50% | PGY-ssRNA-6 | 293T |
| FIG. 32a-e | sphingosine derivative So-74 | 0.00% | 0.60% | 4.00% | 3.10% | 6.60% | PGY-ssRNA-6 | 293T |
| FIG. 33a-e | sphingosine derivative So-75 | 0.00% | 0.60% | 3.00% | 4.20% | 11.40% | PGY-ssRNA-6 | 293T |
| FIG. 34a-e | No. 41 + No. 38 + sphingosine derivative So-1 | 0.10% | 0.40% | | 6.30% | | PGY-ssRNA-6 | THP-1 |
| FIG. 35a-c | No. 41 + No. 38 + sphingosine derivative So-2 | 0.10% | 0.40% | | 37.00% | | PGY-ssRNA-6 | THP-1 |
| FIG. 36a-c | No. 41 + No. 38 + sphingosine derivative So-3 | 0.10% | 0.40% | | 29.00% | | PGY-ssRNA-6 | THP-1 |
| FIG. 37a-c | No. 41 + No. 38 + sphingosine derivative So-4 | 0.10% | 0.40% | | 6.70% | | PGY-ssRNA-6 | THP-1 |
| FIG. 38a-c | No. 41 + No. 38 + sphingosine derivative So-5 | 0.10% | 0.40% | | 20.40% | | PGY-ssRNA-6 | THP-1 |
| FIG. 39a-c | No. 41 + No. 38 + sphingosine derivative So-6 | 0.10% | 0.40% | | 26.60% | | PGY-ssRNA-6 | THP-1 |
| FIG. 40a-c | No. 41 + No. 38 + sphingosine derivative So-7 | 0.10% | 0.40% | | 19.90% | | PGY-ssRNA-6 | THP-1 |
| FIG. 41a-c | No. 41 + No. 38 + sphingosine derivative So-8 | 0.10% | 0.40% | | 54.30% | | PGY-ssRNA-6 | THP-1 |
| FIG. 42a-c | No. 41 + No. 38 + sphingosine derivative So-9 | 0.10% | 0.40% | | 21.20% | | PGY-ssRNA-6 | THP-1 |
| FIG. 43a-c | No. 41 + No. 38 + sphingosine derivative So-10 | 0.10% | 0.40% | | 38.90% | | PGY-ssRNA-6 | THP-1 |
| FIG. 44a-c | No. 41 + No. 38 + sphingosine derivative So-11 | 0.10% | 0.40% | | 7.30% | | PGY-ssRNA-6 | THP-1 |
| FIG. 45a-c | No. 41 + No. 38 + sphingosine derivative So-12 | 0.10% | 0.40% | | 0.40% | | PGY-ssRNA-6 | THP-1 |
| FIG. 46a-c | No. 41 + No. 38 + sphingosine | 0.10% | 0.40% | | 26.20% | | PGY-ssRNA-6 | THP-1 |

TABLE 4-continued

| FIGS. | Name of the lipid | Naïve group | Free uptake group | Lipid delivery group (different concentrations of lipids) | | | Delivery sequence | Cell line |
|---|---|---|---|---|---|---|---|---|
| | | | | 3.75 μg/mL | 12.5 μg/mL | 37.5 μg/mL | | |
| | derivative So-13 | | | | | | | |
| FIG. 47a-c | No. 41 + No. 38 + sphingosine derivative So-14 | 0.10% | 0.40% | | 28.30% | | PGY-ssRNA-6 | THP-1 |
| FIG. 48a-c | No. 41 + No. 38 + sphingosine derivative So-15 | 0.10% | 0.40% | | 31.80% | | PGY-ssRNA-6 | THP-1 |
| FIG. 49a-c | No. 41 + No. 38 + sphingosine derivative So-45 | 0.10% | 0.40% | | 15.50% | | PGY-ssRNA-6 | THP-1 |
| FIG. 50a-c | No. 41 + No. 38 + sphingosine derivative So-46 | 0.10% | 0.40% | | 31.40% | | PGY-ssRNA-6 | THP-1 |
| FIG. 51a-c | No. 41 + No. 38 + sphingosine derivative So-47 | 0.10% | 0.40% | | 32.60% | | PGY-ssRNA-6 | THP-1 |
| FIG. 52a-c | No. 41 + No. 38 + sphingosine derivative So-48 | 0.10% | 0.40% | | 37.40% | | PGY-ssRNA-6 | THP-1 |
| FIG. 53a-c | No. 41 + No. 38 + sphingosine derivative So-49 | 0.10% | 0.40% | | 36.40% | | PGY-ssRNA-6 | THP-1 |
| FIG. 54a-c | No. 41 + No. 38 + sphingosine derivative So-50 | 0.10% | 0.40% | | 34.40% | | PGY-ssRNA-6 | THP-1 |
| FIG. 55a-c | No. 41 + No. 38 + sphingosine derivative So-51 | 0.10% | 0.40% | | 40.80% | | PGY-ssRNA-6 | THP-1 |
| FIG. 56a-c | No. 41 + No. 38 + sphingosine derivative So-52 | 0.10% | 0.40% | | 22.60% | | PGY-ssRNA-6 | THP-1 |
| FIG. 57a-c | No. 41 + No. 38 + sphingosine derivative So-53 | 0.10% | 0.40% | | 20.40% | | PGY-ssRNA-6 | THP-1 |
| FIG. 58a-c | No. 41 + No. 38 + sphingosine derivative So-54 | 0.10% | 0.40% | | 30.70% | | PGY-ssRNA-6 | THP-1 |
| FIG. 59a-c | No. 41 + No. 38 + sphingosine derivative So-55 | 0.10% | 0.40% | | 32.50% | | PGY-ssRNA-6 | THP-1 |
| FIG. 60a-c | No. 41 + No. 38 + sphingosine derivative So-56 | 0.10% | 0.40% | | 41.00% | | PGY-ssRNA-6 | THP-1 |
| FIG. 61a-c | No. 41 + No. 38 + sphingosine derivative So-57 | 0.10% | 0.40% | | 28.00% | | PGY-ssRNA-6 | THP-1 |
| FIG. 62a-c | No. 41 + No. 38 + sphingosine derivative So-58 | 0.10% | 0.40% | | 17.70% | | PGY-ssRNA-6 | THP-1 |
| FIG. 63a-c | No. 41 + No. 38 + sphingosine derivative So-59 | 0.10% | 0.40% | | 26.80% | | PGY-ssRNA-6 | THP-1 |
| FIG. 64a-c | No. 41 + No. 38 + sphingosine derivative So-60 | 0.10% | 0.40% | | 43.80% | | PGY-ssRNA-6 | THP-1 |

TABLE 4-continued

| FIGS. | Name of the lipid | Naïve group | Free uptake group | Lipid delivery group (different concentrations of lipids) | | | Delivery sequence | Cell line |
|---|---|---|---|---|---|---|---|---|
| | | | | 3.75 μg/mL | 12.5 μg/mL | 37.5 μg/mL | | |
| FIG. 65a-c | No. 41 + No. 38 + sphingosine derivative So-61 | 0.10% | 0.40% | | 42.70% | | PGY-ssRNA-6 | THP-1 |
| FIG. 66a-c | No. 41 + No. 38 + sphingosine derivative So-62 | 0.10% | 0.40% | | 39.70% | | PGY-ssRNA-6 | THP-1 |
| FIG. 67a-c | No. 41 + No. 38 + sphingosine derivative So-63 | 0.10% | 0.40% | | 16.80% | | PGY-ssRNA-6 | THP-1 |
| FIG. 68a-c | No. 41 + No. 38 + sphingosine derivative So-64 | 0.10% | 0.40% | | 30.70% | | PGY-ssRNA-6 | THP-1 |
| FIG. 69a-c | No. 41 + No. 38 + sphingosine derivative So-65 | 0.10% | 0.40% | | 40.90% | | PGY-ssRNA-6 | THP-1 |
| FIG. 70a-c | No. 41 + No. 38 + sphingosine derivative So-66 | 0.10% | 0.40% | | 38.40% | | PGY-ssRNA-6 | THP-1 |
| FIG. 71a-c | No. 41 + No. 38 + sphingosine derivative So-67 | 0.10% | 0.40% | | 23.50% | | PGY-ssRNA-6 | THP-1 |
| FIG. 72a-c | No. 41 + No. 38 + sphingosine derivative So-68 | 0.10% | 0.40% | | 26.90% | | PGY-ssRNA-6 | THP-1 |
| FIG. 73a-c | No. 41 + No. 38 + sphingosine derivative So-69 | 0.10% | 0.40% | | 34.60% | | PGY-ssRNA-6 | THP-1 |
| FIG. 74a-c | No. 41 + No. 38 + sphingosine derivative So-70 | 0.10% | 0.40% | | 12.20% | | PGY-ssRNA-6 | THP-1 |
| FIG. 75a-c | No. 41 + No. 38 + sphingosine derivative So-71 | 0.10% | 0.40% | | 14.10% | | PGY-ssRNA-6 | THP-1 |
| FIG. 76a-c | No. 41 + No. 38 + sphingosine derivative So-72 | 0.10% | 0.40% | | 44.40% | | PGY-ssRNA-6 | THP-1 |
| FIG. 77a-c | No. 41 + No. 38 + sphingosine derivative So-73 | 0.10% | 0.40% | | 7.30% | | PGY-ssRNA-6 | THP-1 |
| FIG. 78a-c | No. 41 + No. 38 + sphingosine derivative So-74 | 0.10% | 0.40% | | 30.70% | | PGY-ssRNA-6 | THP-1 |
| FIG. 79a-c | No. 41 + No. 38 + sphingosine derivative So-75 | 0.10% | 0.40% | | 17.70% | | PGY-ssRNA-6 | THP-1 |
| FIG. 80a-c | No. 41 + No. 38 + No. 48 + sphingosine derivative So-42 | 0.10% | 0.40% | | 18.40% | | PGY-ssRNA-6 | THP-1 |
| FIG. 81a-c | No. 41 + No. 38 + No. 48 + sphingosine derivative So-43 | 0.10% | 0.40% | | 19.40% | | PGY-ssRNA-6 | THP-1 |
| FIG. 82a-c | No. 41 + No. 38 + No. 48 + sphingosine derivative So-44 | 0.10% | 0.40% | | 29.70% | | PGY-ssRNA-6 | THP-1 |
| FIG. 83a-c | No. 41 + No. 38 + No. 48 + sphingosine | 0.10% | 0.40% | | 33.20% | | PGY-ssRNA-6 | THP-1 |

TABLE 4-continued

| FIGS. | Name of the lipid | Naïve group | Free uptake group | Lipid delivery group (different concentrations of lipids) | | | Delivery sequence | Cell line |
|---|---|---|---|---|---|---|---|---|
| | | | | 3.75 μg/mL | 12.5 μg/mL | 37.5 μg/mL | | |
| | derivative So-45 | | | | | | | |
| FIG. 84a-c | No. 41 + No. 38 + No. 48 + sphingosine derivative So-46 | 0.10% | 0.40% | | 29.00% | | PGY-ssRNA-6 | THP-1 |
| FIG. 85a-c | No. 41 + No. 38 + No. 48 + sphingosine derivative So-47 | 0.10% | 0.40% | | 34.60% | | PGY-ssRNA-6 | THP-1 |
| FIG. 86a-c | No. 41 + No. 38 + No. 48 + sphingosine derivative So-52 | 0.10% | 0.40% | | 31.20% | | PGY-ssRNA-6 | THP-1 |
| FIG. 87a-c | No. 41 + No. 38 + No. 48 + sphingosine derivative So-56 | 0.10% | 0.40% | | 39.30% | | PGY-ssRNA-6 | THP-1 |
| FIG. 88a-c | No. 41 + No. 38 + No. 48 + sphingosine derivative So-57 | 0.10% | 0.40% | | 32.70% | | PGY-ssRNA-6 | THP-1 |
| FIG. 89a-c | No. 41 + No. 38 + No. 48 + sphingosine derivative So-58 | 0.10% | 0.40% | | 5.00% | | PGY-ssRNA-6 | THP-1 |
| FIG. 90a-c | No. 41 + No. 38 + No. 48 + sphingosine derivative So-59 | 0.10% | 0.40% | | 21.60% | | PGY-ssRNA-6 | THP-1 |
| FIG. 91a-c | No. 41 + No. 38 + No. 48 + sphingosine derivative So-60 | 0.10% | 0.40% | | 22.30% | | PGY-ssRNA-6 | THP-1 |
| FIG. 92a-c | No. 41 + No. 38 + No. 48 + sphingosine derivative So-61 | 0.10% | 0.40% | | 21.40% | | PGY-ssRNA-6 | THP-1 |
| FIG. 93a-c | No. 41 + No. 38 + No. 48 + sphingosine derivative So-62 | 0.10% | 0.40% | | 25.00% | | PGY-ssRNA-6 | THP-1 |
| FIG. 94a-c | No. 41 + No. 38 + No. 48 + sphingosine derivative So-63 | 0.10% | 0.40% | | 30.00% | | PGY-ssRNA-6 | THP-1 |
| FIG. 95a-c | No. 41 + No. 38 + No. 48 + sphingosine derivative So-64 | 0.10% | 0.40% | | 27.60% | | PGY-ssRNA-6 | THP-1 |
| FIG. 96a-c | No. 41 + No. 38 + No. 48 + sphingosine derivative So-67 | 0.10% | 0.40% | | 36.90% | | PGY-ssRNA-6 | THP-1 |
| FIG. 97a-c | No. 41 + No. 38 + No. 48 + sphingosine derivative So-68 | 0.10% | 0.40% | | 41.90% | | PGY-ssRNA-6 | THP-1 |
| FIG. 98a-c | No. 41 + No. 38 + No. 48 + sphingosine derivative So-69 | 0.10% | 0.40% | | 23.20% | | PGY-ssRNA-6 | THP-1 |
| FIG. 99a-c | No. 41 + No. 38 + No. 48 + sphingosine derivative So-70 | 0.10% | 0.40% | | 12.80% | | PGY-ssRNA-6 | THP-1 |

EXPLANATION

1. Compared with the negative control group, the fluorescence shift (shifted to the right, marked with red area) was increased in the experimental group, which indicated that more fluorescently labeled RNA had been taken up by cells, that is, larger amount of RNA was delivered into the cell by lipid, reflecting the higher delivery efficiency;

2. The delivery efficiency varied with lipid concentration, which indicated that the delivery of RNA was dependent on the lipid concentration.

The invention claimed is:

1. A method for delivering a nucleic acid to a cell or a subject, comprising:
   (1) providing an organic solvent solution comprising a lipid composition;
   (2) providing an aqueous solution comprising the nucleic acid;
   (3) adding the organic solvent solution of step (1) to the aqueous solution of step (2), and then heating at a temperature of 60° C. to 100° C. to obtain a lipid-nucleic acid mixture, and
   (4) contacting the lipid-nucleic acid mixture of step (3) with the cell or the subject so that the nucleic acid is delivered to the cell or the subject,
   wherein the lipid composition consists of one or more compounds of Formula (I), a stereoisomer or a pharmaceutical acceptable salt thereof:

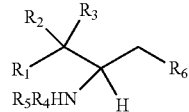

I wherein:
R1 is selected from $C_{1-20}$ alkyl or $C_{2-20}$ alkenyl, which are optionally substituted by one to three hydroxyl groups;
R2 is hydrogen and R3 is hydroxyl; or
R2 and R3 together form oxo (=O);
R4 and R5 are independently selected from the group consisting of hydrogen, $C_{1-20}$ alkyl, $C_{1-30}$ alkylacyl and $C_{1-30}$ alkenylacyl, said $C_{1-30}$ alkylacyl and $C_{1-30}$ alkenylacyl are optionally substituted by one to three groups selected from biotin, acyl or hydroxyl;
R6 is selected from the group consisting of hydrogen, hydroxyl, phosphate ester group, —O-glycosyl, ganglioside, and aminoethoxyphosphonate ester group ($NH_2$—$CH_2$—$CH_2$—O—P(O)OH—).

2. The method of claim 1, wherein:
R1 is selected from $C_{14-20}$ alkyl or $C_{14-20}$ alkenyl containing one double bond;
R4 and R5 are independently selected from the group consisting of hydrogen, $C_{1-6}$ alkyl, $C_{6-30}$ alkylacyl and $C_{6-30}$ alkenylacyl, said $C_{6-30}$ alkylacyl and the $C_{6-30}$ alkenylacyl are optionally substituted at a terminal carbon by biotin, acyl or hydroxyl, or optionally substituted at an α-carbon of the acyl by a hydroxyl.

3. The method of claim 1, wherein
(i) R4 and R5 are both methyl;
(ii) at least one of R4 and R5 is hydrogen and the other is straight-chain $C_{6-30}$ alkylacyl, straight-chain $C_{6-30}$ alkenylacyl or straight-chain $C_{7-14}$ alkyl; or
(iii) R4 and R5 are independently selected from $C_{1-6}$ alkyl.

4. The method of claim 1, wherein R1 is selected from a straight-chain $C_{14-20}$ alkyl or a straight-chain $C_{14-20}$ alkenyl containing one double bond.

5. The method of claim 1, wherein the compound has the following Formula (Ia):

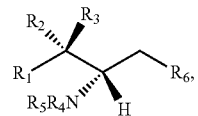

Ia wherein R1, R2, R3, R4, R5 and R6 are as defined in claim 1.

6. The method of claim 1, wherein the lipid composition consists of one or more of the following lipids:

| No. | Structure |
|---|---|
| So-1 | 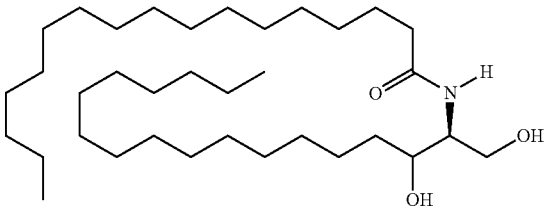 |

-continued
| No. | Structure |
|---|---|
| So-2 | 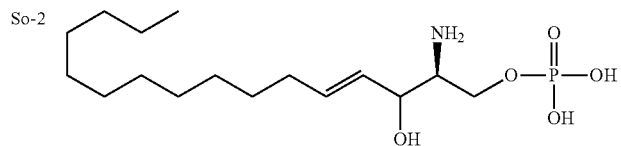 |
| So-3 | 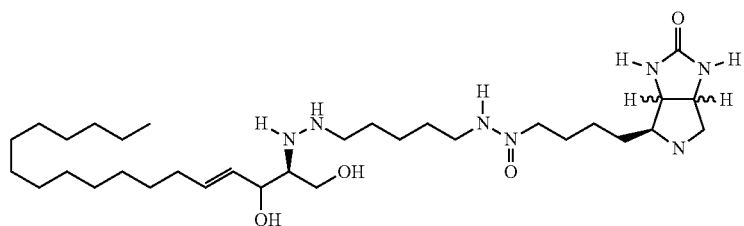 |
| So-4 | 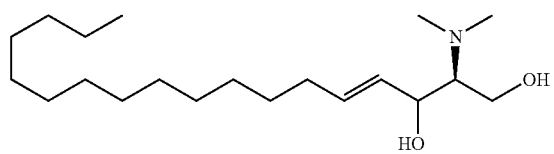 [SMILES: CCCCCCCCCCCCC/C=C/C(O)[C@H](CO)N(C)C] |
| So-5 | 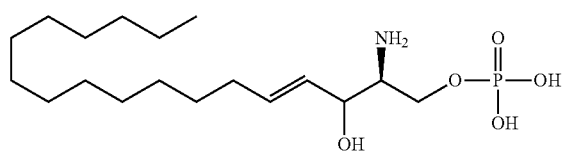 [SMILES: CCCCCCCCCCCCC/C=C/C(O)[C@@H](N)COP(=O)(O)O] |
| So-6 | 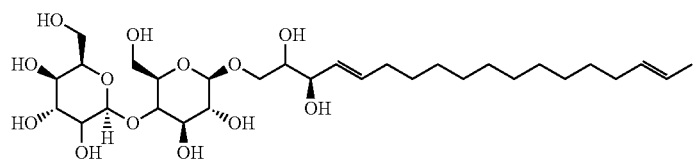 [SMILES: C/C=C/CCCCCCCCCC/C=C/[C@@H](O)C(O)CO[C@@H]1O[C@H](CO)C(O[C@@H]2O[C@H](CO)[C@H](O)[C@@H](O)C2O)[C@H](O)[C@H]1O] |
| So-7 | 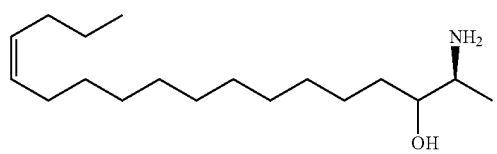 [SMILES: CCC/C=C\CCCCCCCCCCC(O)[C@H](C)N] |
| So-8 | 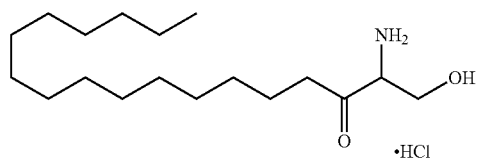 [SMILES: CCCCCCCCCCCCCCCC(=O)C(N)CO ; Cl] |
| So-9 | 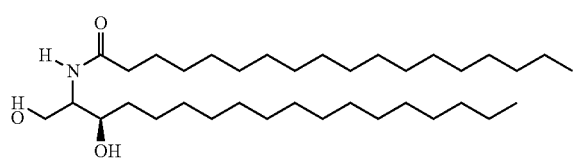 [SMILES: CCCCCCCCCCCCCCCCCC(=O)NC(CO)[C@H](O)CCCCCCCCCCCCCCC] |
| So-10 | 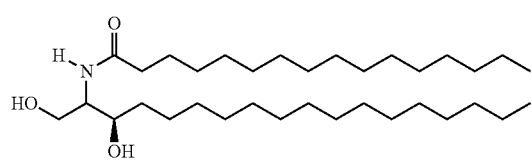 [SMILES: CCCCCCCCCCCCCCCC(=O)NC(CO)[C@H](O)CCCCCCCCCCCCCCC] |

-continued
| No. | Structure |
|---|---|
| So-11 | 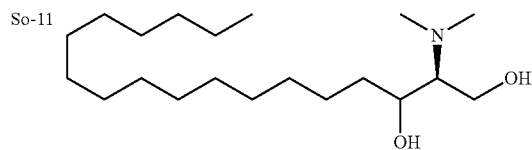 |
| So-12 | 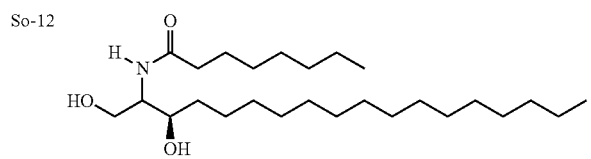 |
| So-13 | 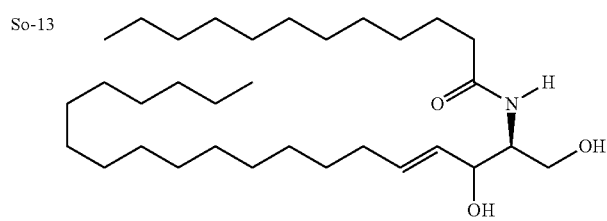 |
| So-14 | 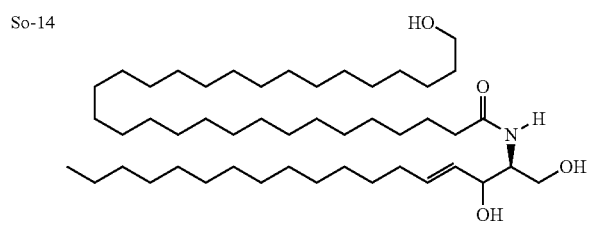 |
| So-15 | 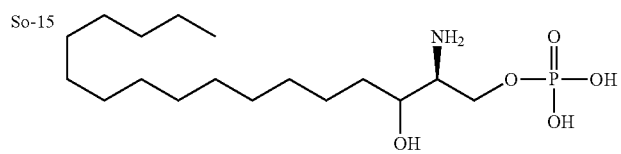 |
| So-16 | 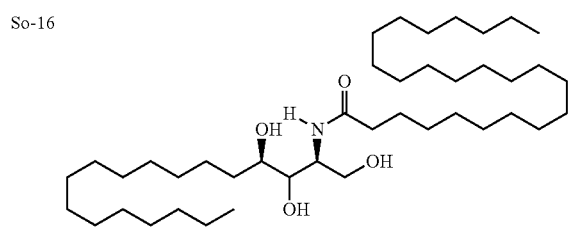 |
| So-17 | 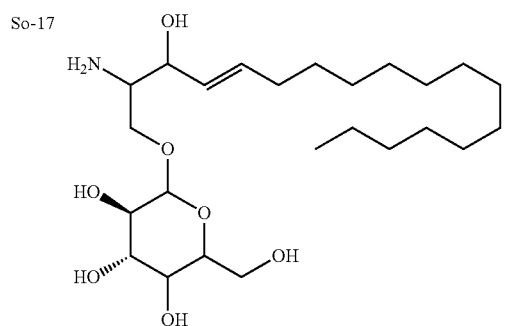 |

-continued
| No. | Structure |
|---|---|
| So-18 | 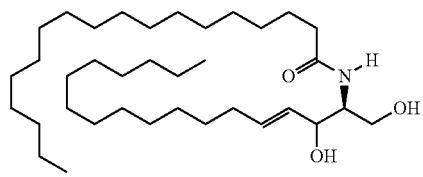 [SMILES: CCCCCCCCCCCCC/C=C/C(O)[C@H](CO)NC(=O)CCCCCCCCCCCCCCCCC] |
| So-19 | 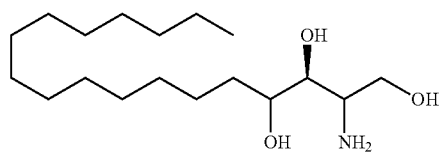 [SMILES: CCCCCCCCCCCCCCC(O)[C@@H](O)C(N)CO] |
| So-20 | 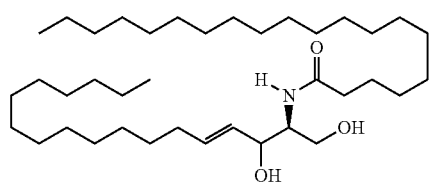 [SMILES: CCCCCCCCCCCCC/C=C/C(O)[C@H](CO)NC(=O)CCCCCCCCCCCCCCCCCCC] |
| So-21 | 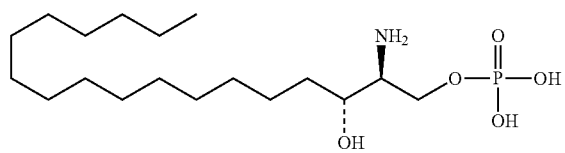 [SMILES: CCCCCCCCCCCCCCC[C@@H](O)[C@@H](N)COP(=O)(O)O] |
| So-23 | 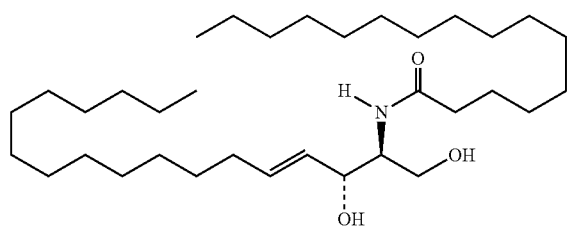 [SMILES: CCCCCCCCCCCCC/C=C/[C@@H](O)[C@H](CO)NC(=O)CCCCCCCCCCCCCCC] |
| So-25 | 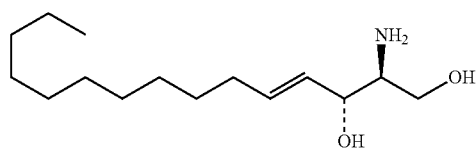 [SMILES: CCCCCCCCCC/C=C/[C@@H](O)[C@@H](N)CO] |
| So-26 | 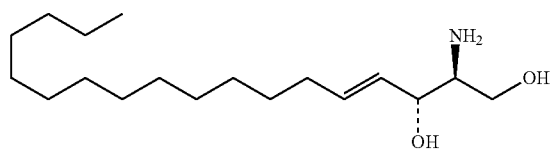 [SMILES: CCCCCCCCCCCCC/C=C/[C@@H](O)[C@@H](N)CO] |
| So-27 | 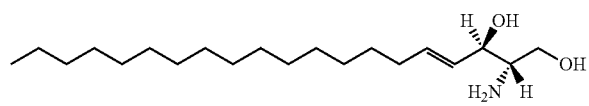 [SMILES: CCCCCCCCCCCCCCC/C=C/[C@@H](O)[C@@H](N)CO] |
| So-30 | 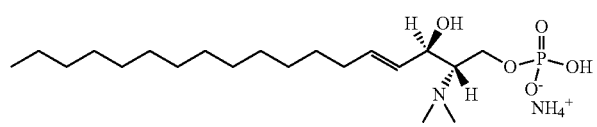 [SMILES: CCCCCCCCCCCCC/C=C/[C@@H](O)[C@H](COP(=O)([O-])O)N(C)C ; [NH4+]] |
| So-36 | 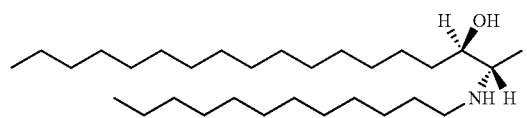 [SMILES: CCCCCCCCCCCCCCC[C@@H](O)[C@H](C)NCCCCCCCCCCCC] |

| No. | Structure |
|---|---|
| So-37 | 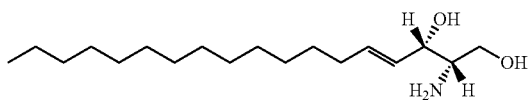 [SMILES: CCCCCCCCCCCCC/C=C/[C@H](O)[C@@H](N)CO] |
| So-38 | 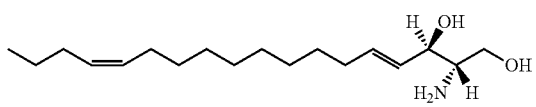 [SMILES: CCC/C=C\CCCCCCCC/C=C/[C@@H](O)[C@@H](N)CO] |
| So-41 | 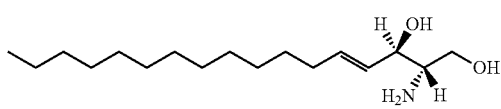 |
| So-42 | 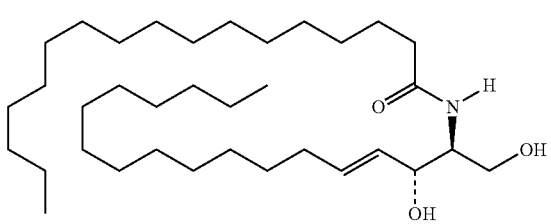 [SMILES: CCCCCCCCCCCCC/C=C/[C@@H](O)[C@H](CO)NC(=O)CCCCCCCCCCCCCCCC] |
| So-43 | 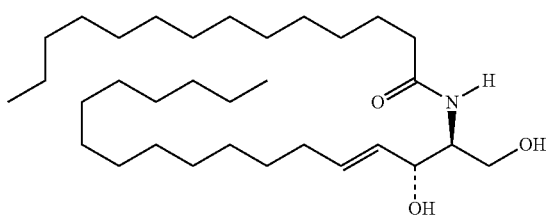 [SMILES: CCCCCCCCCCCCC/C=C/[C@@H](O)[C@H](CO)NC(=O)CCCCCCCCCCCCC] |
| So-44 | 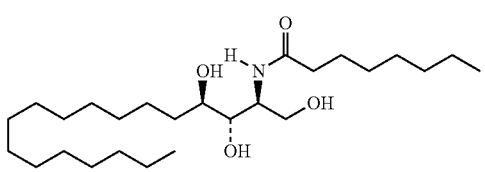 [SMILES: CCCCCCCCCCCCCC[C@@H](O)[C@@H](O)[C@H](CO)NC(=O)CCCCCCC] |
| So-45 | 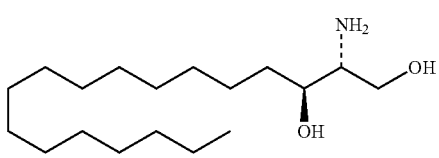 [SMILES: CCCCCCCCCCCCCCC[C@H](O)[C@H](N)CO] |
| So-46 | 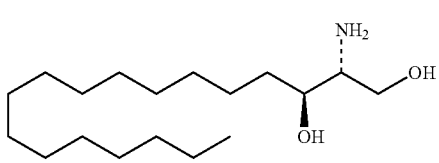 [SMILES: CCCCCCCCCCCCCCC[C@H](O)[C@H](N)CO] |
| So-47 | 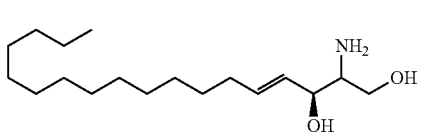 [SMILES: CCCCCCCCCCCCC/C=C/[C@H](O)C(N)CO] |
| So-48 | 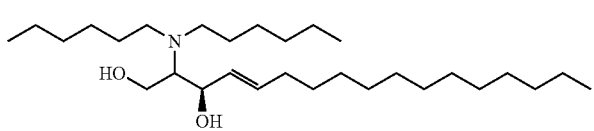 [SMILES: CCCCCCCCCCCC/C=C/[C@@H](O)C(CO)N(CCCCCC)CCCCCC] |

-continued
| No. | Structure |
|---|---|
| So-49 | 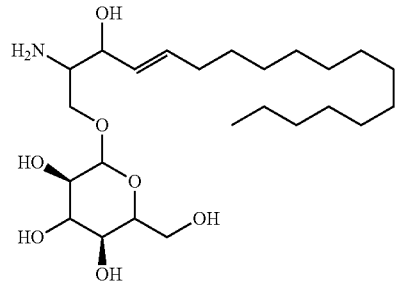 [SMILES: CCCCCCCCCCCCC/C=C/C(O)C(N)COC1OC(CO)[C@@H](O)C(O)[C@H]1O] |
| So-50 | 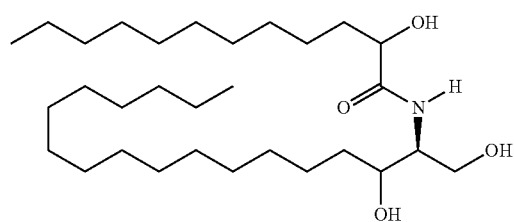 [SMILES: CCCCCCCCCCCCCCCC(O)[C@H](CO)NC(=O)C(O)CCCCCCCCCC] |
| So-51 | 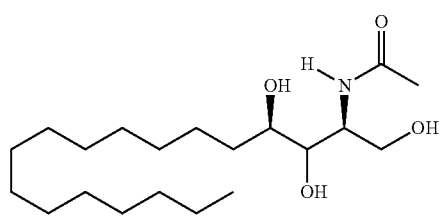 [SMILES: CCCCCCCCCCCCCC[C@@H](O)C(O)[C@H](CO)NC(C)=O] |
| So-52 | 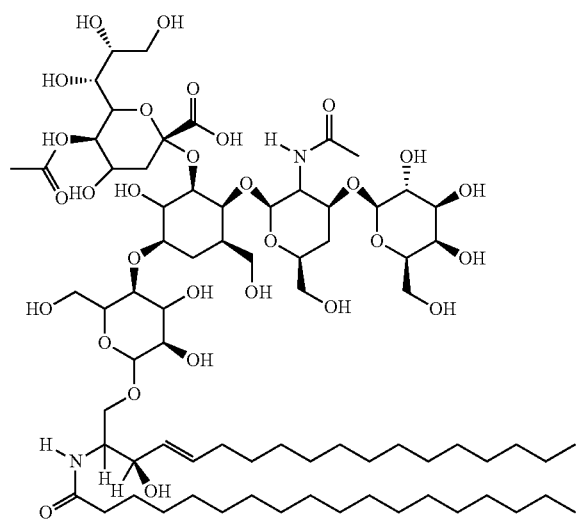 [SMILES: CCCCCCCCCCCCC/C=C/[C@@H](O)C(COC1OC(CO)[C@@H](O[C@@H]2C[C@H](CO)[C@H](O[C@@H]3O[C@H](CO)C[C@H](O[C@@H]4O[C@H](CO)[C@H](O)[C@H](O)[C@H]4O)C3NC(C)=O)[C@H](O[C@]3(C(=O)O)CC(O)[C@@H](OC(C)=O)C([C@H](O)[C@H](O)CO)O3)C2O)C(O)[C@H]1O)NC(=O)CCCCCCCCCCCCCCCCC] |
| So-53 | 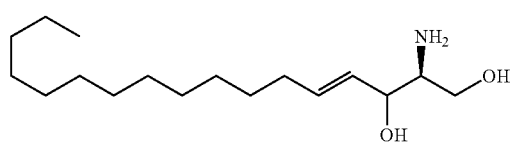 [SMILES: CCCCCCCCCCCC/C=C/C(O)[C@@H](N)CO] |
| So-54 | 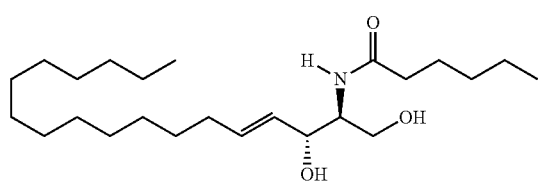 [SMILES: CCCCCCCCCCCCC/C=C/[C@@H](O)[C@H](CO)NC(=O)CCCCC] |

-continued
| No. | Structure |
|-----|-----------|
| So-55 | 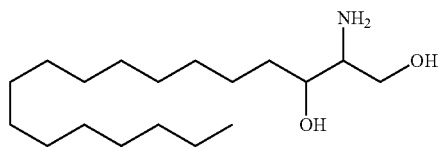 [SMILES: CCCCCCCCCCCCCCCC(O)C(N)CO] |
| So-56 | 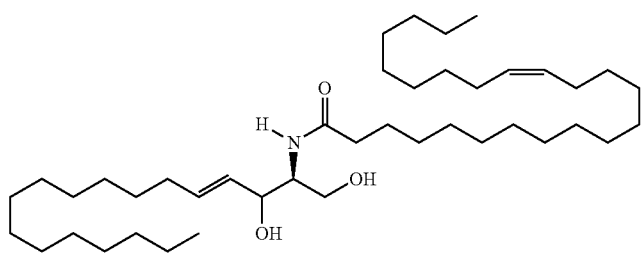 [SMILES: CCCCCCCC/C=C\CCCCCCCCCCCCCC(=O)N[C@@H](CO)C(O)/C=C/CCCCCCCCCCCCC] |
| So-57 | 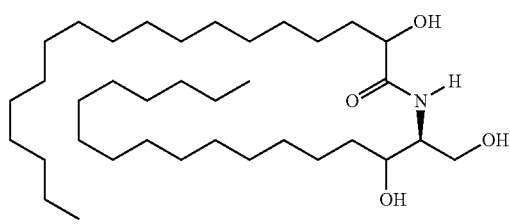 [SMILES: CCCCCCCCCCCCCCCCC(O)C(=O)N[C@@H](CO)C(O)CCCCCCCCCCCCCCC] |
| So-58 | 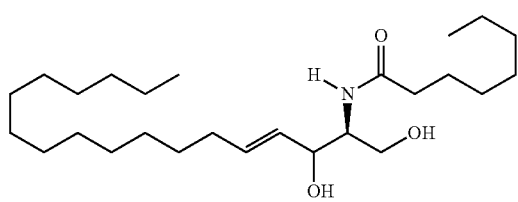 [SMILES: CCCCCCCCCCCCC/C=C/C(O)[C@H](CO)NC(=O)CCCCCCC] |
| So-59 | 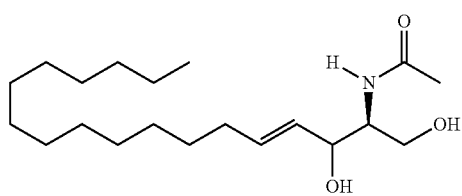 [SMILES: CCCCCCCCCCCCC/C=C/C(O)[C@H](CO)NC(C)=O] |
| So-60 | 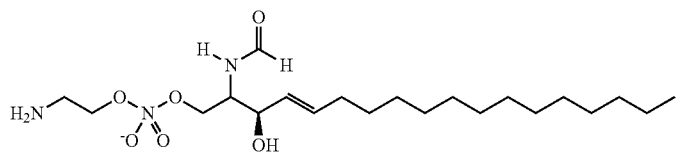 |
| So-61 | 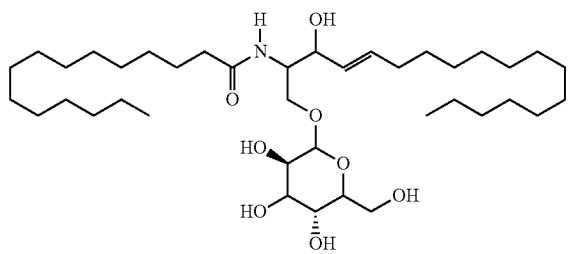 [SMILES: CCCCCCCCCCCCC/C=C/C(O)C(COC1OC(CO)[C@H](O)C(O)[C@H]1O)NC(=O)CCCCCCCCCCCCCC] |

-continued
| No. | Structure |
|---|---|
| So-62 | 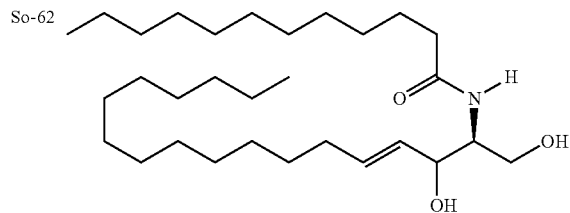 |
| So-63 | 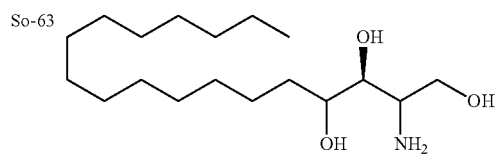 |
| So-64 | 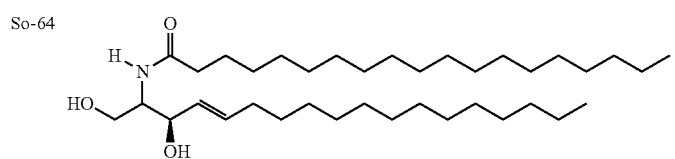 |
| So-65 | 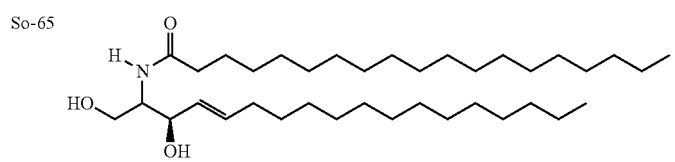 |
| So-66 | 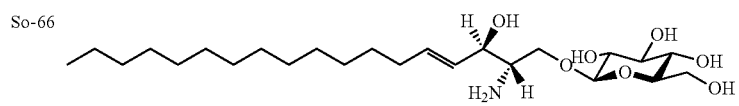 |
| So-67 | 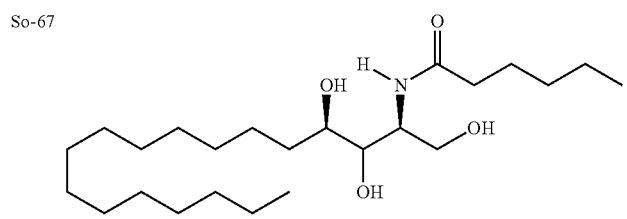 |
| So-68 | 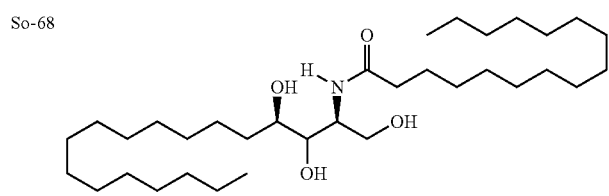 |
| So-69 | 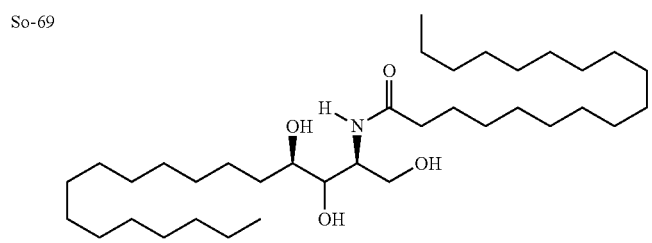 |

-continued

| No. | Structure |
|---|---|
| So-70 | 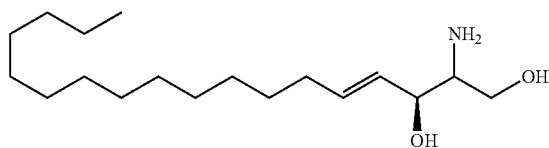 [SMILES: CCCCCCCCCCCCC/C=C/[C@H](O)C(N)CO] |
| So-71 | 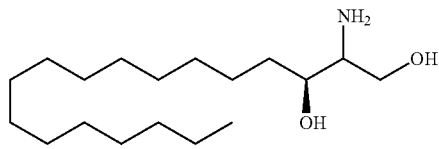 |
| So-72 | 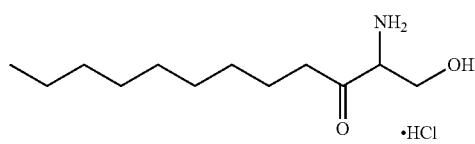 |
| So-73 | 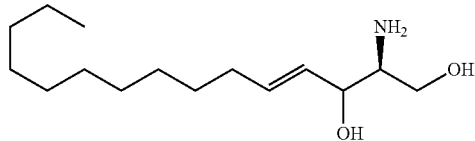 [SMILES: CCCCCCCCCC/C=C/C(O)[C@@H](N)CO] |
| So-74 | 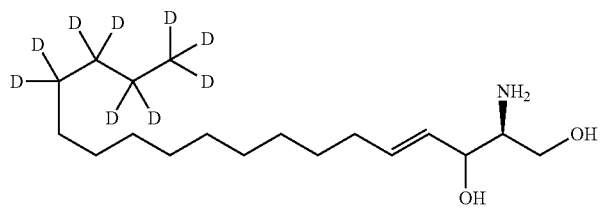 [SMILES: [2H]C([2H])([2H])C([2H])([2H])C([2H])([2H])C([2H])([2H])CCCCCCCCC/C=C/C(O)[C@@H](N)CO] |
| So-75 | 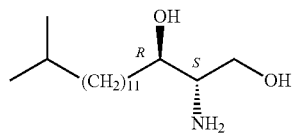 |
| No.41 | 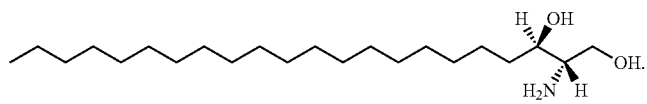 [SMILES: CCCCCCCCCCCCCCCCCCC[C@@H](O)[C@@H](N)CO] |

7. The method of claim 1, wherein the nucleic acid is a therapeutic or diagnostic used to treat or diagnose a disease selected from the group consisting of: inflammatory diseases, pneumonia, myocarditis, acute and chronic gastritis, acute and chronic enteritis, acute and chronic hepatitis, acute and chronic nephritis, dermatitis, encephalitis, lymphitis, conjunctivitis, keratitis, iridocyclitis, otitis media, allergic rhinitis, asthma, pulmonary fibrosis, chronic obstructive pulmonary disease, allergic dermatitis, sickle cell disease, multiple sclerosis, systemic lupus erythematosus, lupus nephritis, lung cancer, gastric cancer, colorectal cancer, liver cancer, pancreatic cancer, cervical cancer, breast cancer, leukemia, multiple myeloma, diabetes, and gout.

8. The method of claim 7, wherein the nucleic acid is a ribonucleic acid (RNA) selected from the group consisting of messenger RNA (mRNA), rRNA (ribosomal RNA), tRNA (transfer RNA), heterogeneous nuclear RNA (hnRNA), small RNA, transfer-messenger RNA (tmRNA), telomerase RNA and antisense RNA.

9. The method of claim 8, wherein the length of the small RNA is 14-32 bp.

10. The method of claim 9, wherein the small RNA comprises the sequence of SEQ ID NO: 1.

11. The method of claim 1, wherein the nucleic acid is delivered in vitro to the cell, or delivered in vivo to the subject.

12. The method of claim 11, wherein delivery in vivo to the subject is by oral administration, intravenous administration, subcutaneous administration, intramuscular administration, intraarterial administration, intraperitoneal administration, intrapulmonary administration, intracerebral administration, intraspinal administration, intra-articular a b administration, intrasynovial administration, or administration via inhalation.

13. The method of claim 8, wherein the small RNA is selected from the group consisting of small nuclear RNA (snRNA), small nucleolar RNA (snoRNA) and small cytoplasmic RNA.

14. The method of claim 9, wherein the length of the small RNA is 16-28 bp.

15. The method of claim 14, wherein the length of the small RNA is 18-24 bp.

16. The method of claim 1, wherein the nucleic acid is synthetic or purified.

17. The method of claim 1, wherein the nucleic acid is single-stranded, double-stranded or partially double-stranded RNA or DNA.

\* \* \* \* \*